(12) United States Patent
Sakamoto

(10) Patent No.: US 12,391,872 B2
(45) Date of Patent: Aug. 19, 2025

(54) LIGHT EMITTING ELEMENT AND MONOAMINE COMPOUND FOR THE SAME

(71) Applicant: Samsung Display Co., Ltd., Yongin-si (KR)

(72) Inventor: Naoya Sakamoto, Yokohama (JP)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 722 days.

(21) Appl. No.: 17/375,524

(22) Filed: Jul. 14, 2021

(65) Prior Publication Data

US 2022/0077396 A1    Mar. 10, 2022

(30) Foreign Application Priority Data

Sep. 10, 2020    (KR) ........................ 10-2020-0116374

(51) Int. Cl.
| | |
|---|---|
| C07D 307/91 | (2006.01) |
| C07D 333/76 | (2006.01) |
| C09K 11/06 | (2006.01) |
| H10K 59/12 | (2023.01) |
| H10K 85/60 | (2023.01) |
| H10K 50/11 | (2023.01) |
| H10K 50/15 | (2023.01) |
| H10K 101/10 | (2023.01) |
| H10K 101/30 | (2023.01) |

(52) U.S. Cl.
CPC ............ *C09K 11/06* (2013.01); *C07D 307/91* (2013.01); *C07D 333/76* (2013.01); *H10K 59/12* (2023.02); *H10K 85/633* (2023.02); *H10K 85/636* (2023.02); *C09K 2211/1018* (2013.01); *H10K 50/11* (2023.02); *H10K 50/156* (2023.02); *H10K 85/626* (2023.02); *H10K 85/6574* (2023.02); *H10K 85/6576* (2023.02); *H10K 2101/10* (2023.02); *H10K 2101/30* (2023.02)

(58) Field of Classification Search
None
See application file for complete search history.

(56) References Cited

U.S. PATENT DOCUMENTS

| | | | |
|---|---|---|---|
| 9,065,060 B2 | 6/2015 | Hong et al. | |
| 2016/0372665 A1* | 12/2016 | Takada | ............... H10K 85/636 |
| 2016/0372677 A1* | 12/2016 | Miyake | ............... H10K 85/626 |
| 2017/0133591 A1 | 5/2017 | Takada et al. | |
| 2018/0105534 A1* | 4/2018 | Kim | ..................... C09K 11/06 |
| 2018/0331290 A1* | 11/2018 | Miyake | ............... C07D 409/12 |
| 2019/0207117 A1* | 7/2019 | Miyake | ............... C09B 57/008 |
| 2019/0237668 A1* | 8/2019 | Miyake | ............... C07C 211/54 |
| 2019/0237676 A1* | 8/2019 | Miyake | ............... C07D 311/96 |
| 2020/0235297 A1* | 7/2020 | Miyake | ............... C07C 211/54 |
| 2020/0365814 A1 | 11/2020 | Ha et al. | |

FOREIGN PATENT DOCUMENTS

| | | | |
|---|---|---|---|
| CN | 102850334 A * | 1/2013 | ........... C07D 405/14 |
| CN | 108863813 | 11/2018 | |
| CN | 109694328 | 4/2019 | |
| CN | 110003018 | 7/2019 | |
| CN | 112585114 | 3/2021 | |
| KR | 10-1380009 | 4/2014 | |
| KR | 10-2016-0149977 | 12/2016 | |
| KR | 10-1868505 | 6/2018 | |
| KR | 10-2019-0077158 | 7/2019 | |
| KR | 10-2019-0091409 | 8/2019 | |
| KR | 10-2083707 | 3/2020 | |
| KR | 10-2020-0061302 | 6/2020 | |
| KR | 10-2134379 | 7/2020 | |
| WO | 2016/024792 | 2/2016 | |
| WO | 2019/050153 | 3/2019 | |
| WO | 2019/093649 | 5/2019 | |
| WO | 2019/164327 | 8/2019 | |
| WO | WO-2020106098 A1 * | 5/2020 | ........... C07C 211/54 |

* cited by examiner

*Primary Examiner* — Robert S Loewe
(74) *Attorney, Agent, or Firm* — KILE PARK REED & HOUTTEMAN PLLC

(57) ABSTRACT

A light emitting element of an embodiment includes a first electrode, a second electrode facing the first electrode, and functional layers disposed between the first electrode and the second electrode. At least one functional layer among the functional layers includes a monoamine compound of an embodiment thereby showing high efficiency and long life characteristics. The monoamine compound includes a substituted or unsubstituted phenanthryl group directly bonded to a nitrogen atom, a substituted or unsubstituted dibenzoheterole group directly bonded to the nitrogen atom, and a substituted or unsubstituted naphthyl group bonded to the nitrogen atom via a linker.

14 Claims, 7 Drawing Sheets

LIGHT EMITTING ELEMENT AND MONOAMINE COMPOUND FOR THE SAME

CROSS-REFERENCE TO RELATED APPLICATION(S)

This application claims priority to and benefits of Korean Patent Application No. 10-2020-0116374 under 35 U.S.C. § 119, filed on Sep. 10, 2020 in the Korean Intellectual Property Office, the entire contents of which are incorporated herein by reference.

BACKGROUND

1. Technical Field

The disclosure relates to a hole transport layer of a light emitting element and a compound used as a material of the hole transport layer.

2. Description of the Related Art

Active development continues for an organic electroluminescence display as an image display. The organic electroluminescence display is different from a liquid crystal display and is a so-called self-luminescent display in which holes and electrons respectively injected from a first electrode and a second electrode recombine in an emission layer so that a light-emitting material including an organic compound in the emission layer emits light to achieve display.

In the application of a light emitting element to a display, there is an ongoing need for the reduction of driving voltage, as well as improvements in emission efficiency and the life of the light emitting element. Continuous development is required for materials for a light emitting element which stably achieves such characteristics.

SUMMARY

The disclosure provides a light emitting element showing excellent emission efficiency and long life and provides a monoamine compound used in the light emitting element.

An embodiment of the inventive concept provides a light emitting element that may include a first electrode, a second electrode facing the first electrode, and functional layers disposed between the first electrode and the second electrode, wherein at least one functional layer among the functional layers may include a monoamine compound including a substituted or unsubstituted phenanthryl group directly bonded to a nitrogen atom, a substituted or unsubstituted dibenzoheterole group directly bonded to the nitrogen atom, and a substituted or unsubstituted naphthyl group bonded to the nitrogen atom via a linker.

In an embodiment, the dibenzoheterole group may be a dibenzothiophene group or a dibenzofuran group.

In an embodiment, the linker may be a substituted or unsubstituted phenylene group or a substituted or unsubstituted divalent biphenyl group.

In an embodiment, the linker may be an unsubstituted phenylene group, and the naphthyl group may be bonded to the phenylene group at a para position with respect to the nitrogen atom.

In an embodiment, the phenanthryl group may be an unsubstituted phenanthryl group or a phenanthryl group substituted with a deuterium atom, the naphthyl group may be an unsubstituted naphthyl group, a naphthyl group substituted with a phenyl group, or a naphthyl group substituted with a deuterium atom, and the dibenzoheterole group may be an unsubstituted dibenzoheterole group, a dibenzoheterole group substituted with a deuterium atom, or a dibenzoheterole group substituted with a substituted or unsubstituted phenyl group.

In an embodiment, the monoamine compound may be one selected from Compound Group 1 below.

[Compound Group 1]

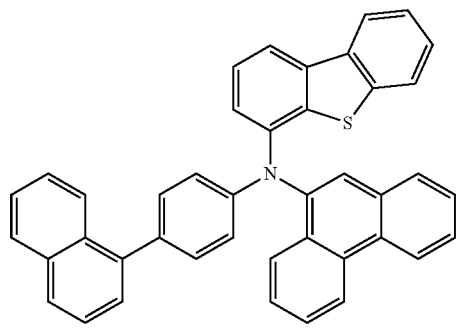

1

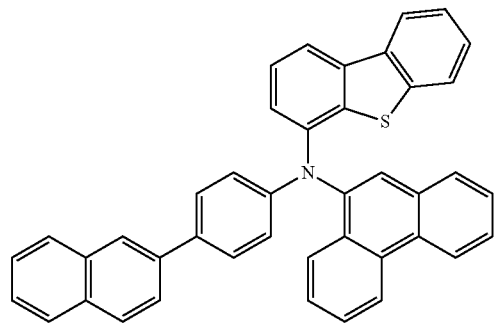

2

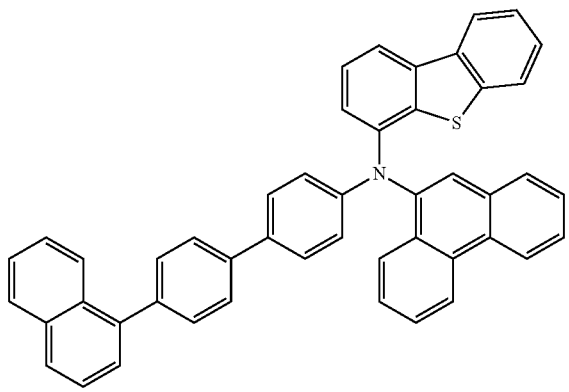

3

4
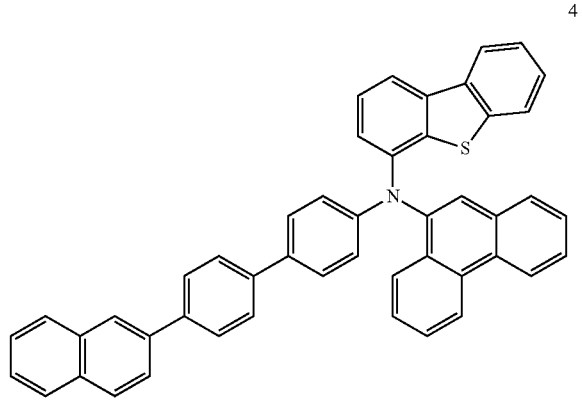
5
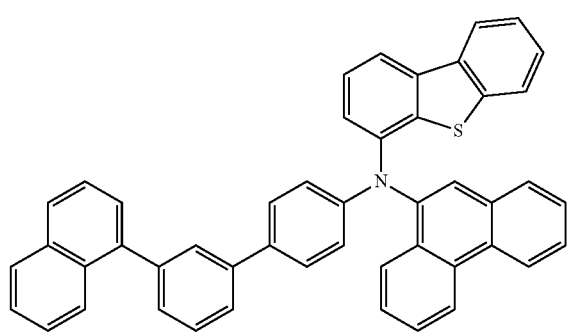
6
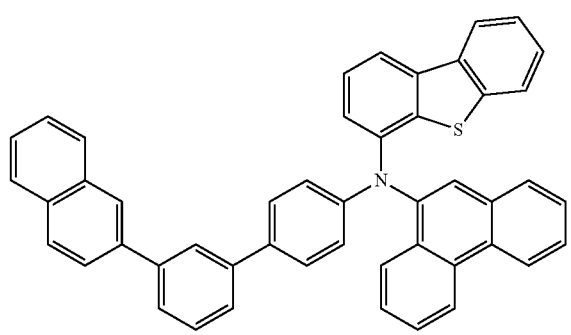
7
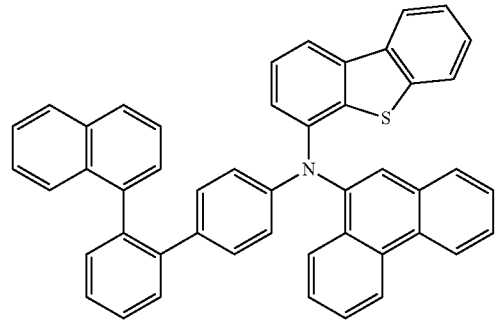
8
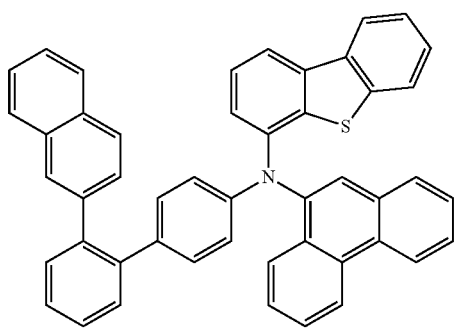
9
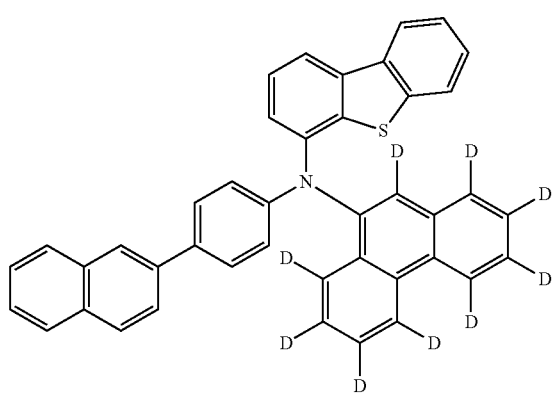

12
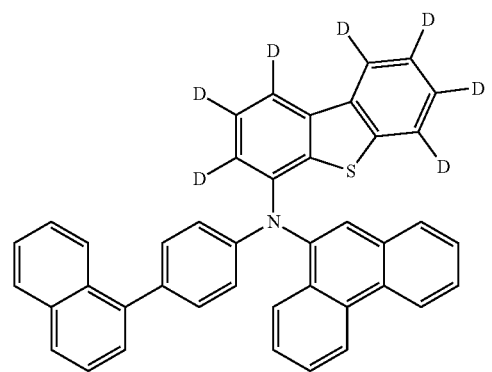
13
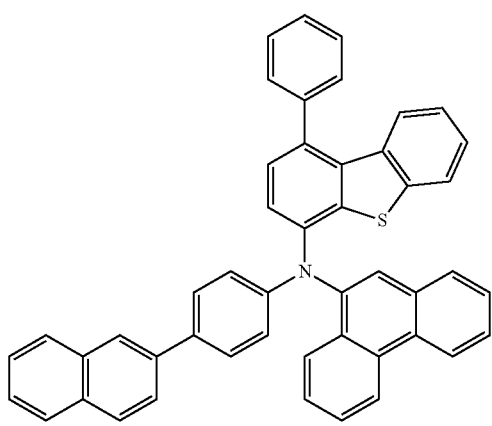
14
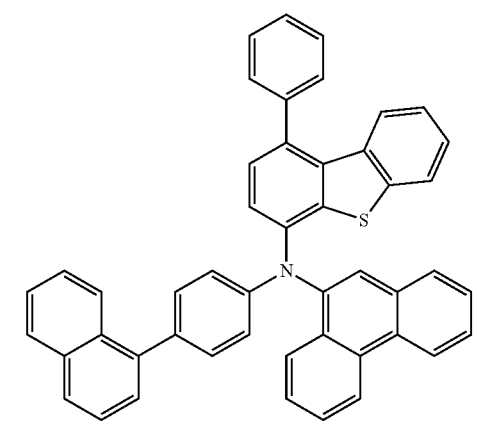
15
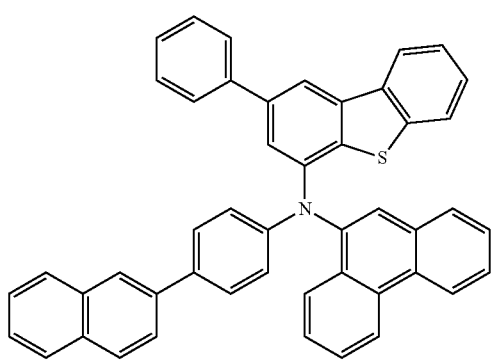
16
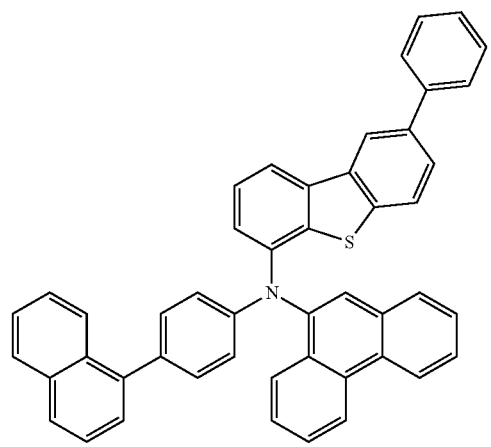
17
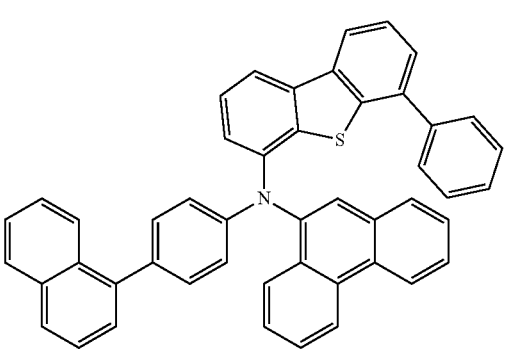
18
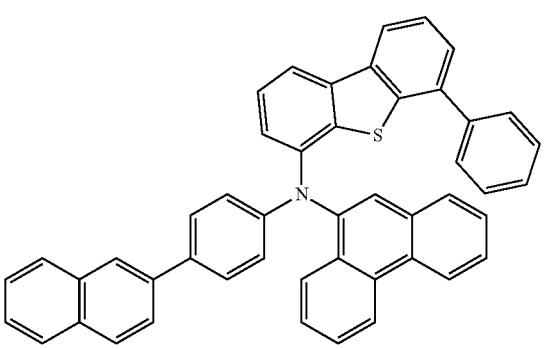
19
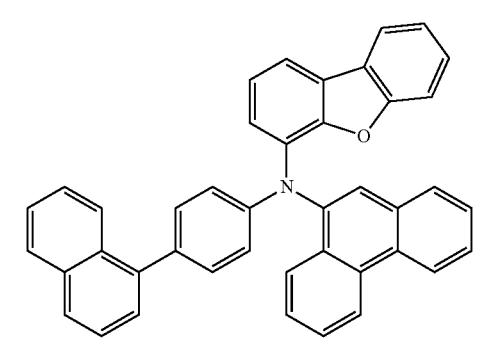

20
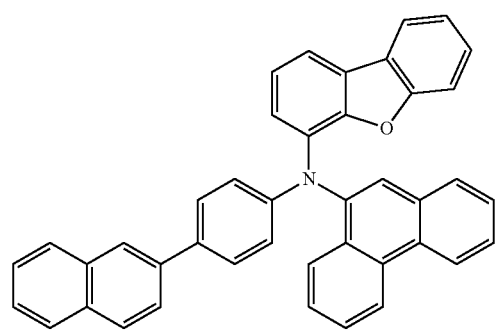
21
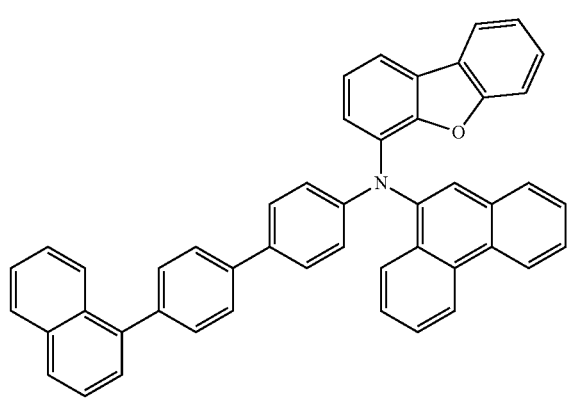
22
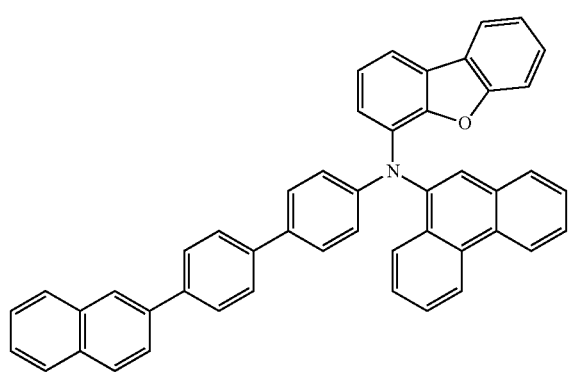
23
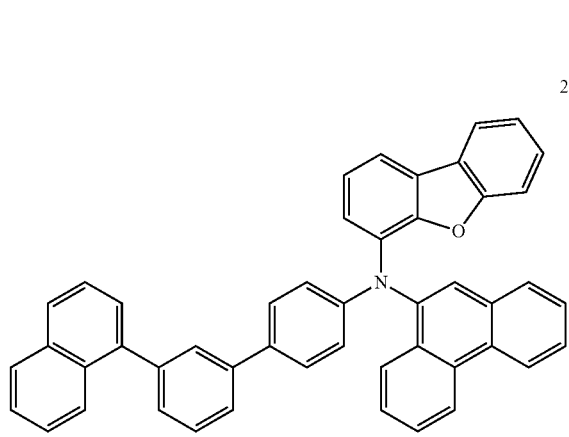
24
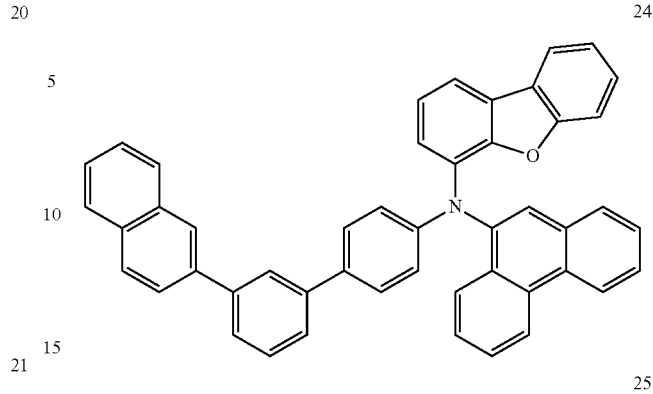
25
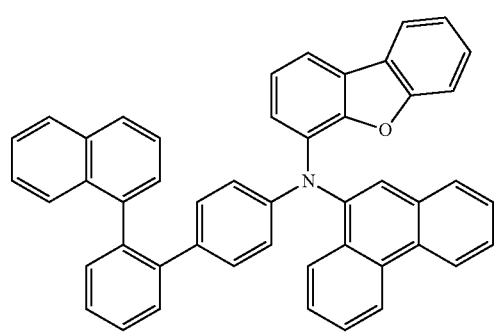
26
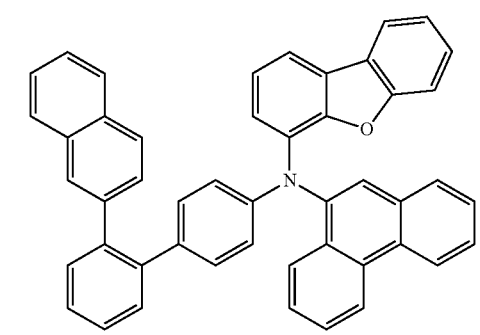
27
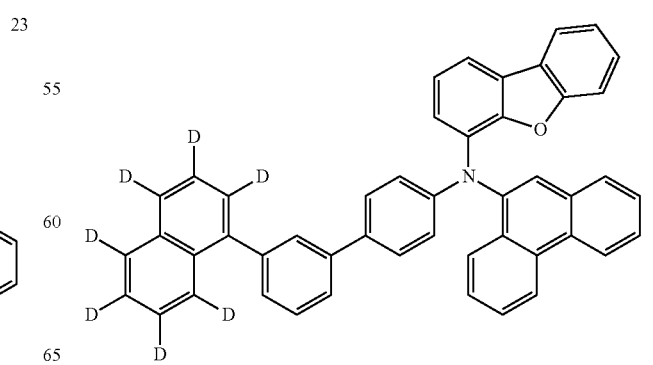

28
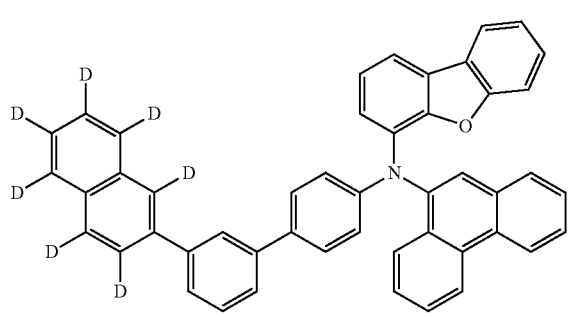
29
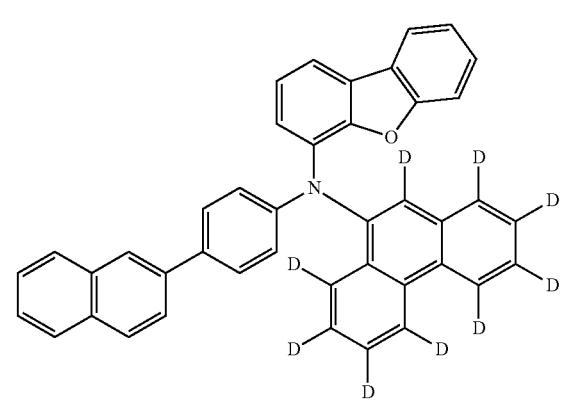
30
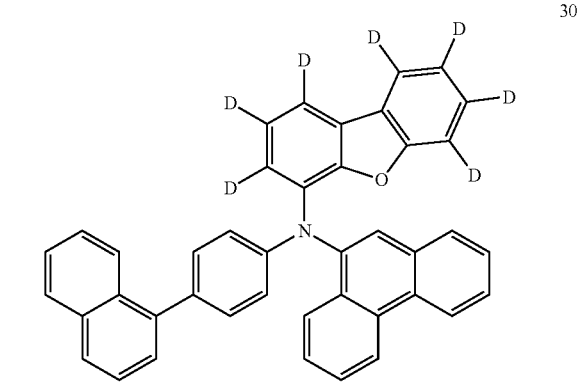
31
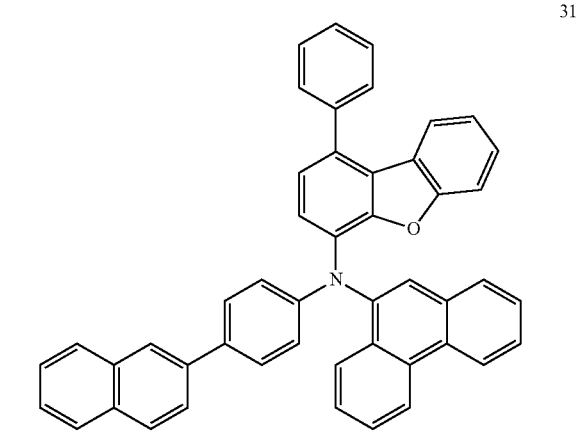
32
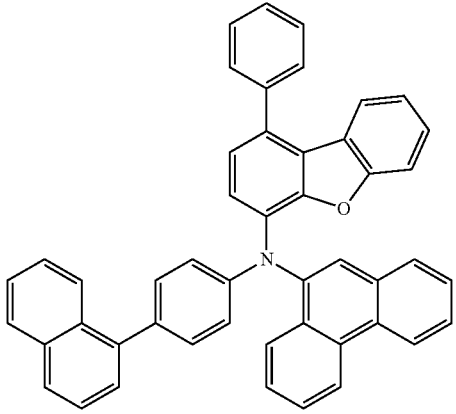
33
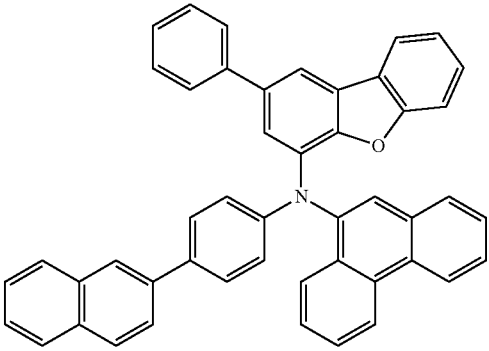
34
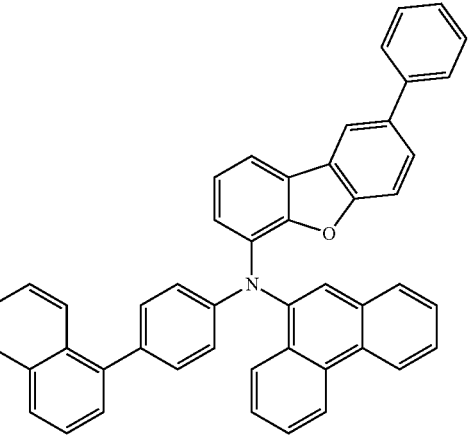
35
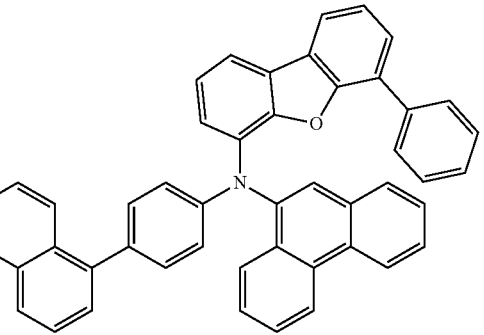

36
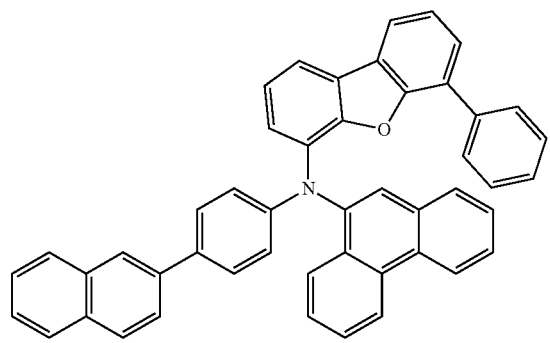
37
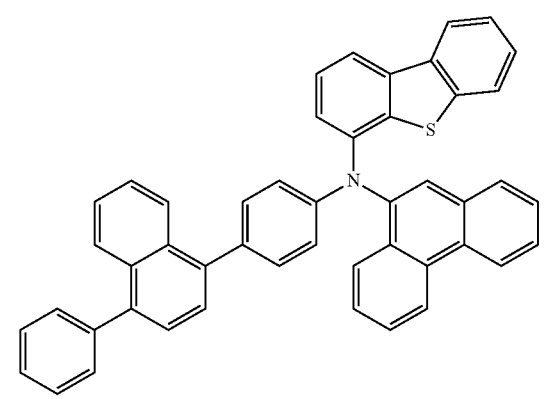
38
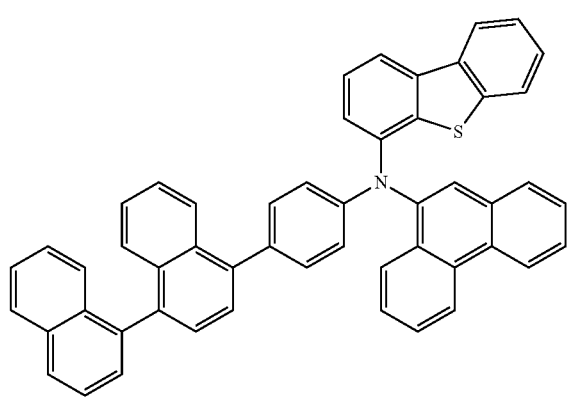
39
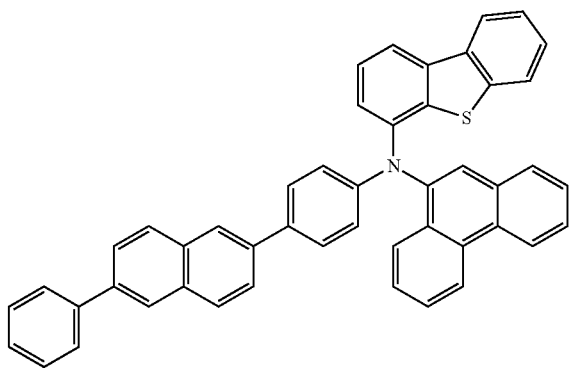
40
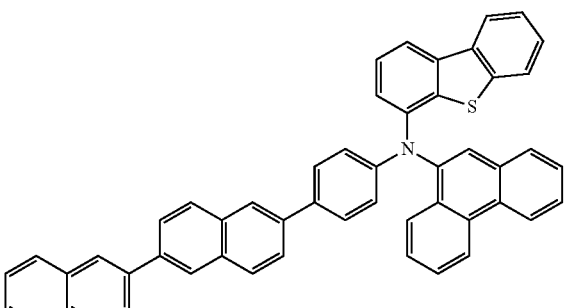
41
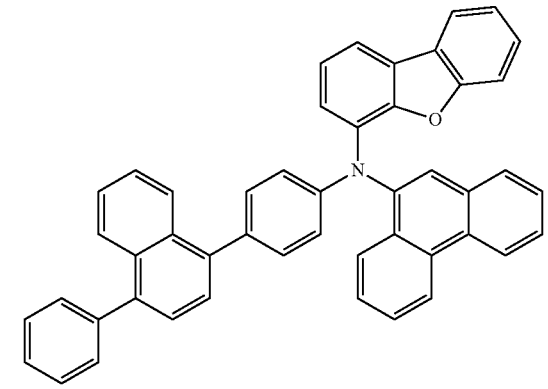
42
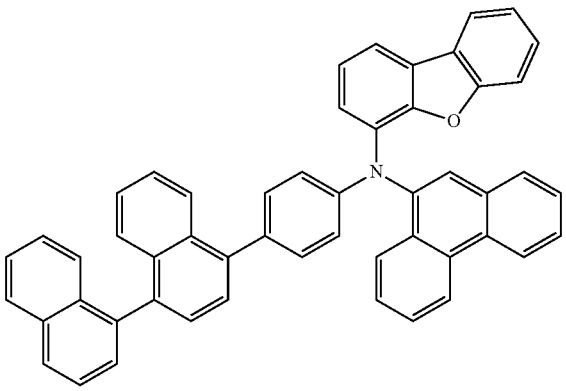
43
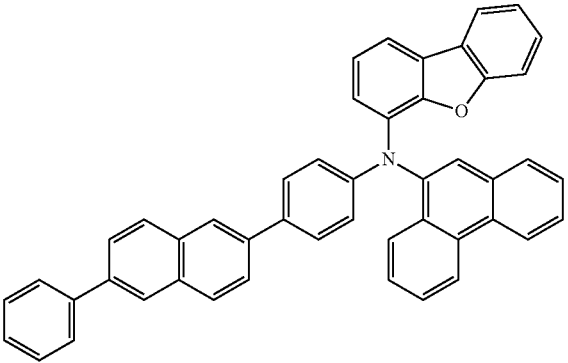

44
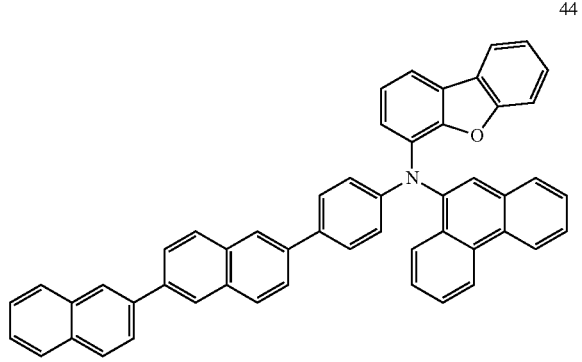
45
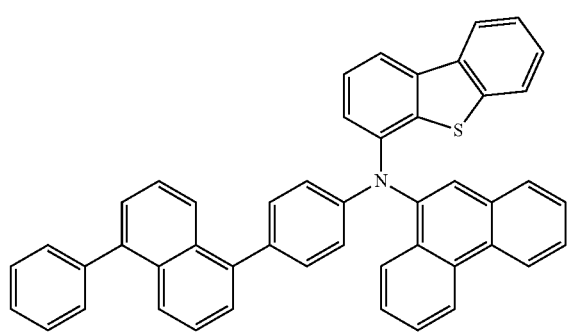
46
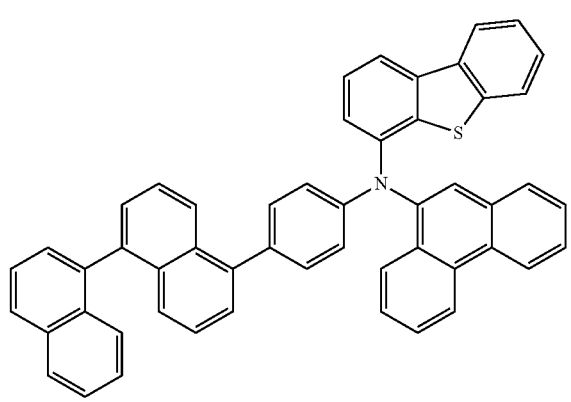
47
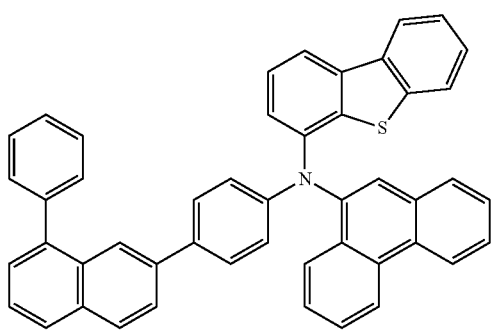
48
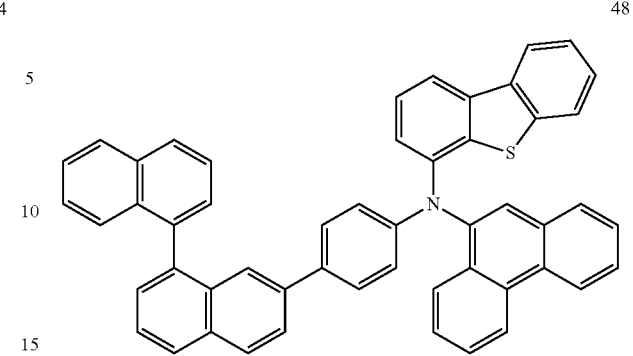
49
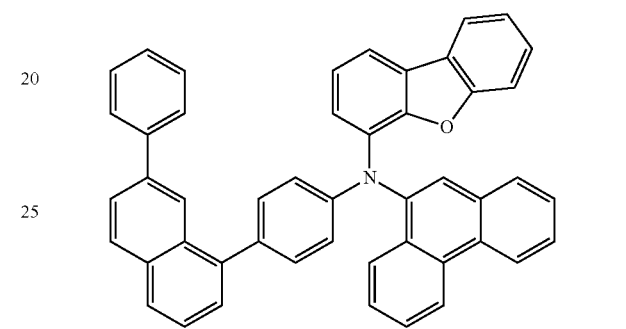
50
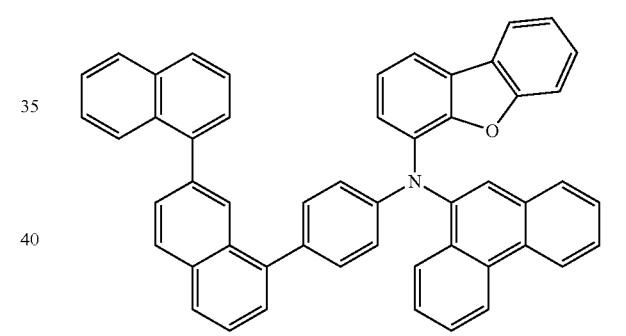
51
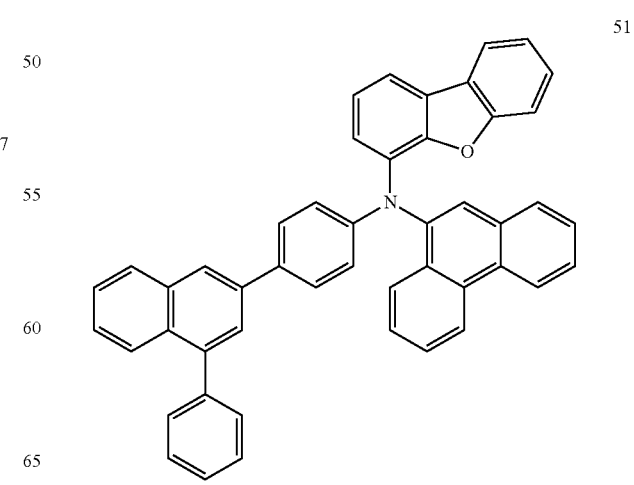

52
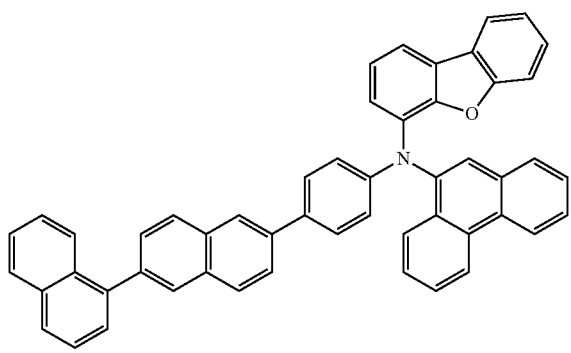
53
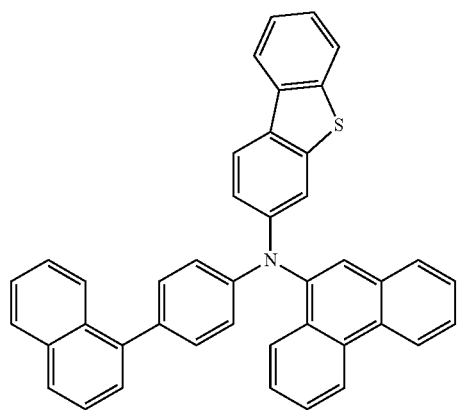
54
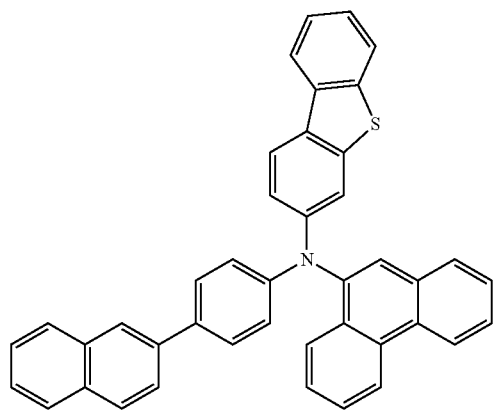
55
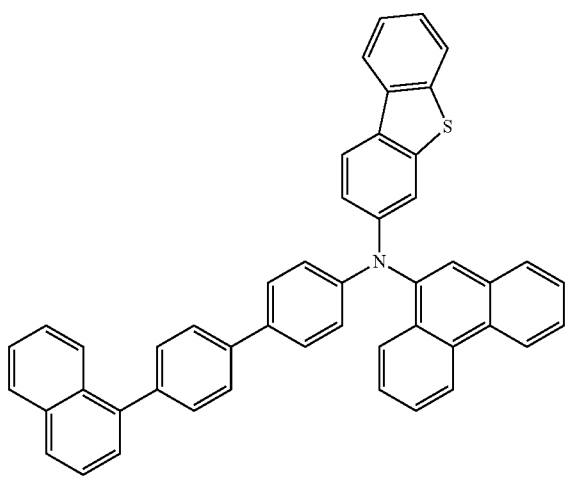
56
57
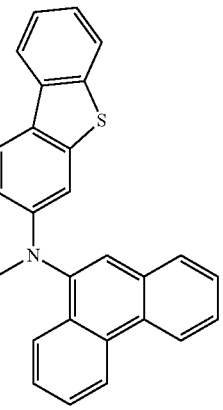

58
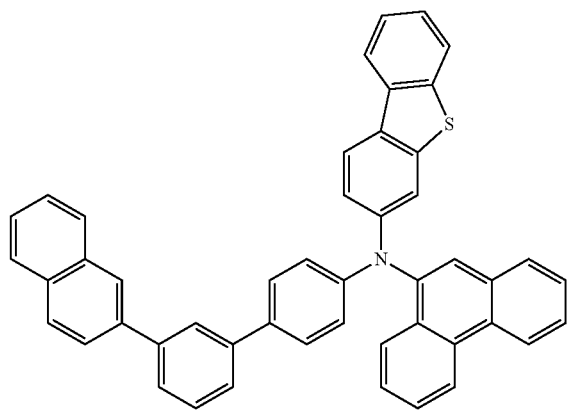
59
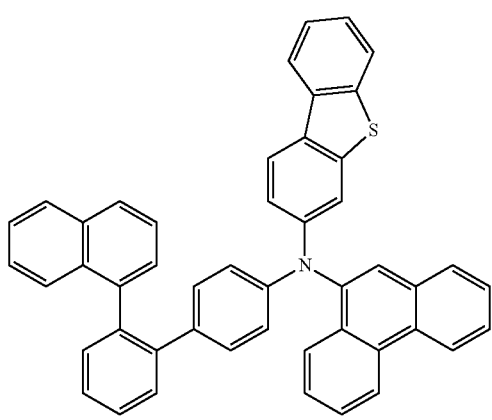
60
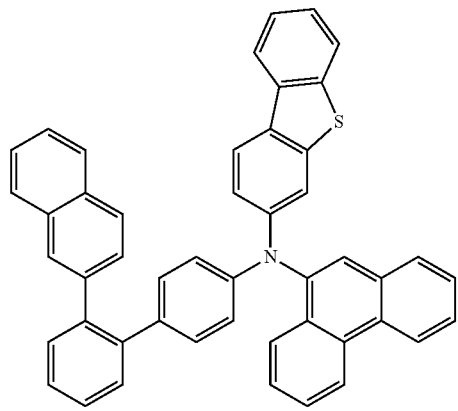
61
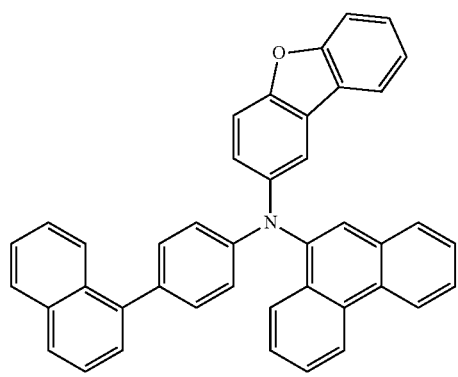
62
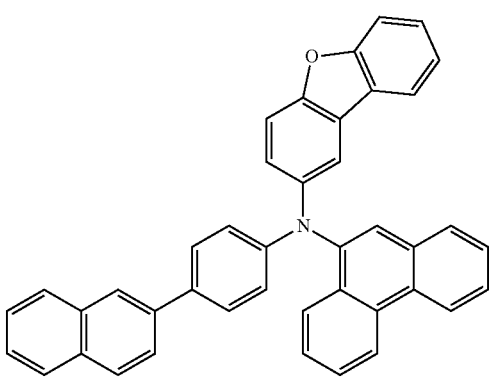
63
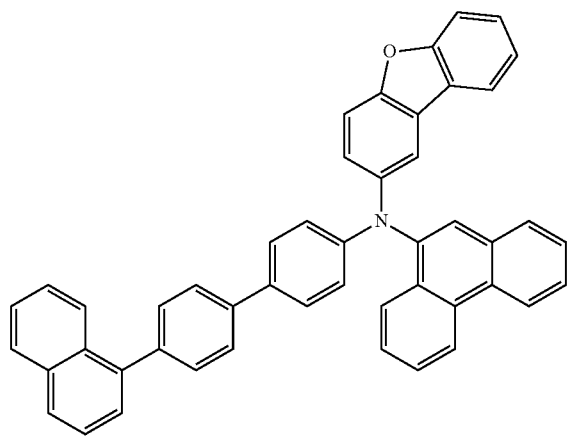
64
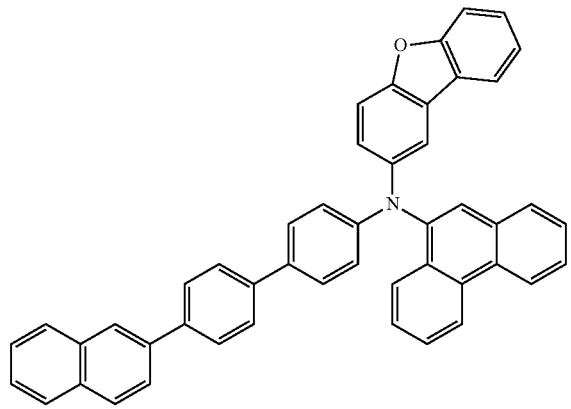

65
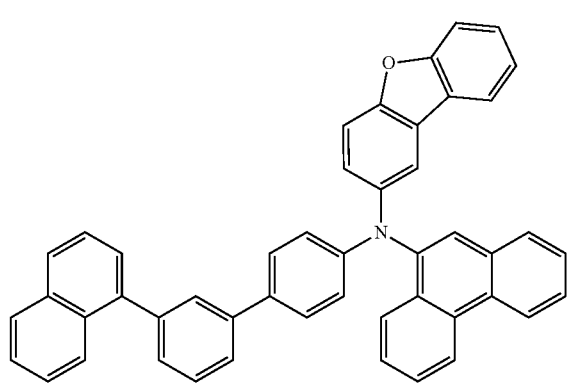
66
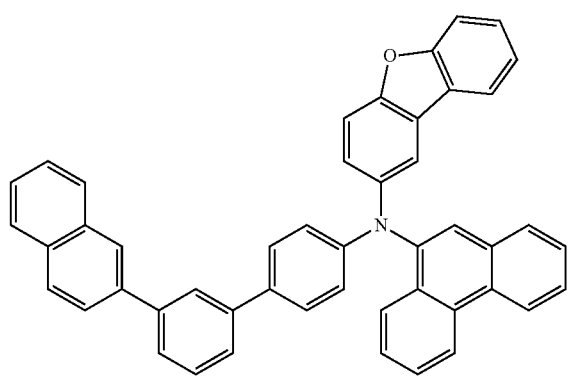
66
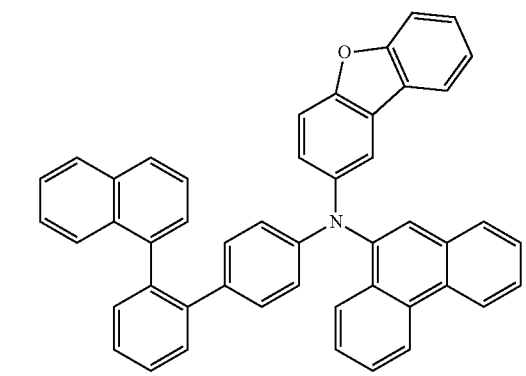
67
68
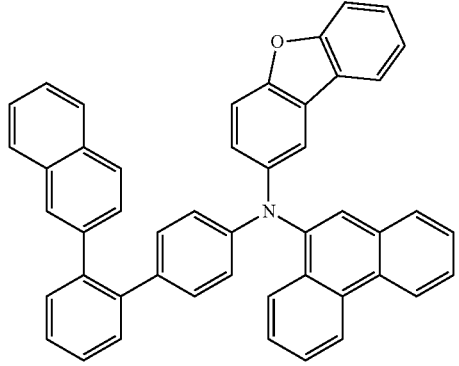
69
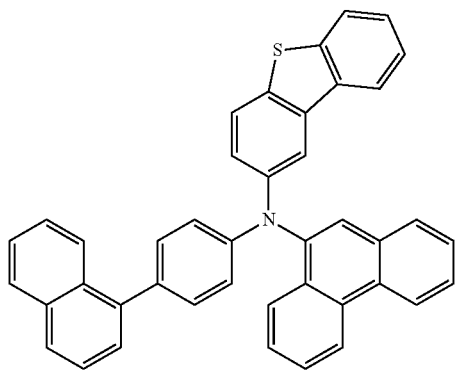
70
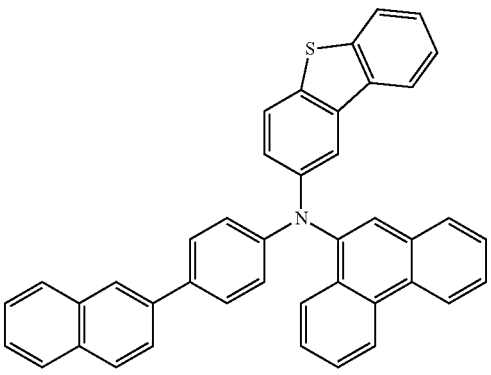
71

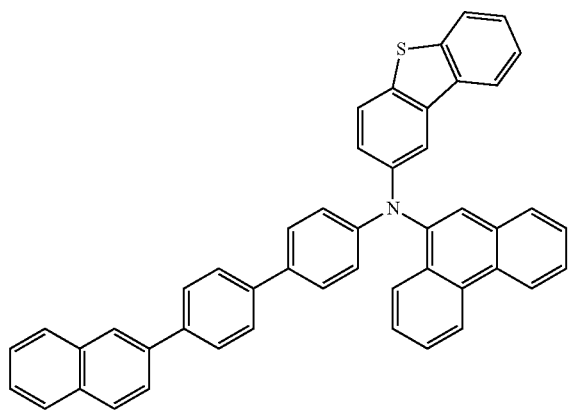
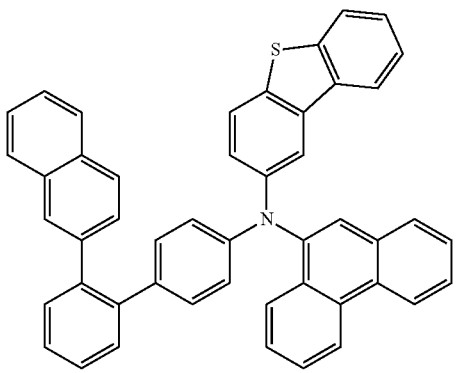
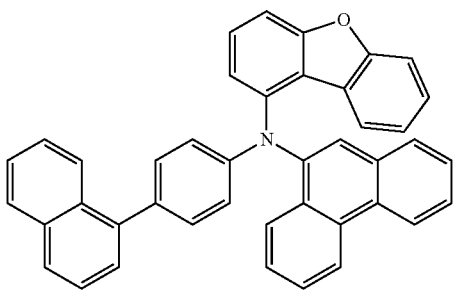
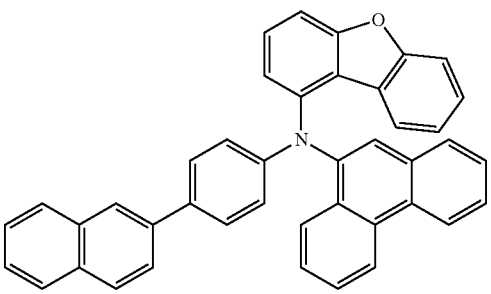
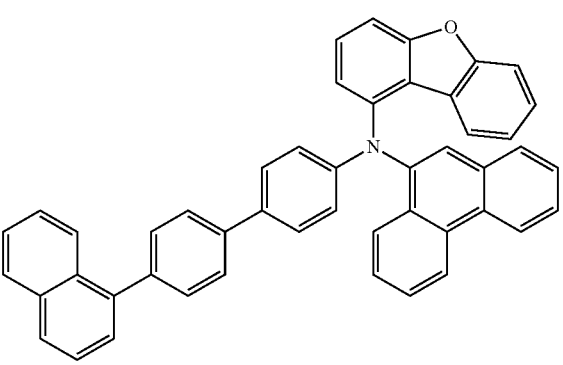

-continued
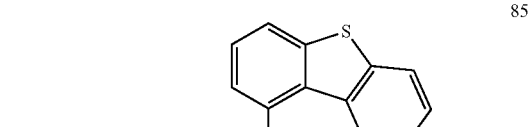
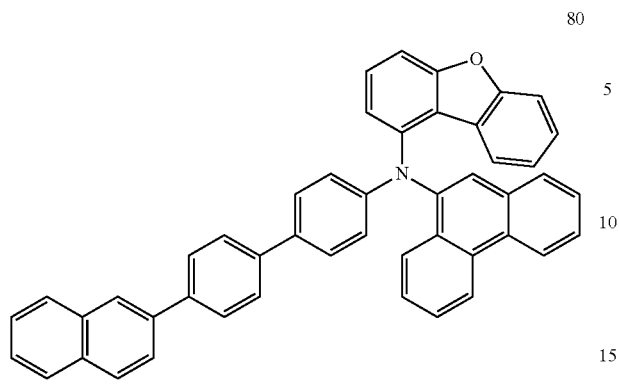
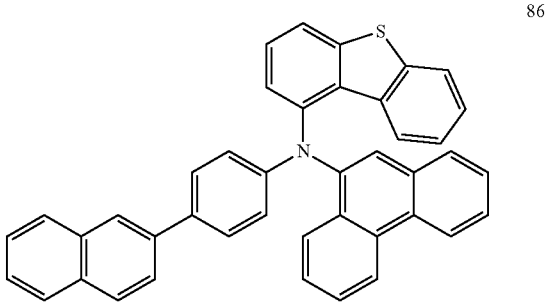
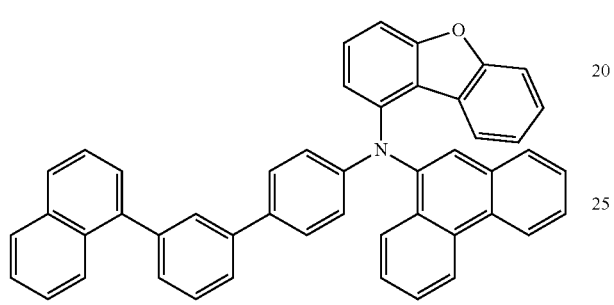
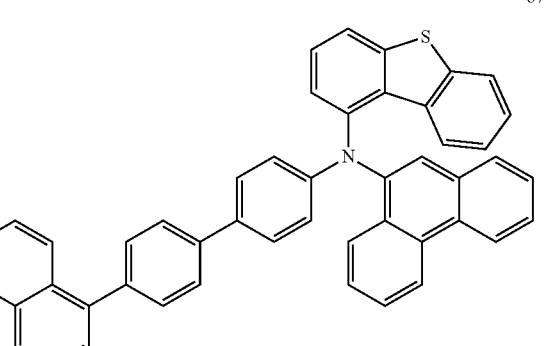
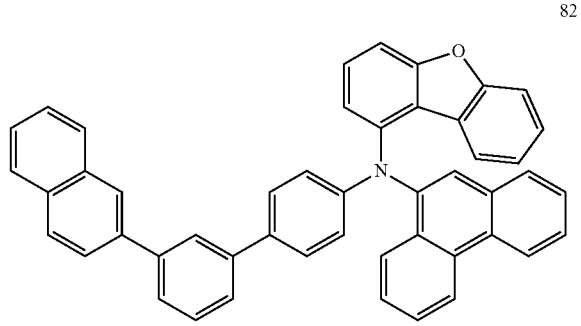
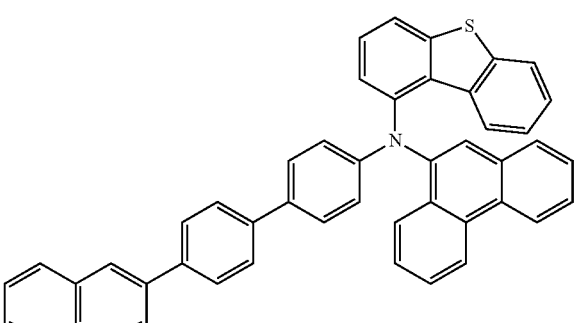
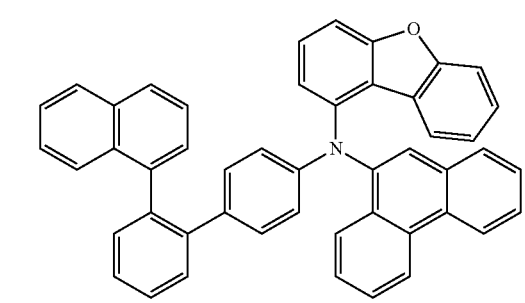
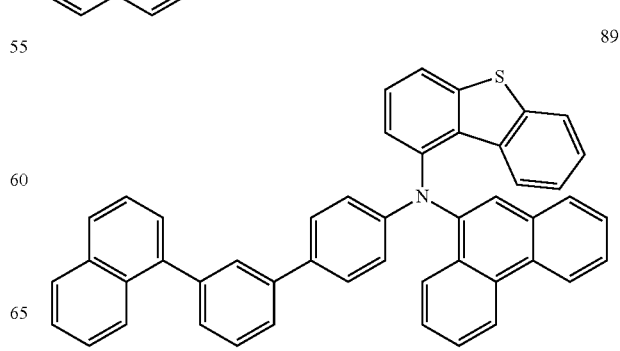
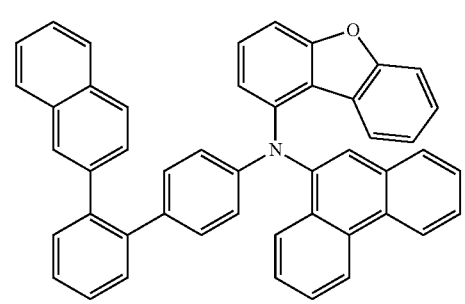

-continued

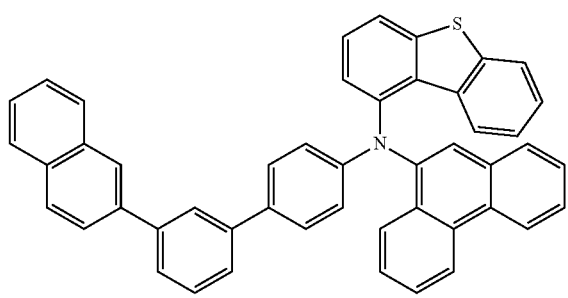

90

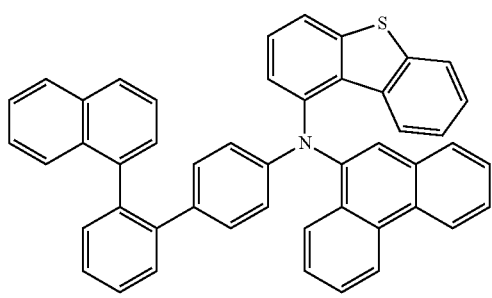

91

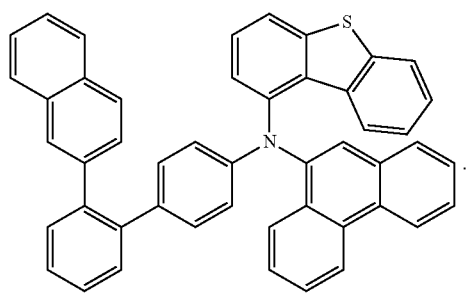

92

An embodiment of the inventive concept provides a light emitting element that may include a first electrode, a second electrode facing the first electrode, and functional layers disposed between the first electrode and the second electrode, wherein at least one functional layer among the functional layers may include a monoamine compound represented by Formula 1 below.

[Formula 1]

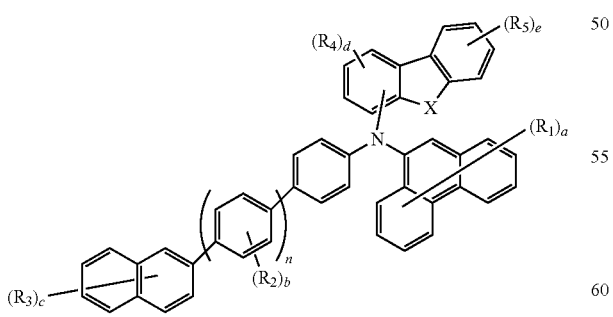

In Formula 1, X may be O or S, n may be 0 or 1, a may be an integer from 0 to 9, b and e may each independently be an integer from 0 to 4, c may be an integer from 0 to 7, d may be an integer from 0 to 3, and $R_1$ to $R_5$ may each independently be a substituted or unsubstituted alkyl group of 1 to 15 carbon atoms, a substituted or unsubstituted aryl group of 6 to 30 carbon atoms, a substituted or unsubstituted heteroaryl group of 1 to 30 carbon atoms, a substituted or unsubstituted silyl group, a halogen atom, a hydrogen atom, or a deuterium atom.

In an embodiment, Formula 1 may be represented by Formula 2-1 or Formula 2-2 below.

[Formula 2-1]

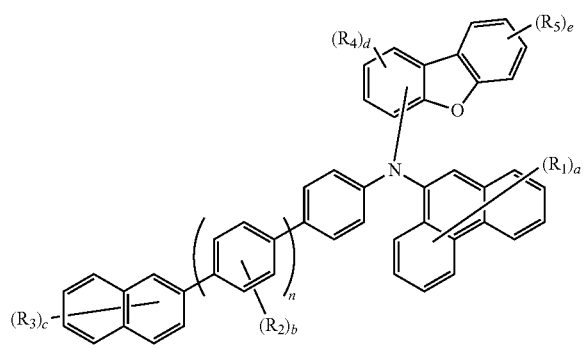

[Formula 2-2]

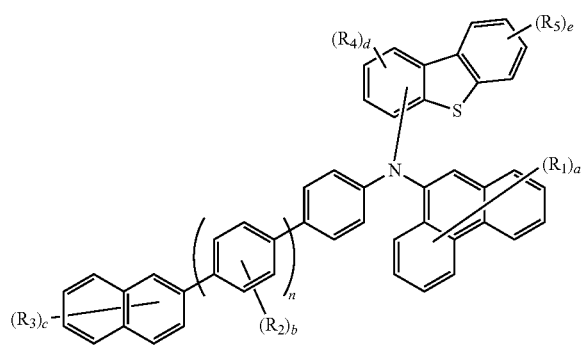

In Formula 2-1 and Formula 2-2, a to e, n, and $R_1$ to $R_5$ may be the same as defined in Formula 1.

In an embodiment, Formula 1 may be represented by one of Formula 3-1 to Formula 3-4 below.

[Formula 3-1]

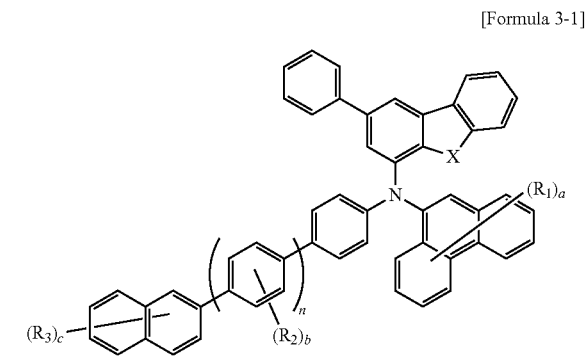

[Formula 3-2]

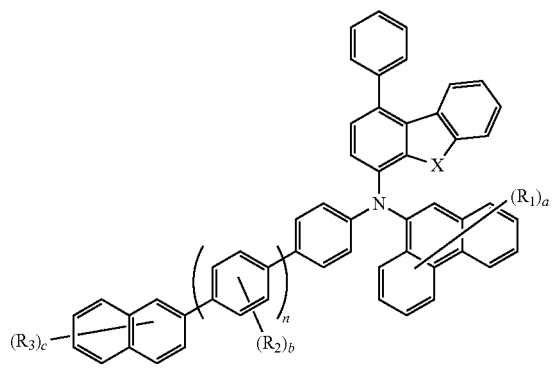

[Formula 3-3]

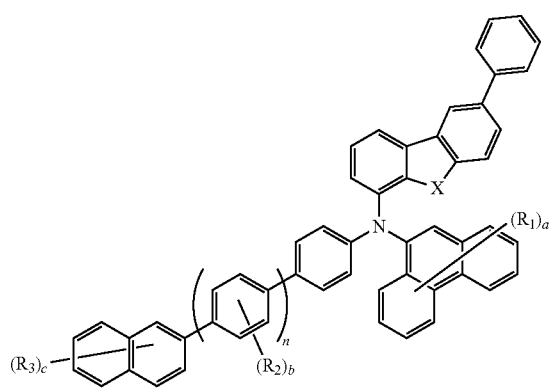

[Formula 3-4]

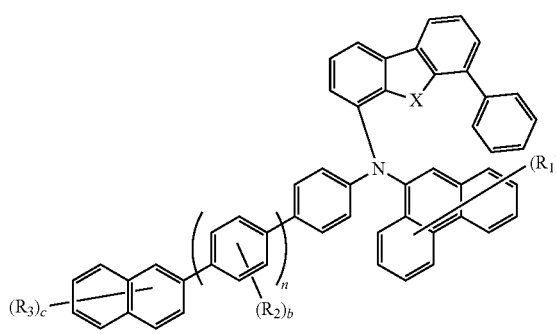

In Formula 3-1 to Formula 3-4, a to c, n, X, and $R_1$ to $R_3$ may be the same as defined in Formula 1.

In an embodiment, Formula 1 may be represented by Formula 4-1 or Formula 4-2 below.

[Formula 4-1]

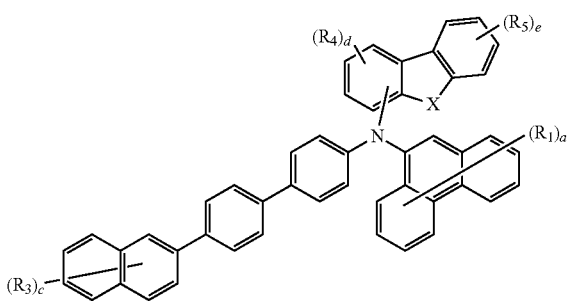

[Formula 4-2]

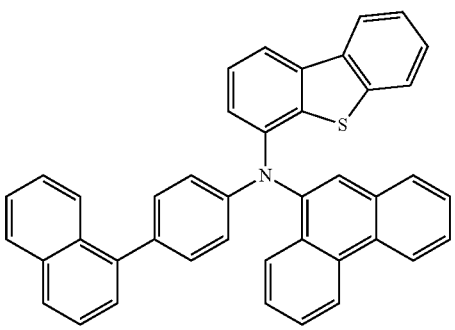

In Formula 4-1 and Formula 4-2, a, c to e, X, $R_1$, and $R_3$ to $R_5$ may be the same as defined in Formula 1.

In an embodiment, the functional layers may include a hole transport region, and an emission layer disposed on the hole transport region, and the hole transport region may include the monoamine compound.

In an embodiment, the hole transport region may include hole transport layers, and a hole transport layer adjacent to the emission layer among the hole transport layers may include the monoamine compound.

In an embodiment, the emission layer may emit blue light.

In an embodiment, the monoamine compound may have a highest occupied molecular orbital (HOMO) energy level in a range of about −5.02 eV to about −4.80 eV.

In an embodiment, at least one functional layer among the functional layers may include at least one monoamine compounds represented by Compound Group 1 below.

[Compound Group 1]

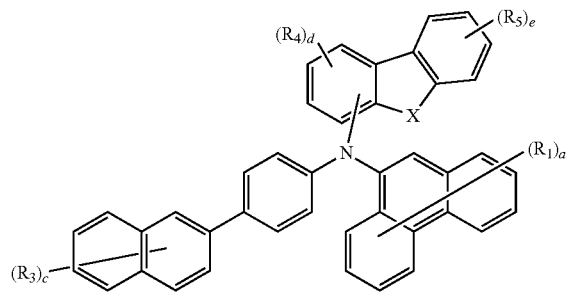

3
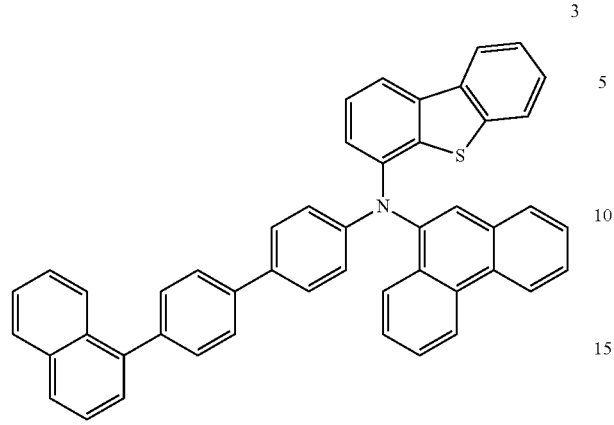
4
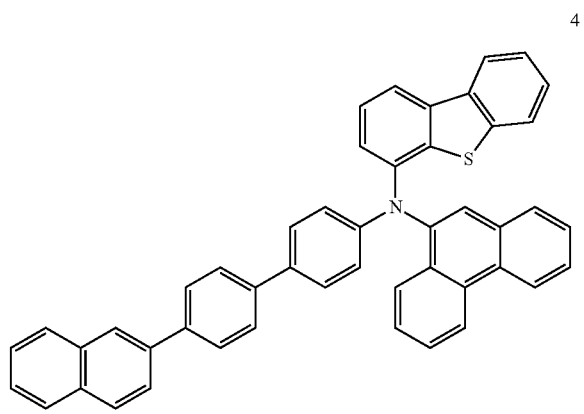
5
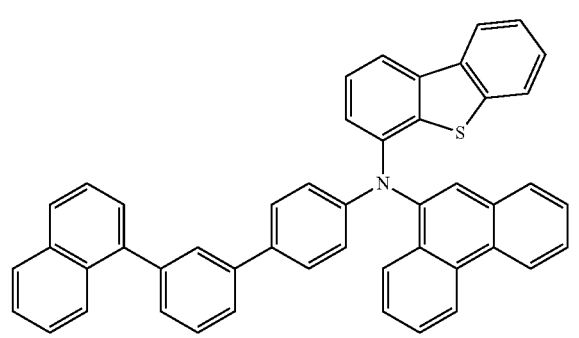
6
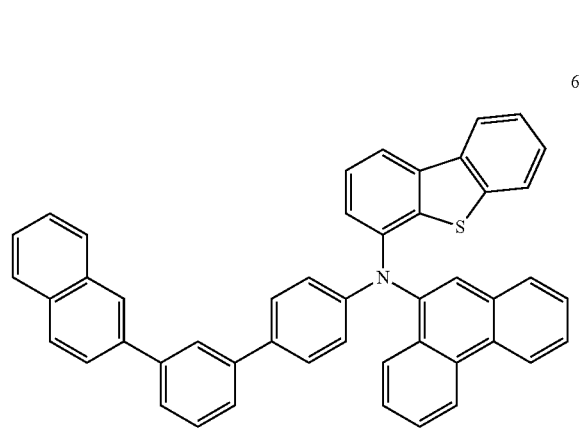
7
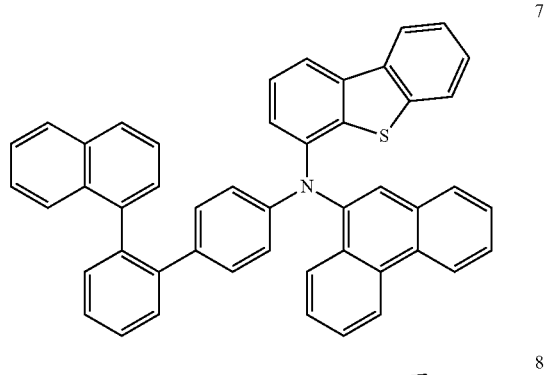
8
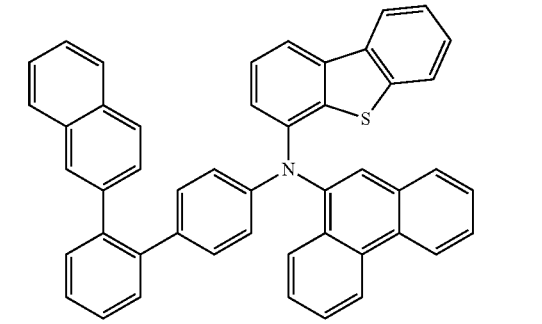
9
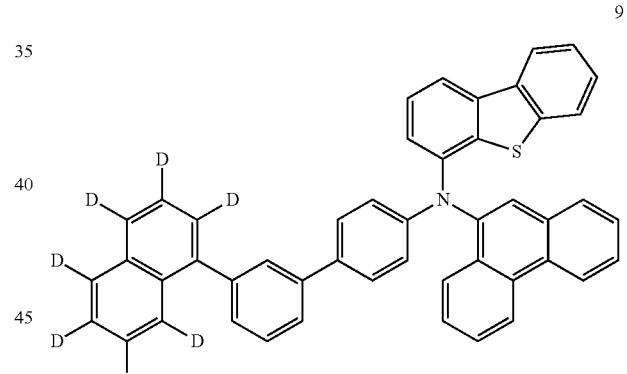
10
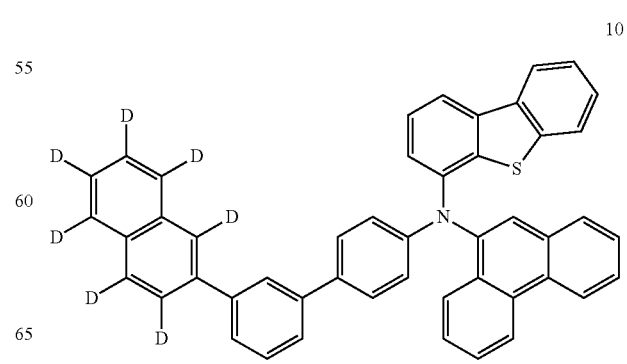

11
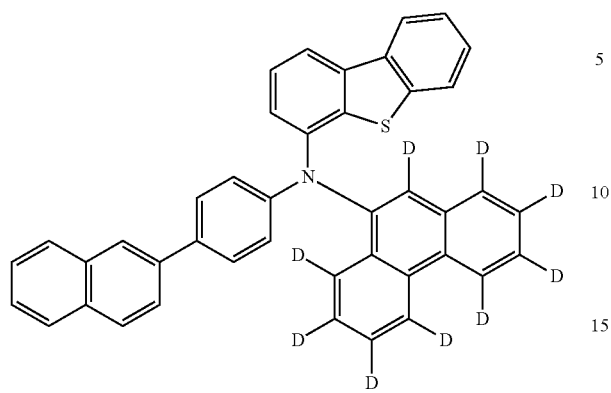
12
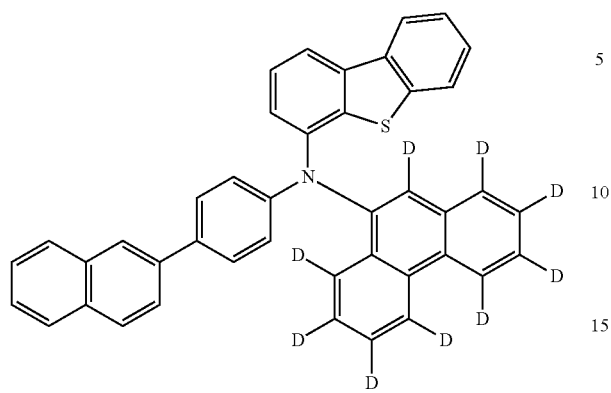
13
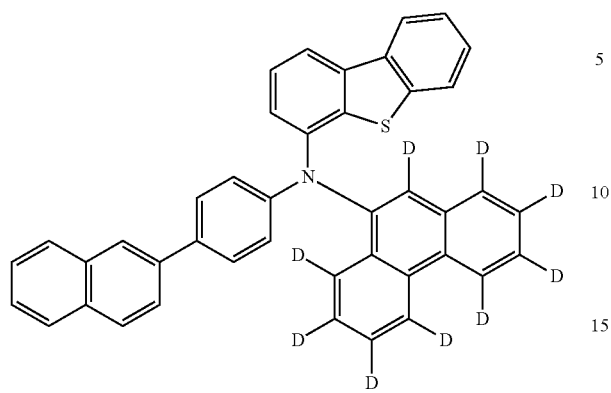
14
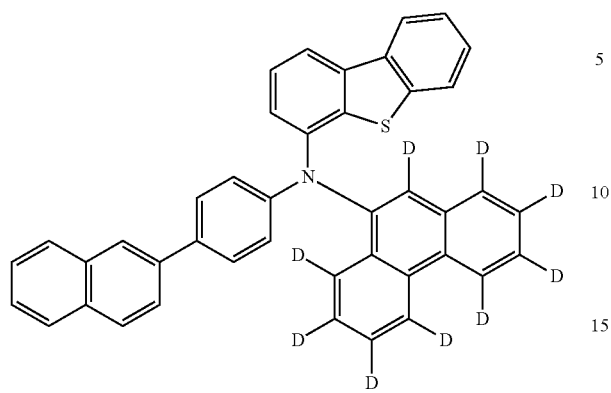
15
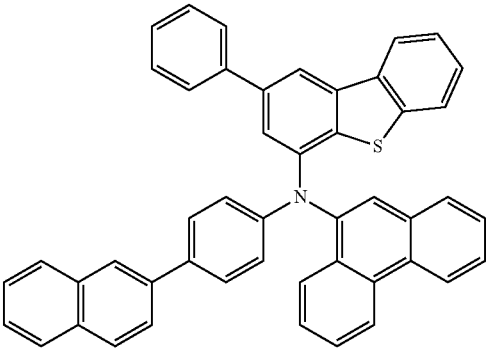
16
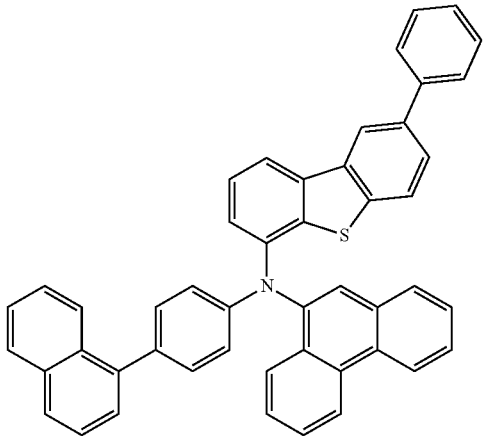
17
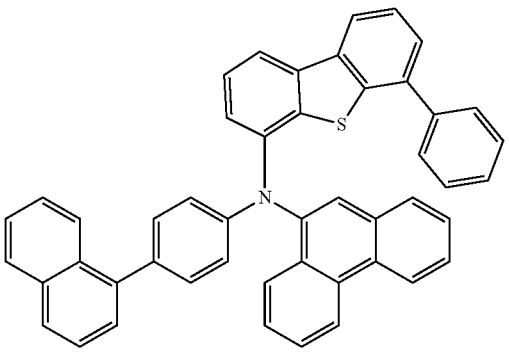
18
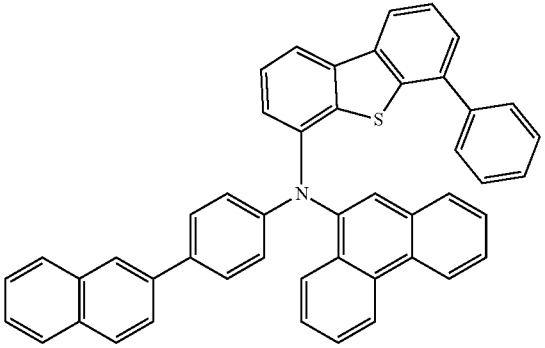

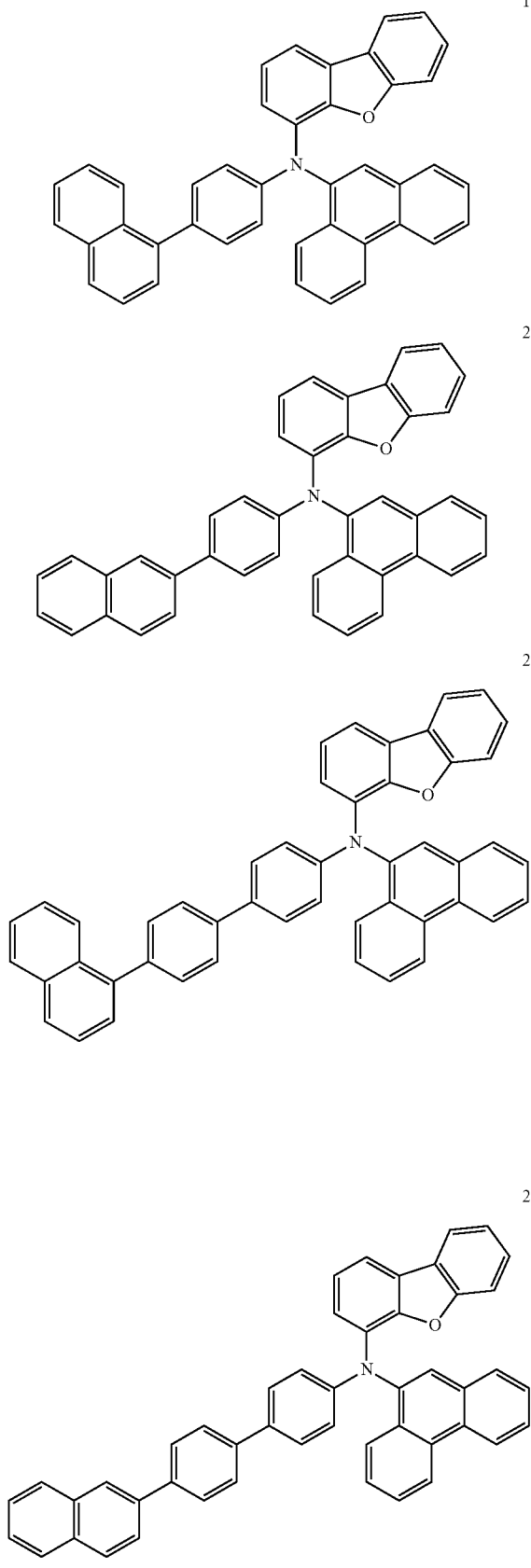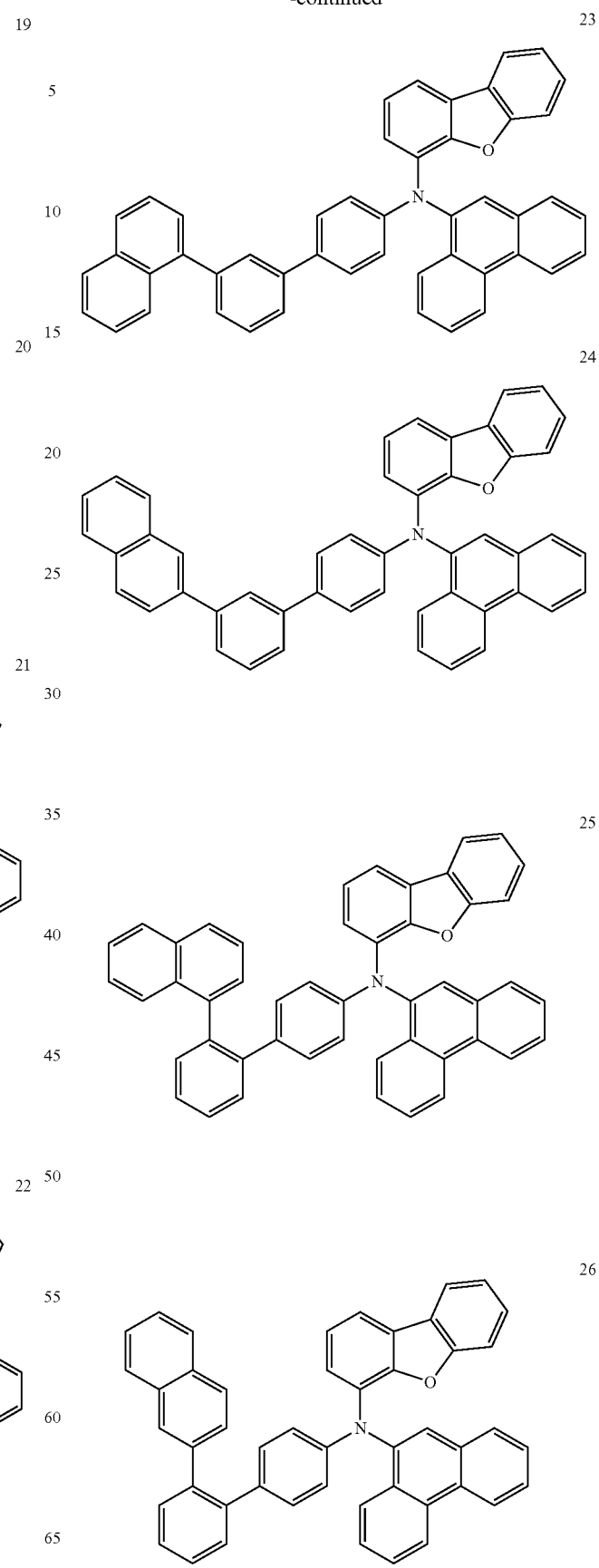

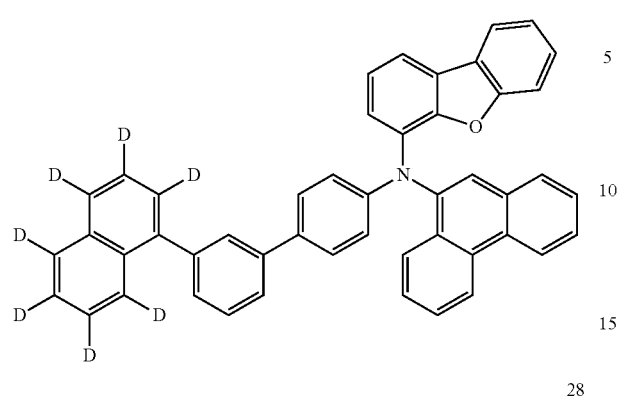
27
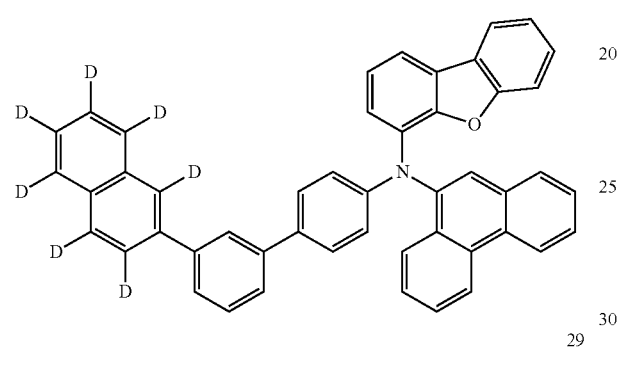
28
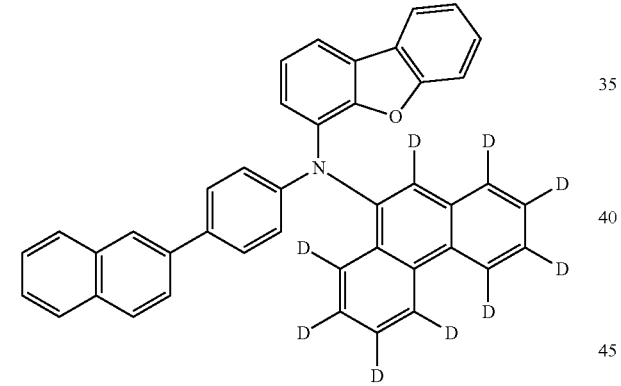
29
30
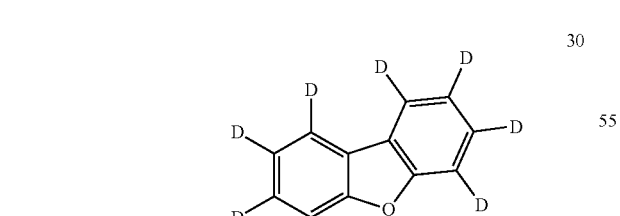
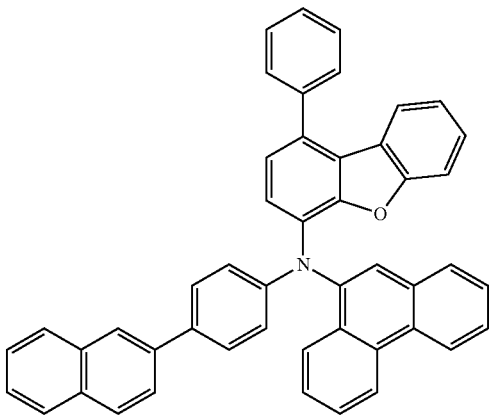
31
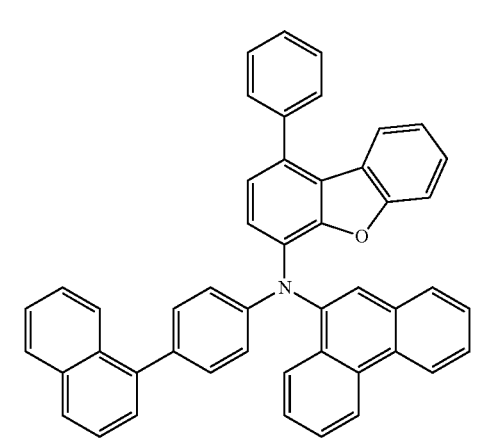
32
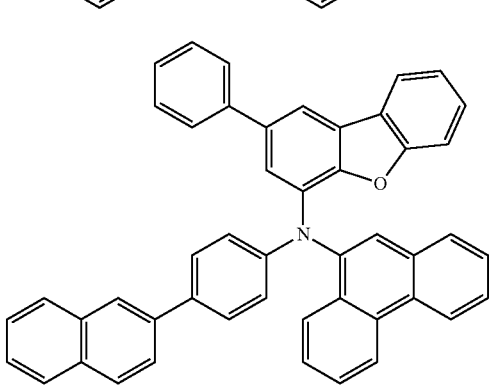
33
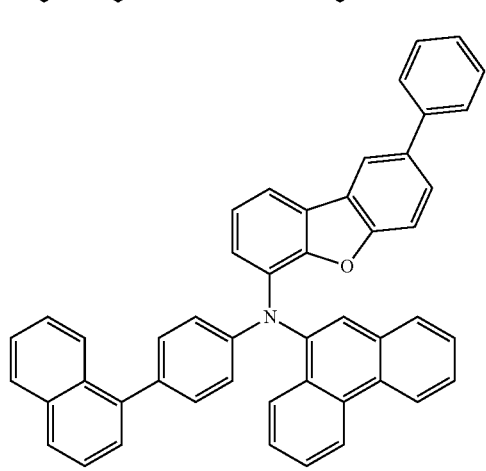
34

35
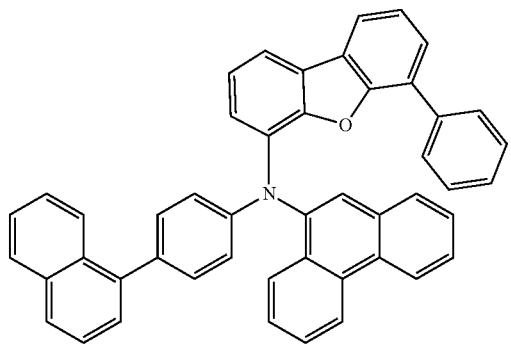
36
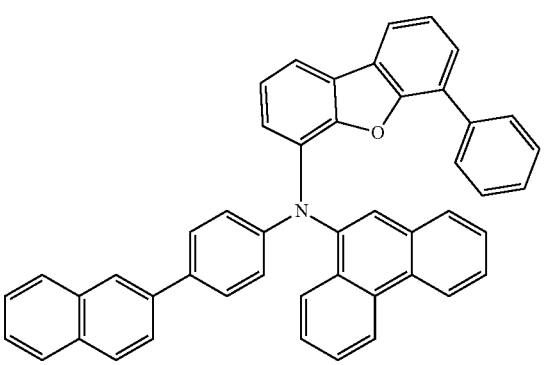
37
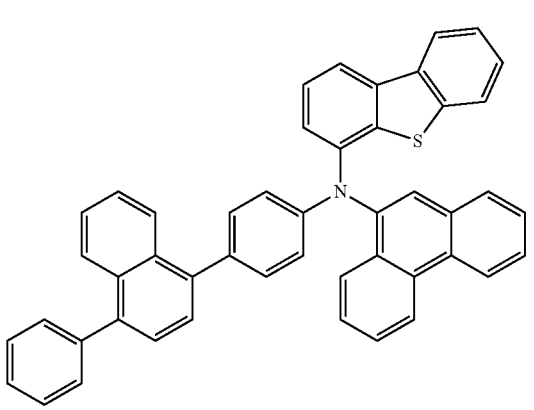
38
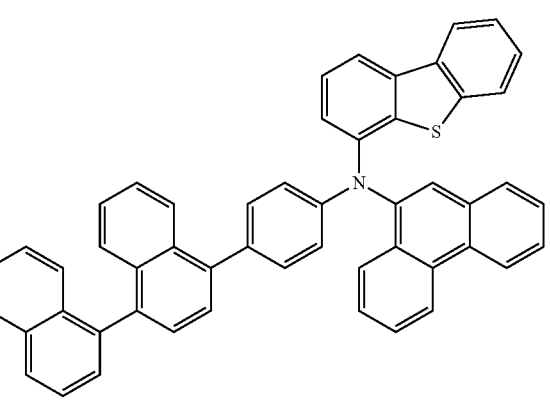
39
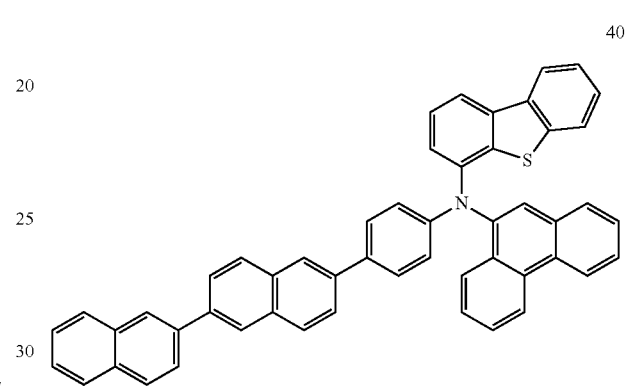
40
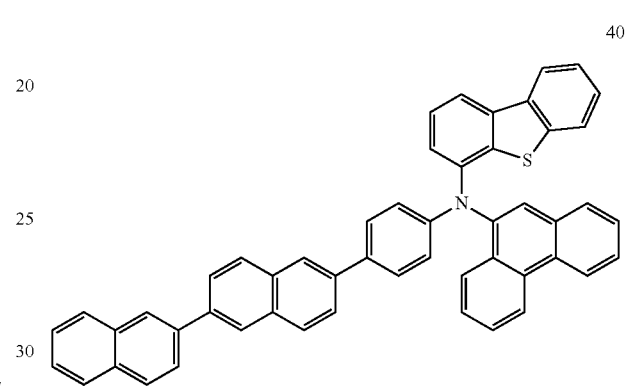
41
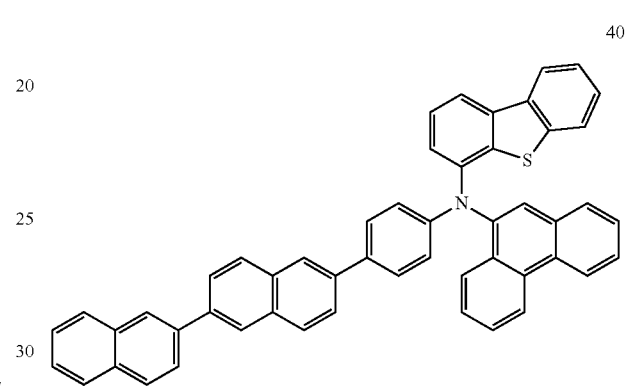
42
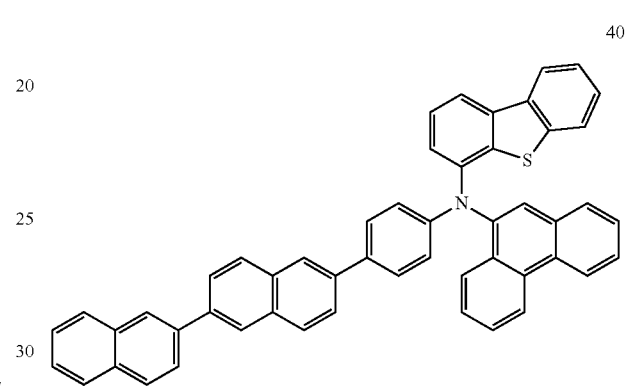

-continued
43
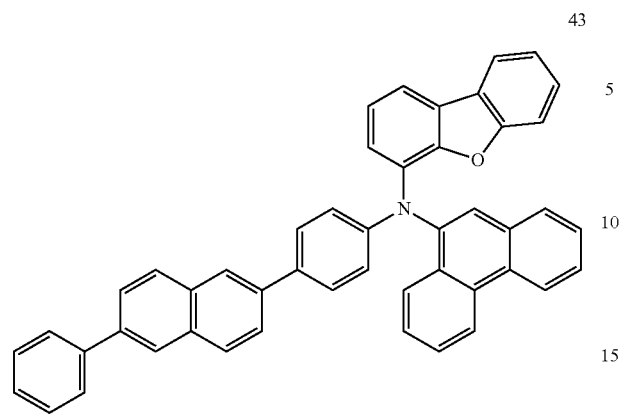
44
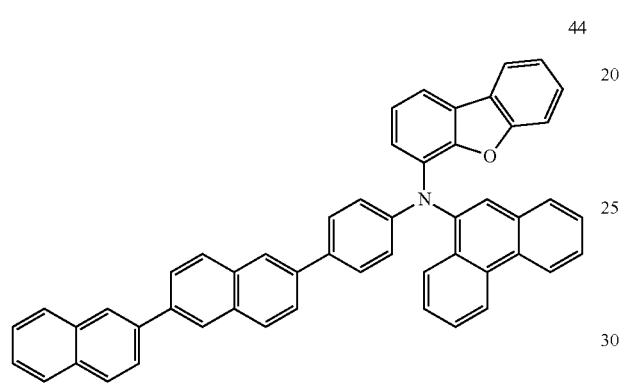
45
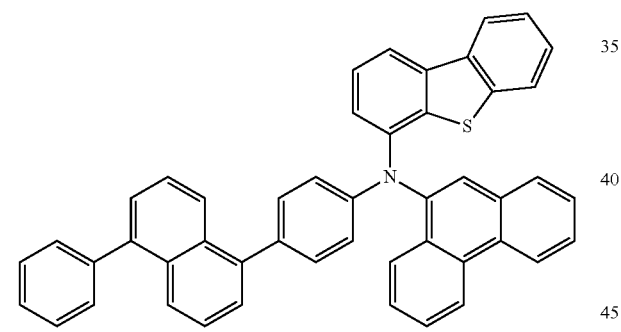
46
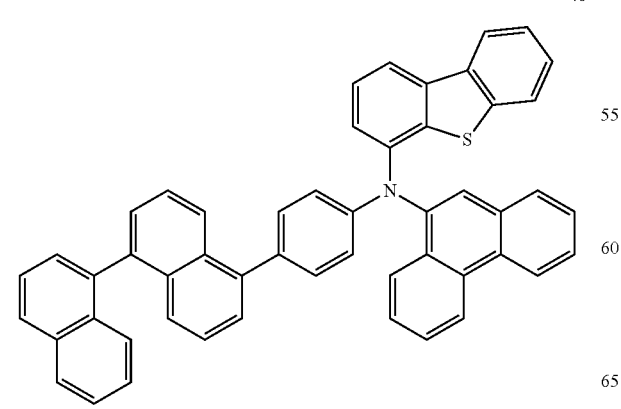
-continued
47
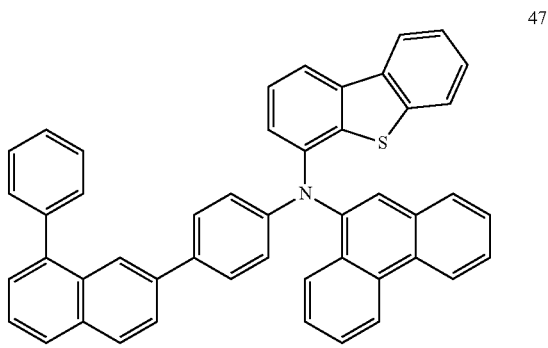
48
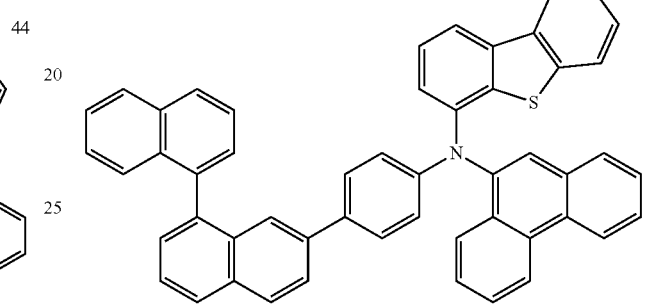
49
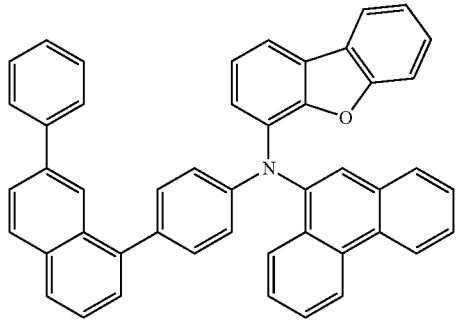
50
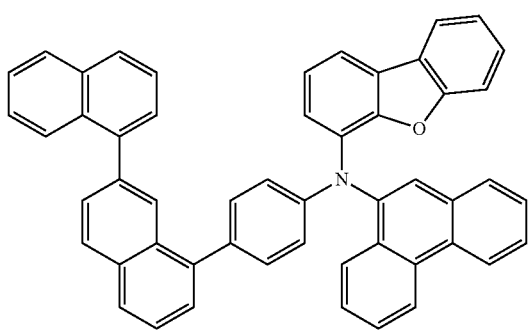

51
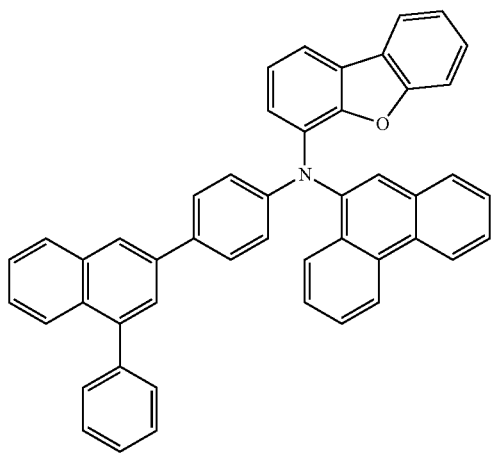
52
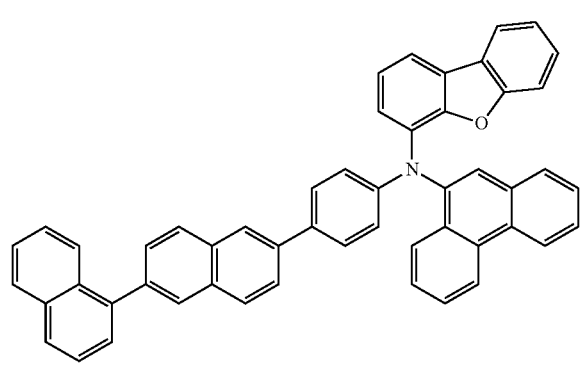
53
54
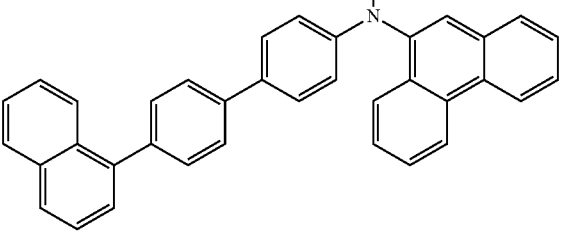
55
56
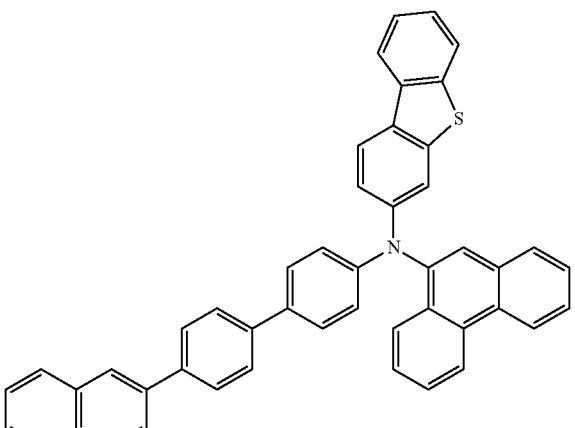
57
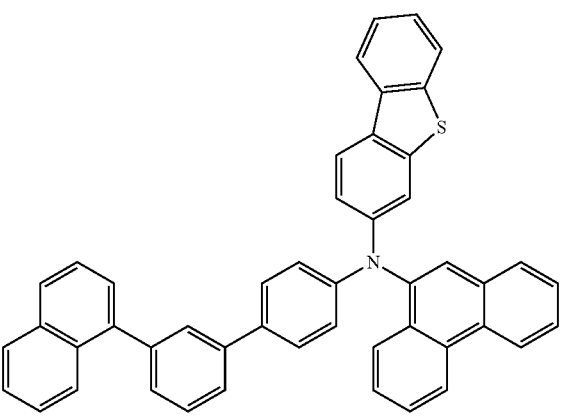

-continued
58
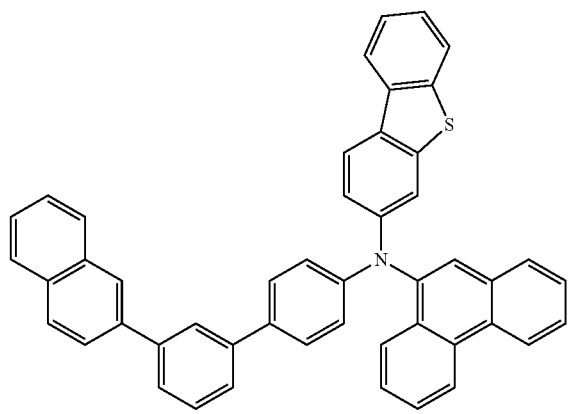
59
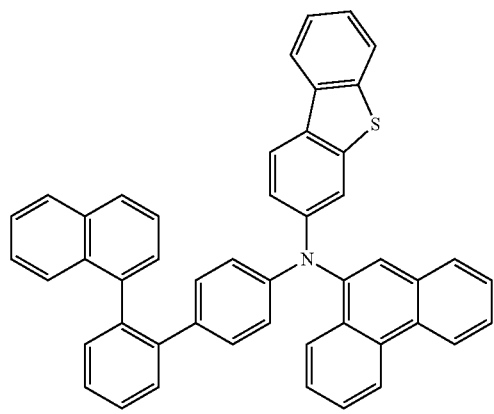
60
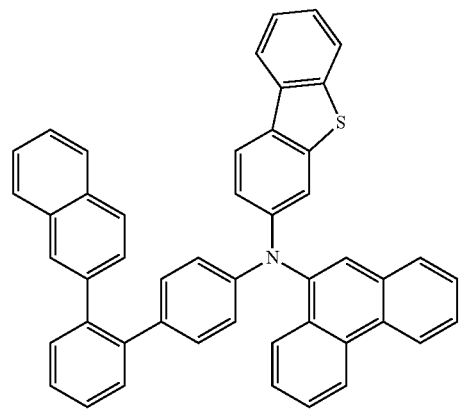
61
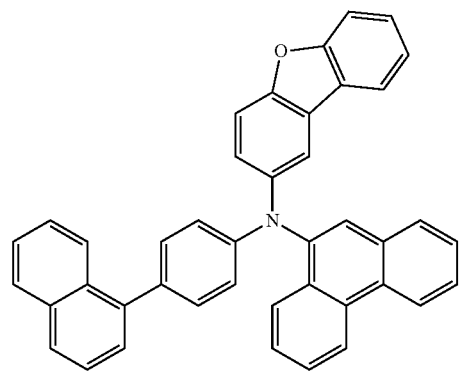
-continued
62
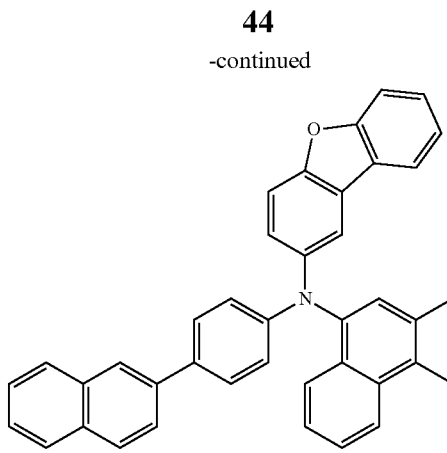
63
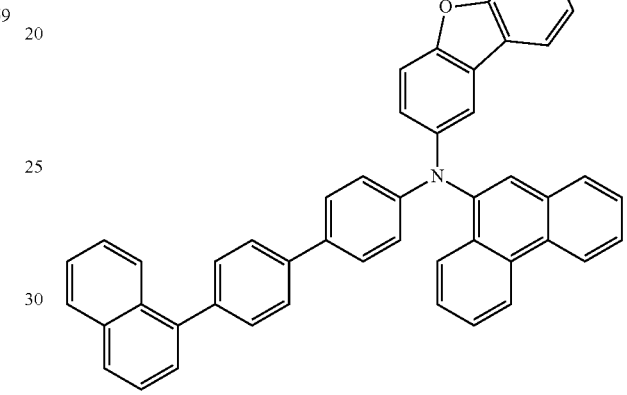
64
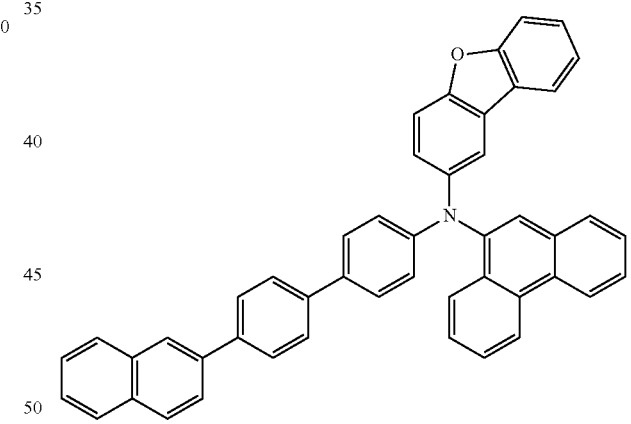
65
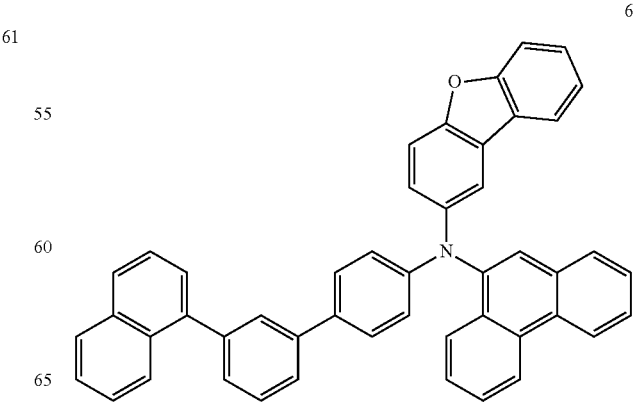

66
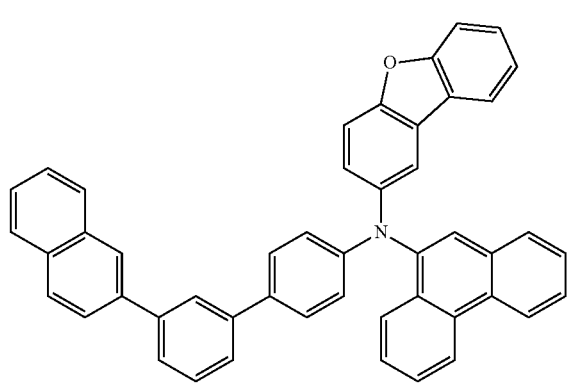
66
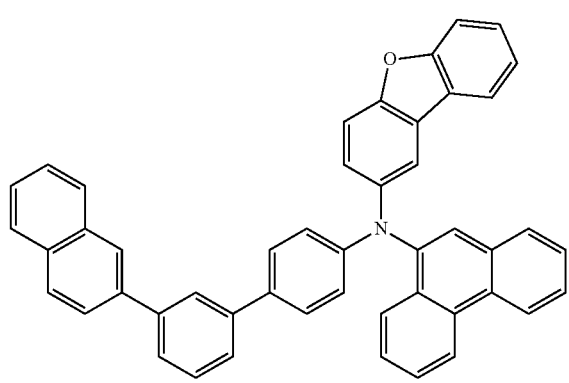
67
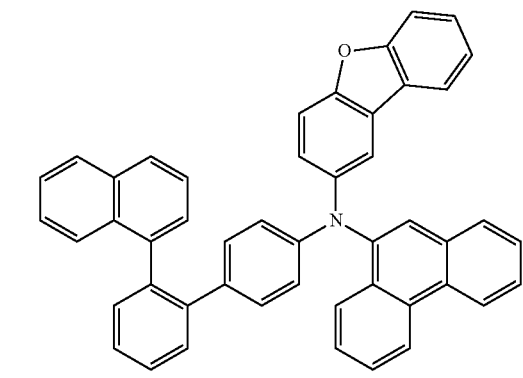
68
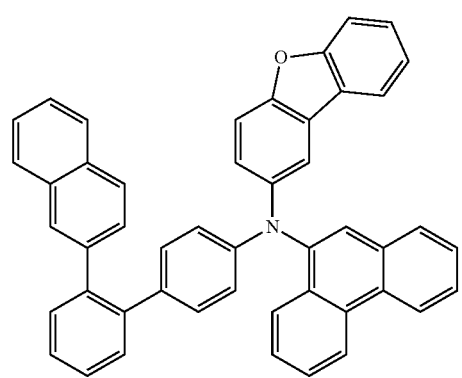
69
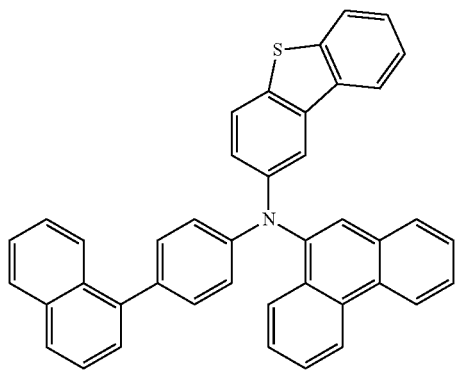
70
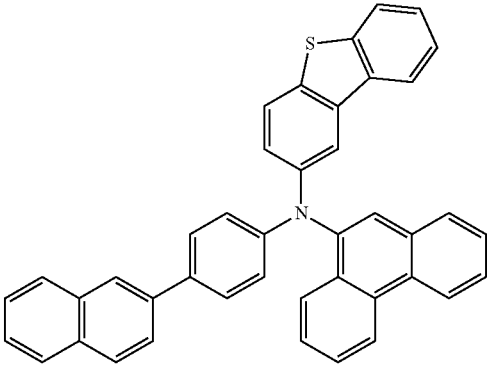
71
72
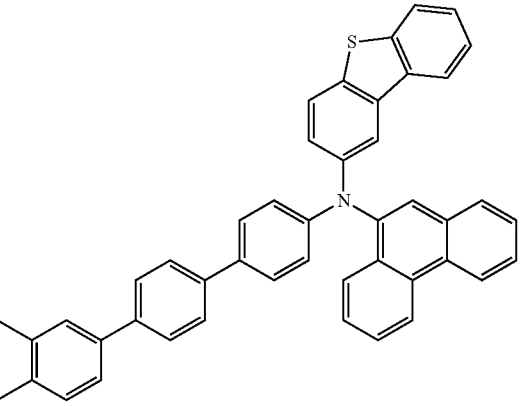

73
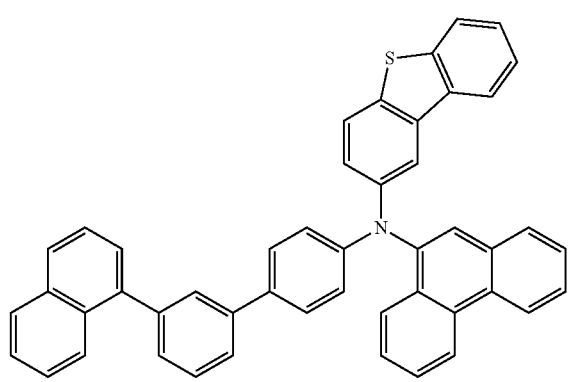
74
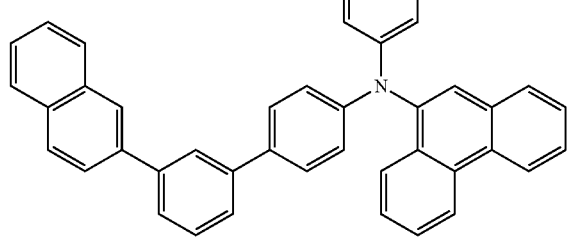
75
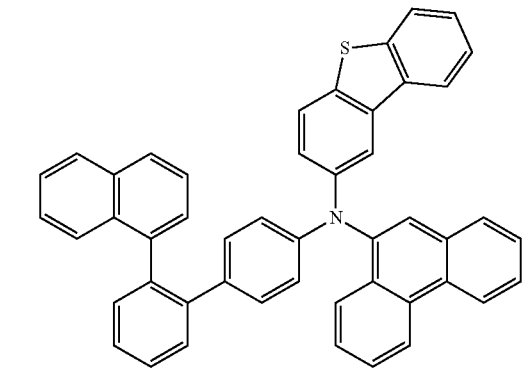
76
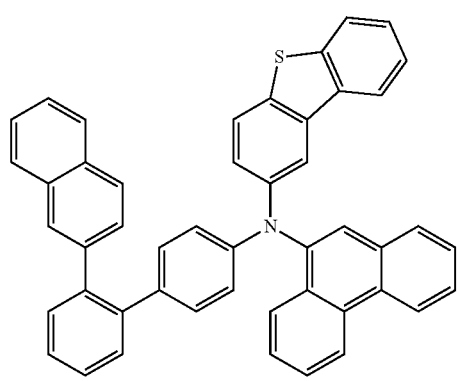
77
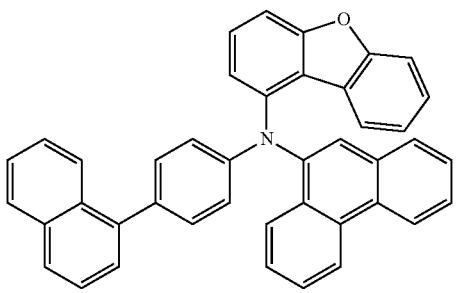
78
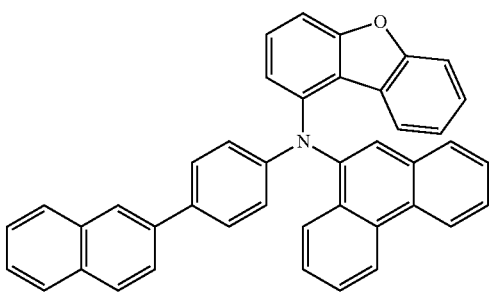
79
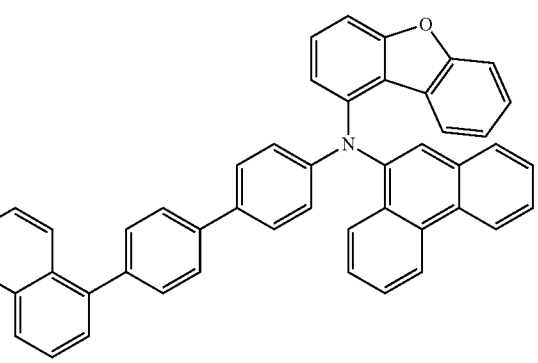
80
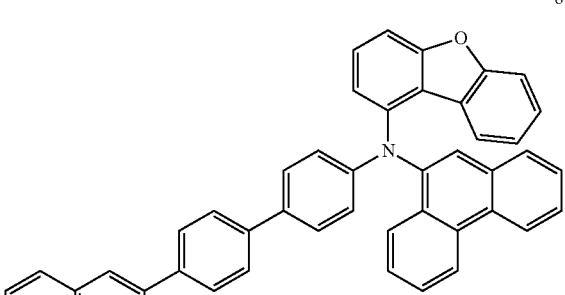
81
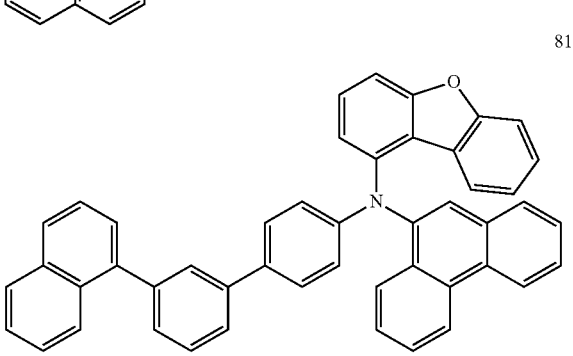

82
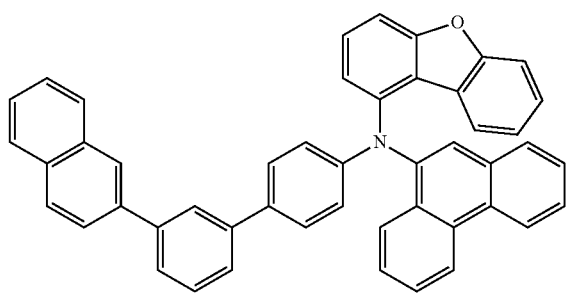
83
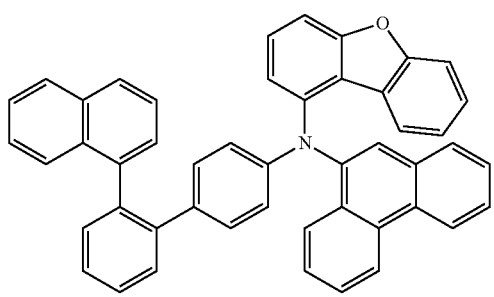
84
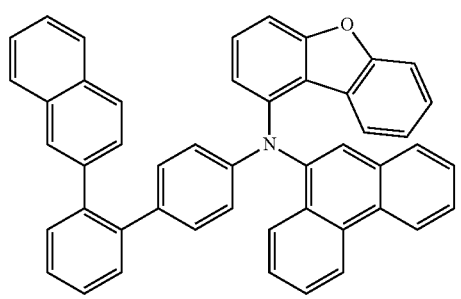
85
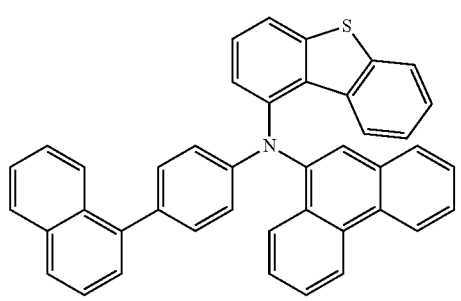
86
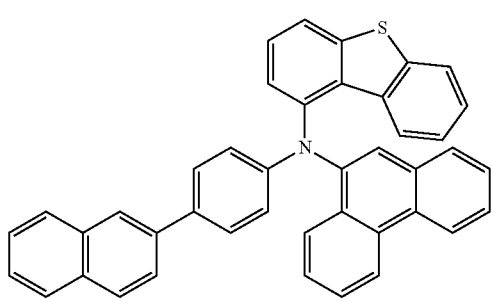
87
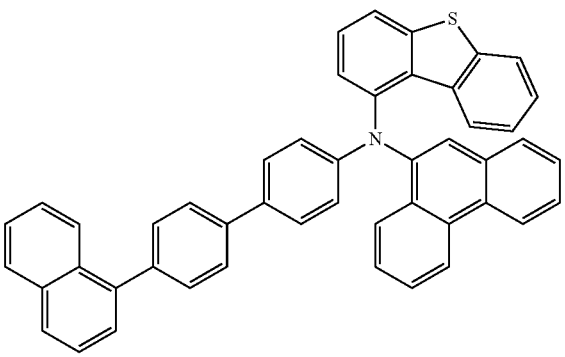
88
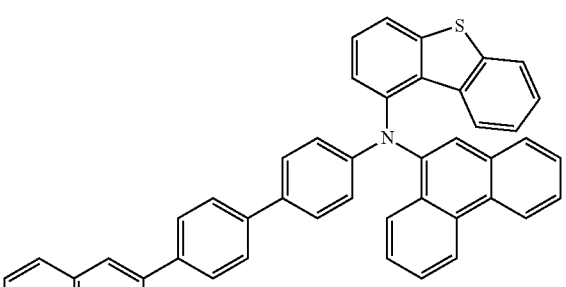
89
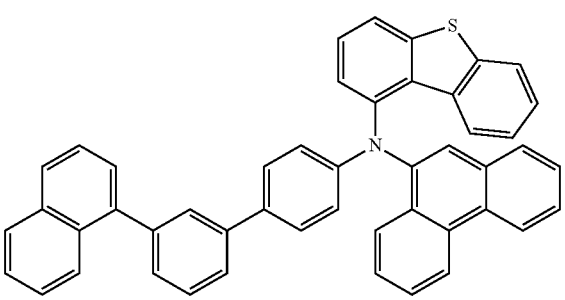
90
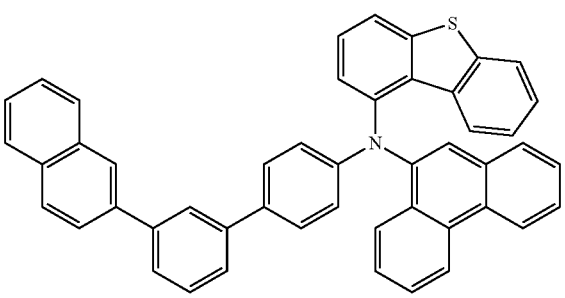
91
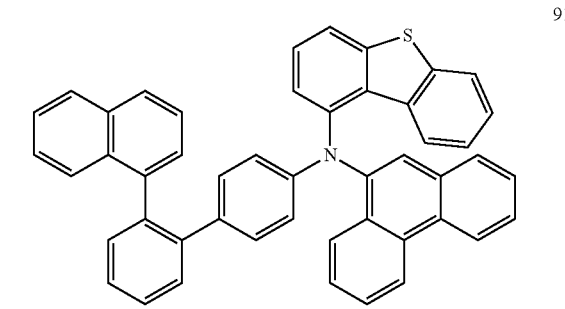

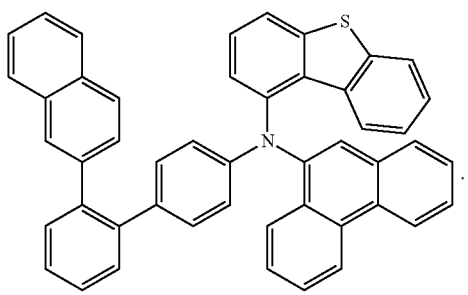

92

An embodiment of the inventive concept provides a monoamine compound that may be represented by Formula 1 below.

[Formula 1]

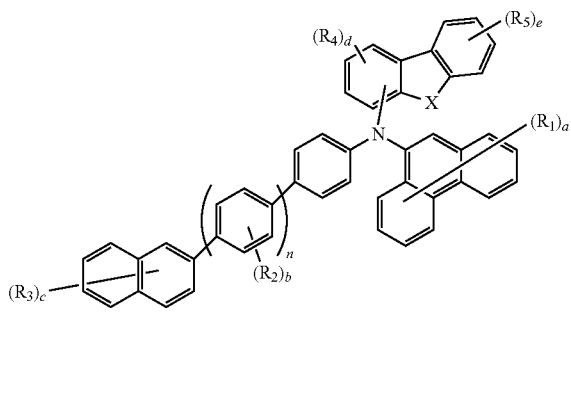

In Formula 1, X may be O or S n may be 0 or 1, a may be an integer from 0 to 9, b and e may each independently be an integer from 0 to 4, c may be an integer from 0 to 7, d may be an integer from 0 to 3, and $R_1$ to $R_5$ may each independently be a substituted or unsubstituted alkyl group of 1 to 15 carbon atoms, a substituted or unsubstituted aryl group of 6 to 30 carbon atoms, a substituted or unsubstituted heteroaryl group of 1 to 30 carbon atoms, a substituted or unsubstituted silyl group, a halogen atom, a hydrogen atom, or a deuterium atom.

In an embodiment, Formula 1 may be represented by Formula 2-1 or Formula 2-2 below.

[Formula 2-1]

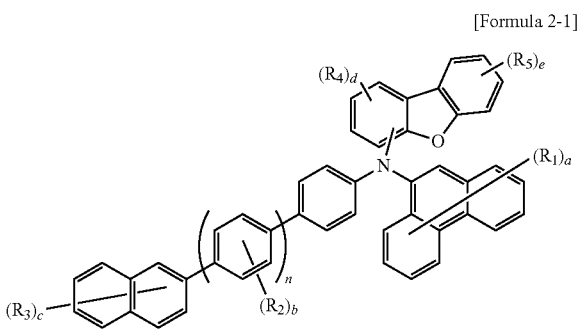

[Formula 2-2]

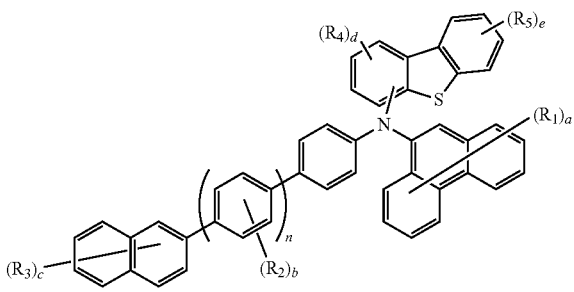

In Formula 2-1 and Formula 2-2, a to e, n, and $R_1$ to $R_5$ may be the same as defined in Formula 1.

In an embodiment, Formula 1 may be represented by one of Formula 3-1 to Formula 3-4 below.

[Formula 3-1]

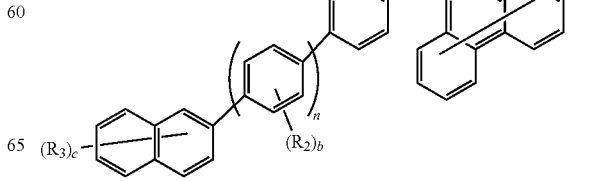

[Formula 3-2]

[Formula 3-3]

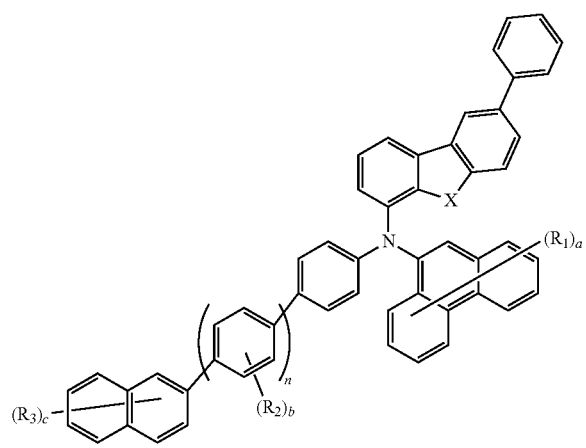

[Formula 4-2]

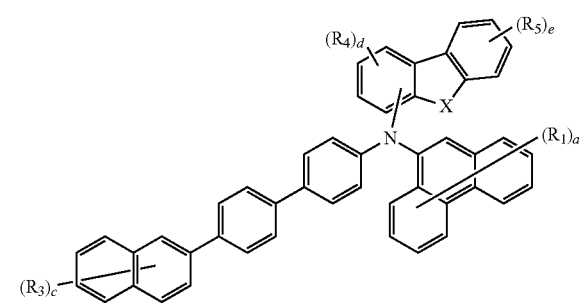

In Formula 4-1 and Formula 4-2, a, c to e, X, $R_1$, and $R_3$ to $R_5$ may be the same as defined in Formula 1.

In an embodiment, the monoamine compound may be selected from Compound Group 1 below.

[Compound Group 1]

1

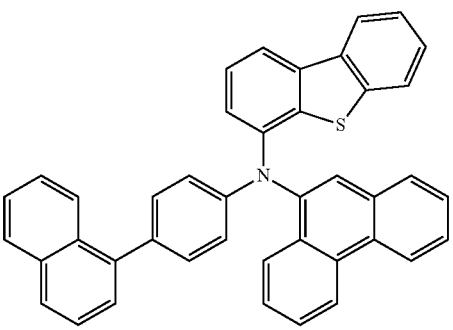

[Formula 3-4]

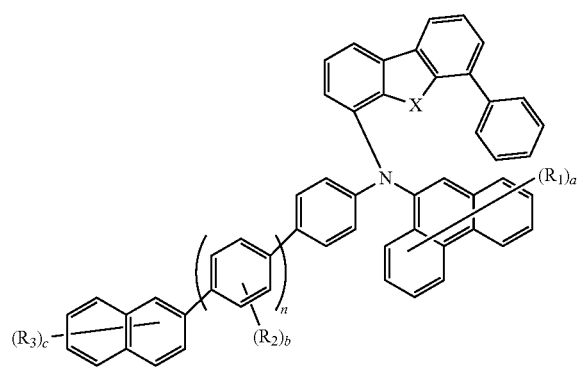

2

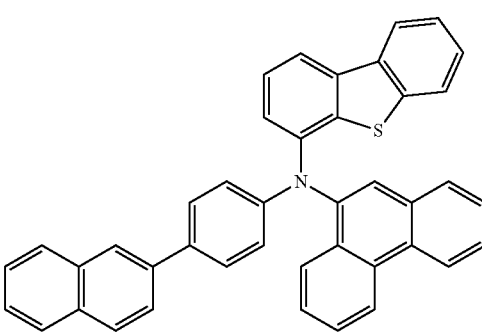

In Formula 3-1 to Formula 3-4, a to c, n, X, and $R_1$ to $R_3$ may be the same as defined in Formula 1.

In an embodiment, Formula 1 may be represented by Formula 4-1 or Formula 4-2 below.

3

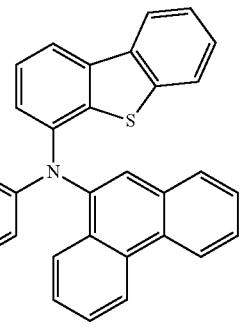

[Formula 4-1]

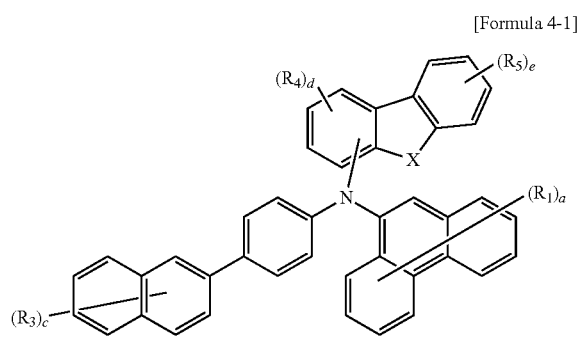

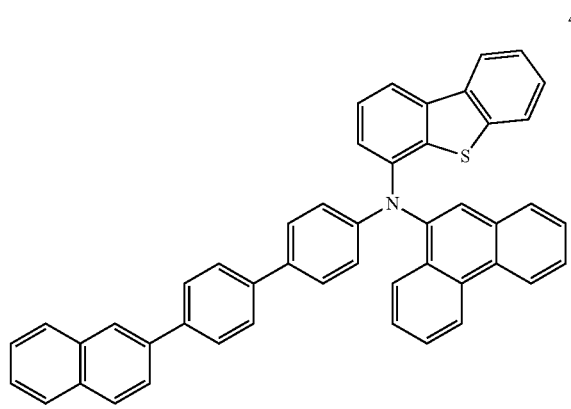
4
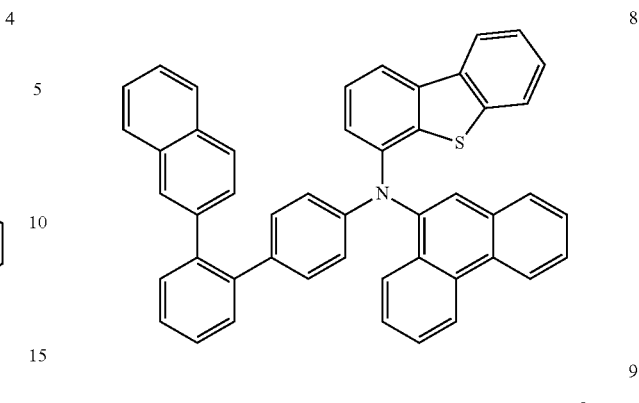
8
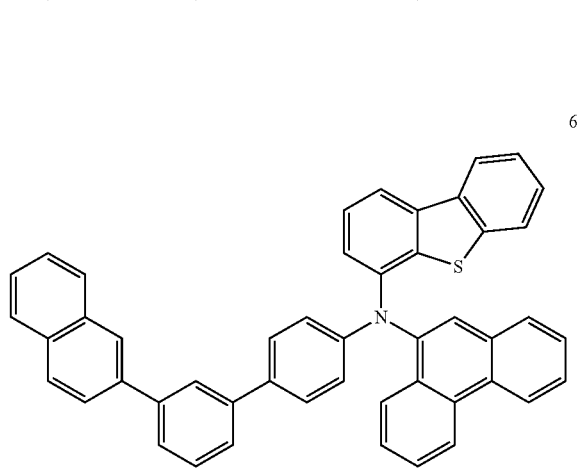
5
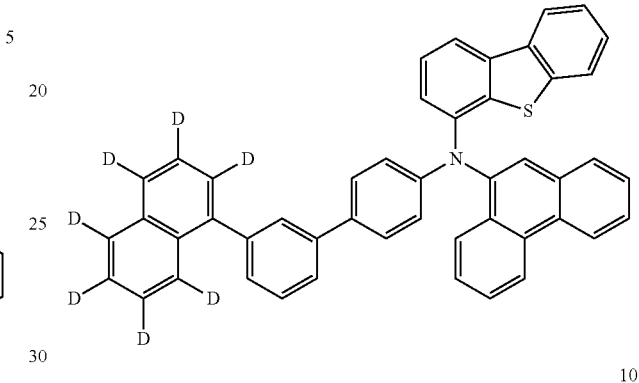
9
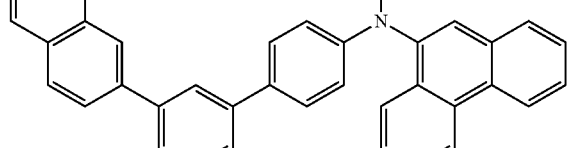
6
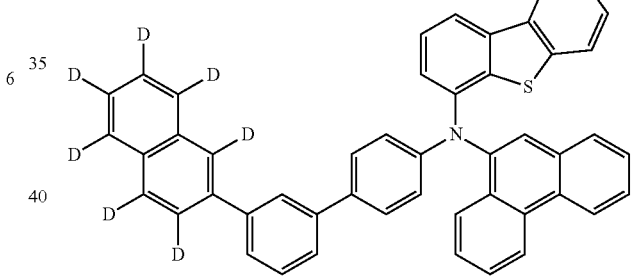
10
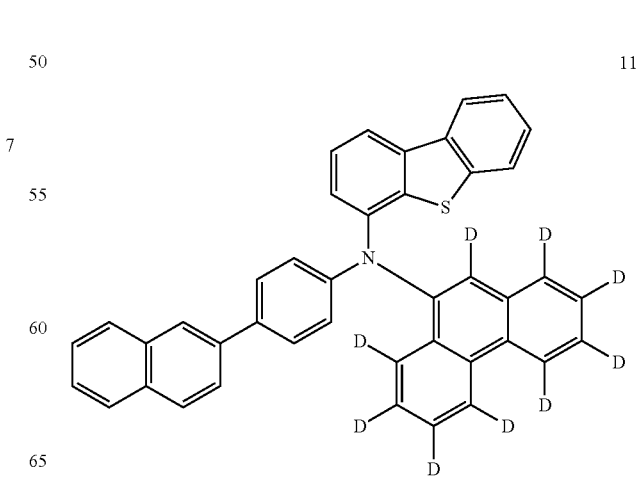
11

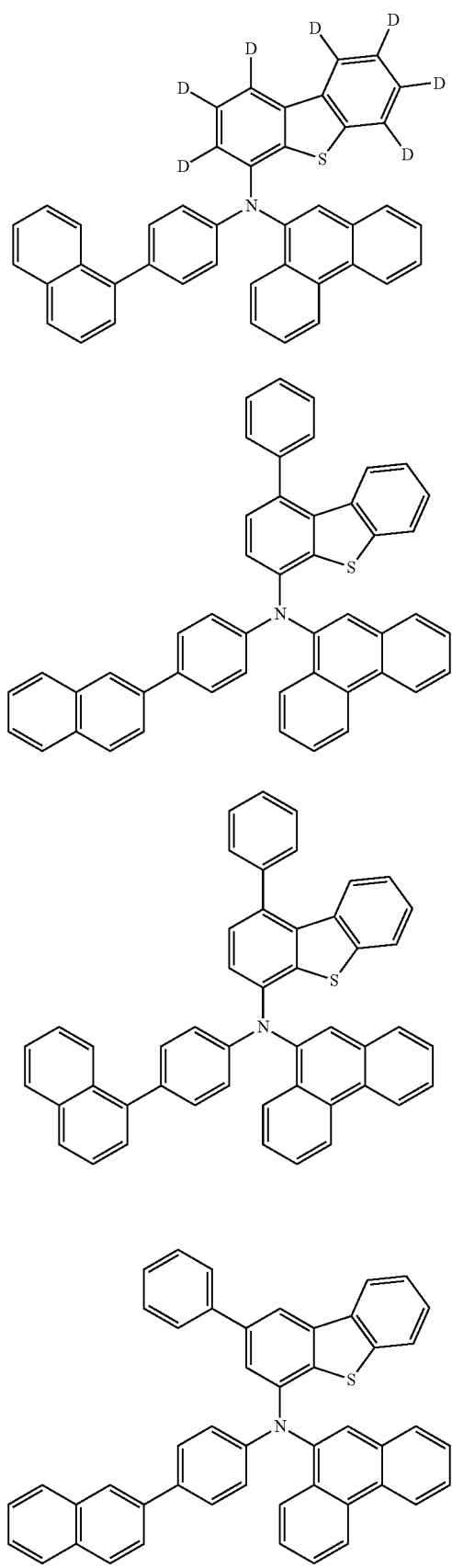
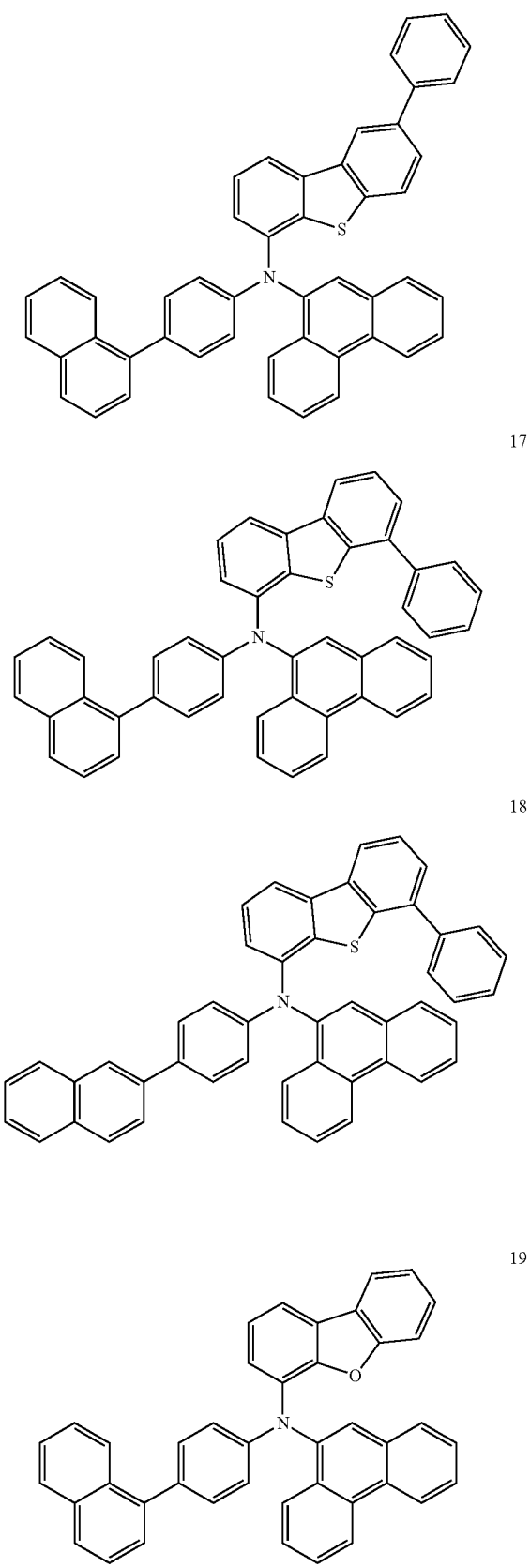

20
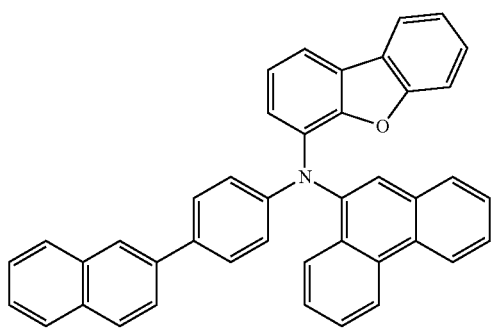
21
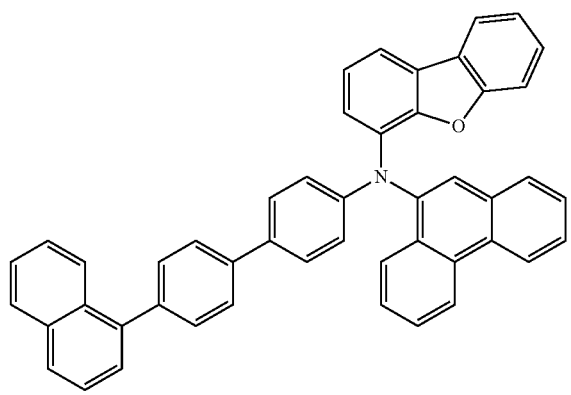
22
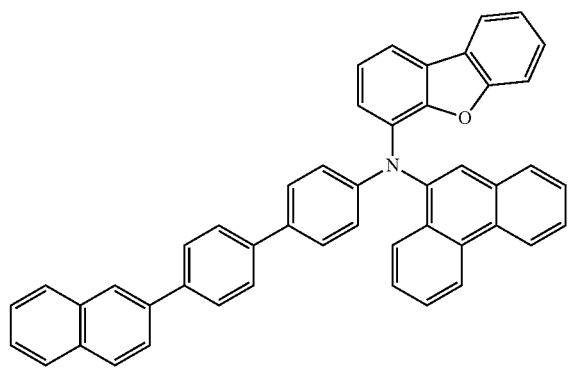
23
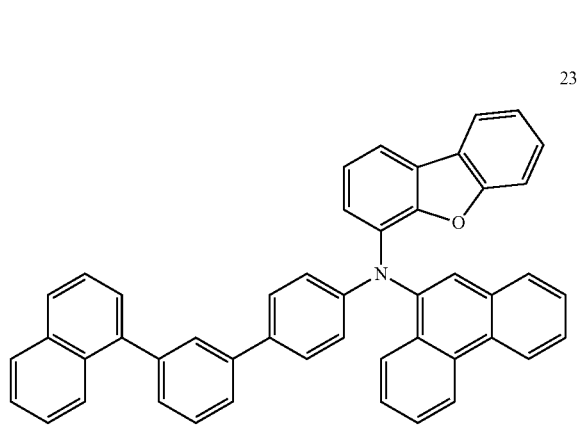
24
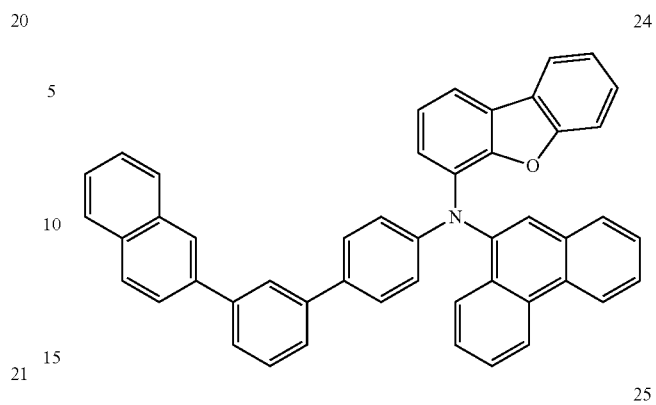
25
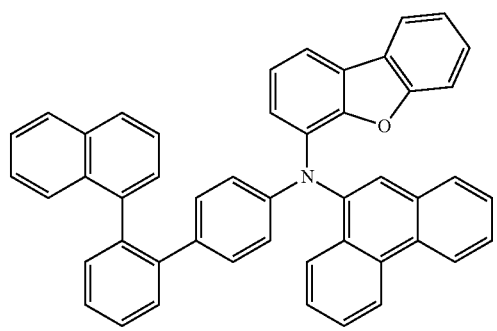
26
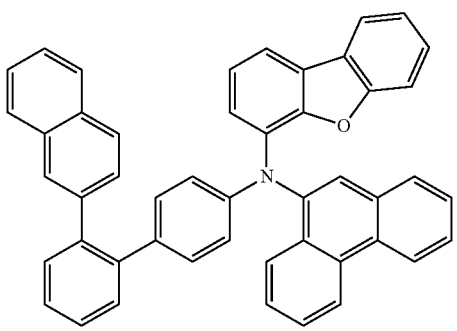
27
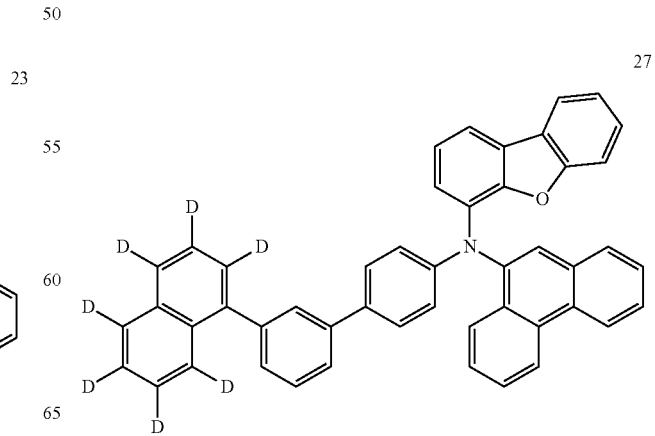

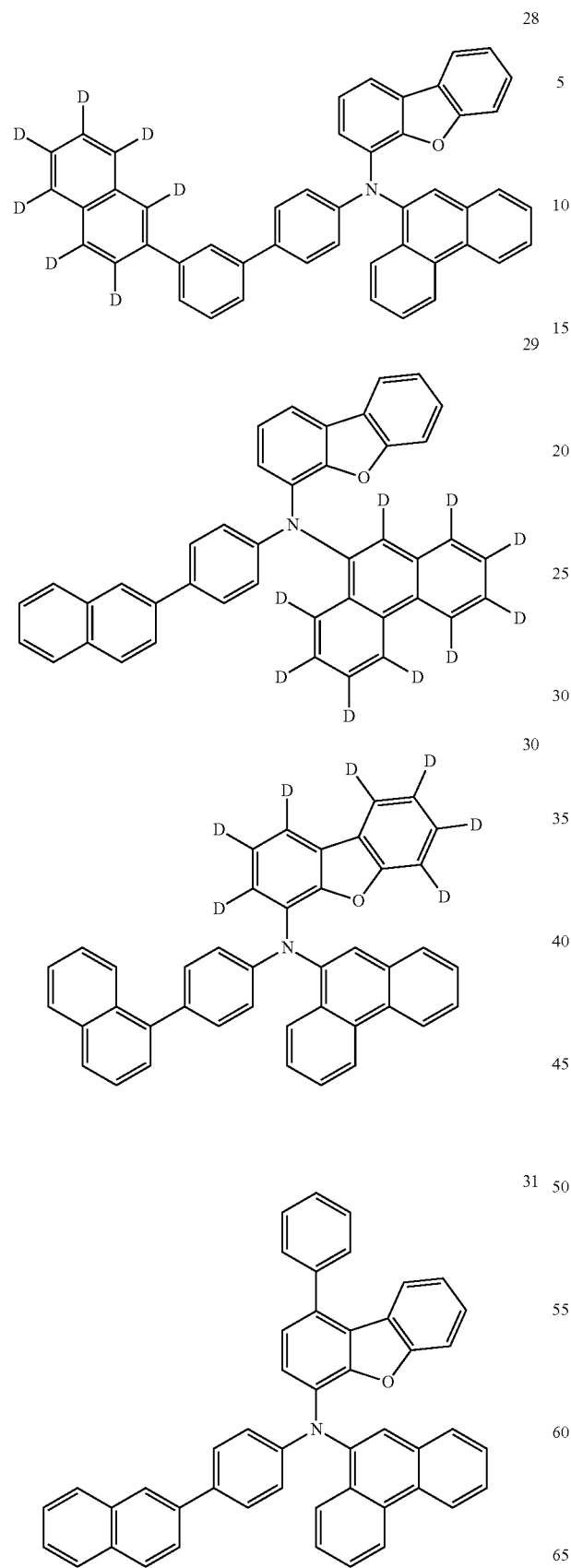
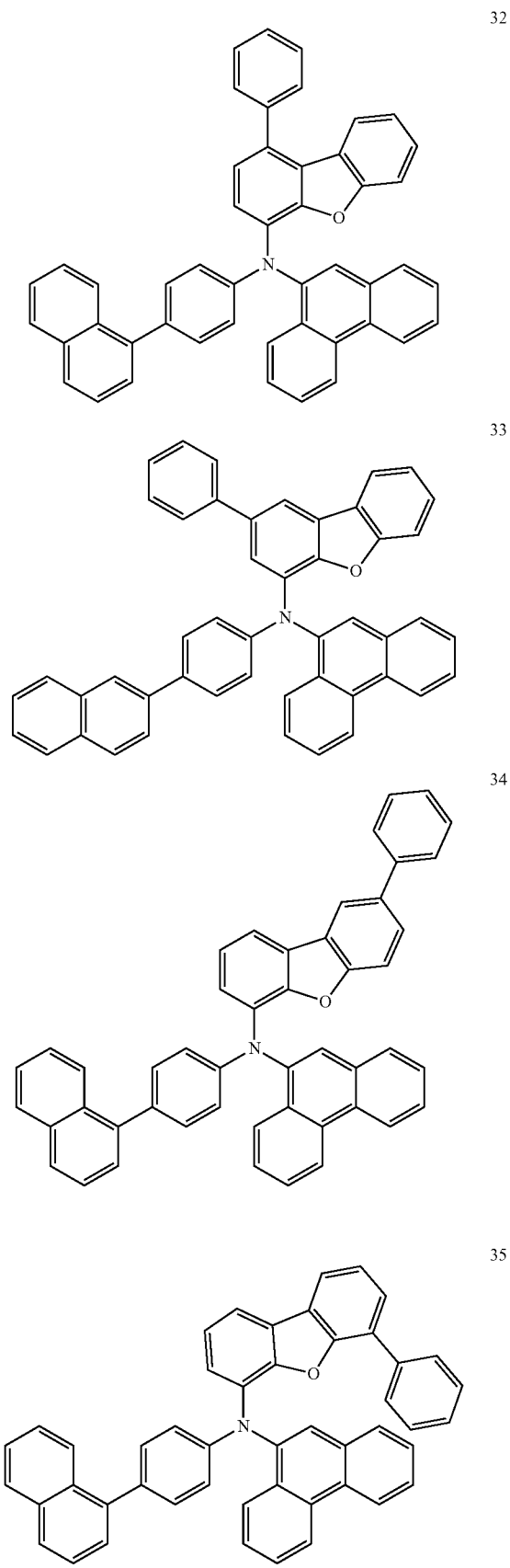

36
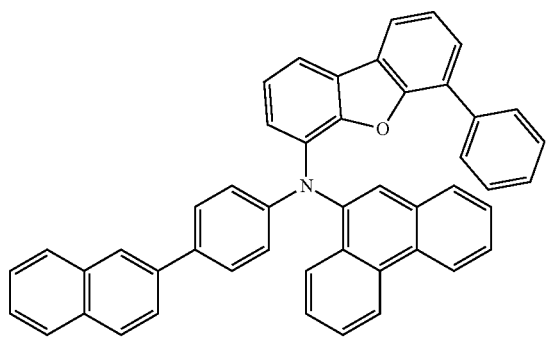
37
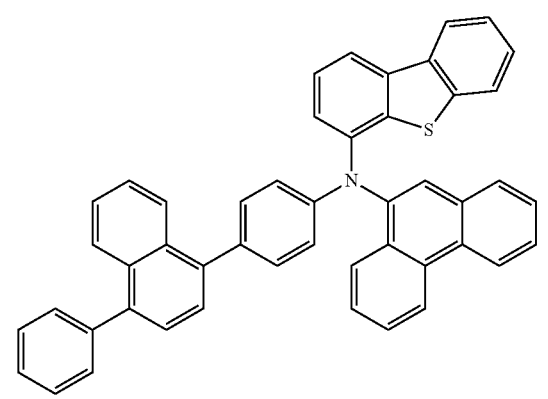
38
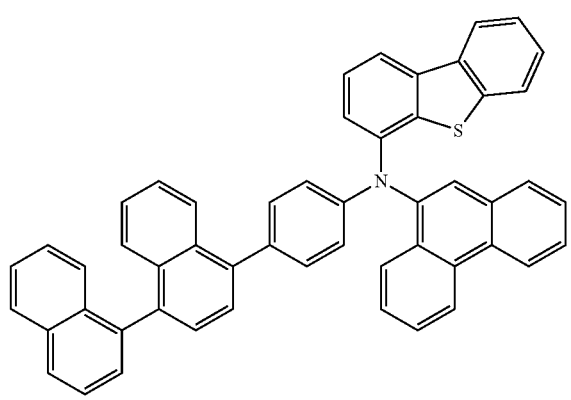
39
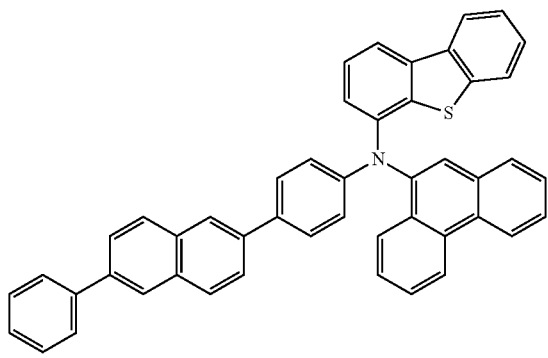
40
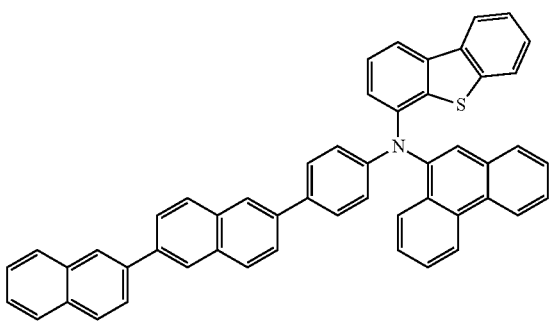
41
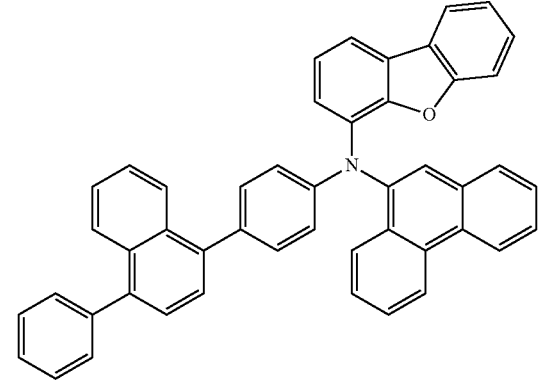
42
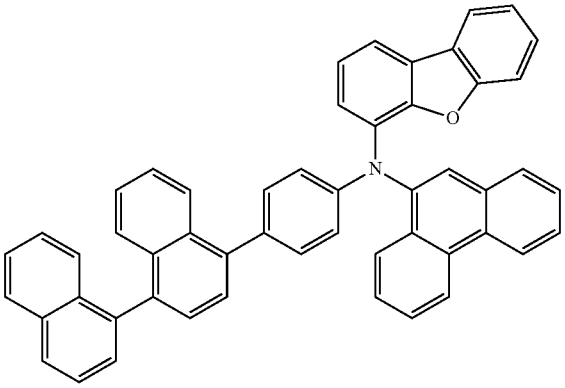
43
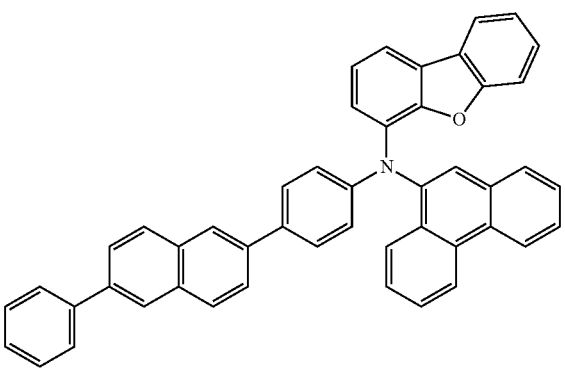

44
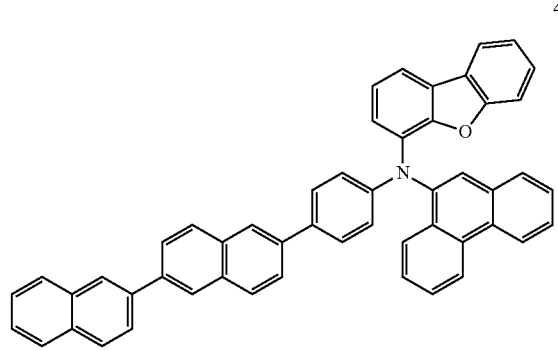
45
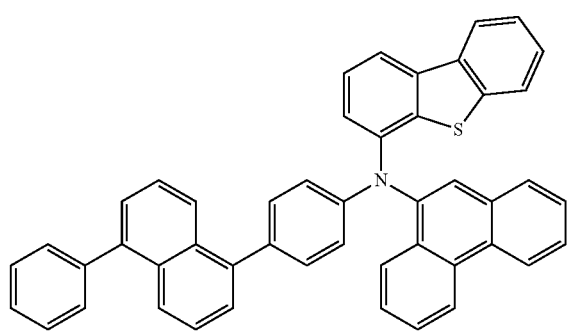
46
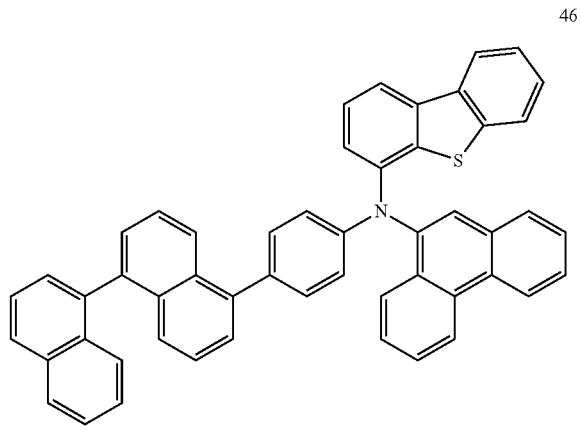
47
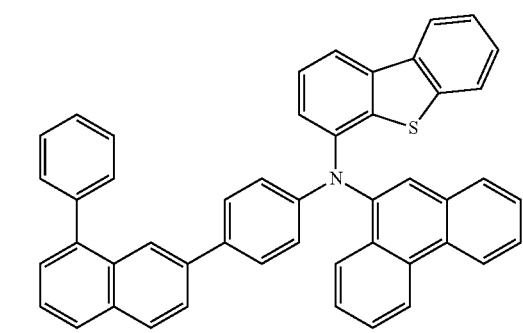
48
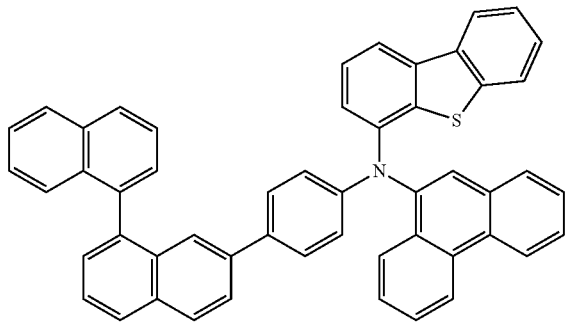
49
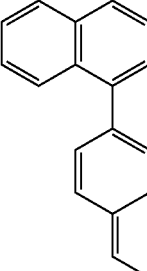
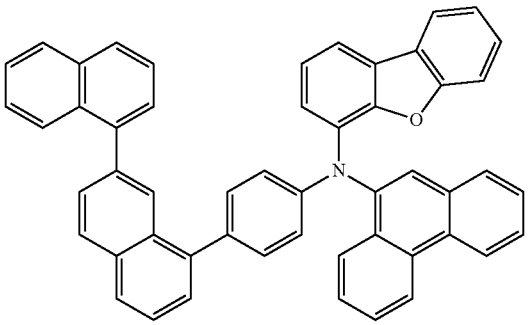
50
51

-continued
52
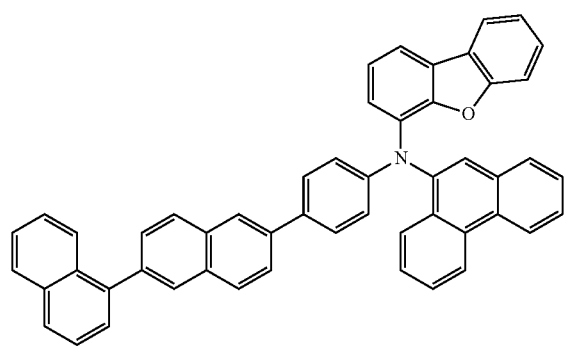
53
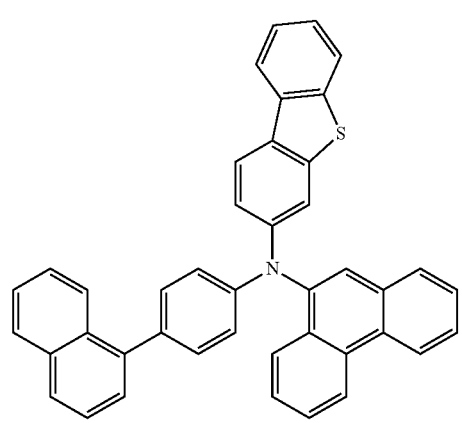
54
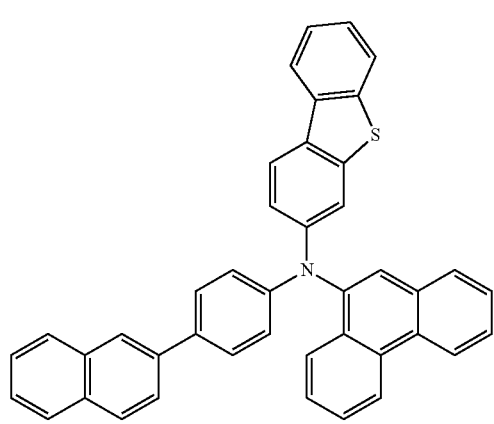
-continued
55
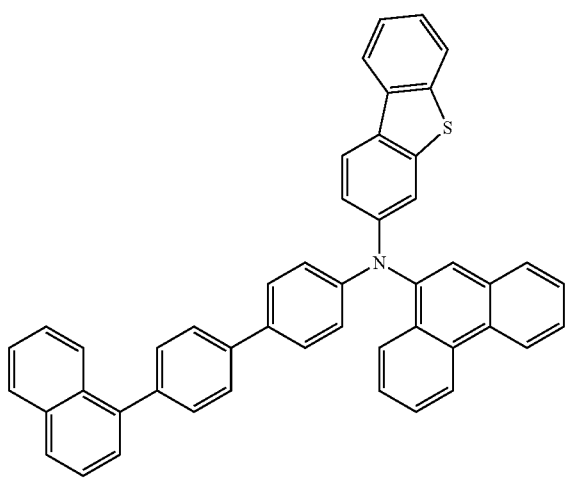
56
57
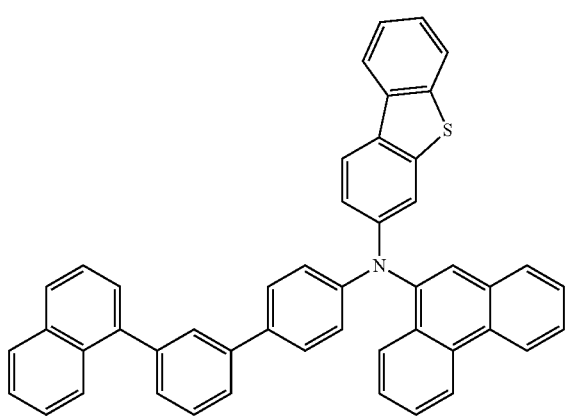

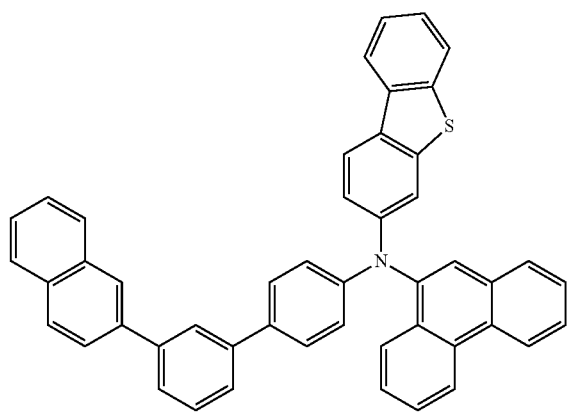
58
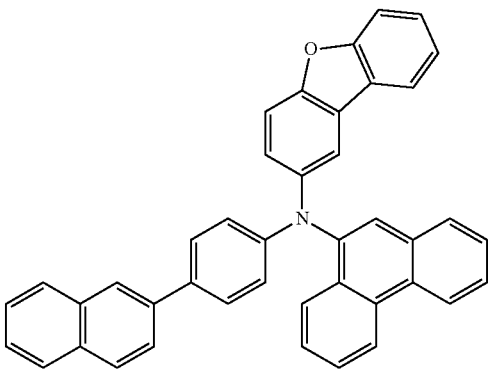
62
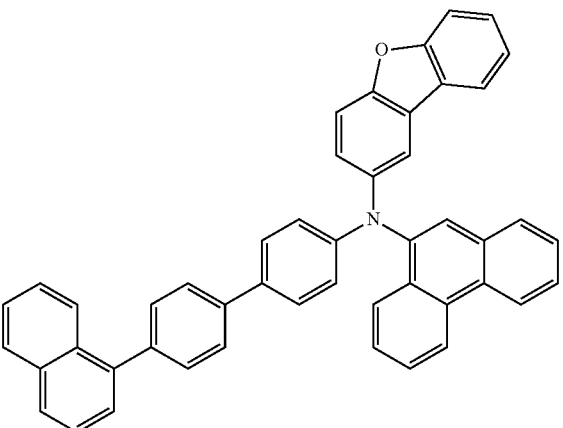
63
59
60
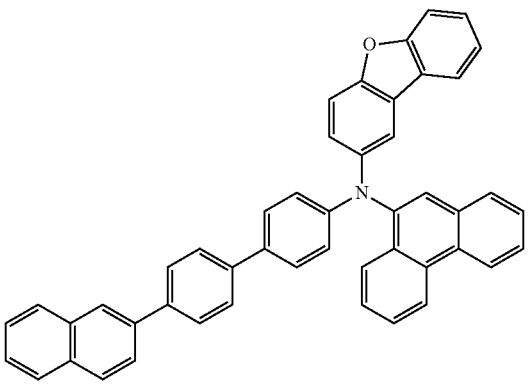
64
61
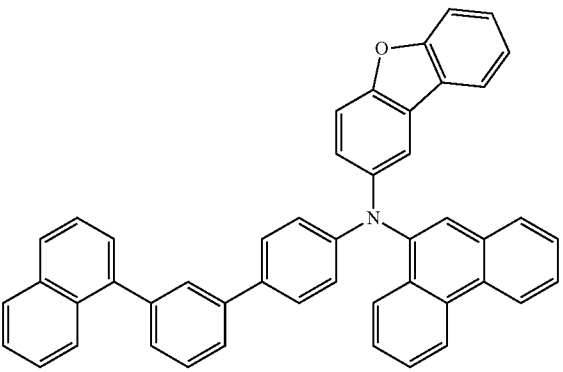
65

-continued
66
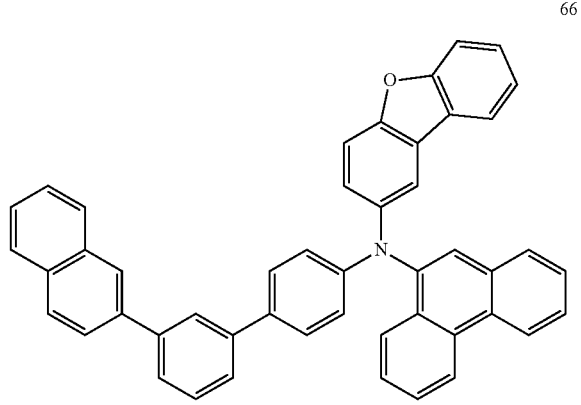 [SMILES: c1cc(-c2ccc(N(c3ccc4oc5ccccc5c4c3)c3cc4ccccc4c4ccccc34)cc2)cc(-c2ccc3ccccc3c2)c1]
66
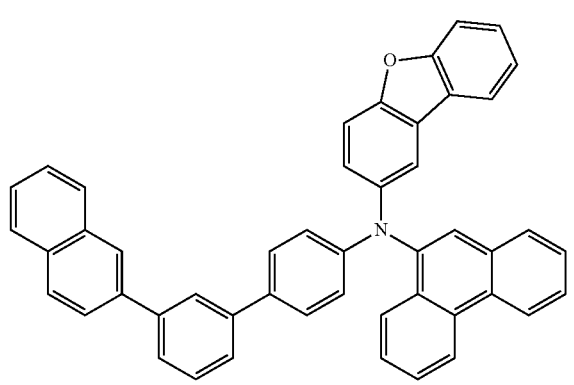
67
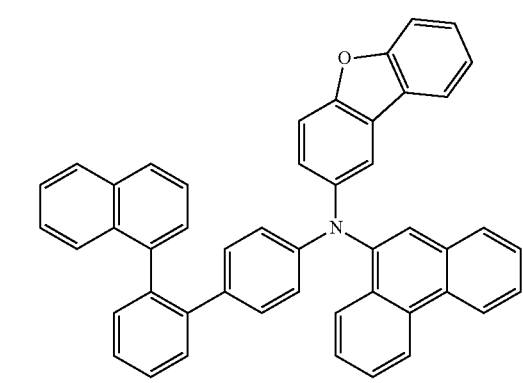
68
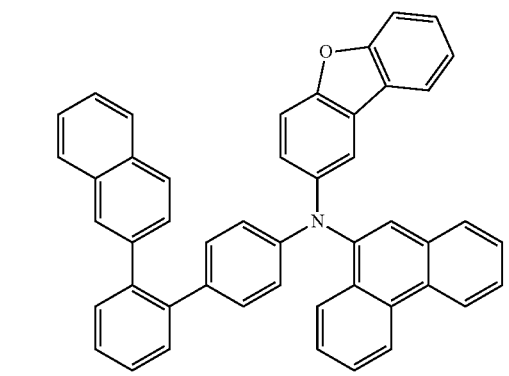
-continued
69
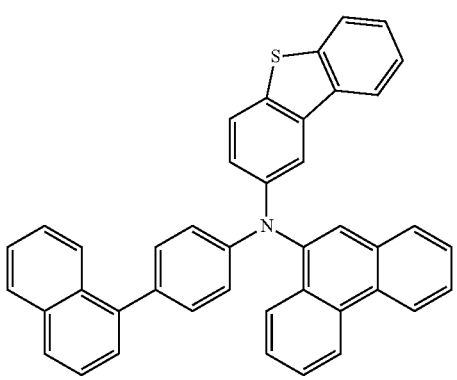
70
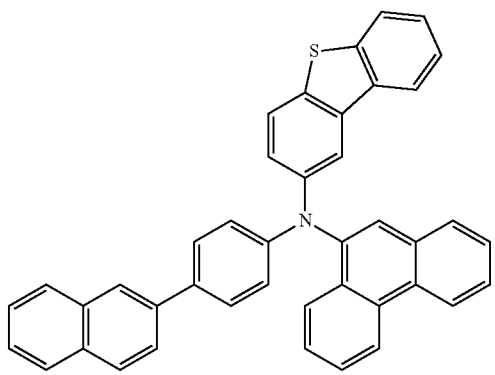
71
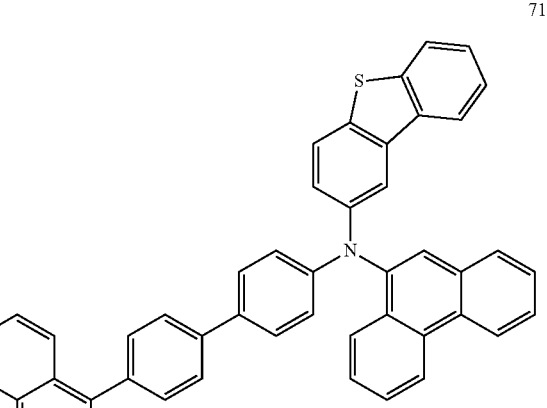
72
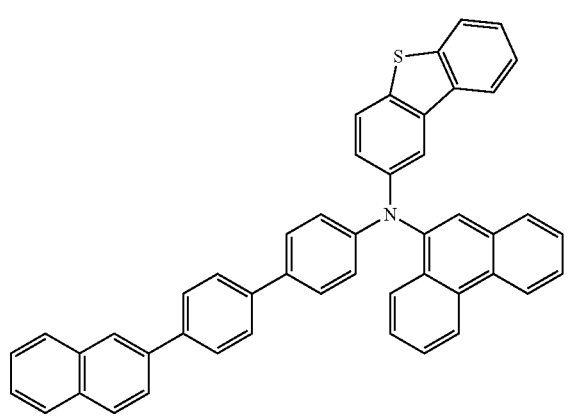

73
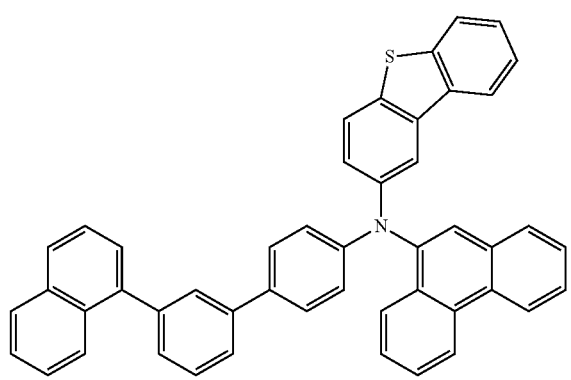
74
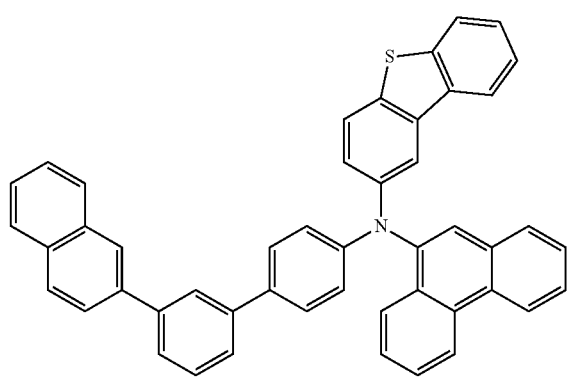
75
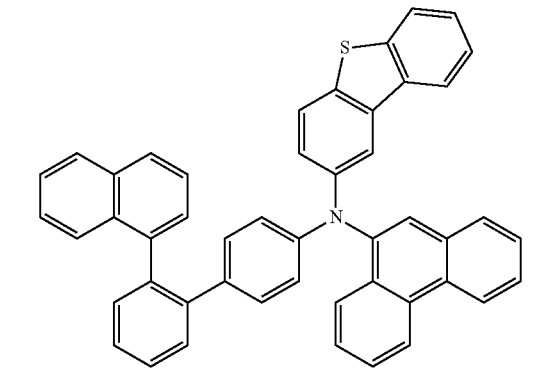
76
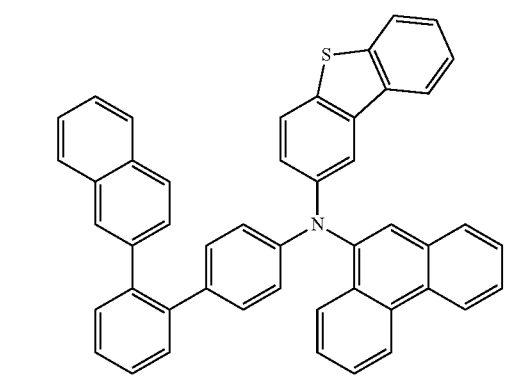
77
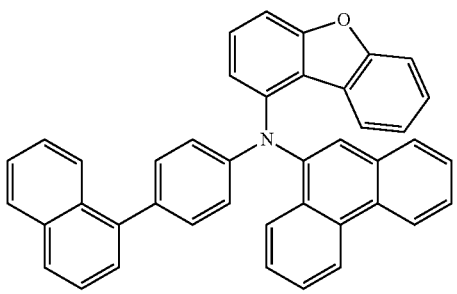
78
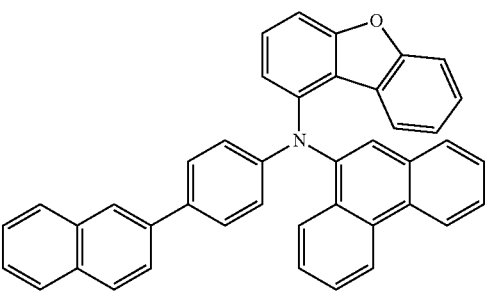
79
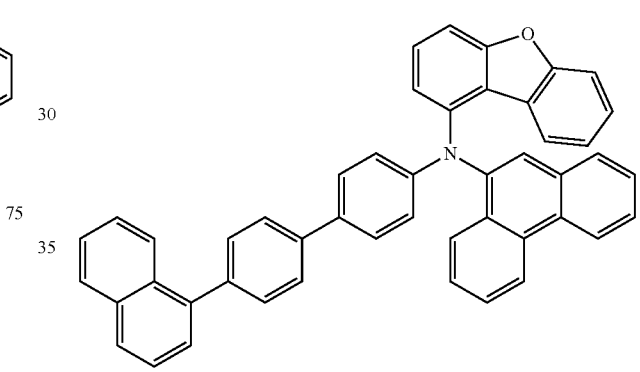
80
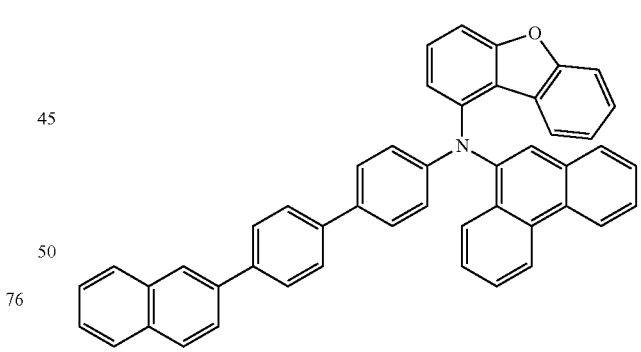
81
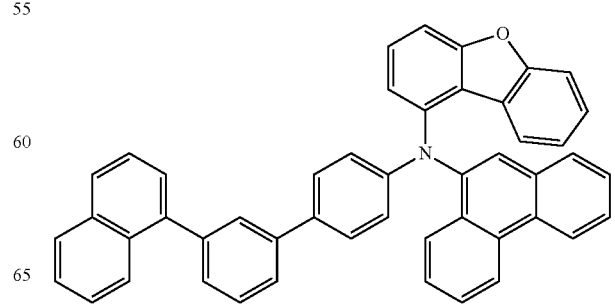

82
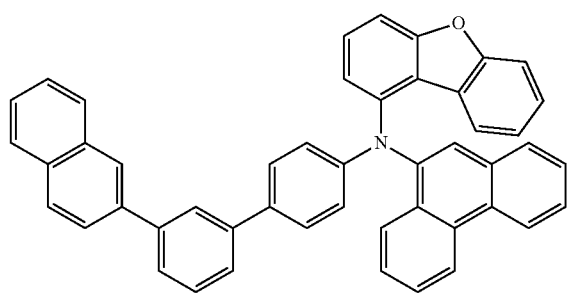
83
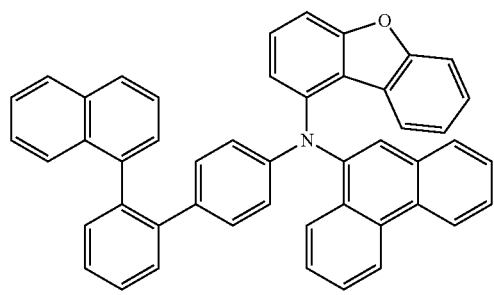
84
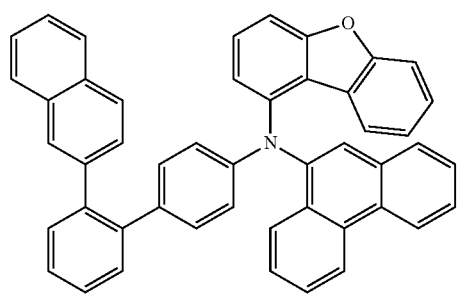
85
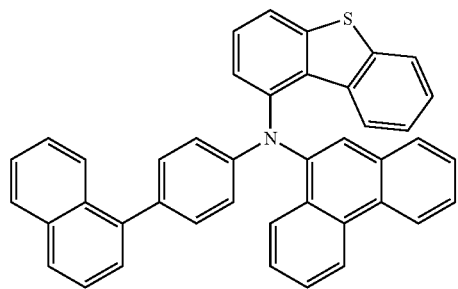
86
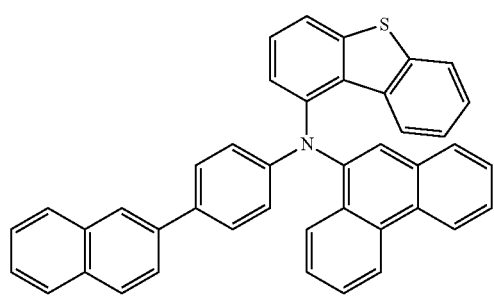
87
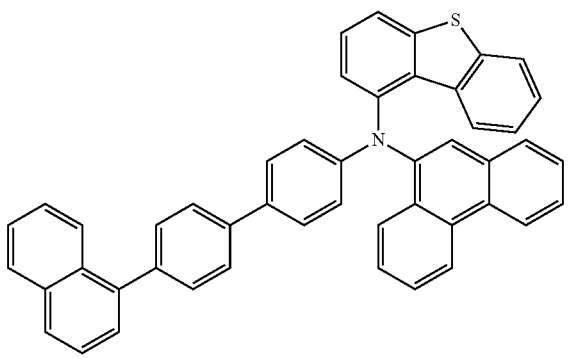
88
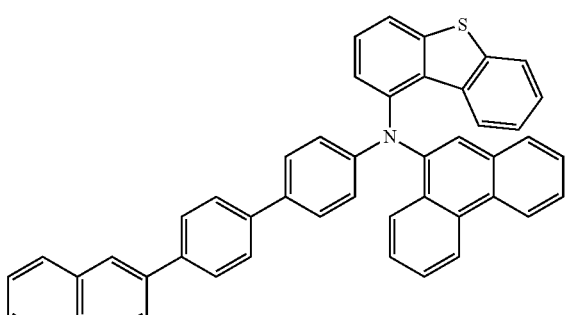
89
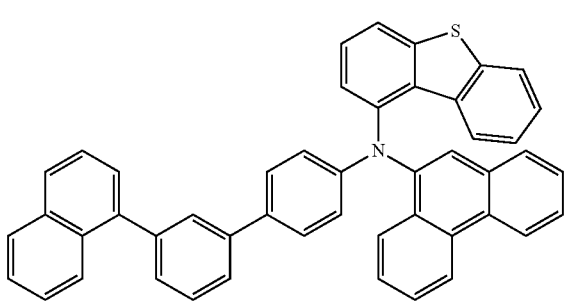
90
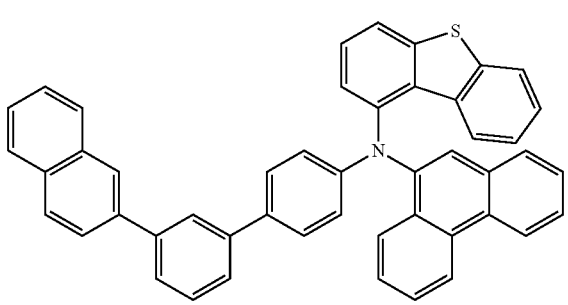
91
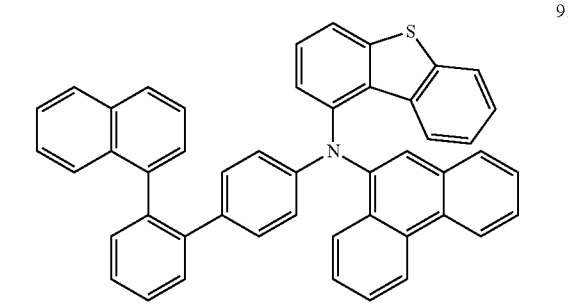

-continued

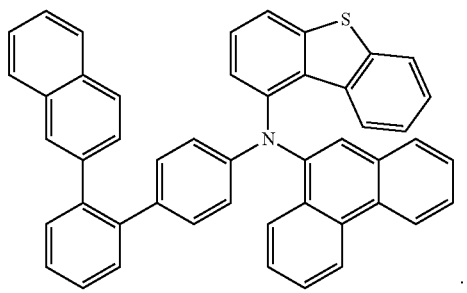

92

BRIEF DESCRIPTION OF THE DRAWINGS

The accompanying drawings are included to provide a further understanding of the inventive concept and are incorporated in and constitute a part of this specification. The drawings illustrate embodiments of the inventive concept and, together with the description, serve to explain principles of the inventive concept. The above and other aspects and features of the disclosure will become more apparent by describing in detail embodiments thereof with reference to the attached drawings, in which.

DETAILED DESCRIPTION OF THE EMBODIMENTS

Figure 1:
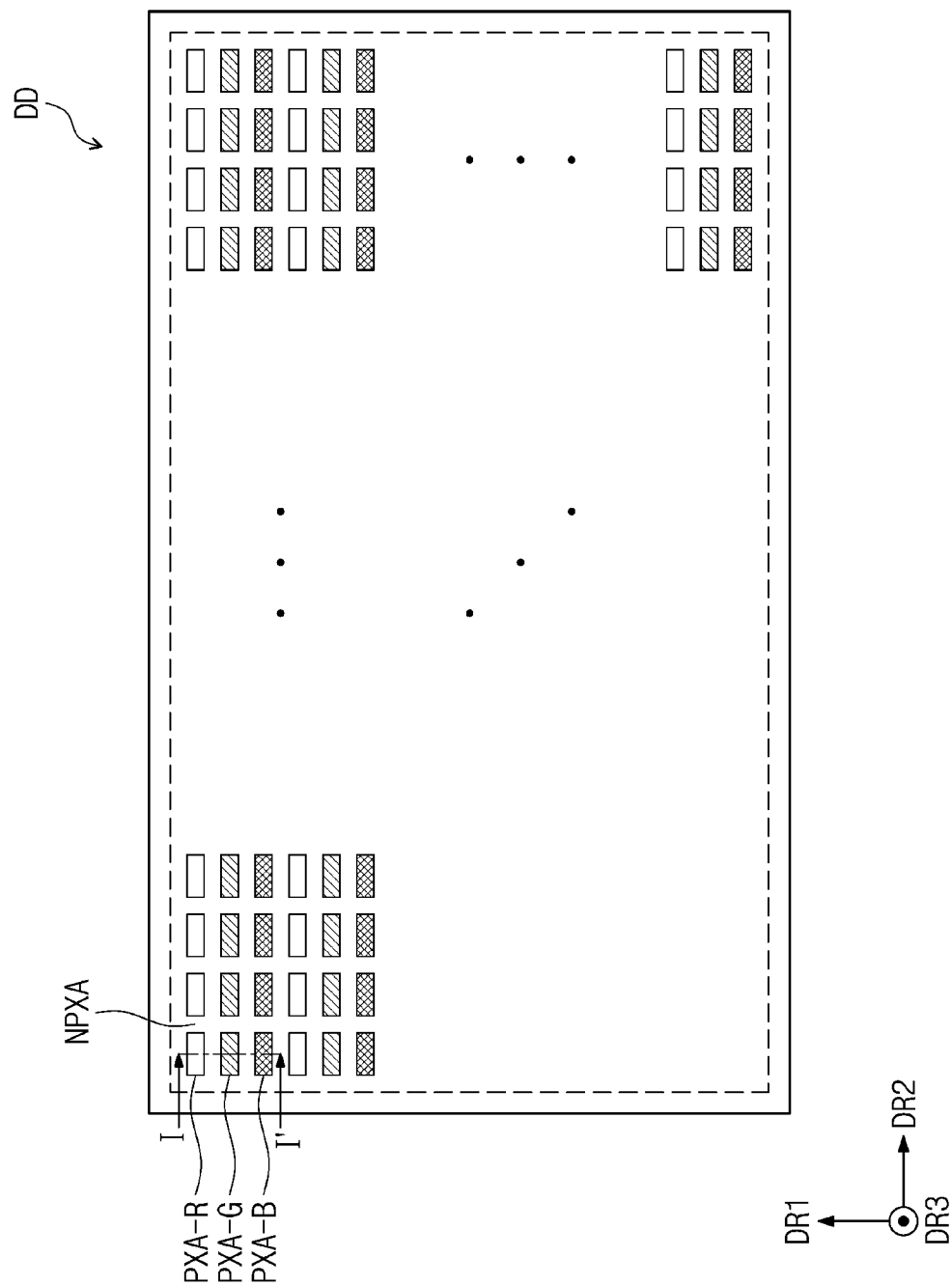
FIG. 1 is a plan view showing an embodiment of a display apparatus.

The inventive concept may have various modifications and may be embodied in different forms, and embodiments will be explained with reference to the accompanying drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

Like reference numerals refer to like elements throughout the specification. In the drawings, the thicknesses, the ratios, and the dimensions of structures and constituent elements may be exaggerated for effective explanation of their technical contents. Therefore, as the sizes and thicknesses of components in the drawings may be arbitrarily illustrated for convenience of explanation, such embodiments of the disclosure are not limited thereto.

As used herein, the expressions used in the singular such as "a," "an," and "the" are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the embodiments of the inventive concept.

It should be understood that the terms "comprises," "comprising," "includes," "including," "have," "having," "contains," "containing," and the like are intended to specify the presence of stated features, numerals, steps, operations, elements, parts, or combinations thereof, but do not preclude the presence or addition of one or more other features, numerals, steps, operations, elements, parts, or combinations thereof.

It will be understood that when an element such as a layer, film, region, or substrate is referred to as being "on," "connected to," or "coupled to" another element, it can be directly on, connected to, or coupled to the other element, or one or more intervening elements may also be present. When an element is referred to as being "directly on", "directly connected to," or "directly coupled to" another element, there are no intervening elements present. Throughout the specification, the word "on" a target element will be understood to be positioned above or below the target element, and will not necessarily be understood to be positioned "at an upper side" based on an opposite to gravity direction.

Throughout the specification, the phrase "in a plan view" means viewing the object from the top, and the phrase "in a schematic cross-sectional view" means viewing a cross-section of which the object is vertically cut from the side.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "overlap" or "overlapped" mean that a first object may be above or below or to a side of a second object, and vice versa. Additionally, the term "overlap" may include layer, stack, face or facing, extending over, covering, or partly covering or any other suitable term as would be appreciated and understood by those of ordinary skill in the art.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, 10%, or 5% of the stated value.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the description, the term "substituted or unsubstituted" corresponds to substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the exemplified substituents may be substituted or unsubstituted. For example, a biphenyl group may be interpreted as an aryl group or a phenyl group substituted with a phenyl group.

In the description, the term "forming a ring via the combination with an adjacent group" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocycles or polycycles. The ring formed via the combination with an adjacent group may be combined with another ring to form a spiro structure.

In the description, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the halogen atom may be a fluorine atom, a chlorine atom, a bromine atom, or an iodine atom.

In the description, the alkyl group may be a linear, branched, or cyclic type. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring group means an optional functional group or substituent derived from an aliphatic hydrocarbon ring. The hydrocarbon ring group may be a saturated hydrocarbon ring group of 5 to 20 ring-forming carbon atoms.

In the description, the aryl group means an optional functional group or substituent derived from an aromatic hydrocarbon ring. The aryl group may be a monocyclic aryl group or a polycyclic aryl group. The carbon number for forming rings in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of a substituted fluorenyl group are as follows, but an embodiment of the inventive concept is not limited thereto.

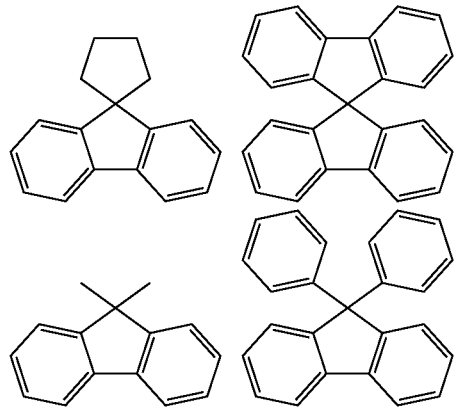

In the description, the heterocyclic group means an optional functional group or substituent derived from a ring including one or more among B, O, N, P, Si and S as heteroatoms. The heterocyclic group includes an aliphatic heterocyclic group and an aromatic heterocyclic group. The aromatic heterocyclic group may be a heteroaryl group. The aliphatic heterocyclic group and the aromatic heterocyclic group may be a monocycle or a polycycle.

In the description, the heterocyclic group may include one or more among B, O, N, P, Si and S as heteroatoms. If the heterocyclic group includes two or more heteroatoms, two or more heteroatoms may be the same or different. The heterocyclic group may be a monocyclic heterocyclic group or a polycyclic heterocyclic group, and has the concept including a heteroaryl group. The carbon number for forming rings of the heteroaryl group may be 2 to 30, 2 to 20, 2 to 12, or 2 to 10.

In the description, the aliphatic heterocyclic group may include one or more among B, O, N, P, Si and S as heteroatoms. The number of ring-forming carbon atoms of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more among B, O, N, P, Si and S as heteroatoms. If the heteroaryl group includes two or more heteroatoms, two or more heteroatoms may be the same or different. The heteroaryl group may be a monocyclic heterocyclic group or polycyclic heterocyclic group. The carbon number for forming rings of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofurane, phenanthroline, thiazole, isooxazole, oxazole, oxadiazole, thiadiazole, phenothiazine, dibenzosilole, dibenzofuran, etc., without limitation.

In the description, the explanation on the aryl group may be applied to the arylene group except that the arylene group is a divalent group. The explanation on the heteroaryl group may be applied to the heteroarylene group except that the heteroarylene group is a divalent group.

In the description, the silyl group includes an alkyl silyl group and an aryl silyl group. Examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the description, the carbon number of the amino group is not specifically limited, but may be 1 to 30. The amino group may include an alkyl amino group, an aryl amino group, or a heteroaryl amino group. Examples of the amino group include a methylamino group, a dimethylamino group, a phenylamino group, a diphenylamino group, a naphthylamino group, a 9-methyl-anthracenylamino group, a triphenylamino group, etc., without limitation.

In the description, the carbon number of a carbonyl group is not specifically limited, but the carbon number may be 1 to 40, 1 to 30, or 1 to 20. For example, the carbonyl group may have the structures below, but is not limited thereto.

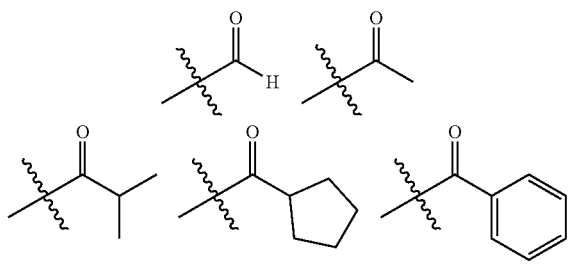

In the description, the carbon number of the sulfinyl group and sulfonyl group is not specifically limited, but may be 1 to 30. The sulfinyl group may include an alkyl sulfinyl group and an aryl sulfinyl group. The sulfonyl group may include an alkyl sulfonyl group and an aryl sulfonyl group.

In the description, the thiol group may include an alkyl thio group and an aryl thio group. The thiol group may mean the above-defined alkyl group or aryl group combined with a sulfur atom. Examples of the thiol group include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the description, the oxy group may mean the above-defined alkyl group or aryl group which is combined with an oxygen atom. The oxy group may include an alkoxy group and an aryl oxy group. The alkoxy group may be a linear, branched, or cyclic chain. The carbon number of the alkoxy group is not specifically limited but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, an embodiment of the inventive concept is not limited thereto.

In the description, the boron group may mean the above-defined alkyl group or aryl group which is combined with a boron atom. The boron group includes an alkyl boron group and an aryl boron group. Examples of the boron group include a trimethylboron group, a triethylboron group, a t-butyldimethylboron group, a triphenylboron group, a diphenylboron group, a phenylboron group, etc., without limitation.

In the description, the alkenyl group may be a linear chain or a branched chain. The carbon number is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the carbon number of the amine group is not specifically limited, but may be 1 to 30. The amine group may include an alkyl amine group and an aryl amine group. Examples of the amine group include a methylamine group, a dimethylamine group, a phenylamine group, a diphenylamine group, a naphthylamine group, a 9-methylanthracenylamine group, a triphenylamine group, etc., without limitation.

In the description, an alkyl group in the alkylthio group, alkylsulfoxy group, alkylaryl group, alkylamino group, alkylboron group, alkyl silyl group, and alkyl amine group may be the same as the examples of the above-described alkyl group.

In the description, the aryl group in the aryloxy group, arylthio group, arylsulfoxy group, aryl amino group, arylboron group, and aryl silyl group may be the same as the examples of the above-described aryl group.

In the description, a direct linkage may mean a single bond.

In the description,

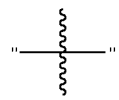

and "———*" each indicate a binding site to a neighboring atom.

Hereinafter, embodiments of the inventive concept will be explained in reference to the drawings.

Figure 2:
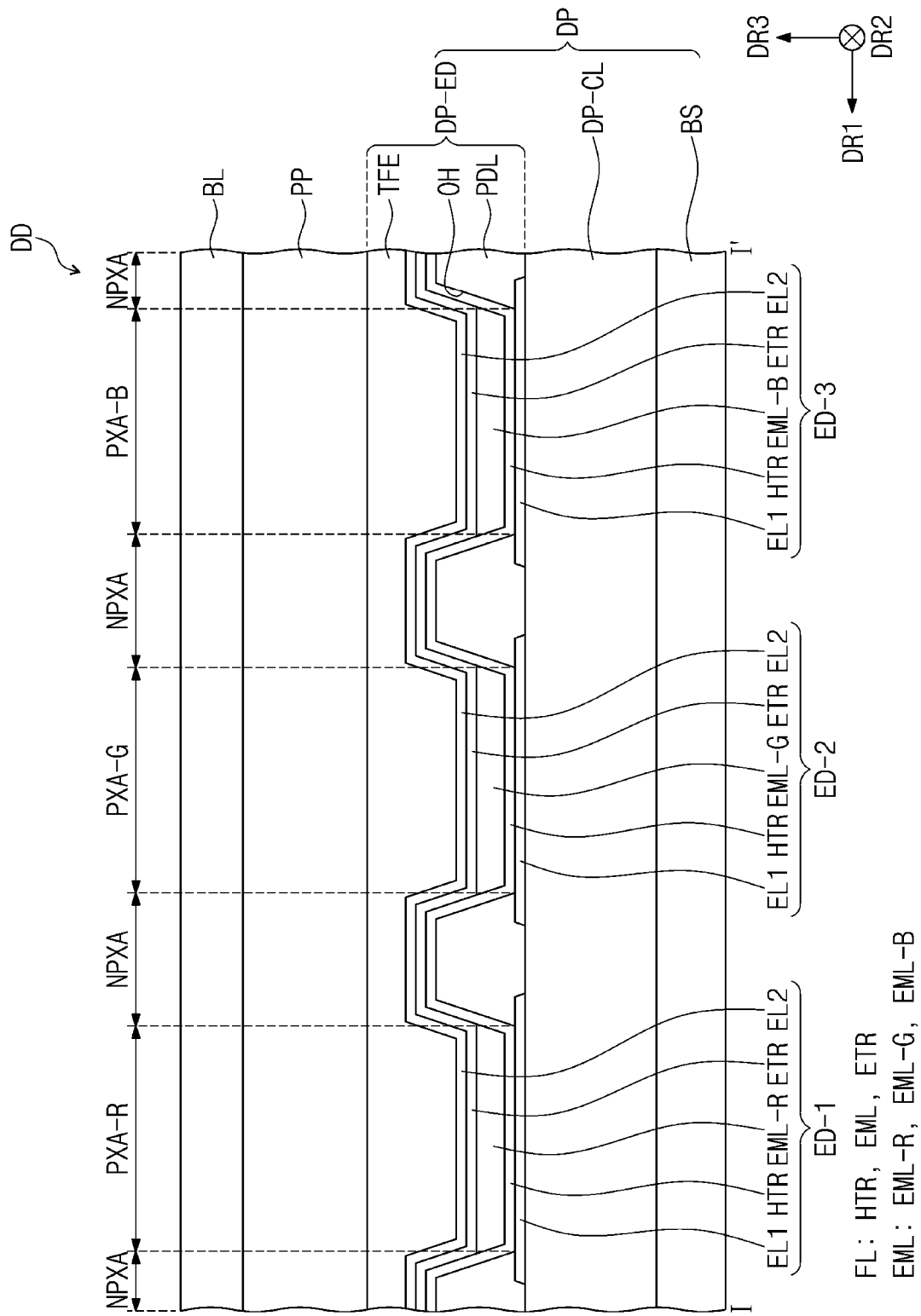
FIG. 2 is a schematic cross-sectional view of a display apparatus of an embodiment.

FIG. 1 is a plan view showing an embodiment of a display apparatus DD. FIG. 2 is a schematic cross-sectional view of a display apparatus DD of an embodiment. FIG. 2 is a schematic cross-sectional view showing a part corresponding to line I-I'.

The display apparatus DD may include a display panel DP and an optical layer PP disposed on the display panel DP. The display panel DP includes light emitting elements ED-1, ED-2, and ED-3. The display apparatus DD may include multiple light emitting elements ED-1, ED-2, and ED-3. The optical layer PP may be disposed on the display panel DP and control light reflected from external light at the display panel DP. The optical layer PP may include, for example, a polarization layer or a color filter layer. Different from the drawings, the optical layer PP may be omitted in the display apparatus DD of an embodiment.

On the optical layer PP, a base substrate BL may be disposed. The base substrate BL may be a member providing a base surface where the optical layer PP is disposed. The base substrate BL may be a glass substrate, a metal substrate, a plastic substrate, etc. However, an embodiment of the inventive concept is not limited thereto, and the base substrate BL may be an inorganic layer, an organic layer, or a composite material layer. Different from the drawings, the base substrate BL may be omitted in an embodiment.

The display apparatus DD according to an embodiment may further include a plugging layer (not shown). The plugging layer (not shown) may be disposed between a display device layer DP-ED and a base substrate BL. The plugging layer (not shown) may be an organic layer. The plugging layer (not shown) may include at least one among an acrylic resin, a silicon-based resin, and an epoxy-based resin.

The display panel DP may include a base layer BS, a circuit layer DP-CL provided on the base layer BS, and a display device layer DP-ED. The display device layer DP-ED may include a pixel definition layer PDL, light emitting elements ED-1, ED-2, and ED-3 disposed in the pixel definition layer PDL, and an encapsulating layer TFE disposed on the light emitting elements ED-1, ED-2, and ED-3.

The base layer BS may be a member providing a base surface where the display device layer DP-ED is disposed. The base layer BS may be a glass substrate, a metal substrate, a plastic substrate, etc. However, an embodiment of the inventive concept is not limited thereto, and the base layer BS may be an inorganic layer, an organic layer, or a composite material layer.

In an embodiment, the circuit layer DP-CL is disposed on the base layer BS, and the circuit layer DP-CL may include multiple transistors (not shown). Each of the transistors (not shown) may include a control electrode, an input electrode, and an output electrode. For example, the circuit layer DP-CL may include switching transistors and driving transistors for driving the light emitting elements ED-1, ED-2, and ED-3 of the display device layer DP-ED.

Each of the light emitting elements ED-1, ED-2, and ED-3 may have the structures of light emitting elements ED of embodiments according to FIG. 3 to FIG. 7, which will be explained later. Each of the light emitting elements ED-1, ED-2, and ED-3 may include a first electrode EL1, a second electrode EL2 disposed on the first electrode EL1, and a functional layer FL disposed between the first electrode EL1 and the second electrode EL2. The functional layer FL may include a hole transport region HTR, emission layers EML-R, EML-G, and EML-B, and an electron transport region ETR.

In FIG. 2, shown is an embodiment where the emission layers EML-R, EML-G, and EML-B of light emitting elements ED-1, ED-2, and ED-3, which are in opening portions OH defined in a pixel definition layer PDL, are disposed, and a hole transport region HTR, an electron transport region ETR and a second electrode EL2 are provided as common layers in all light emitting elements ED-1, ED-2, and ED-3. However, an embodiment of the inventive concept is not limited thereto. Different from FIG. 2, in an embodiment, the hole transport region HTR and the electron transport region ETR may be patterned and provided in the opening portions OH defined in the pixel definition layer PDL. For example, in an embodiment, the hole transport region HTR, the emission layers EML-R, EML-G, and EML-B, and the electron transport region ETR of the light emitting elements ED-1, ED-2, and ED-3 may be patterned by an ink jet printing method and provided.

An encapsulating layer TFE may cover the light emitting elements ED-1, ED-2, and ED-3. The encapsulating layer TFE may encapsulate the display device layer DP-ED. The encapsulating layer TFE may be a thin film encapsulating layer. The encapsulating layer TFE may be one layer or a stack of multiple layers. The encapsulating layer TFE includes at least one insulating layer. The encapsulating layer TFE according to an embodiment may include at least one inorganic layer (hereinafter, encapsulating inorganic layer). The encapsulating layer TFE according to an embodiment may include at least one organic layer (hereinafter, encapsulating organic layer) and at least one encapsulating inorganic layer.

The encapsulating inorganic layer protects the display device layer DP-ED from moisture/oxygen, and the encapsulating organic layer protects the display device layer DP-ED from foreign materials such as dust particles. The encapsulating inorganic layer may include silicon nitride, silicon oxy nitride, silicon oxide, titanium oxide, or aluminum oxide, without specific limitation. The encapsulating organic layer may include an acrylic compound, an epoxy-based compound, etc. The encapsulating organic layer may include a photopolymerizable organic material, without specific limitation.

The encapsulating layer TFE may be disposed on the second electrode EL2 and may be disposed while filling the opening portion OH.

Referring to FIG. 1 and FIG. 2, the display apparatus DD may include a non-luminous area NPXA and luminous areas PXA-R, PXA-G, and PXA-B. The luminous areas PXA-R, PXA-G, and PXA-B may be areas emitting light produced from the light emitting elements ED-1, ED-2, and ED-3, respectively. The luminous areas PXA-R, PXA-G, and PXA-B may be separated from each other on a plane.

The luminous areas PXA-R, PXA-G, and PXA-B may be areas separated by the pixel definition layer PDL. The non-luminous areas NPXA may be areas between neighboring luminous areas PXA-R, PXA-G, and PXA-B and may be areas corresponding to the pixel definition layer PDL. In the disclosure, each of the luminous areas PXA-R, PXA-G, and PXA-B may correspond to each pixel. The pixel definition layer PDL may divide the light emitting elements ED-1, ED-2, and ED-3. The emission layers EML-R, EML-G, and EML-B of the respective light emitting elements ED-1, ED-2, and ED-3 may be disposed and divided in the opening portions OH defined in the pixel definition layer PDL.

The luminous areas PXA-R, PXA-G, and PXA-B may be divided into multiple groups according to the color of light produced from the light emitting elements ED-1, ED-2, and ED-3. In the display apparatus DD of an embodiment, shown in FIG. 1 and FIG. 2, three luminous areas PXA-R, PXA-G, and PXA-B respectively emitting red light, green light, and blue light are illustrated as an embodiment. For example, the display apparatus DD of an embodiment may include a red luminous area PXA-R, a green luminous area PXA-G, and a blue luminous area PXA-B, which are separated from each other.

In the display apparatus DD according to an embodiment, multiple light emitting elements ED-1, ED-2, and ED-3 may emit light having different wavelength regions. For example, in an embodiment, the display apparatus DD may include a first light emitting element ED-1 emitting red light, a second light emitting element ED-2 emitting green light, and a third light emitting element ED-3 emitting blue light. For example, each of the red luminous area PXA-R, the green luminous area PXA-G, and the blue luminous area PXA-B of the display apparatus DD may correspond to the first light emitting element ED-1, the second light emitting element ED-2, and the third light emitting element ED-3.

However, an embodiment of the inventive concept is not limited thereto, and the first to third light emitting elements ED-1, ED-2, and ED-3 may emit light in the same wavelength region, or at least one thereof may emit light in a different wavelength region. For example, the first to third light emitting elements ED-1, ED-2, and ED-3 may all emit blue light.

The luminous areas PXA-R, PXA-G, and PXA-B in the display apparatus DD according to an embodiment may be arranged in a stripe shape. Referring to FIG. 1, multiple red luminous areas PXA-R, multiple green luminous areas PXA-G, and multiple blue luminous areas PXA-B may be arranged along a second directional axis DR2. The red luminous area PXA-R, the green luminous area PXA-G, and the blue luminous area PXA-B may be arranged by turns along a first directional axis DR1.

In FIG. 1 and FIG. 2, the areas of the luminous areas PXA-R, PXA-G, and PXA-B are shown as having similar sizes, but an embodiment of the inventive concept is not limited thereto. The areas of the luminous areas PXA-R, PXA-G, and PXA-B may be different from each other according to the wavelength region of light emitted. The areas of the luminous areas PXA-R, PXA-G, and PXA-B may mean areas on a plane defined by the first directional axis DR1 and the second directional axis DR2.

The arrangement type of the luminous areas PXA-R, PXA-G, and PXA-B is not limited to the configuration shown in FIG. 1, and the arrangement order of the red luminous areas PXA-R, the green luminous areas PXA-G, and the blue luminous areas PXA-B may be provided in various combinations according to the properties of display quality required for the display apparatus DD. For example, the arrangement type of the luminous areas PXA-R, PXA-G, and PXA-B may be a PenTile® arrangement type, or a diamond arrangement type.

The areas of the luminous areas PXA-R, PXA-G, and PXA-B may be different from each other. For example, in an embodiment, the area of the green luminous area PXA-G may be smaller than the area of the blue luminous area PXA-B, but an embodiment of the inventive concept is not limited thereto.

Hereinafter, FIG. 3 to FIG. 7 are schematic cross-sectional views showing light emitting elements according to embodiments. The light emitting element ED according to an embodiment may include a first electrode EL1, a hole transport region HTR, an emission layer EML, an electron transport region ETR, and a second electrode EL2 stacked in order.

Figure 3:
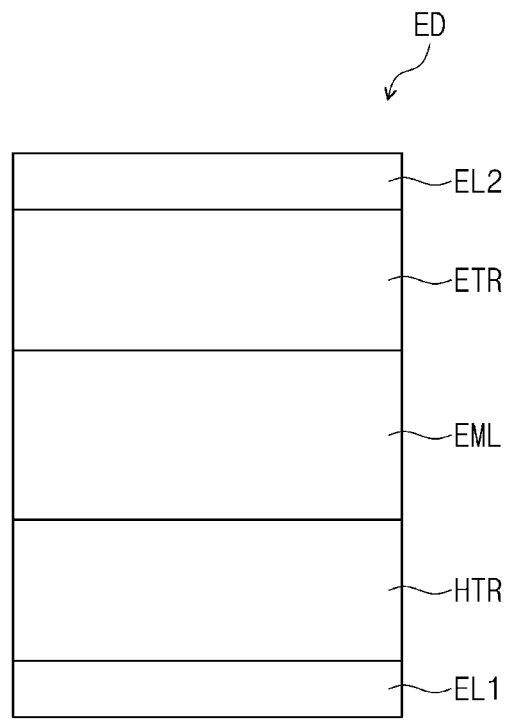
FIG. 3 is a schematic cross-sectional view showing a light emitting element according to an embodiment.
Figure 4:
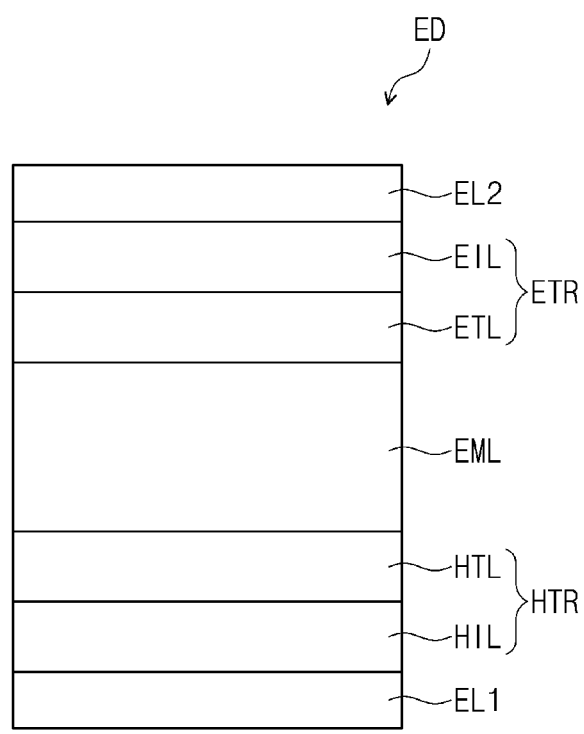
FIG. 4 is a schematic cross-sectional view showing a light emitting element according to an embodiment.
Figure 5:
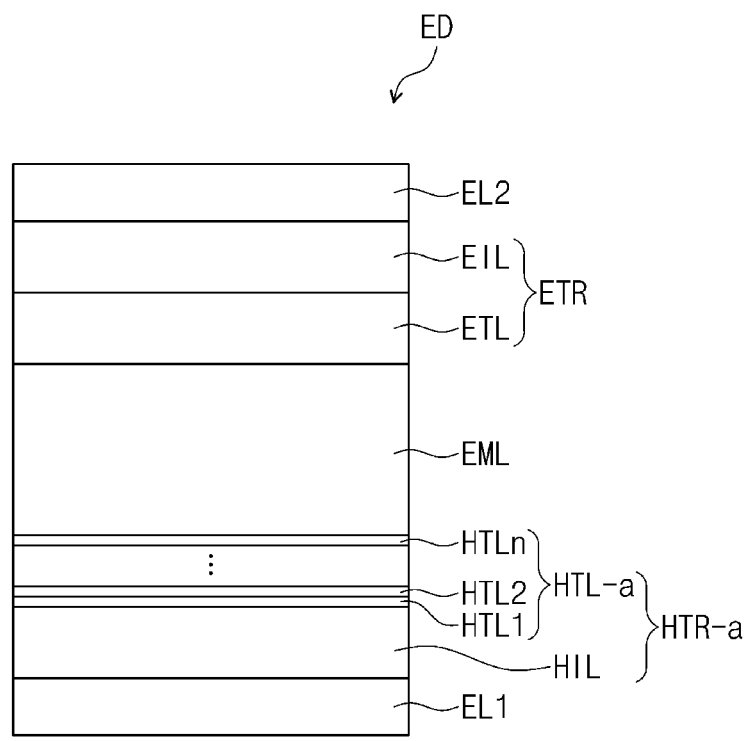
FIG. 5 is a schematic cross-sectional view showing a light emitting element according to an embodiment.
Figure 6:
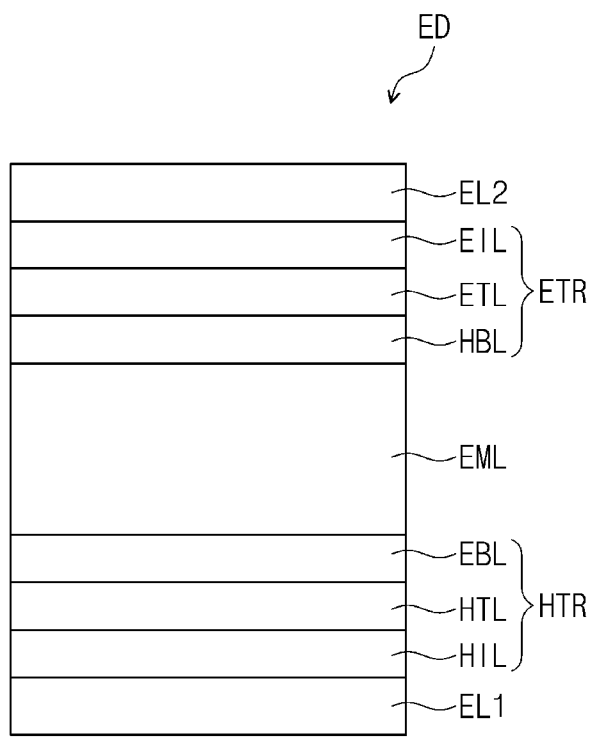
FIG. 6 is a schematic cross-sectional view showing a light emitting element according to an embodiment.
Figure 7:
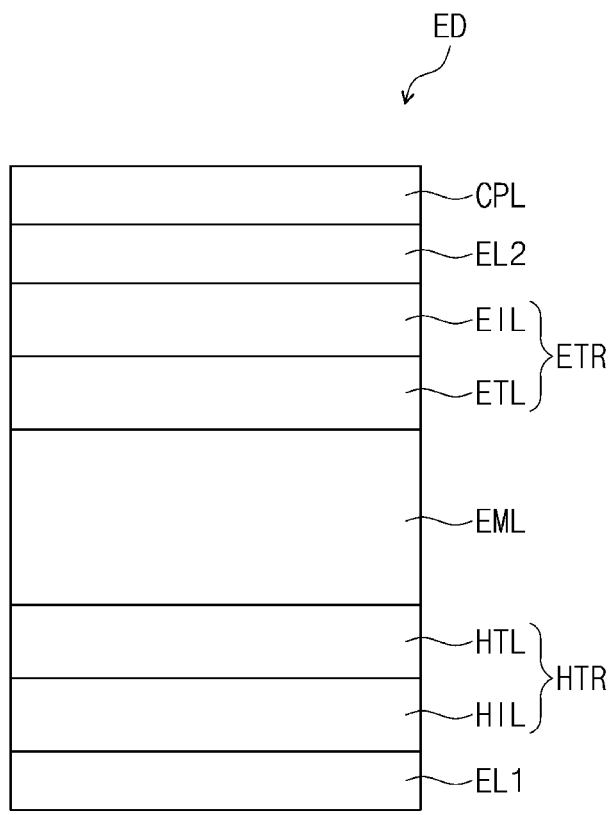
FIG. 7 is a schematic cross-sectional view showing a light emitting element according to an embodiment.

In comparison to FIG. 3, FIG. 4 shows the schematic cross-sectional view of a light emitting element ED of an embodiment, wherein a hole transport region HTR includes a hole injection layer HIL and a hole transport layer HTL, and an electron transport region ETR includes an electron injection layer EIL and an electron transport layer ETL. In comparison to FIG. 4, FIG. 5 shows the schematic cross-sectional view of a light emitting element ED of an embodiment, wherein a hole transport layer HTL-a includes hole transport layers HTL1, HTL2, . . . , HTLn. In comparison to FIG. 3, FIG. 6 shows the schematic cross-sectional view of a light emitting element ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 7 shows the schematic cross-sectional view of a light emitting element ED of an embodiment, including a capping layer CPL disposed on the second electrode EL2.

The first electrode EL1 has conductivity. The first electrode EL1 may be formed using a metal material, a metal alloy, or a conductive compound. The first electrode EL1 may be an anode or a cathode. However, an embodiment of the inventive concept is not limited thereto. The first electrode EL1 may be a pixel electrode. The first electrode EL1 may be a transmissive electrode, a transflective electrode, or a reflective electrode. If the first electrode EL1 is the transmissive electrode, the first electrode EL1 may include a transparent metal oxide such as indium tin oxide (ITO), indium zinc oxide (IZO), zinc oxide (ZnO), and indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, compounds thereof, or mixtures thereof (for example, a mixture of Ag and Mg). Also, the first electrode EL1 may have a structure including layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, an embodiment of the inventive concept is not limited thereto. The first electrode EL1 may include the above-described metal materials, combinations of two or more metal materials selected from the above-described metal materials, or oxides of the above-described metal materials. A thickness of the first electrode EL1 may be in a range of about 700 Å to about 10,000 Å. For example, the thickness of the first electrode EL1 may be in a range of about 1,000 Å to about 3,000 Å.

The hole transport region HTR is provided on the first electrode EL1. The hole transport region HTR may include at least one of a hole injection layer HIL, a hole transport layer HTL, a buffer layer, an emission auxiliary layer (not shown), and an electron blocking layer EBL. A thickness of the hole transport region HTR may be in a range of about 50 Å to about 15,000 Å.

The hole transport region HTR may have a single layer formed using a single material, a single layer formed using multiple different materials, or a multilayer structure including layers formed using multiple different materials.

For example, the hole transport region HTR may have the structure of a single layer of a hole injection layer HIL or a hole transport layer HTL, and may have a structure of a single layer formed using a hole injection material and a hole transport material. In another embodiment, the hole transport region HTR may have a structure of a single layer formed using different materials, or a structure stacked from the first electrode EL1 of hole injection layer HIL/hole transport layer HTL, hole injection layer HIL/hole transport layer HTL/buffer layer (not shown), hole injection layer HIL/buffer layer (not shown), hole transport layer HTL/ buffer layer (not shown), or hole injection layer HIL/hole transport layer HTL/electron blocking layer EBL, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the monoamine compound according to an embodiment. The monoamine compound of an embodiment may include a substituted or unsubstituted phenanthryl group which is directly bonded to the nitrogen atom of an amine, a substituted or unsubstituted dibenzoheterole group which is directly bonded to the nitrogen atom of an amine, and a substituted or unsubstituted naphtyl group which is bonded to the nitrogen atom of an amine via a linker.

The phenanthryl group

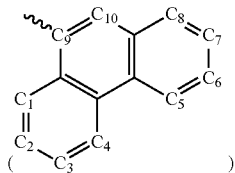

may be one in which $C_9$ of the phenanthryl group is bonded to the nitrogen atom of an amine. The phenanthryl group may be an unsubstituted phenanthryl group, or a phenanthryl group substituted with a deuterium atom. The phenanthryl group substituted with a deuterium atom may be one in which $C_1$ to $C_8$ and $C_{10}$ excluding $C_9$ are substituted with deuterium atoms. However, these are only examples, and an embodiment of the inventive concept is not limited thereto. The phenanthryl group may be one in which deuterium is substituted at least one position excluding a carbon bonded to the nitrogen atom of an amine.

The dibenzoheterole group

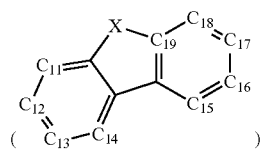

may be one in which one carbon selected among $C_{11}$, $C_{12}$, $C_{13}$, and $C_{14}$ of the dibenzoheterole group is bonded to the nitrogen atom of an amine. In the dibenzoheterole group, a heteroatom X may be a sulfur atom or an oxygen atom. For example, the dibenzoheterole group may be a dibenzothiophene group or a dibenzofuran group. The dibenzoheterole group may be an unsubstituted dibenzoheterole group, a dibenzoheterole group substituted with a deuterium atom, or a dibenzoheterole group substituted with a substituted or unsubstituted phenyl group.

In the dibenzoheterole group substituted with a deuterium atom, deuterium atoms may be substituted at all carbon atoms, excluding the carbon at a position bonded to the nitrogen atom of an amine group. However, this is only an illustration, and an embodiment of the inventive concept is not limited thereto. In an embodiment, in the dibenzoheterole group substituted with a deuterium atom, a deuterium atom may be substituted at least one carbon excluding a carbon bonded to the nitrogen atom of an amine group.

In the dibenzoheterole group substituted with an unsubstituted phenyl group, the unsubstituted phenyl group may be substituted at a benzene ring to which the nitrogen atom of an amine group is bonded, or may be substituted at a benzene ring to which the nitrogen atom of an amine group is not bonded. In the dibenzoheterole group, the phenyl group substituted at a benzene ring to which the nitrogen atom of an amine group is bonded may be at a para position or meta position with respect to the nitrogen atom of an amine in the dibenzoheterole group. The phenyl group substituted at a benzene ring to which the nitrogen atom of an amine group is not bonded may be at an ortho position or para position with respect to the heteroatom of a heterole group.

The naphthyl group may be bonded to the nitrogen atom of an amine via a linker. For example, the naphthyl group may not be directly bonded to the nitrogen atom of an amine. The linker may be a substituted or unsubstituted phenylene group or a substituted or unsubstituted divalent biphenyl group. The naphthyl group may be combined with a substituted or unsubstituted phenylene group which is bonded to the nitrogen atom of an amine, or combined with a substituted or unsubstituted divalent biphenyl group which is bonded to the nitrogen atom of an amine. The naphtyl group may be an unsubstituted naphthyl group, a naphthyl group substituted with a deuterium atom, or a naphthyl group substituted with a substituted or unsubstituted naphthyl group. In the description, in the naphthyl group substituted with a naphthyl group, the naphthyl group combined with the phenylene group is defined as a first naphthyl group, and the naphthyl group substituted at the first naphthyl group is defined as a second naphthyl group.

The naphthyl group may be combined with an unsubstituted phenylene group which is bonded to the nitrogen atom of an amine. The naphthyl group may be at a para position with respect to the nitrogen atom of an amine in the unsubstituted phenylene group. The naphthyl group

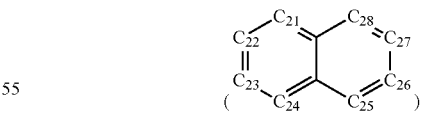

may be combined with the phenylene group at $C_{27}$ or $C_{28}$ of the naphthyl group.

The naphthyl group may be combined with an unsubstituted divalent biphenyl group which is bonded to the nitrogen atom of an amine. The naphthyl group may be combined with a phenyl group which is not bonded to the nitrogen atom of an amine in the divalent biphenyl group.

In the naphthyl group substituted with a deuterium atom, deuterium may be substituted at all carbon atoms excluding a carbon at a position where the naphthyl group is bonded to a linker. However, this is only an illustration, and an embodiment of the inventive concept is not limited thereto. In an embodiment, in the naphthyl group, deuterium may be substituted on at least one carbon atom excluding a carbon at a position where the naphthyl group is bonded to a linker.

In an embodiment, a hole transport region HTR included in a light emitting element ED may include a monoamine compound of an embodiment, represented by Formula 1 below.

[Formula 1]

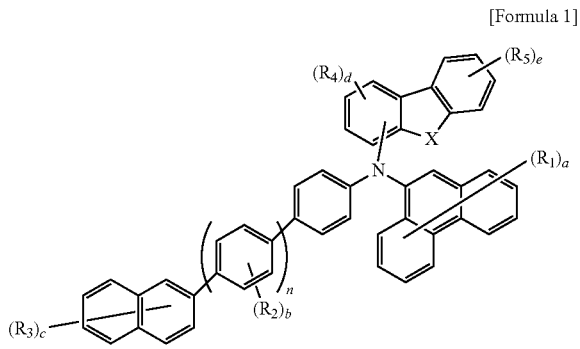

In Formula 1, X may be O or S. For example, the dibenzoheterole group substituted at the nitrogen of an amine may be a substituted or unsubstituted dibenzofuran group or a substituted or unsubstituted dibenzothiophene group.

In Formula 1, n may be 0 or 1. If n is 0, the naphthyl group may be combined with a phenylene group which is bonded to the nitrogen of an amine. If n is 1, the naphthyl group may be combined with a divalent biphenyl group which is bonded to the nitrogen of an amine.

In Formula 1, a may be an integer from 0 to 9, b and e may each independently be an integer from 0 to 4, c may be an integer from 0 to 7, and d may be an integer from 0 to 3. $R_1$ to $R_5$ may each independently be a substituted or unsubstituted alkyl group of 1 to 15 carbon atoms, a substituted or unsubstituted aryl group of 6 to 30 carbon atoms, a substituted or unsubstituted heteroaryl group of 1 to 30 carbon atoms, a substituted or unsubstituted silyl group, a halogen atom, a hydrogen atom, or a deuterium atom.

If a is 0, the phenanthryl group may be an unsubstituted phenanthryl group. If a is 1, the phenanthryl group may be a phenanthryl group which is substituted with one $R_1$ group. If a is an integer of 2 or more, the phenanthryl group may be substituted with multiple $R_1$ groups. If a is an integer of 2 or more, all the multiple $R_1$ groups may be the same substituents, or at least one thereof may be different.

If b is 0, the phenylene group may be an unsubstituted phenylene group. If b is 1, the phenylene group may be a phenylene group which is mono-substituted with a $R_2$ group. If b is an integer of 2 or more, the phenylene group may be substituted with multiple $R_2$ groups, and all the multiple $R_2$ groups may be the same substituents, or at least one thereof may be different.

If c is 0, the naphthyl group may be an unsubstituted naphthyl group. If c is 1, the naphthyl group may be a naphthyl group which is mono-substituted with a $R_3$ group. If c is an integer of 2 or more, the naphthyl group may be substituted with multiple $R_3$ groups, and all the multiple $R_3$ groups may be the same substituents, or at least one thereof may be different.

If both d and e are 0, the dibenzoheterole group may be an unsubstituted dibenzoheterole group. If d is 0, and e is 1, the dibenzoheterole group may be one in which $R_5$ is mono-substituted at a benzene ring which is not bonded to the nitrogen atom of an amine. If d is 1, and e is 0, the dibenzoheterole group may be one in which $R_4$ is mono-substituted at a benzene ring which is bonded to the nitrogen atom of an amine. If d is 2 or more, the dibenzoheterole group may be substituted with multiple $R_4$ groups, and all the multiple $R_4$ groups may be the same substituents, or at least one thereof may be different. If e is 2 or more, the dibenzoheterole group may be substituted with multiple $R_5$ groups, and all the multiple $R_5$ groups may be the same substituents, or at least one thereof may be different.

In an embodiment, the monoamine compound of an embodiment represented by Formula 1 and included in the hole transport region HTR may be represented by Formula 2-1 or Formula 2-2 below.

[Formula 2-1]

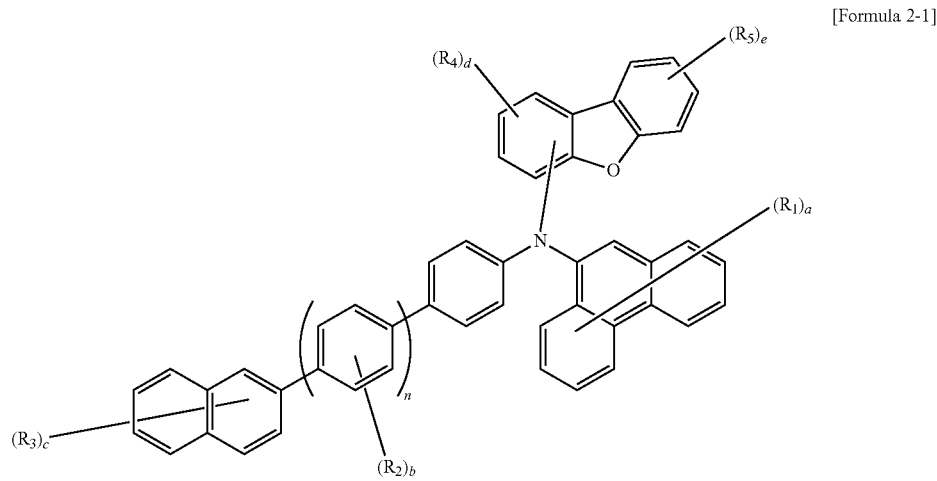

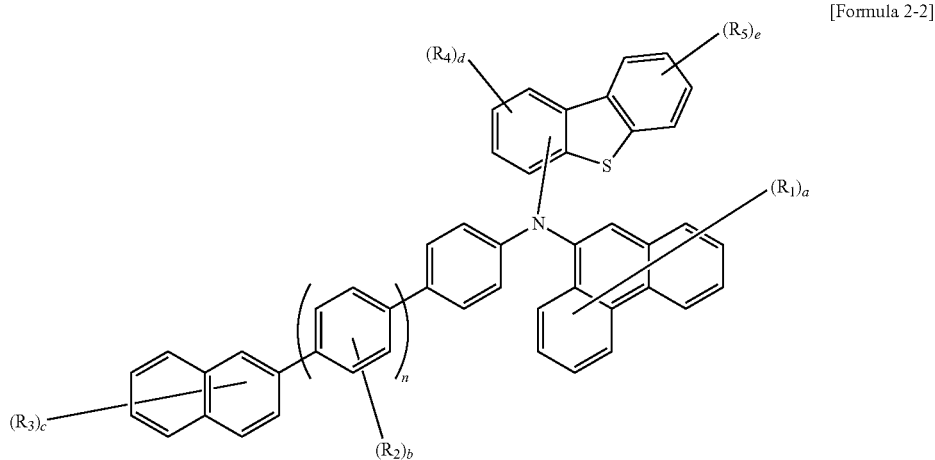

[Formula 2-2]

In Formula 2-1 and Formula 2-2, the same explanation on a to e, n, and $R_1$ to $R_5$ referring to Formula 1 above may be applied.

Formula 2-1 corresponds to Formula 1 where the heteroatom included in the dibenzoheterole is an oxygen atom, and Formula 2-2 corresponds to Formula 1 where the heteroatom included in the dibenzoheterole is a sulfur atom.

The monoamine compound of an embodiment represented by Formula 1 may be represented by one among Formula 3-1 to Formula 3-4 below.

[Formula 3-1]

[Formula 3-2]

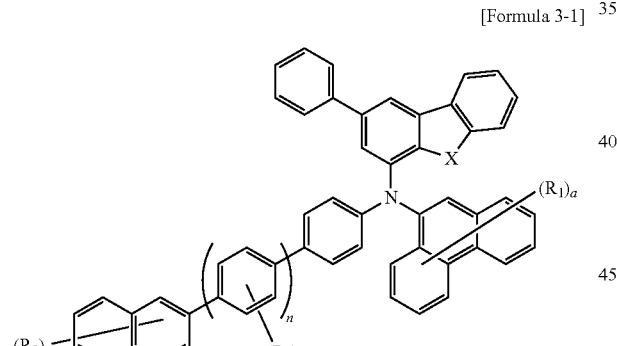

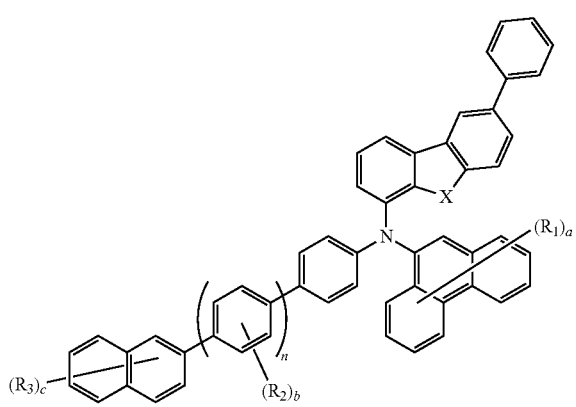

[Formula 3-3]

[Formula 3-4]

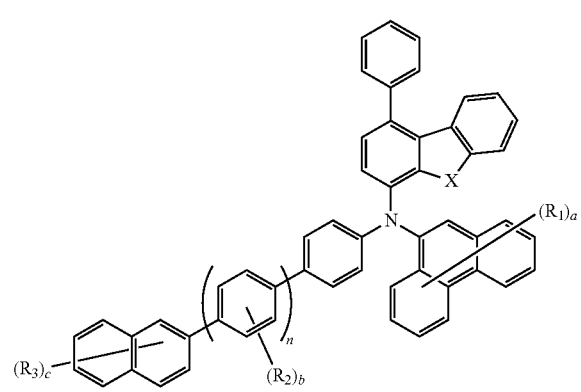

In Formula 3-1 to Formula 3-4, the same explanation on a to c, n, X, and $R_1$ to $R_3$ referring to Formula 1 may be applied.

In Formulae 3-1 to 3-4, in contrast to Formula 1, the bonding position of the nitrogen atom of an amine to the dibenzoheterole group is fixed, and the dibenzoheterole group is substituted with one phenyl group. In Formula 3-1 and Formula 3-2, a phenyl group may be substituted at a benzene ring where the nitrogen of an amine is bonded to the dibenzoheterole group, and in Formula 3-3 and Formula 3-4, a phenyl group may be substituted at a benzene ring where the nitrogen of an amine is not bonded to the dibenzoheterole group. The phenyl group substituted at the dibenzoheterole group may be at a meta position with respect to the nitrogen of an amine at a benzene ring where the nitrogen of the amine of the dibenzoheterole is bonded in Formula 3-1, and may be at a para position with respect to the nitrogen of an amine at a benzene ring where the nitrogen of the amine of the dibenzoheterole is bonded in Formula 3-2. The phenyl group substituted at the dibenzoheterole group may be at a para position with respect to the heterole atom in a benzene ring where the nitrogen of the amine of the dibenzoheterole is not bonded in Formula 3-3, and may be at an ortho position with respect to the heterole atom in a benzene ring where the nitrogen of the amine of the dibenzoheterole is not bonded in Formula 3-4.

The monoamine compound represented by Formula 1 may be represented by Formula 4-1 or Formula 4-2 below.

[Formula 4-1]

[Formula 4-2]

In Formula 4-1 and Formula 4-2, the same explanation on a, c to e, X, $R_1$, and $R_3$ to $R_5$ referring to Formula 1 may be applied.

The monoamine compound of an embodiment may be any one among the compounds represented in Compound Group 1 below. For example, the hole transport region may include at least one among the monoamine compounds represented in Compound Group 1 below.

[Compound Group 1]

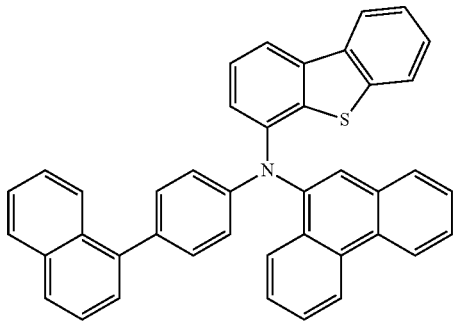

1

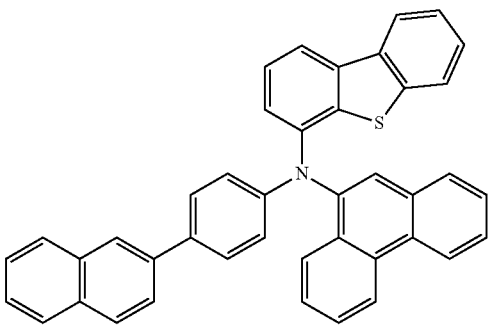

2

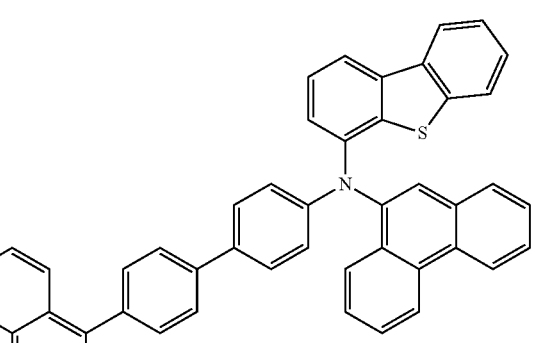

3

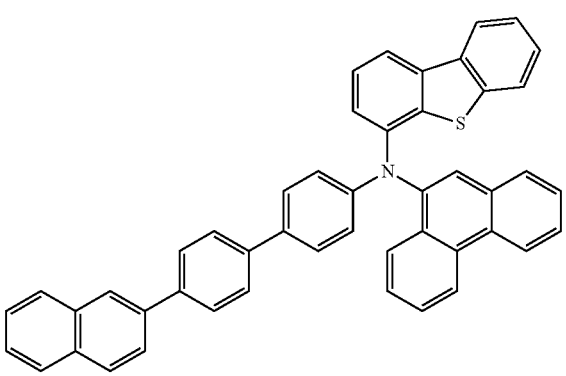

4

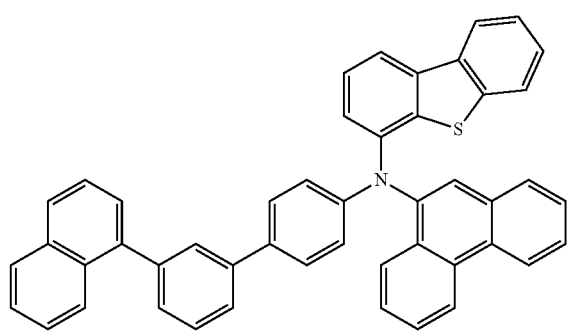
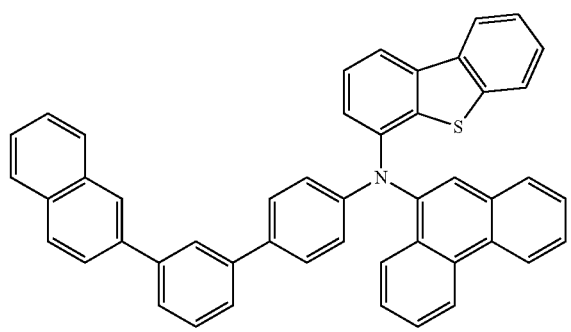
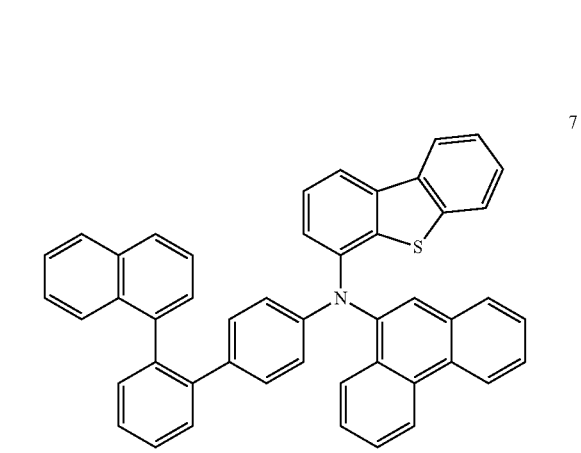
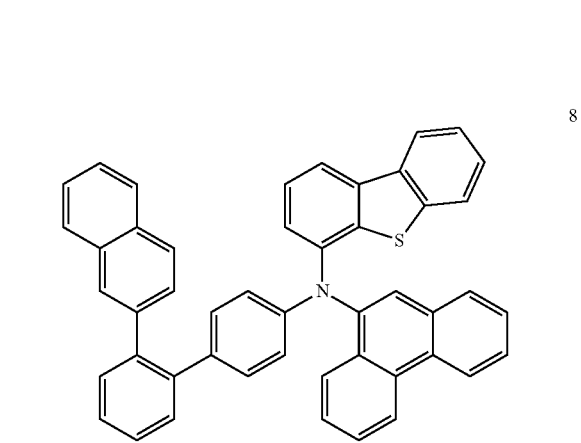
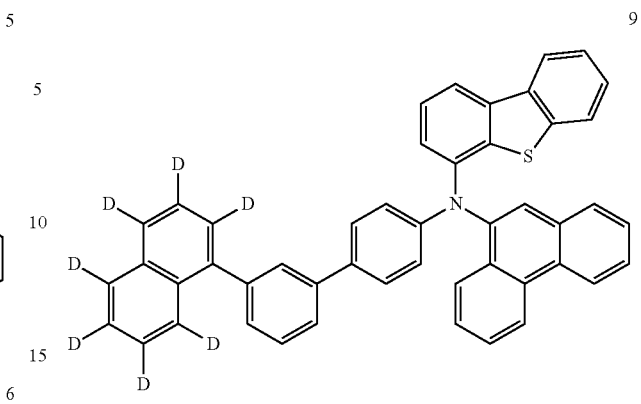
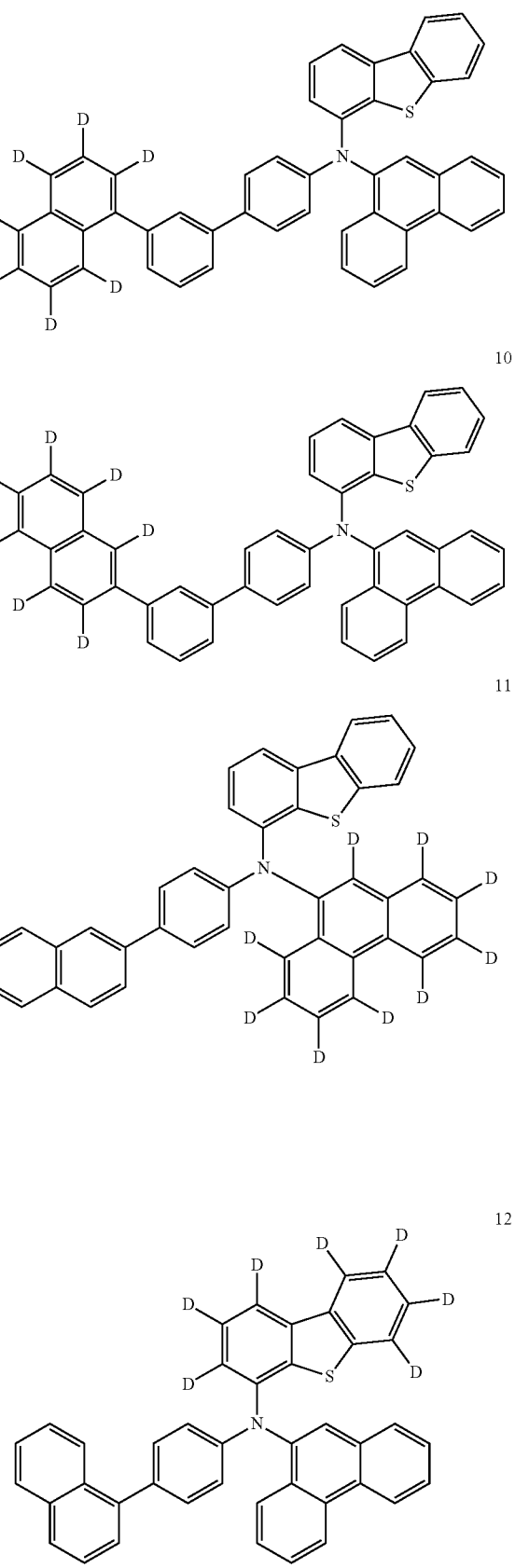

13
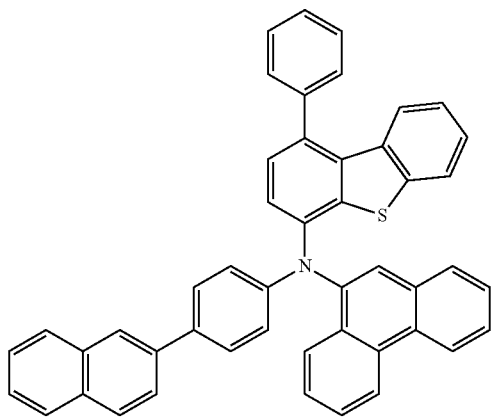
14
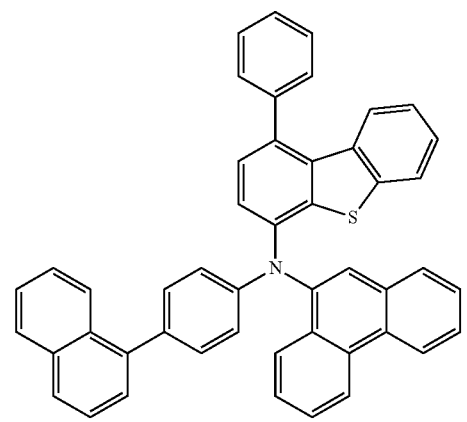
15
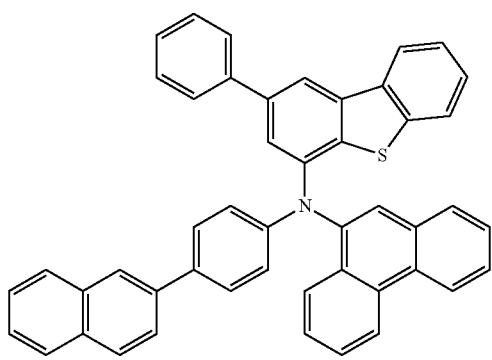
16
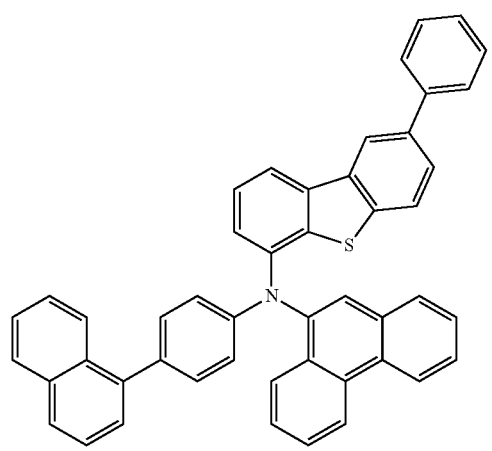
17
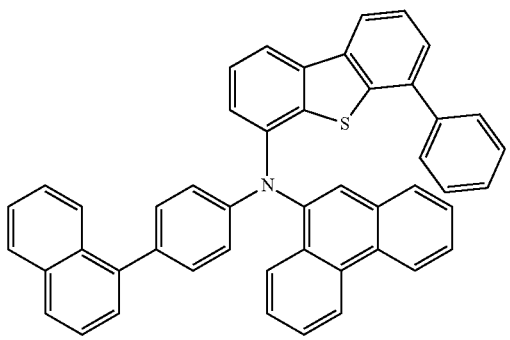
18
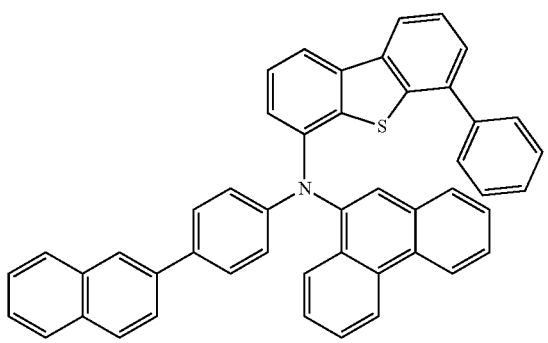
19
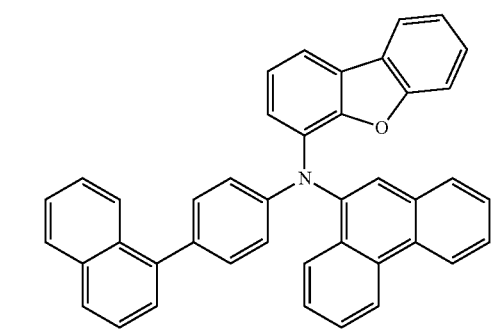
20
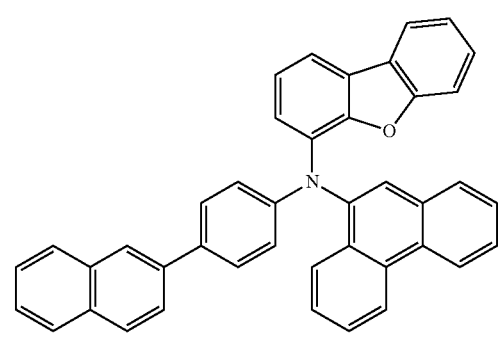

21
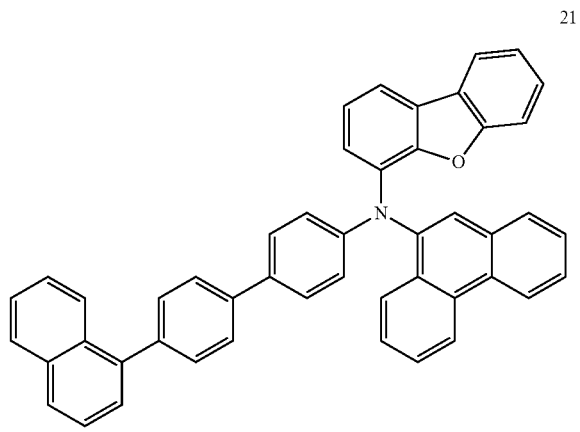
22
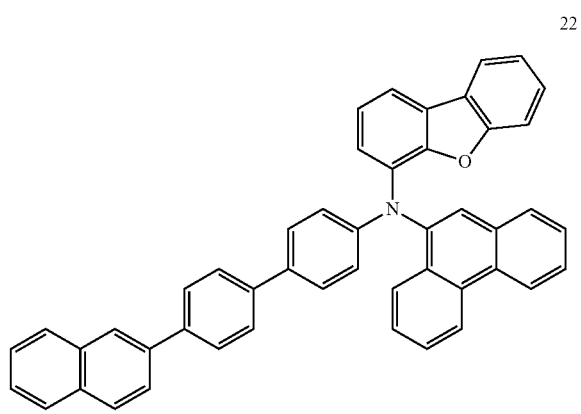
23
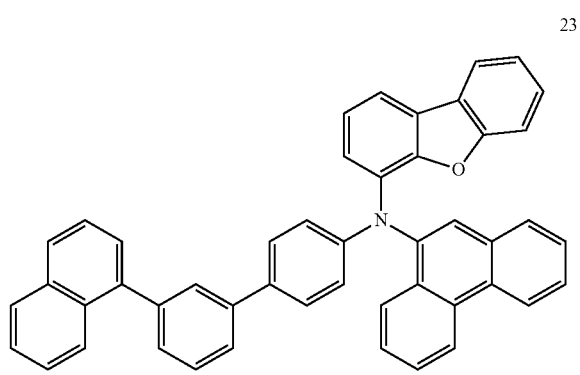
24
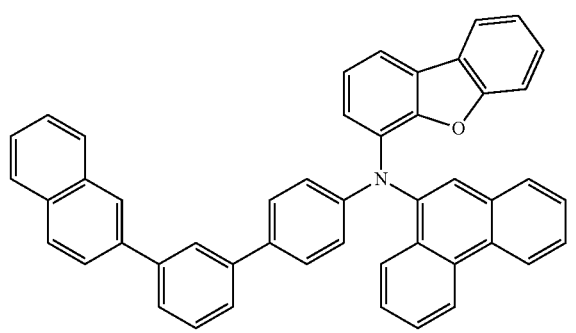
25
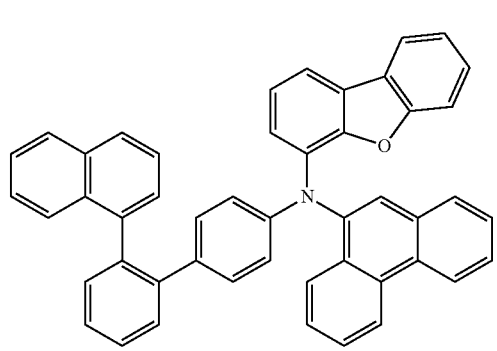
26
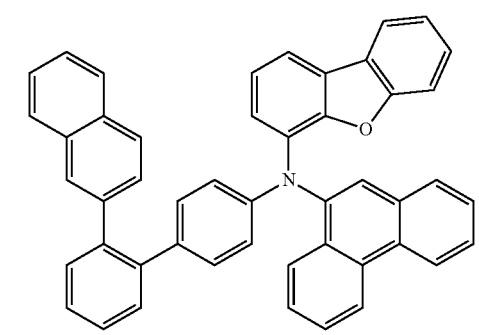
27
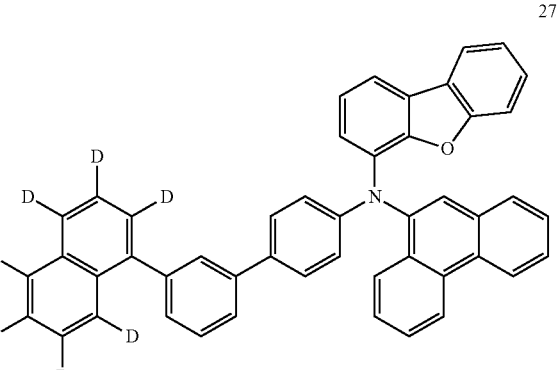
28
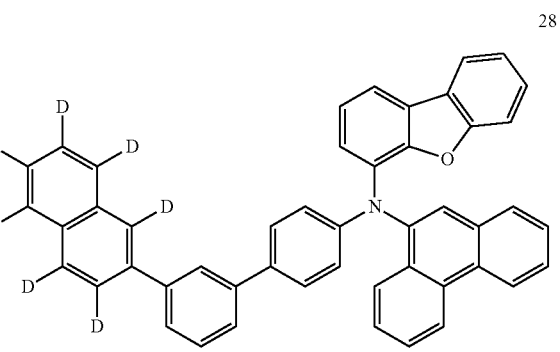

101
-continued
29
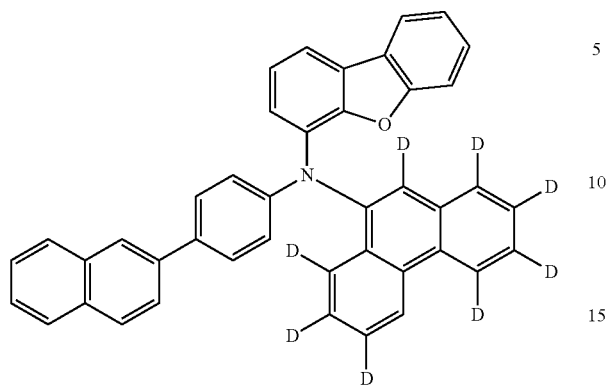
30
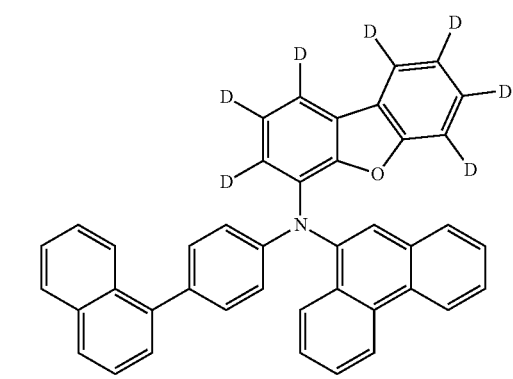
31
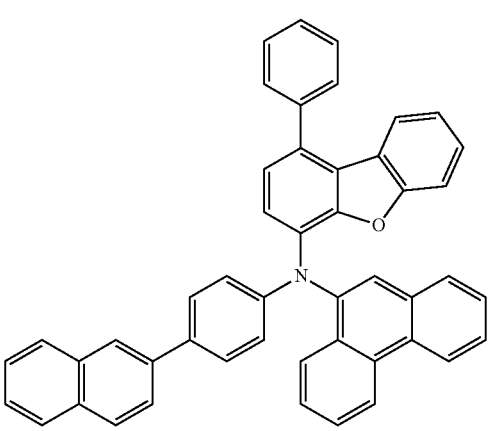
32
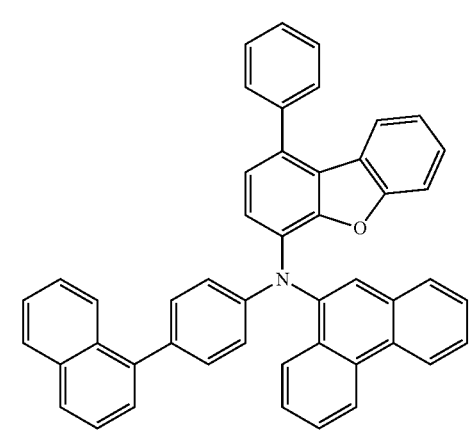
102
-continued
33
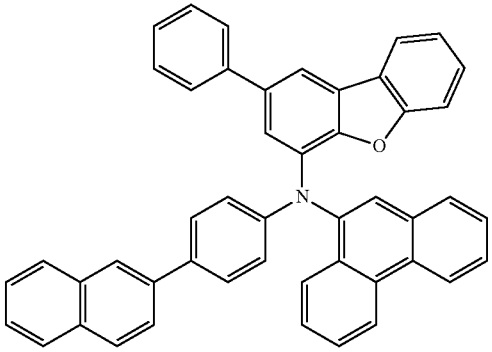
34
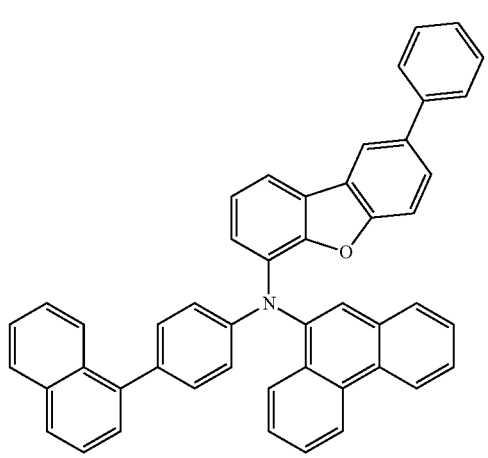
35
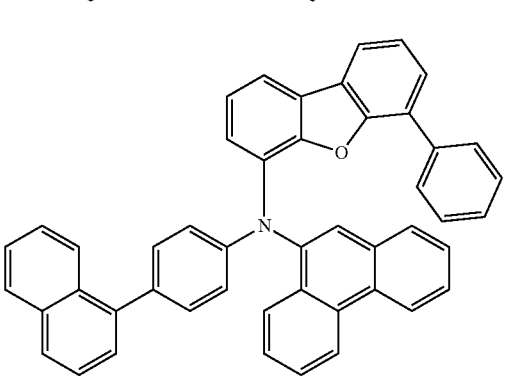
36
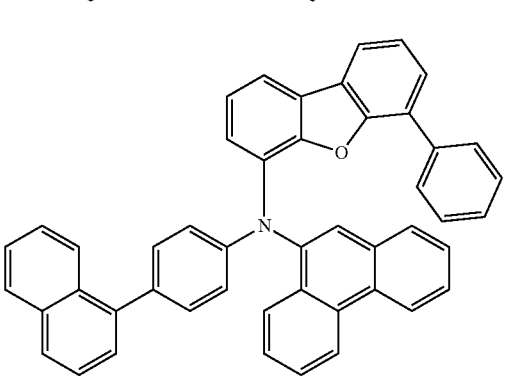

103
-continued
37
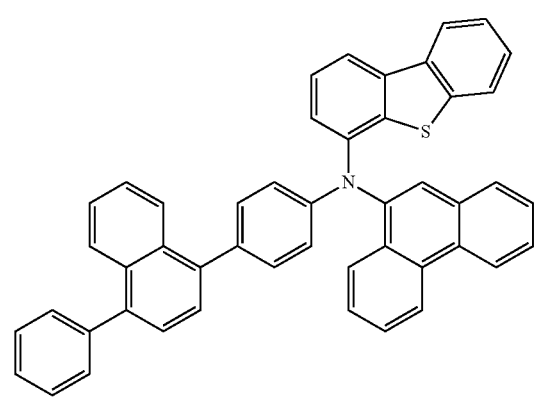
38
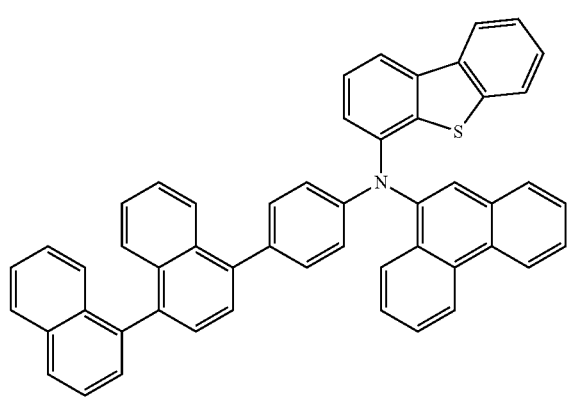
39
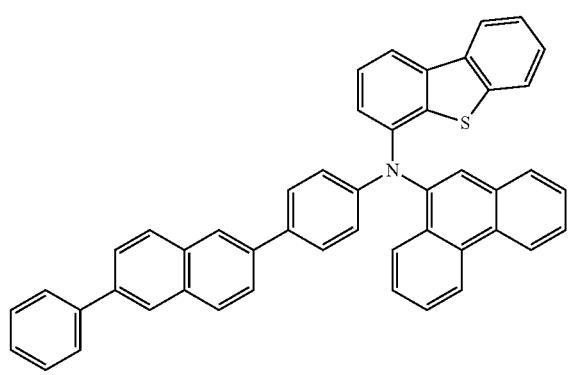
40
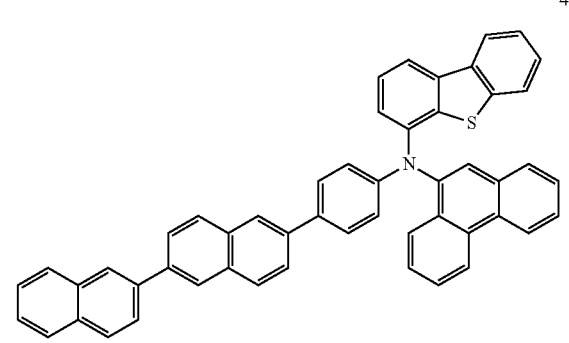
104
-continued
41
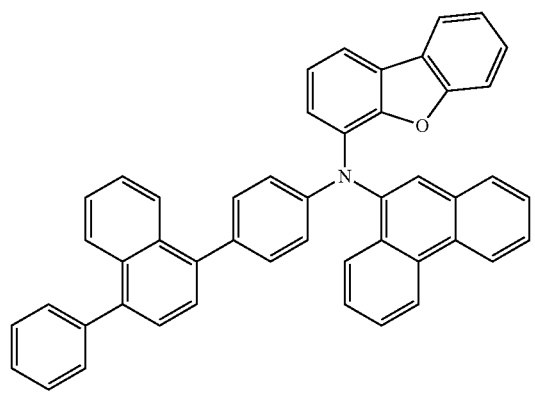
42
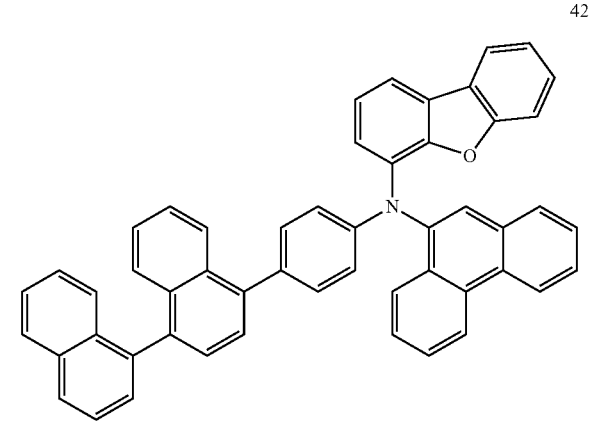
43
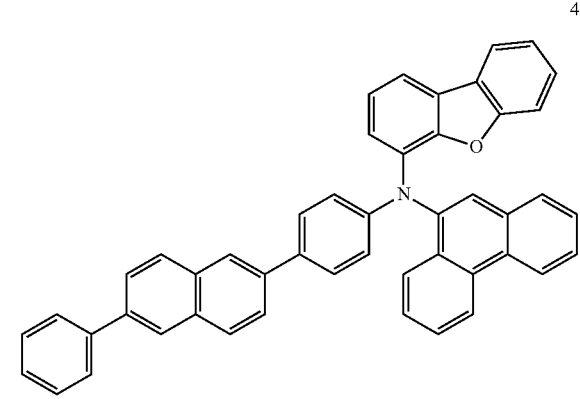
44
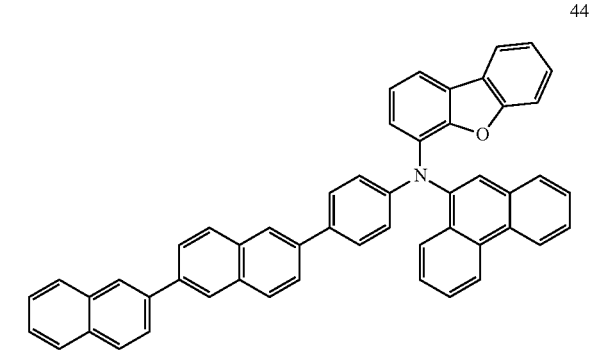

105
-continued
45
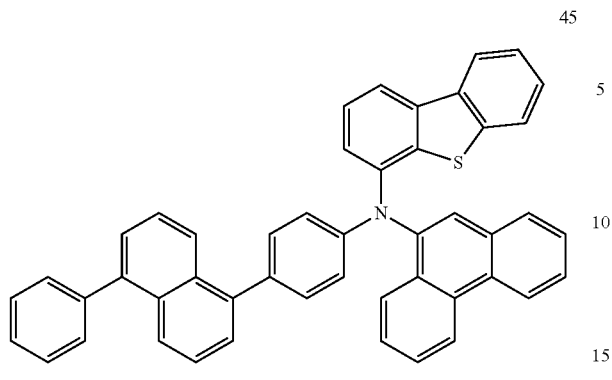
46
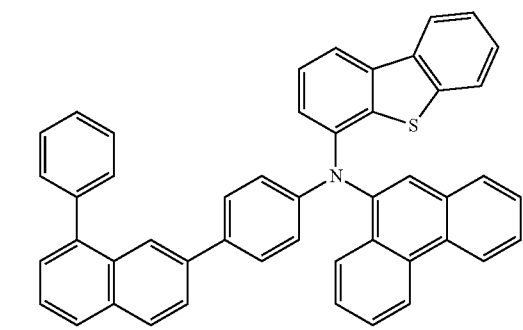
47
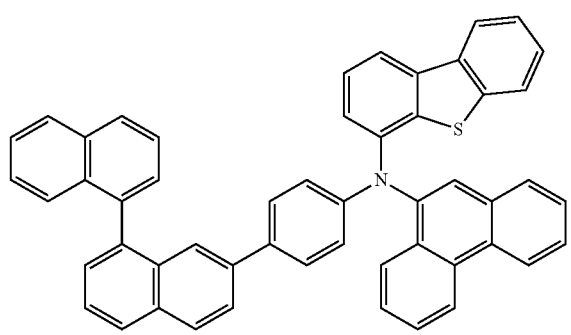
48
106
-continued
49
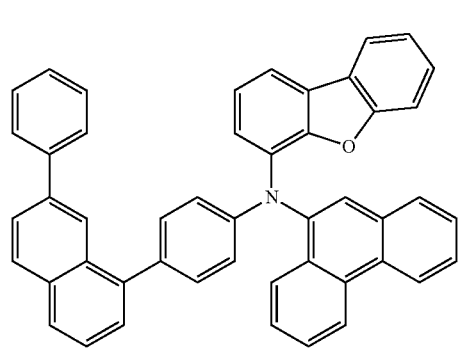
50
51
52
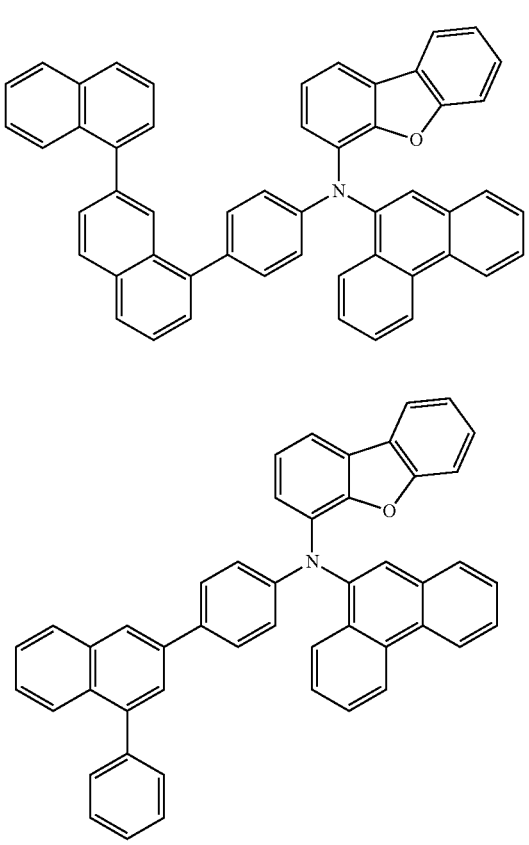

53
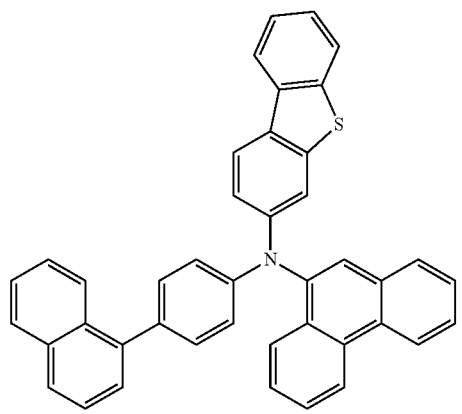
54
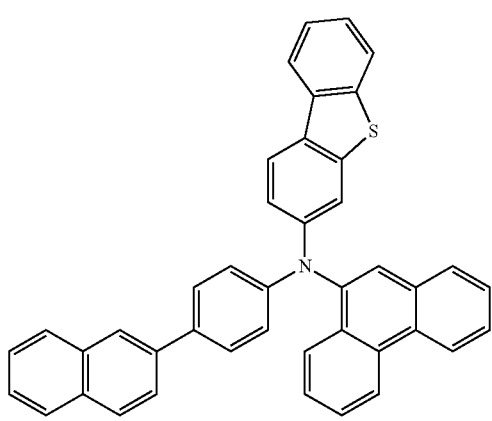
55
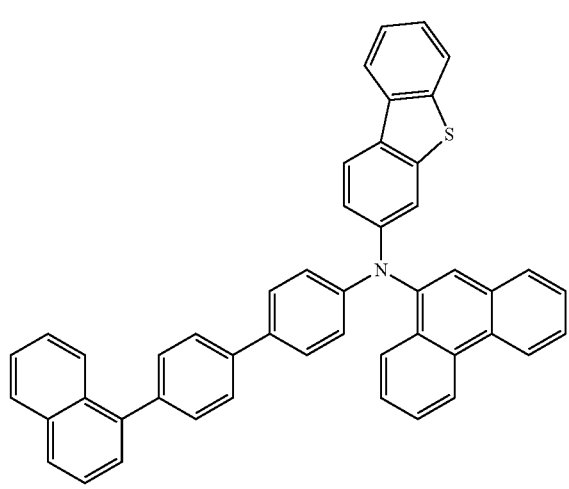
56
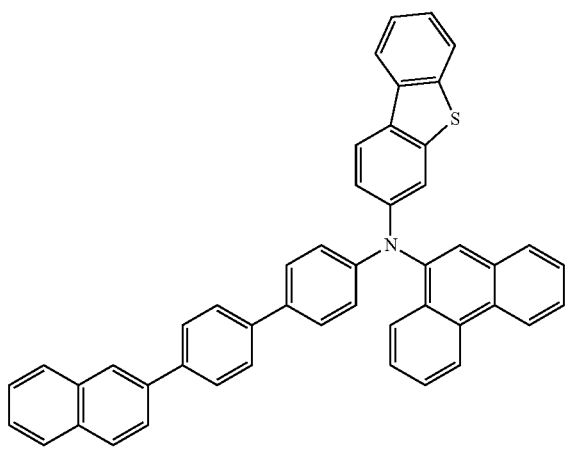
57
58
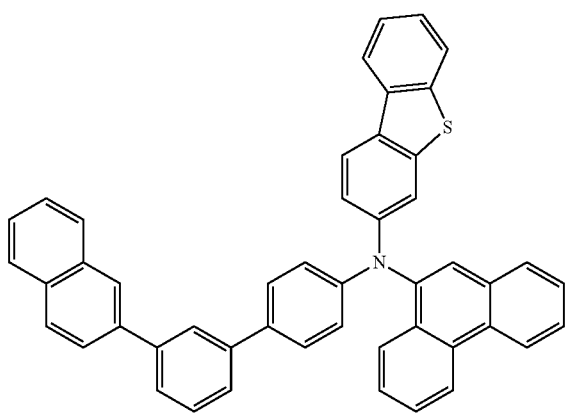

59
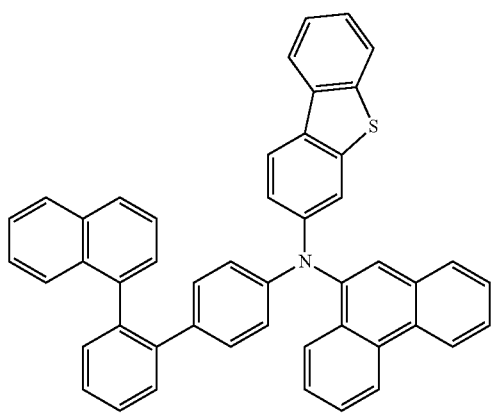
60
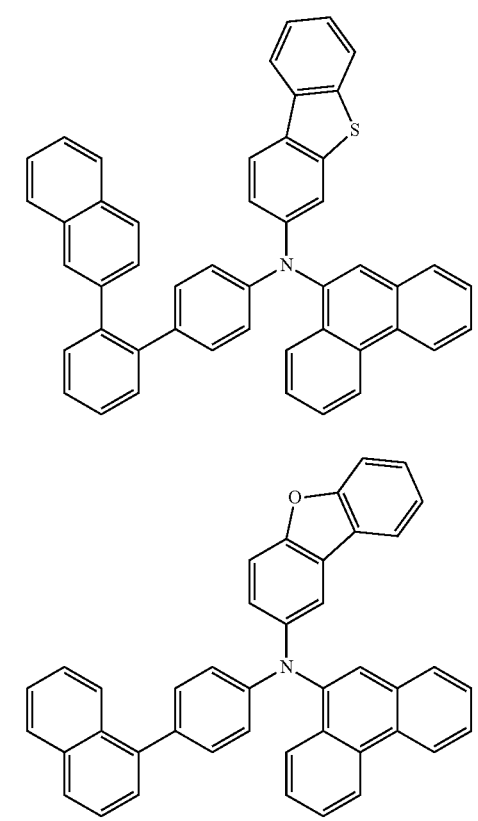
61
62
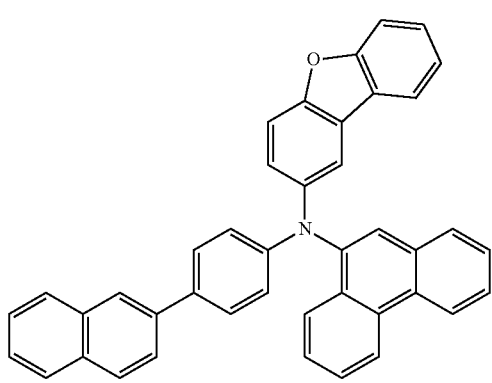
63
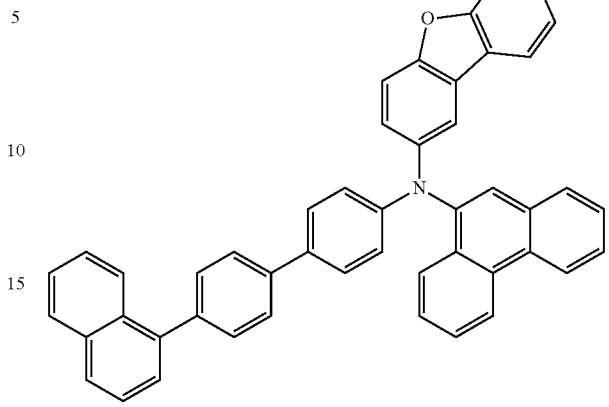
64
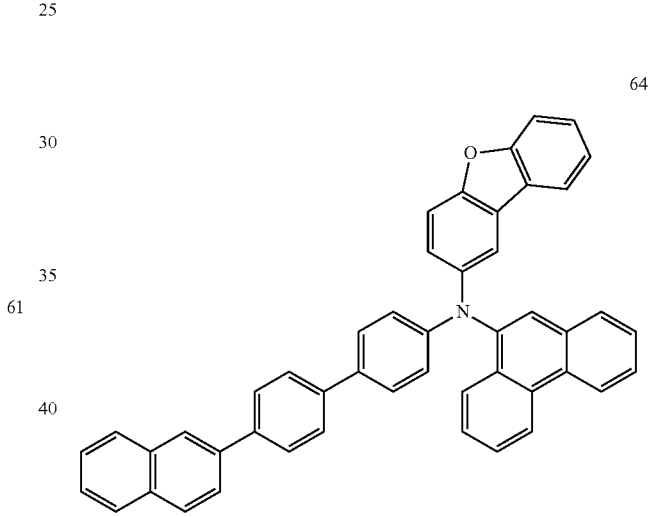
65
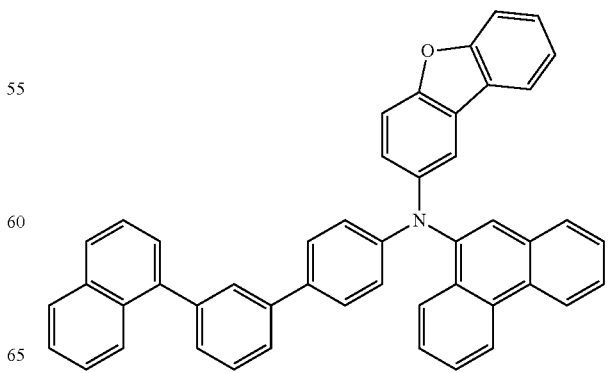

66
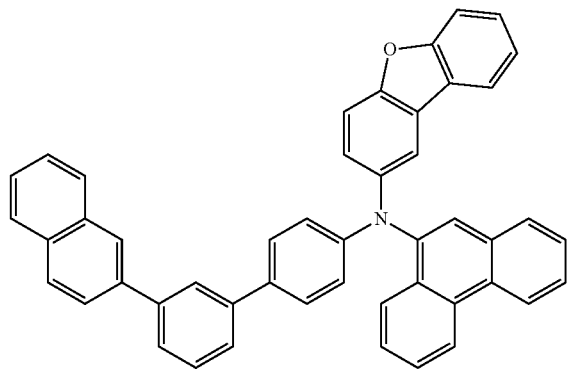
67
68
69
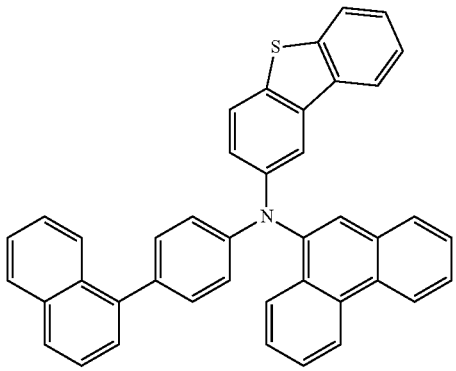
70
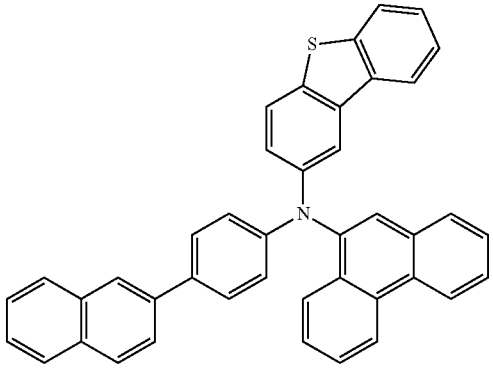
71
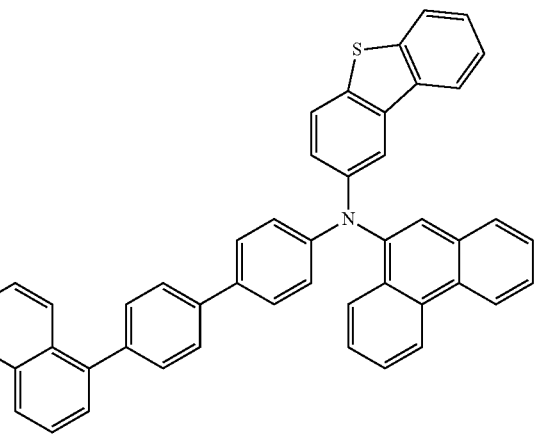
72
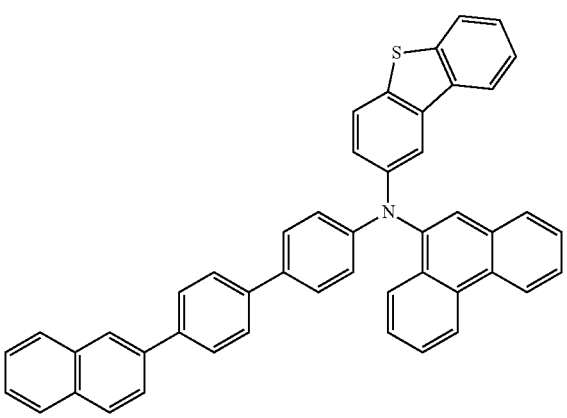

73
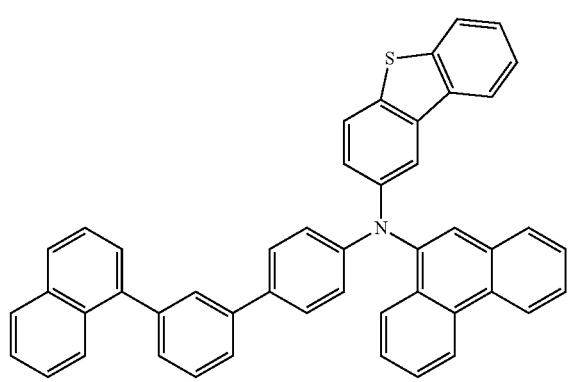
74
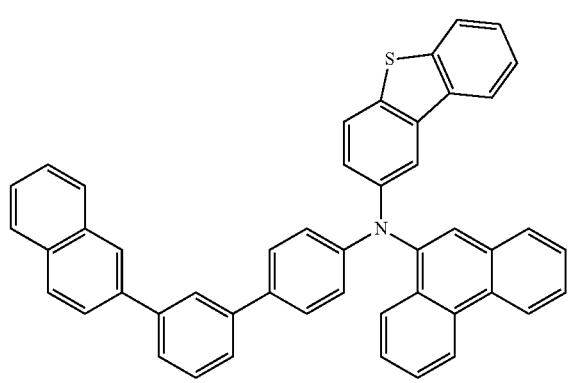
75
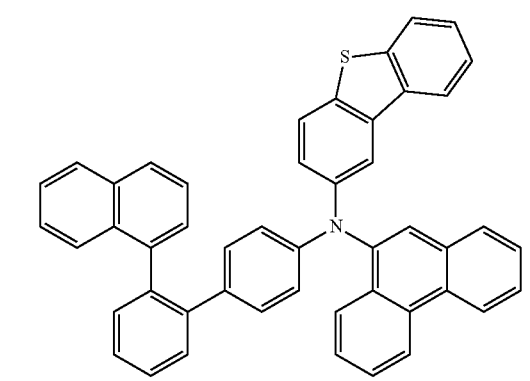
76
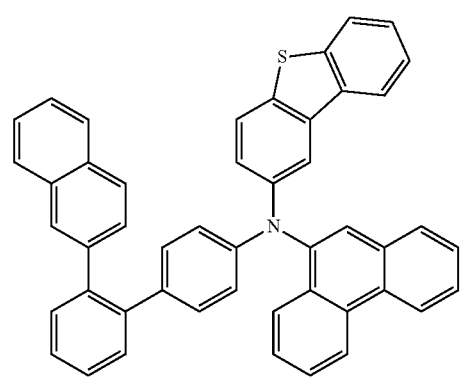
77
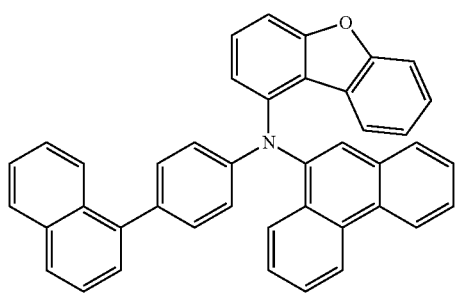
78
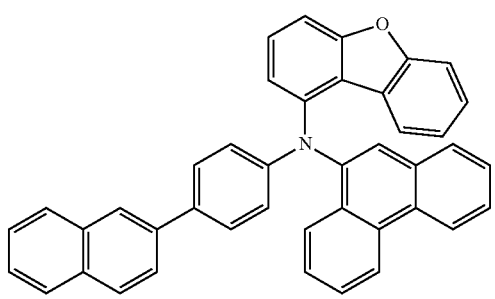
79
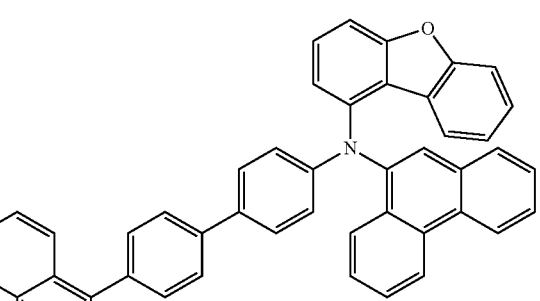
80
81

82
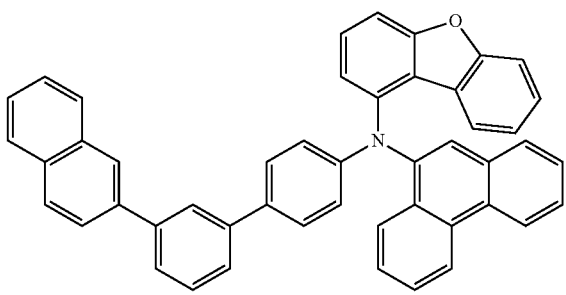
83
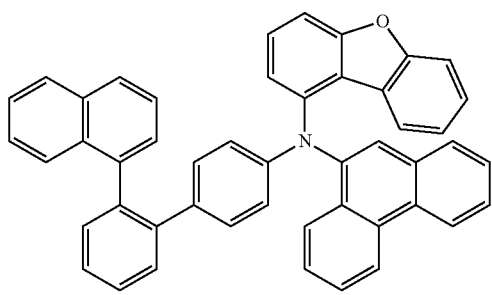
84
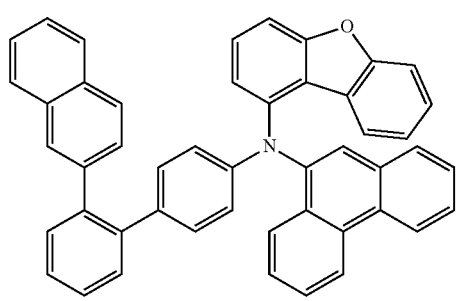
85
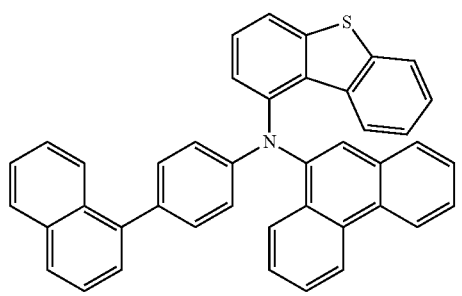
86
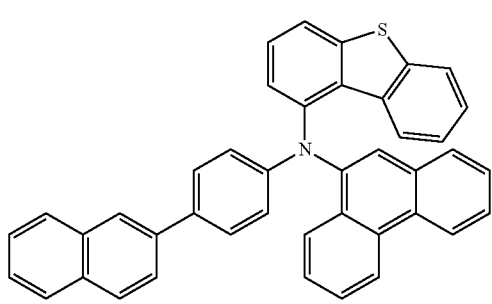
87
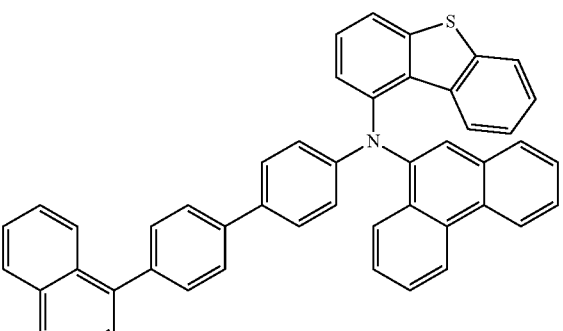
88
89
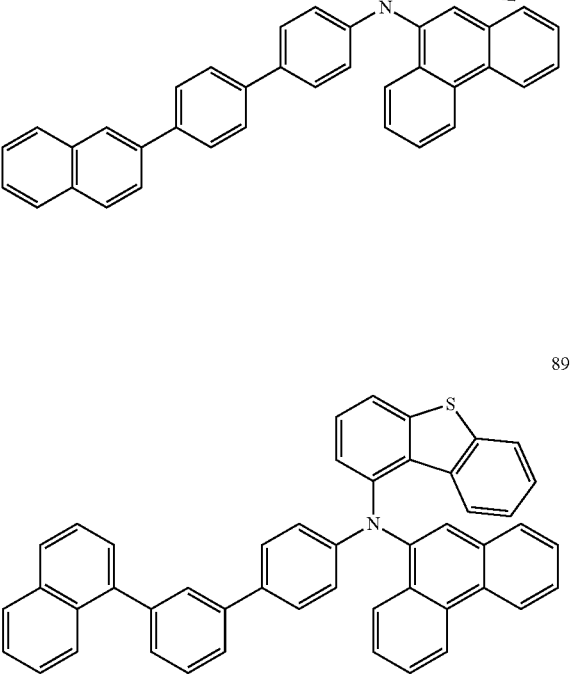
90
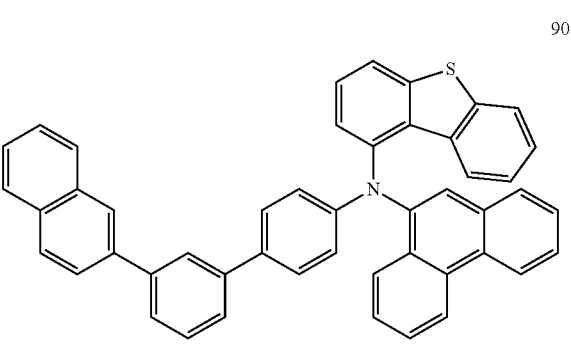

91

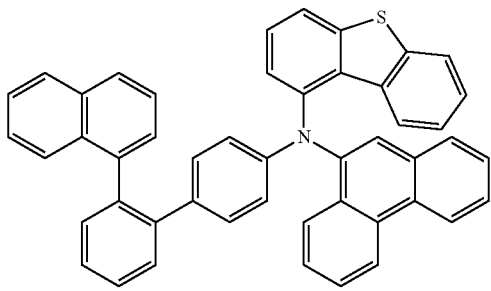

92

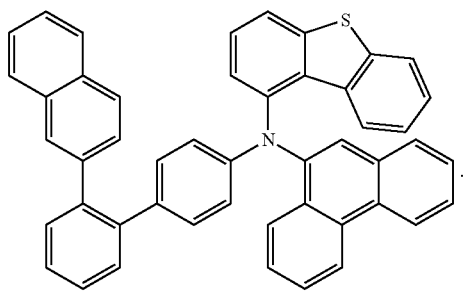

The monoamine compound of an embodiment may be included in a hole transport layer HTL which is included in a hole transport region HTR. However, this in only an illustration, and an embodiment of the inventive concept is not limited thereto. In an embodiment, the monoamine compound may be included in other functional layers in addition to the hole transport region HTR. For example, the monoamine compound may be included in at least one among an electron transport region ETR, an emission layer EML, and a hole transport region HTR.

The light emitting element ED according to an embodiment may include the monoamine compound of an embodiment in at least one functional layer disposed between a first electrode EL1 and a second electrode EL2 and may show improved emission efficiency and improved life characteristics. For example, the monoamine compound according to an embodiment may be included in the hole transport region HTR of the light emitting element ED of an embodiment, and the light emitting element of an embodiment may show excellent emission efficiency and long life characteristics.

Referring to FIG. 5, the hole transport region HTR-a of an embodiment may include a hole transport layer HTL-a and a hole injection layer HIL. The hole transport layer HTL-a of an embodiment may include hole transport layers HTL1, HTL2, . . . , HTLn. A hole transport layer HTLn adjacent to the emission layer EML among the hole transport layers HTL1, HTL2, . . . , HTLn may include the monoamine compound of an embodiment. A hole transport layer HTLn positioned at the uppermost part among the hole transport layers HTL1, HTL2, . . . , HTLn may directly contact the emission layer EML. The hole transport layer HTLn adjacent to the emission layer EML may include a monoamine compound having a low highest occupied molecular orbital (HOMO) energy level, and the transfer of holes may be restricted. The transfer-restricted holes may recombine with electrons at the interface of the emission layer EML and the hole transport layer HTLn adjacent to the emission layer EML. The recombination of the holes and electrons at the interface of the emission layer EML and the hole transport layer HTLn adjacent to the emission layer EML may increase emission efficiency.

A thickness of the hole transport region HTR may be in a range of about 100 Å to about 10,000 Å. For example, the thickness of the hole transport region HTR may be in a range of about 100 Å to about 5,000 Å. In case where the hole transport region HTR includes a hole injection layer HIL, a thickness of the hole injection region IL may be, for example, in a range of about 30 Å to about 1,000 Å. In case where the hole transport region HTR includes a hole transport layer HTL, a thickness of the hole transport layer HTL may be in a range of about 30 Å to about 1,000 Å. For example, in case where the hole transport region HTR includes an electron blocking layer, a thickness of the electron blocking layer EBL may be in a range of about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without substantial increase of a driving voltage. The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include at least one of metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as tungsten oxide and molybdenum oxide, cyano group-containing compounds such as dipyrazino[2,3-f. 2',3'-h]quinoxaline-2,3,6,7,10,11-hexacarbonitrile (HATCN) and 4-[[2,3-bis[cyano-(4-cyano-2,3,5,6-tetrafluorophenyl)methylidene]cyclopropylidene]-cyanomethyl]-2,3,5,6-tetrafluorobenzonitrile, etc., without limitation.

In an embodiment, the hole transport region HTR may further include a compound represented by Formula H-1 below in addition to the monoamine compound of an embodiment.

[Formula H-1]

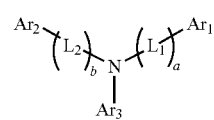

In Formula H-1 above, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula H-1, a and b may each independently be an integer from 0 to 10. If a or b is an integer of 2 or more, multiple $L_1$ and $L_2$ may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In Formula H-1, $Ar_3$ may be a substituted or unsubstituted aryl group of 6 to 30 ring-forming carbon atoms.

The compound represented by Formula H-1 may be a monoamine compound. Otherwise, the compound represented by Formula H-1 may be a diamine compound in which at least one among $Ar_1$ to $Ar_3$ includes an amine group as a substituent. The compound represented by Formula H-1 may be a carbazole-based compound in which at least one among $Ar_1$ to $Ar_3$ includes a substituted or unsubstituted carbazole group, or a fluorene-based compound in which at least one among $Ar_1$ to $Ar_3$ includes a substituted or unsubstituted fluorene group.

The compound represented by Formula H-1 may be represented by any one among the compounds in Compound Group H below. However, the compounds shown in Compound Group H are only examples, and the compound represented by Formula H-1 is not limited to the compounds represented in Compound Group H below.

[Compound Group H]

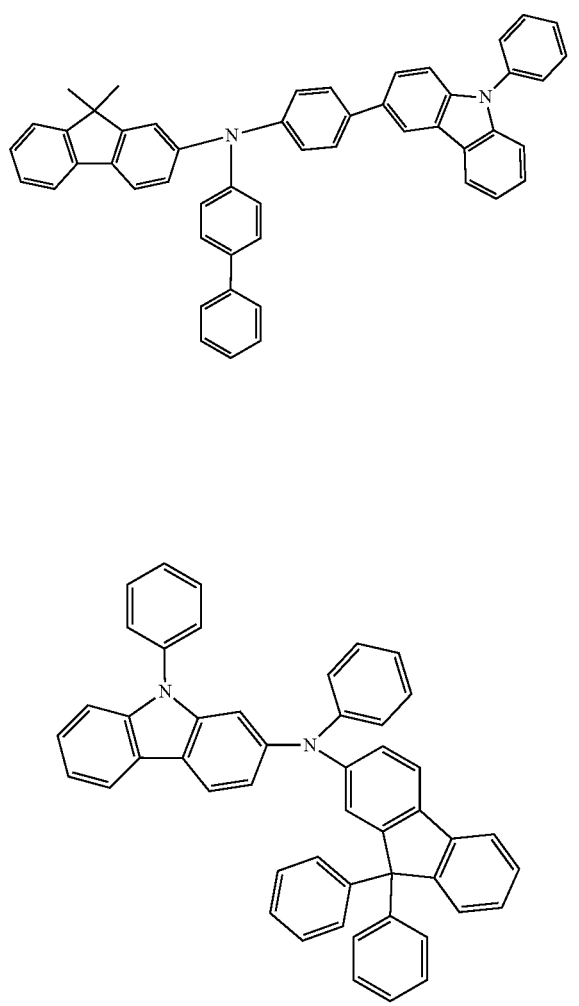

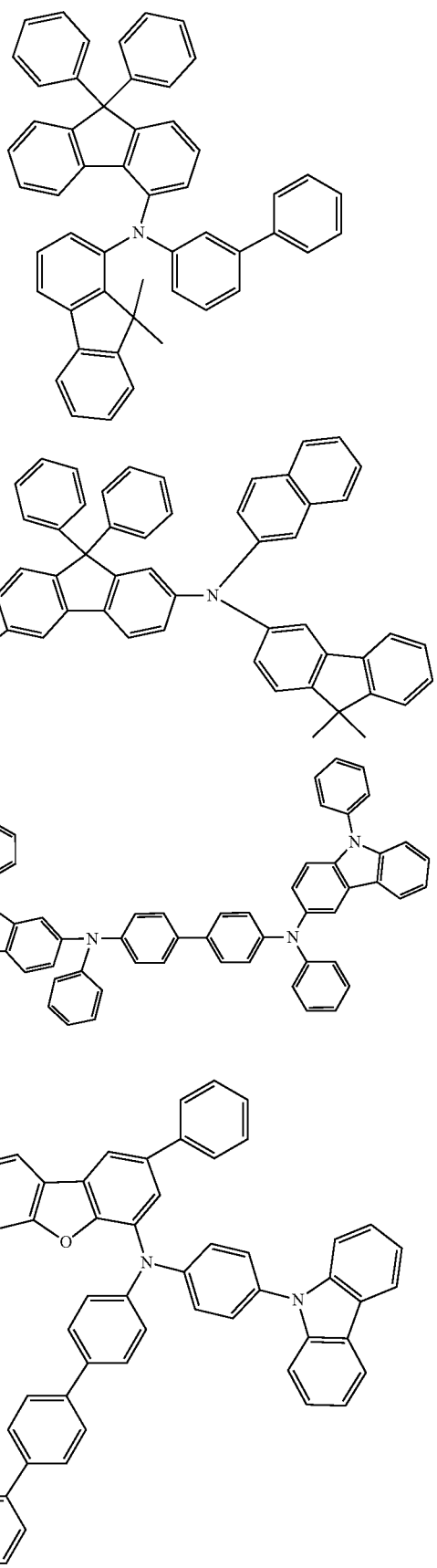

121
-continued
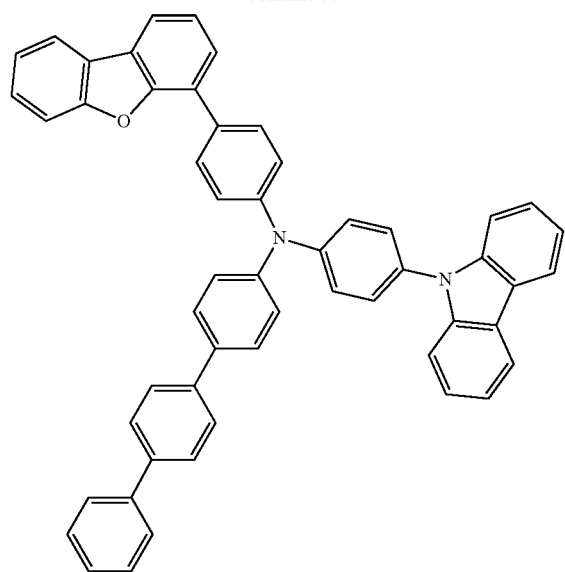
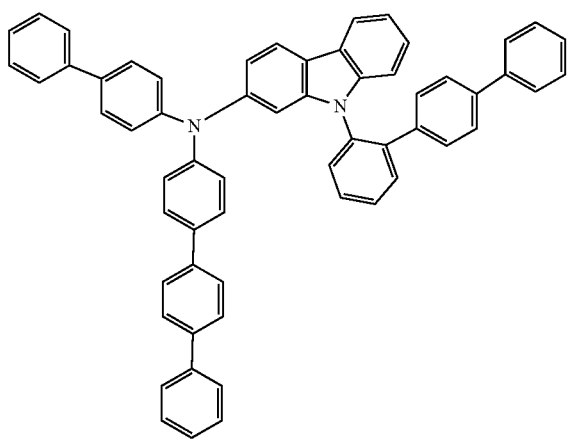
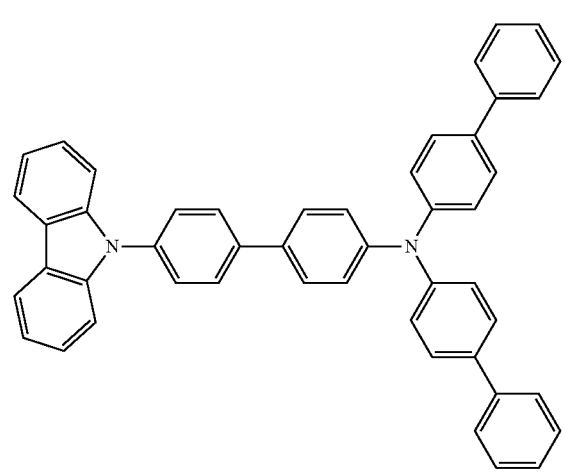
122
-continued
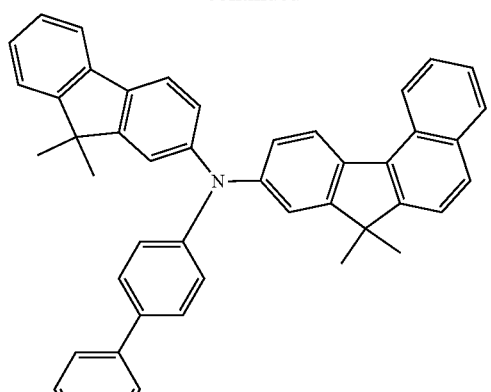
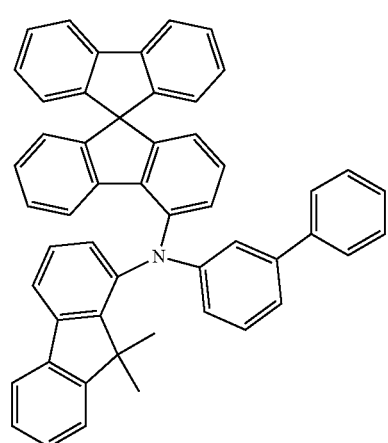
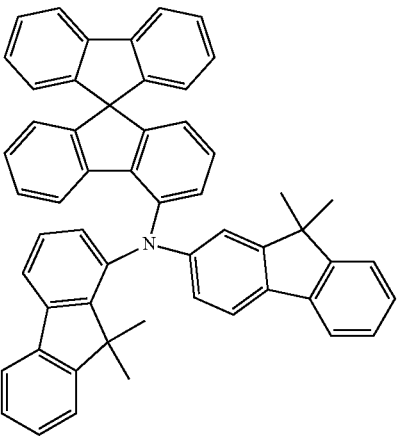
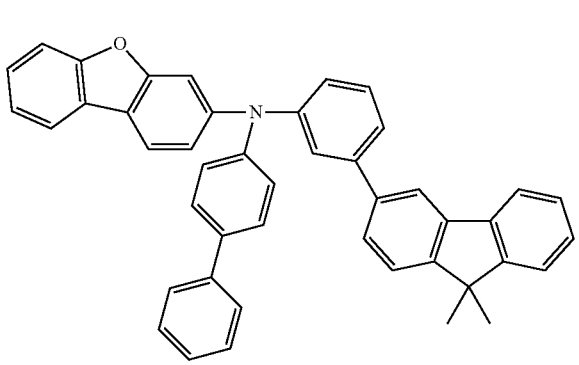

123
-continued

124
-continued

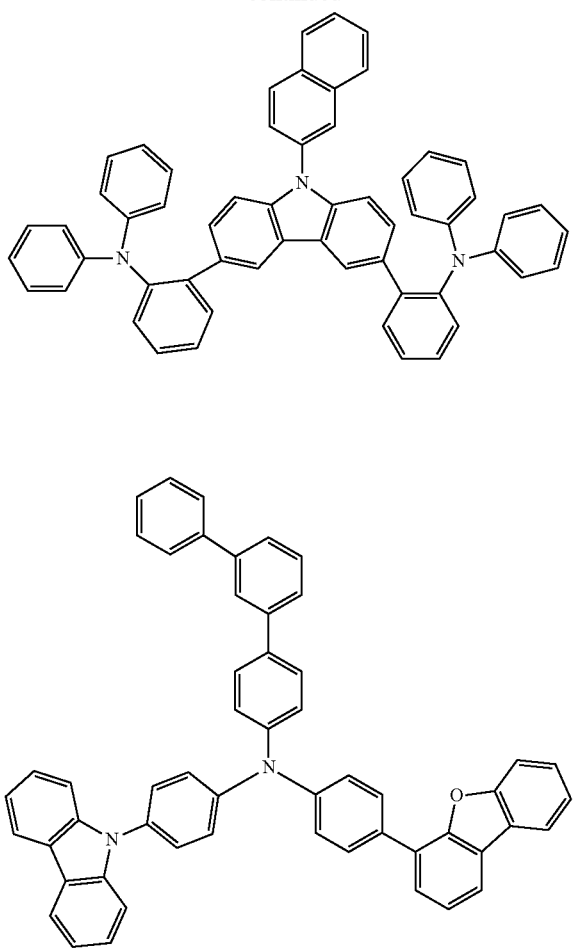

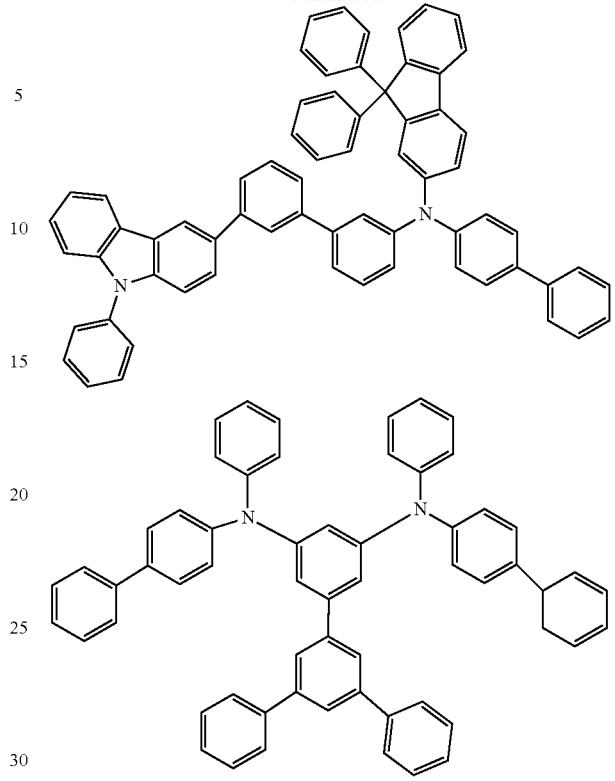

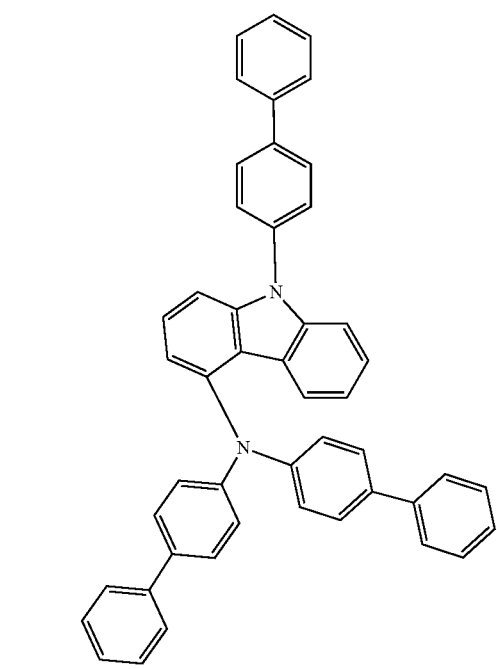

The hole transport region HTR may include a phthalocyanine compound such as copper phthalocyanine, $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4''-[tris(3-methylphenyl)phenylamino]triphenylamine (m-MTDATA), 4,4',4''-tris(N,N-diphenylamino)triphenylamine (TDATA), 4,4',4''-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], and dipyrazino[2,3-f:2',3'-h]quinoxaline-2,3,6,7,10,11-hexacarbonitrile (HAT-CN).

The hole transport region HTR may include carbazole derivatives such as N-phenyl carbazole and polyvinyl carbazole, fluorene-based derivatives, N,N'-bis(3-methylphenyl)-N,N'-diphenyl-[1,1'-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3-bis(N-carbazolyl)benzene (mCP), etc.

The hole transport region HTR may include carbazole derivatives such as N-phenyl carbazole and polyvinyl carbazole, fluorene-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl)benzene (mCP), 1,3-bis(1,8-dimethyl-9H-carbazol-9-yl)benzene (mDCP), etc.

The hole transport region HTR may include the compounds of the hole transport region in at least one among the hole injection layer HIL, hole transport layer HTL, and electron blocking layer EBL.

The emission layer EML is provided on the hole transport region HTR. The emission layer EML may have a thickness in a range of, for example, about 100 Å to about 1,000 Å. For example, the thickness of the emission layer EML may be in a range of about 100 Å to about 300 Å. The emission layer EML may have a single layer formed using a single material, a single layer formed using multiple different materials, or a multilayer structure having layers formed using multiple different materials.

In the light emitting element ED of an embodiment, the emission layer EML may include anthracene derivatives, pyrene derivatives, fluoranthene derivatives, chrysene derivatives, dihydrobenzanthracene derivatives, or triphenylene derivatives. For example, the emission layer EML may include anthracene derivatives or pyrene derivatives.

In the light emitting elements ED of embodiments, shown in FIG. 3 to FIG. 7, the emission layer EML may include a host and a dopant, and the emission layer EML may include a compound represented by Formula E-1 below. The compound represented by Formula E-1 below may be used as a fluorescence host material.

[Formula E-1]

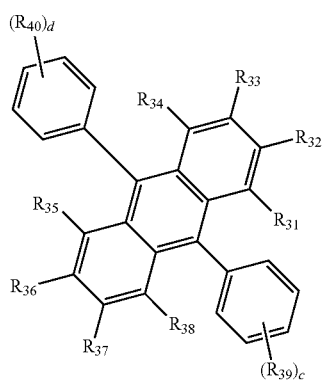

In Formula E-1, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring. $R_{31}$ to $R_{40}$ may be combined with an adjacent group to form a saturated hydrocarbon ring or an unsaturated hydrocarbon ring.

In Formula E-1, c and d may each independently be an integer from 0 to 5.

Formula E-1 may be represented by any one among Compound E1 to Compound E19 below.

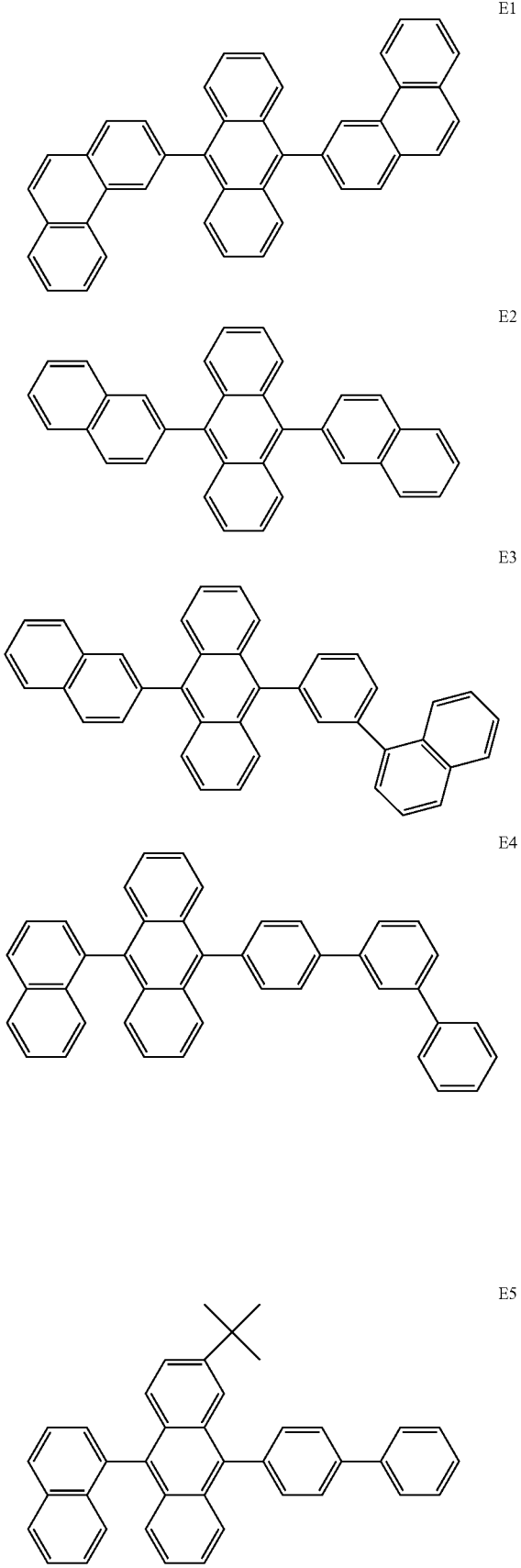

E6
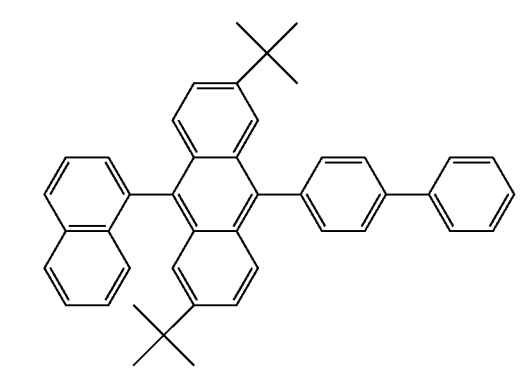
E7
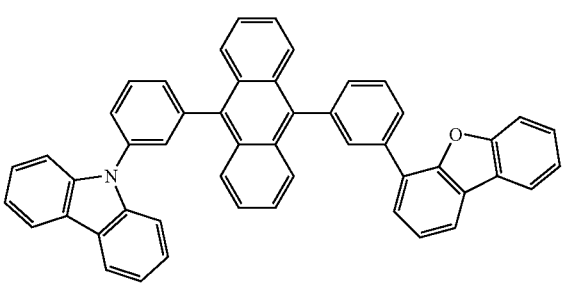
E8
E9
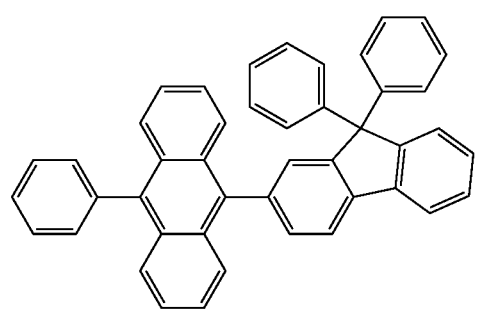
E10
E11
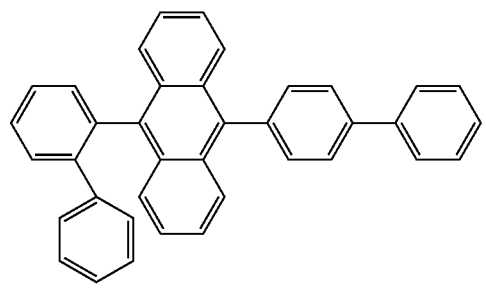
E12
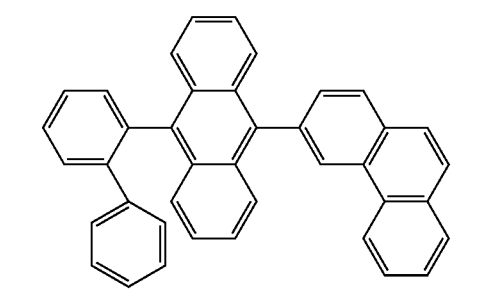
E13
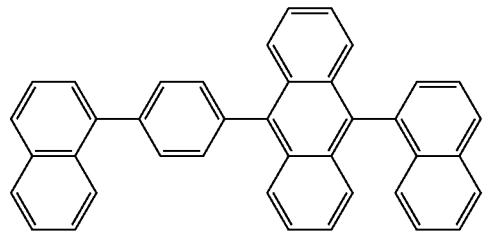
E14
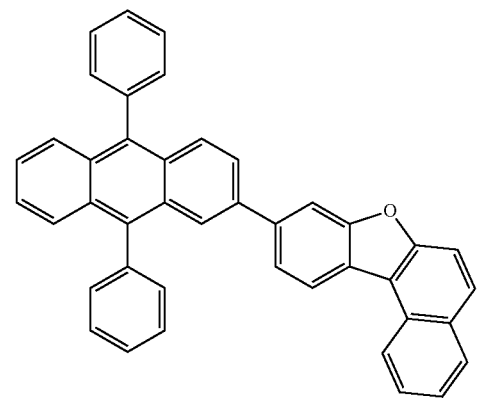

E15

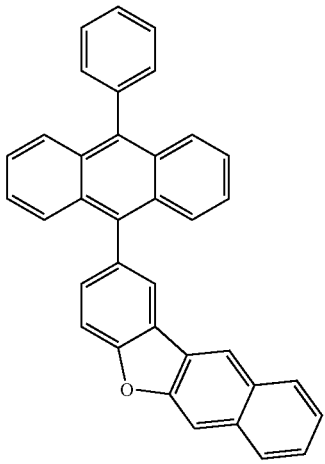

E16

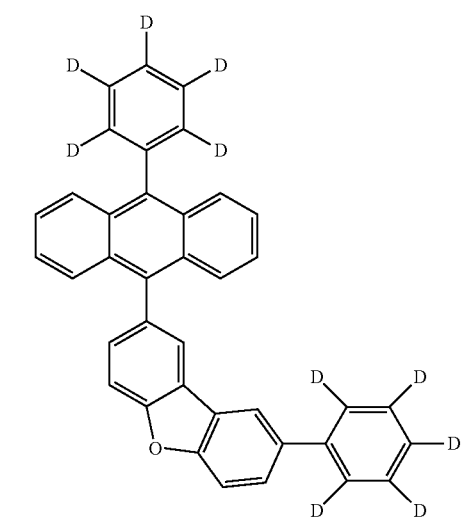

E17

E18

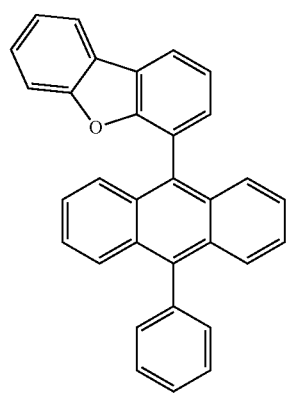

E19

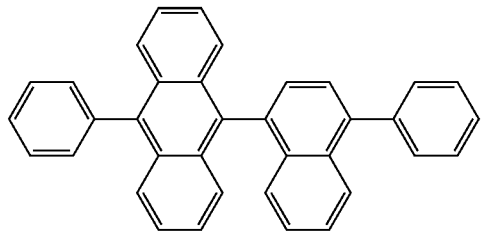

In an embodiment, the emission layer EML may include a compound represented by Formula E-2a or Formula E-2b below. The compound represented by Formula E-2a or Formula E-2b below may be used as a phosphorescence host material.

[Formula E-2a]

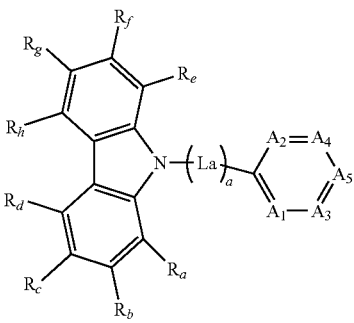

In Formula E-2a, a may be an integer from 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms. If a is an integer of 2 or more, multiple $L_a$ may each independently be a substituted or unsubstituted arylene group of 6 to 30 ring-forming carbon atoms, or a substituted or unsubstituted heteroarylene group of 2 to 30 ring-forming carbon atoms.

In Formula E-2a, $A_1$ to $A_5$ may each independently be N or $CR_i$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_a$ to $R_i$ may be combined with an adjacent group to form a hydrocarbon ring or a heterocycle including N, O, S, etc. as a ring-forming atom.

In Formula E-2a, two or three selected from $A_1$ to $A_5$ may be N, and the remainder may be $CR_i$.

[Formula E-2b]

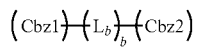

In Formula E-2b, Cbz1 and Cbz2 may each independently be an unsubstituted carbazole group, or a carbazole group substituted with an aryl group of 6 to 30 ring-forming carbon atoms. L$_b$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2b, b may be an integer from 0 to 10, and if b is an integer of 2 or more, multiple L$_b$ may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be represented by any one among the compounds in Compound Group E-2 below. However, the compounds shown in Compound Group E-2 below are only examples, and the compound represented by Formula E-2a or Formula E-2b is not limited to the compounds represented in Compound Group E-2 below.

[Compound Group E-2]

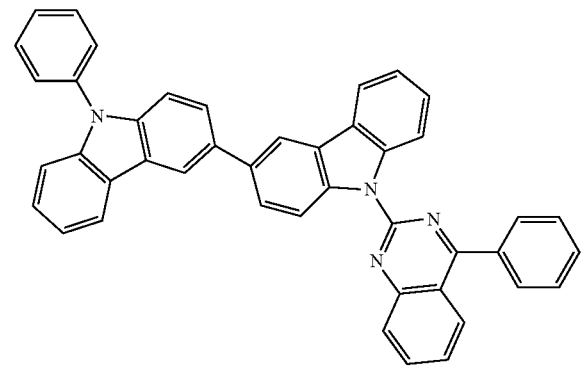

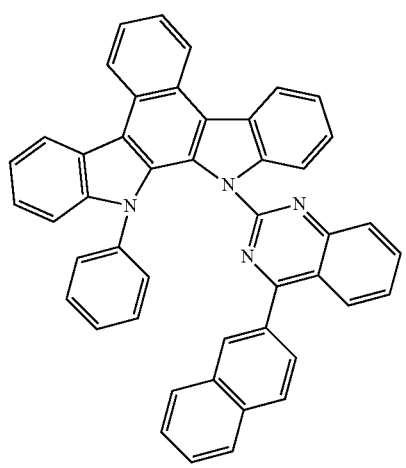

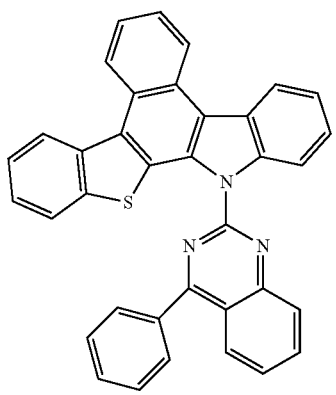

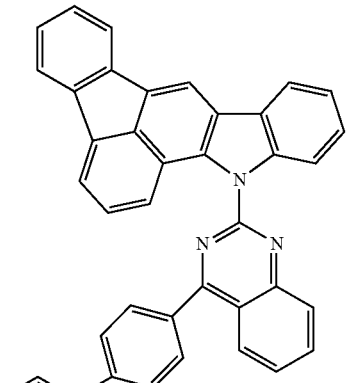

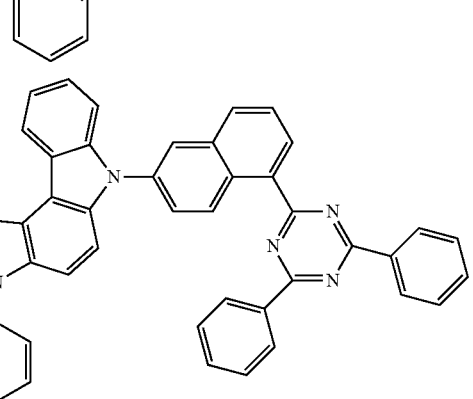

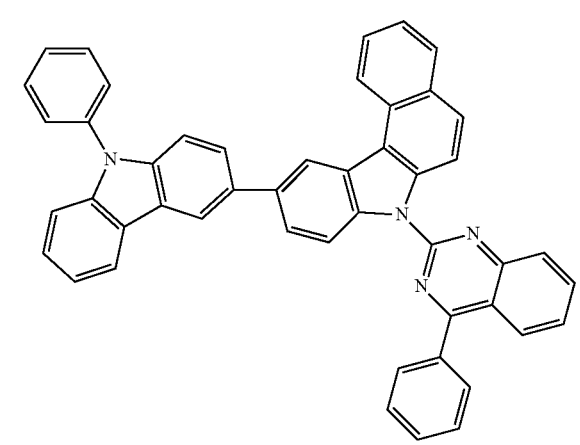

133
-continued
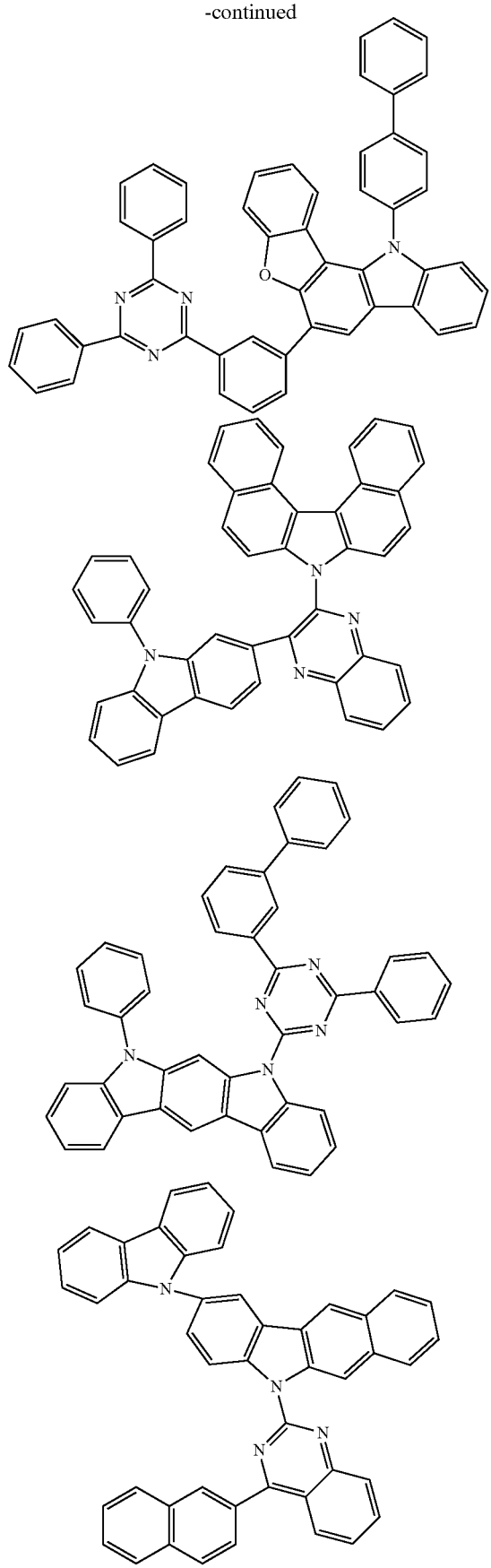
134
-continued
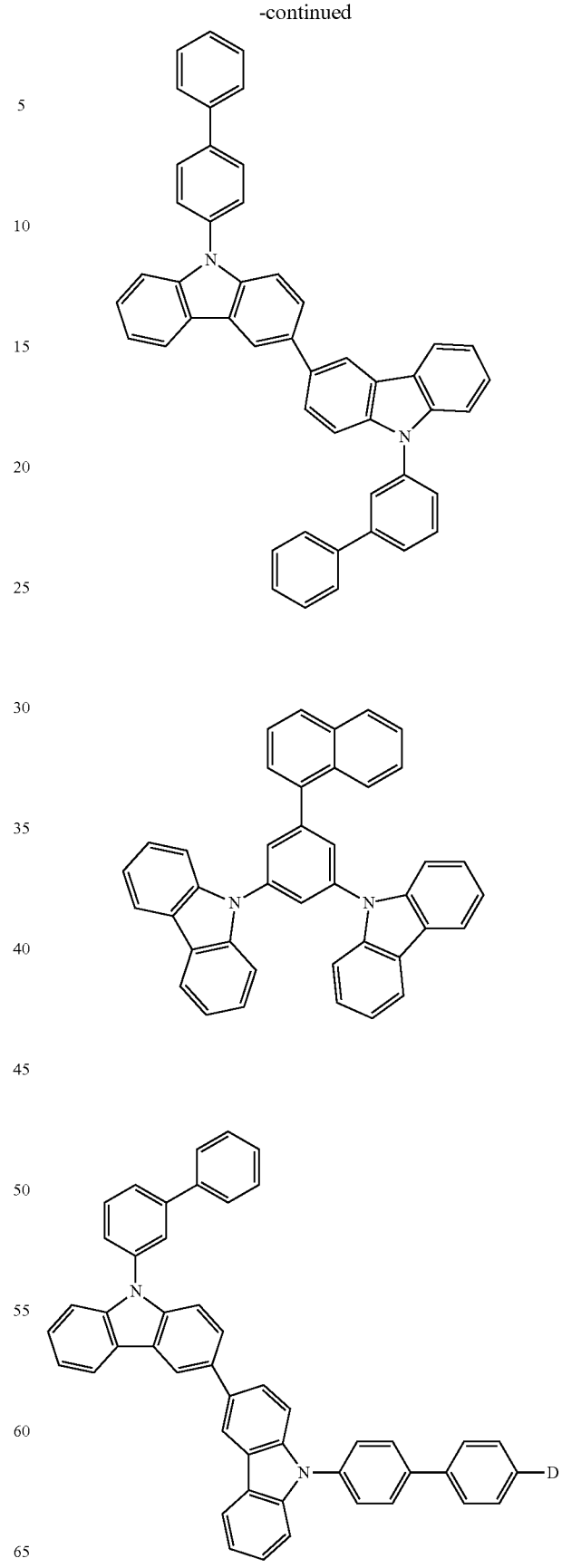

135
-continued
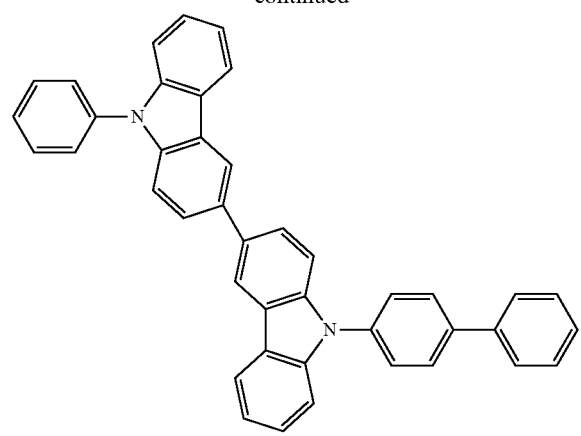
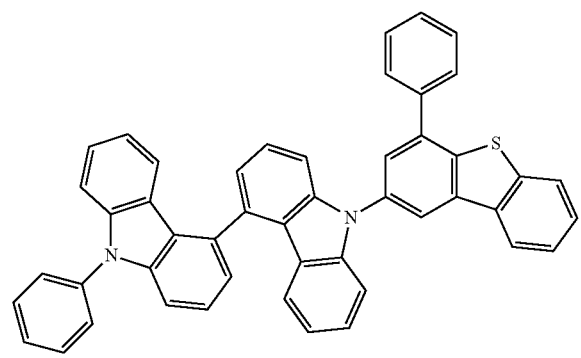
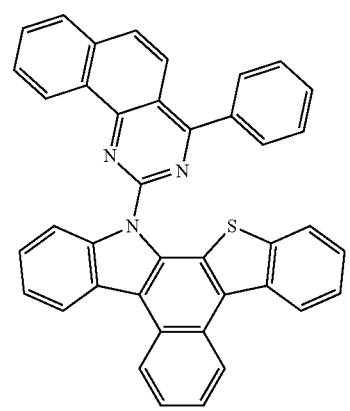
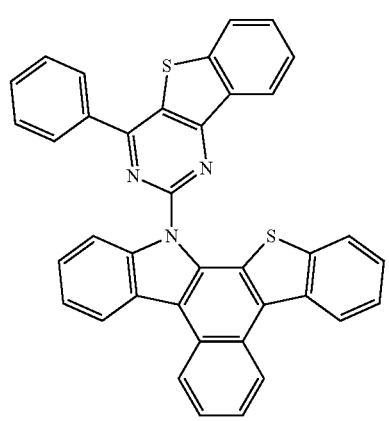
136
-continued
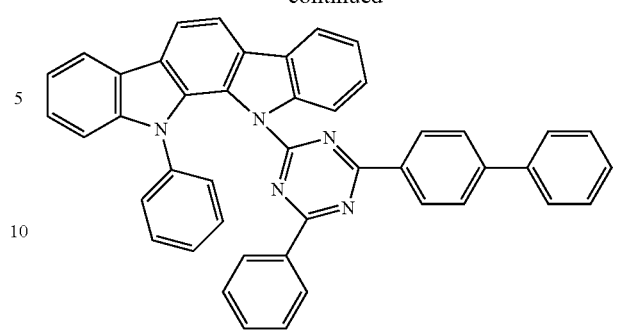
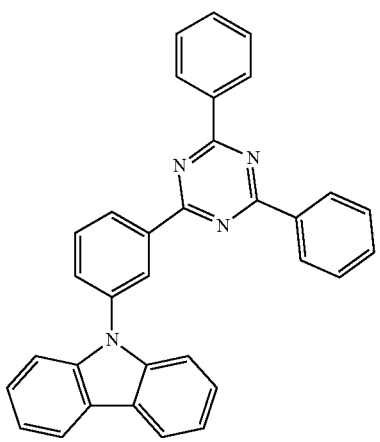

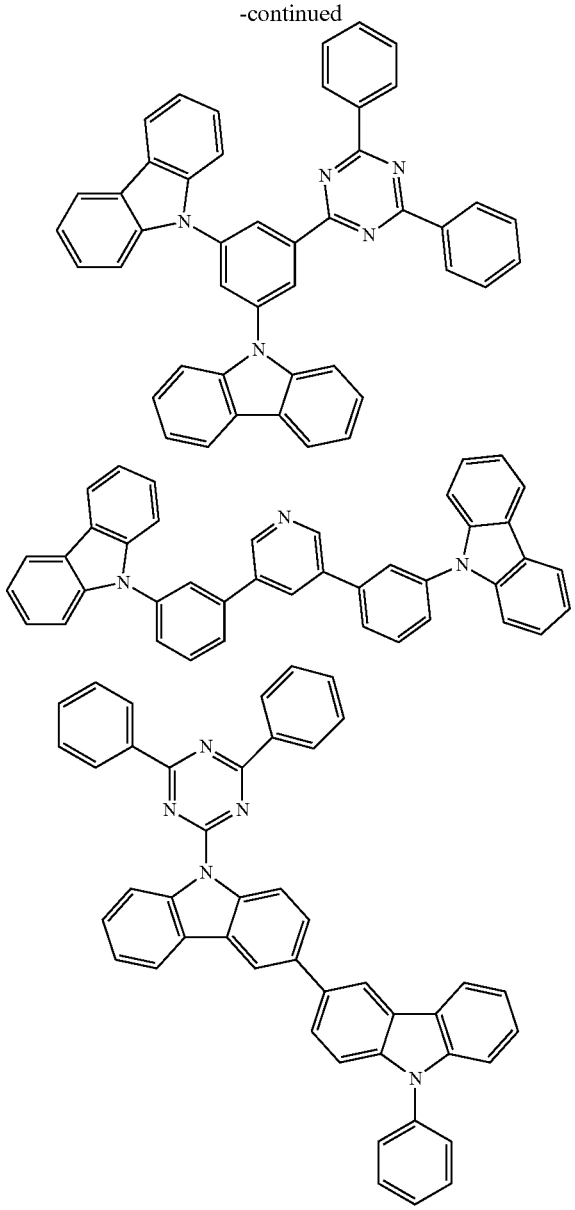

The emission layer EML may further include a material common in the art as a host material. For example, the emission layer EML may include as a host material, at least one of bis[2-(diphenylphosphino)phenyl]ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4', 4''-tris(carbazol-9-yl)-triphenylamine (TCTA), and 1,3,5-tris(1-phenyl-1H-benzo[d]imidazole-2-yl)benzene (TPBi). However, an embodiment of the inventive concept is not limited thereto. For example, tris(8-hydroxyquinolino)aluminum (Alq₃), 4,4'-bis(N-carbazolyl)-1,1'-biphenyl (CBP), poly(N-vinylcarbazole) (PVK), 9,10-di(naphthalene-2-yl)anthracene (ADN), 4,4', 4''-tris(carbazol-9-yl)-triphenylamine (TCTA), 1,3,5-tris(N-phenylbenzimidazole-2-yl)benzene (TPBi), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO₃), octaphenylcyclotetra siloxane (DPSiO₄), 2,8-bis(diphenylphosphoryl)dibenzofuran (PPF), etc. may be used as the host material.

The emission layer EML may include a compound represented by Formula M-a or Formula M-b below. The compound represented by Formula M-a or Formula M-b may be used as a phosphorescence dopant material.

[Formula M-a]

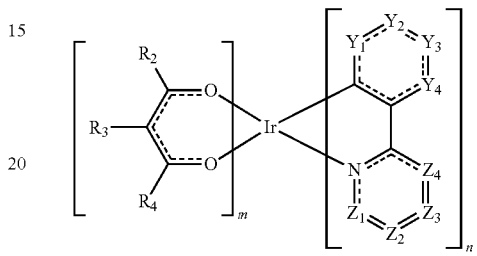

In Formula M-a, $Y_1$ to $Y_4$, and $Z_1$ to $Z_4$ may each independently be $CR_1$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, m may be 0 or 1, and n may be 2 or 3. In Formula M-a, if m is 0, n is 3, and if m is 1, n is 2.

The compound represented by Formula M-a may be used as a red phosphorescence dopant or a green phosphorescence dopant.

The compound represented by Formula M-a may be represented by any one among Compounds M-a1 to M-a19 below. However, Compounds M-a1 to M-a19 below are examples, and the compound represented by Formula M-a is not limited to the compounds represented by Compounds M-a1 to M-a19 below.

M-a1

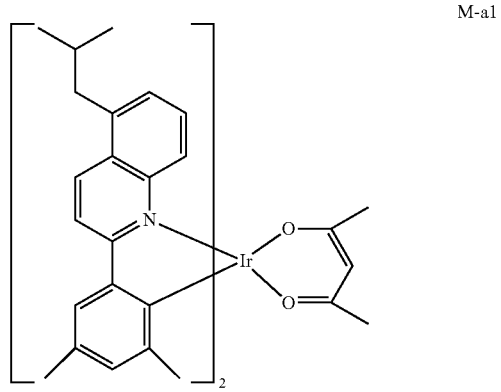

M-a2
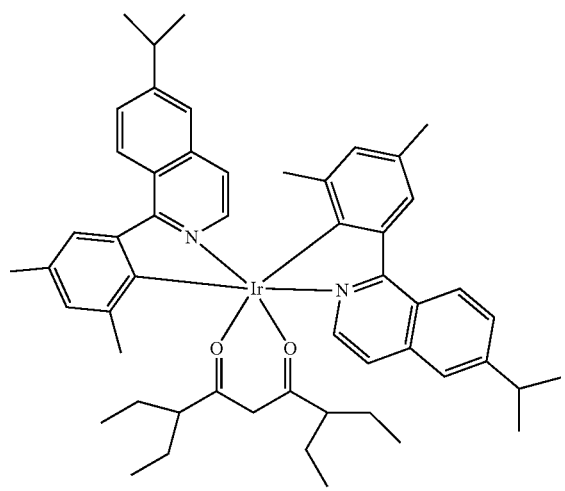
M-a3
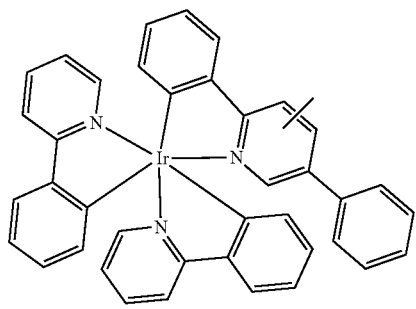
M-a4
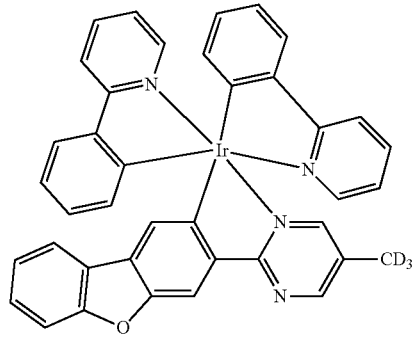
M-a5
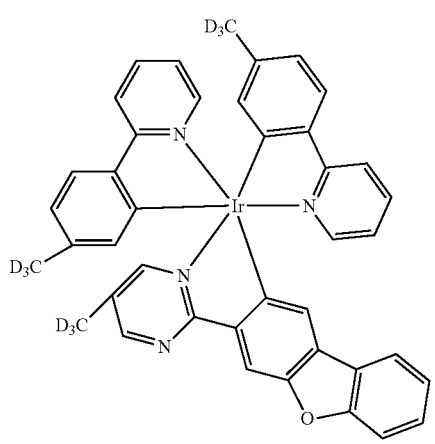
M-a6
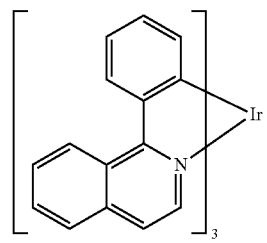
M-a7
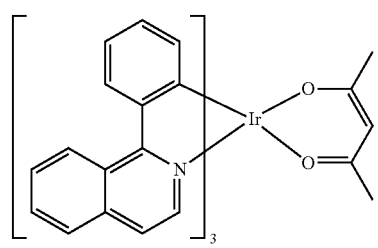
M-a8
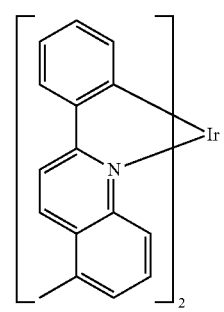
M-a9
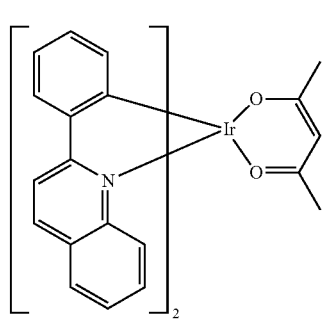
M-a10
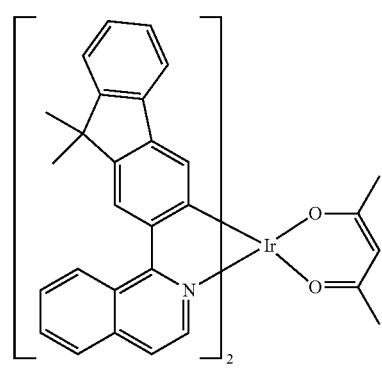

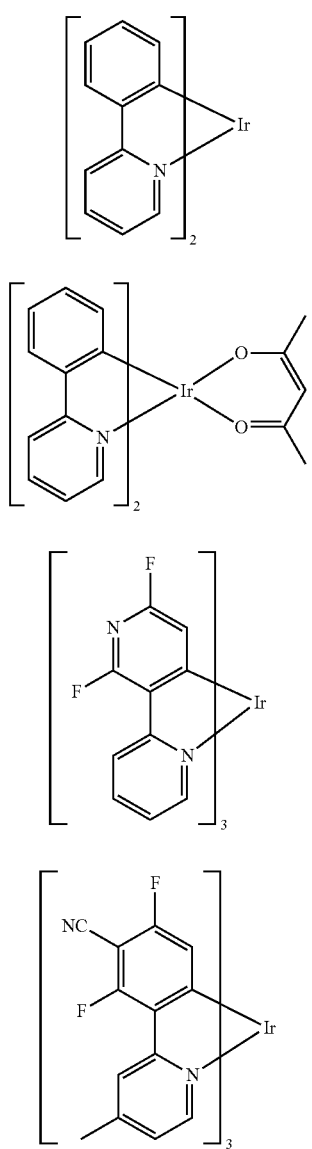
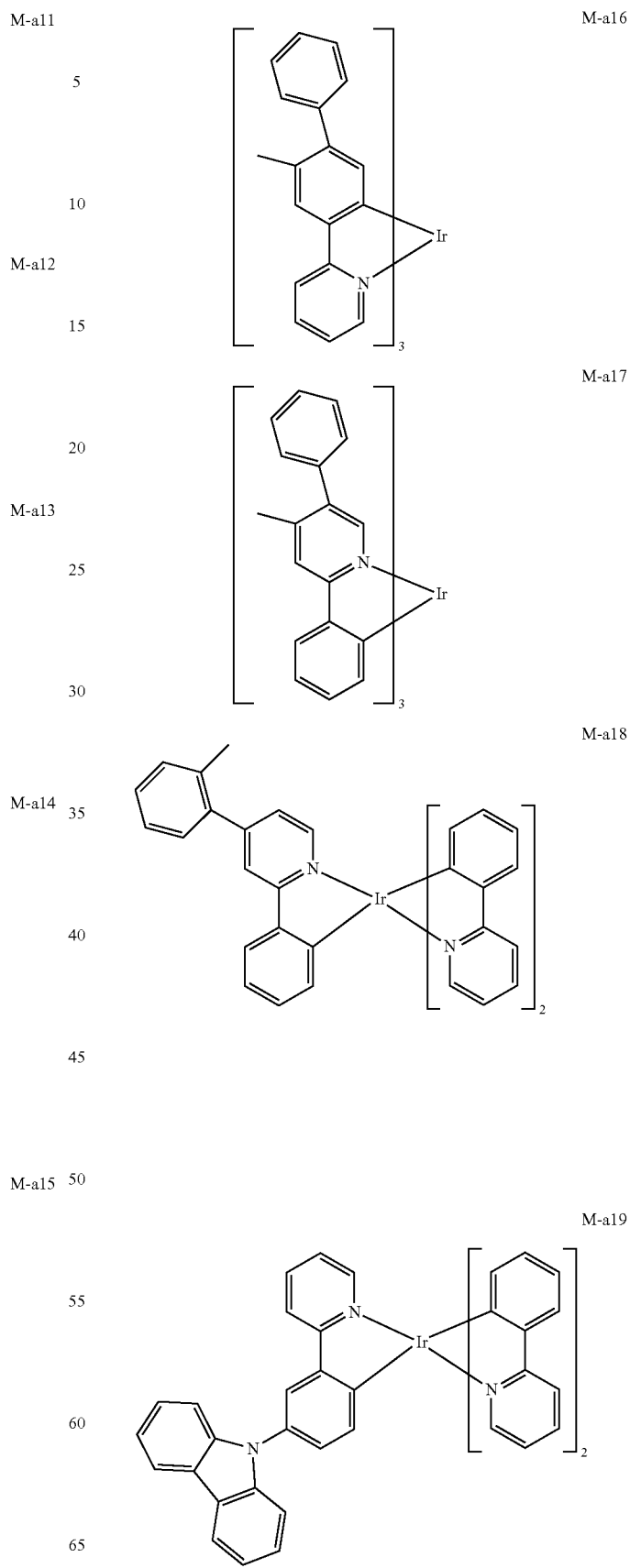

[Formula M-b]

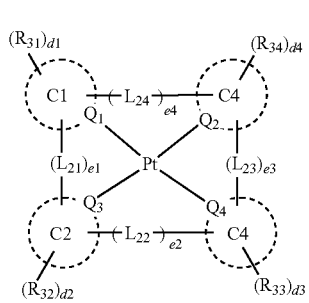

In Formula M-b, $Q_1$ to $Q_4$ may each independently be C or N, C1 to C4 may each independently be a substituted or unsubstituted hydrocarbon ring of 5 to 30 ring-forming carbon atoms, or a substituted or unsubstituted heterocycle of 2 to 30 ring-forming carbon atoms. $L_{21}$ to $L_{24}$ may each independently be a direct linkage,

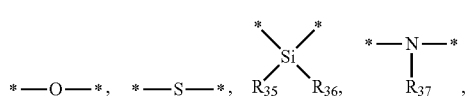

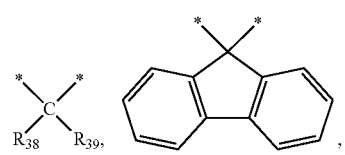

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 may each independently be 0 or 1. $R_{31}$ to $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be represented by any one among the compounds below. However, the compounds below are examples, and the compound represented by Formula M-b is not limited to the compounds represented below.

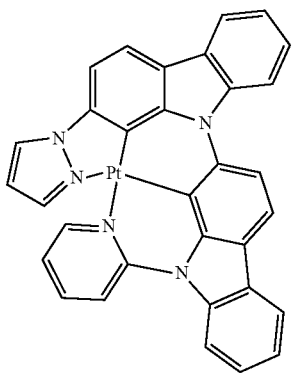

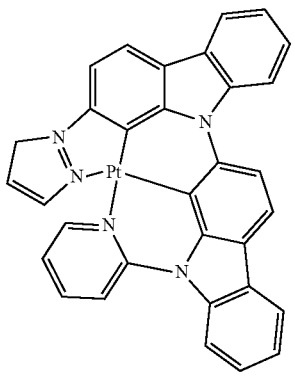

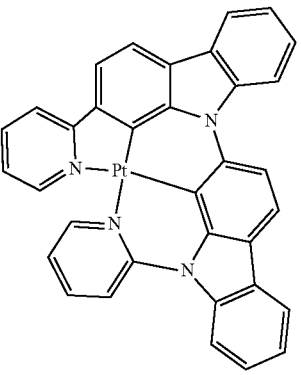

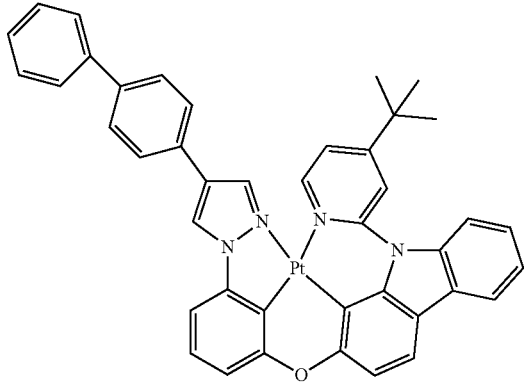

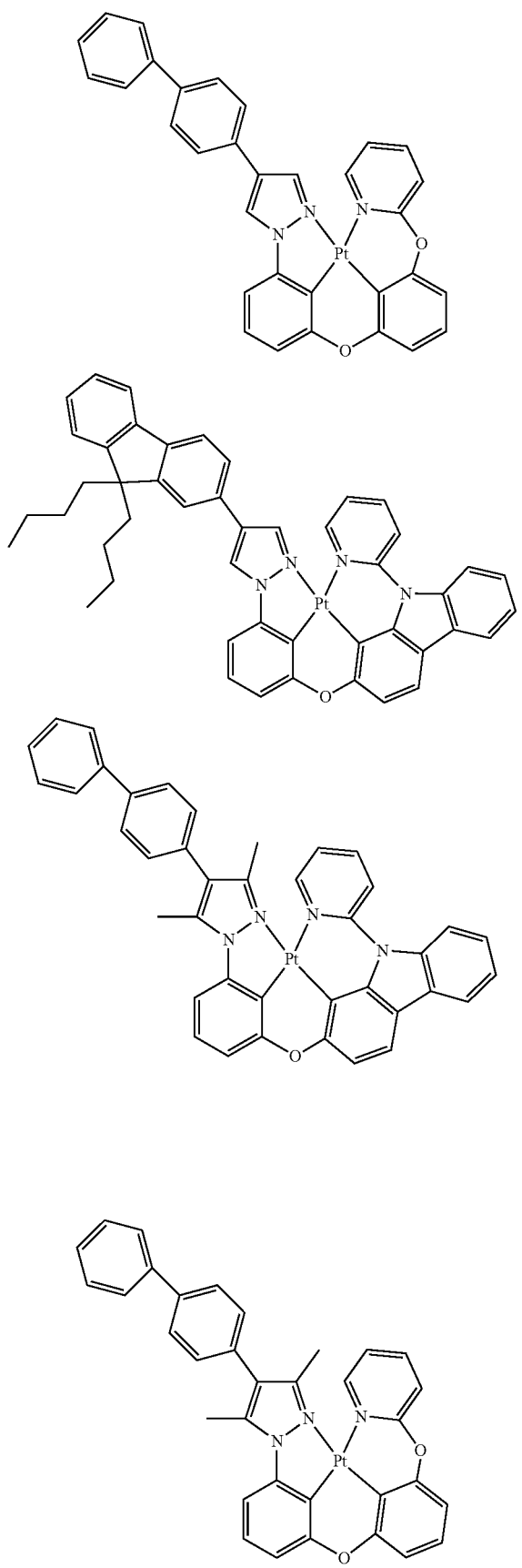
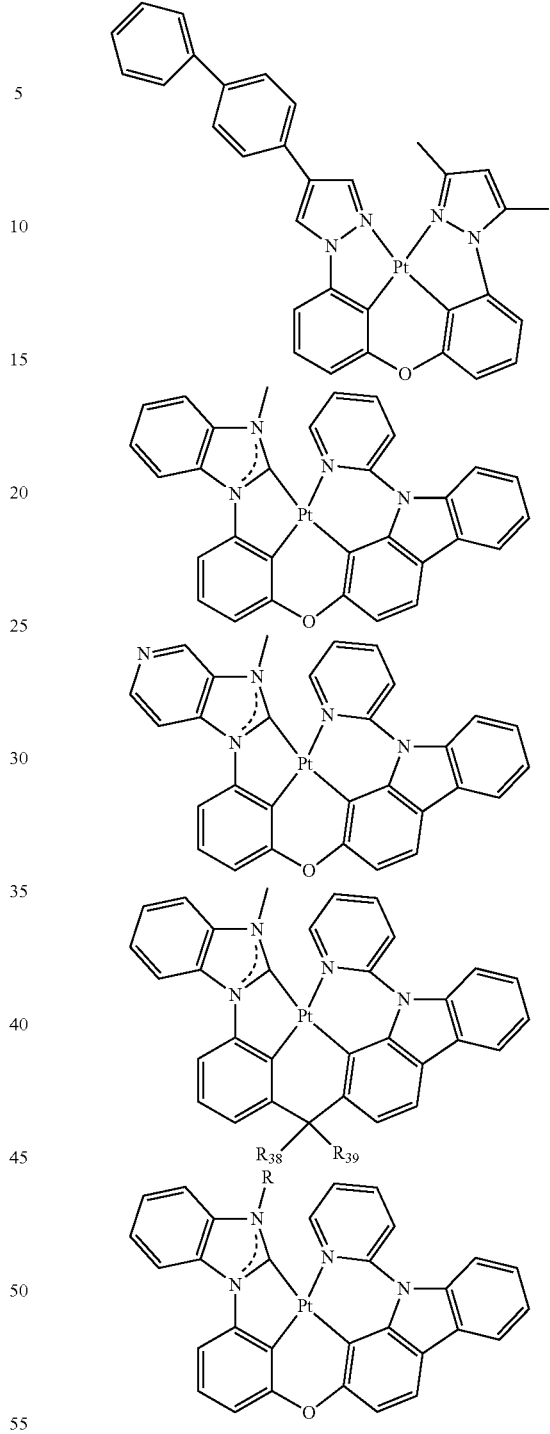

In the compounds above, R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include any one among Formula F-a to Formula F-c below. The compounds represented by Formula F-a to Formula F-c below may be used as fluorescence dopant materials.

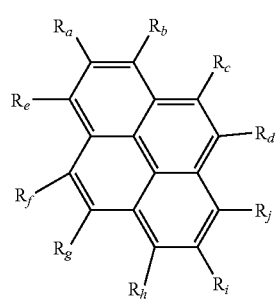

[Formula F-a]

In Formula F-a, two selected from $R_a$ to $R_j$ may each independently be substituted with *—$NAr_1Ar_2$. The remainder of $R_a$ to $R_j$ not substituted with *—$NAr_1Ar_2$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In *—$NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one among $Ar_1$ and $Ar_2$ may be a heteroaryl group including O or S as a ring-forming atom.

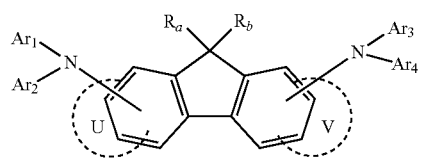

[Formula F-b]

In Formula F-b, $R_a$ and $R_b$ may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may each independently be 0 or 1. For example, in Formula F-b, if the number of U or V is 1, one ring forms a fused ring at the designated part by U or V, and if the number of U or V is 0, a ring is not present at the designated part by U or V. For example, if the number of U is 0 and the number of V is 1, or if the number of U is 1 and the number of V is 0, a fused ring having the fluorene core of Formula F-b may be a ring compound with four rings. If the number of both U and V is 0, the fused ring of Formula F-b may be a ring compound with three rings. If the number of both U and V is 1, a fused ring having the fluorene core of Formula F-b may be a ring compound with five rings.

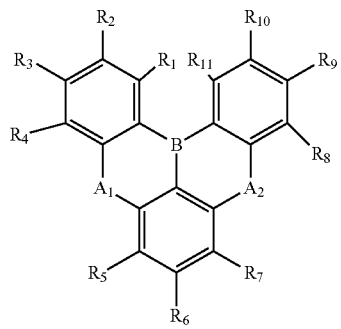

[Formula F-c]

In Formula F-c, $A_1$ and $A_2$ may each independently be O, S, Se, or $NR_m$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring.

In Formula F-c, $A_1$ and $A_2$ may each independently be combined with the substituents of an adjacent ring to form a fused ring. For example, if $A_1$ and $A_2$ may each independently be $NR_m$, $A_1$ may be combined with $R_4$ or $R_5$ to form a ring. For example, $A_2$ may be combined with $R_7$ or $R_8$ to form a ring.

In an embodiment, the emission layer EML may include as a dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl) naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layer EML may include a phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb) or thulium (Tm). For example, iridium(III) bis[2-(4,6-difluorophenylpyridinato-C2,N](picolinato) (FIrpic), bis(2,4-difluorophenylpyridinato)-tetrakis(1-pyrazolyl)borate iridium(III) (FIr6), or platinum octaethyl porphyrin (PtOEP) may be used as the phosphorescence dopant. However, an embodiment of the inventive concept is not limited thereto.

The emission layer EML may include a quantum dot material. The core of the quantum dot may be selected from a II-VI group compound, a III-VI group compound, a IV-VI group compound, a IV group element, a IV group compound, and combinations thereof.

The II-VI group compound may be selected from the group consisting of: a binary compound selected from the group consisting of CdSe, CdTe, CdS, ZnS, ZnSe, ZnTe, ZnO, HgS, HgSe, HgTe, MgSe, MgS, and mixtures thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The III-V group compound may include a binary compound such as $In_2S_3$, and $In_2Se_3$, a ternary compound such as $InGaS_3$, and $InGaSe_3$, or optional combinations thereof.

The I-III-VI group compound may be selected from a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof, or a quaternary compound such as $AgInGaS_2$, and $CuInGaS_2$.

The III-V group compound may be selected from the group consisting of a binary compound selected from the group consisting of GaN, GaP, GaAs, GaSb, AlN, AlP, AlAs, AlSb, InN, InP, InAs, InSb, and mixtures thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. The III-V group compound may further include a II group metal. For example, InZnP, etc. may be selected as a III-II-V group compound.

The IV-VI group compound may be selected from the group consisting of a binary compound selected from the group consisting of SnS, SnSe, SnTe, PbS, PbSe, PbTe, and mixtures thereof, a ternary compound selected from the group consisting of SnSeS, SnSeTe, SnSTe, PbSeS, PbSeTe, PbSTe, SnPbS, SnPbSe, SnPbTe, and mixtures thereof, and a quaternary compound selected from the group consisting of SnPbSSe, SnPbSeTe, SnPbSTe, and mixtures thereof. The IV group element may be selected from the group consisting of Si, Ge, and a mixture thereof. The IV group compound may be a binary compound selected from the group consisting of SiC, SiGe, and a mixture thereof.

The binary compound, the ternary compound, or the quaternary compound may be present at uniform concentration in a particle or may be present at a partially different concentration distribution state in the same particle. A core/shell structure in which one quantum dot wraps another quantum dot may be possible. The interface of the core and the shell may have a concentration gradient in which the concentration of an element present in the shell is decreased toward the center.

In some embodiments, the quantum dot may have the above-described core-shell structure including a core including a nanocrystal and a shell wrapping the core. The shell of the quantum dot may play the role of a protection layer for preventing the chemical deformation of the core to maintain semiconductor properties and/or a charging layer for imparting the quantum dot with electrophoretic properties. The shell may have a single layer or a multilayer. The interface of the core and the shell may have a concentration gradient in which the concentration of an element present in the shell is decreased toward the center. Examples of the shell of the quantum dot may include a metal or non-metal oxide, a semiconductor compound, or combinations thereof.

For example, the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO, or a ternary compound such as $MgAl_2O_4$, $CoFe_2O_4$, $NiFe_2O_4$ and $CoMn_2O_4$, but an embodiment of the inventive concept is not limited thereto.

Also, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but an embodiment of the inventive concept is not limited thereto.

The quantum dot may have a full width of half maximum (FWHM) of emission wavelength spectrum equal to or less than about 45 nm. For example, the quantum dot may have a FWHM of emission wavelength spectrum equal to or less than about 40 nm. For example, the quantum dot may have a FWHM of emission wavelength spectrum equal to or less than about 30 nm. Within this range, color purity or color reproducibility may be improved. Light emitted via such quantum dot may be emitted in all directions, and light view angle properties may be improved.

The shape of the quantum dot may be generally used shapes in the art, without specific limitation. For example, the shape of a spherical, a pyramidal, a multi-arm, or a cubic nanoparticle, nanotube, nanowire, nanofiber, nanoplate particle, etc. may be used.

The quantum dot may control the color of light emitted according to the particle size, and accordingly, the quantum dot may have various emission colors such as blue, red, and green.

In the light emitting element ED of an embodiment, as shown in FIG. 2 to FIG. 8, the electron transport region ETR is provided on the emission layer EML. The electron transport region ETR may include at least one of an electron blocking layer HBL, an electron transport layer ETL, and an electron injection layer EIL. However, an embodiment of the inventive concept is not limited thereto.

The electron transport region ETR may have a single layer formed using a single material, a single layer formed using multiple different materials, or a multilayer structure having layers formed using multiple different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure formed using multiple different materials, or a structure stacked from the emission layer EML of electron transport layer ETL/electron injection layer EIL, or hole blocking layer HBL/electron transport layer ETL/electron injection layer EIL, without limitation. A thickness of the electron transport region ETR may be, for example, in a range of about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

The electron transport region ETR may include a compound represented by Formula ET-1 below.

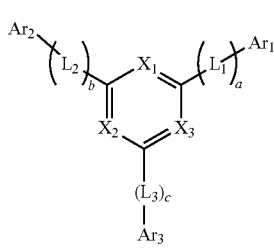

[Formula ET-1]

In Formula ET-1, at least one among $X_1$ to $X_3$ may be N, and the remainder may be $CR_a$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $Ar_1$ to $Ar_3$ may each independently be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group of 6 to 30 ring-forming carbon atoms, or a substituted or unsubstituted heteroarylene group of 2 to 30 ring-forming carbon atoms. If a to c are integers of 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, an embodiment of the inventive concept is not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq$_2$), 9,10-di(naphthalene-2-yl)anthracene (ADN), 1,3-bis[3,5-di(pyridin-3-yl)phenyl]benzene (BmPyPhB), and mixtures thereof, without limitation.

The electron transport region ETR may include a metal halide such as LiF, NaCl, CsF, RbCl, RbI, CuI and KI, a lanthanide metal such as Yb, or a co-depositing material of the metal halide and the lanthanide metal. For example, the electron transport region ETR may include KI:Yb, RbI:Yb, etc., as the co-depositing material. The electron transport region ETR may use a metal oxide such as $Li_2O$ and BaO, or 8-hydroxy-lithium quinolate (Liq). However, an embodiment of the inventive concept is not limited thereto. The electron transport region ETR also may be formed using a mixture material of an electron transport material and an insulating organo metal salt. The organo metal salt may be a material having an energy band gap equal to or greater than about 4 eV. For example, the organo metal salt may include metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP), and 4,7-diphenyl-1,10-phenanthroline (Bphen) in addition to the aforementioned materials. However, an embodiment of the inventive concept is not limited thereto.

The electron transport region ETR may include the compounds of the electron transport region in at least one among an electron injection layer EIL, an electron transport layer ETL, and a hole blocking layer HBL.

If the electron transport region ETR includes the electron transport layer ETL, a thickness of the electron transport layer ETL may be in a range of about 100 Å to about 1,000 Å. For example, the thickness of the electron transport layer ETL may be in a range of about 150 Å to about 500 Å. If the thickness of the electron transport layer ETL satisfies the above-described range, satisfactory electron transport properties may be obtained without substantial increase of a driving voltage. If the electron transport region ETR includes the electron injection layer EIL, a thickness of the electron injection layer EIL may be in a range of about 1 Å to about 100 Å. For example, the thickness of the electron injection layer EIL may be in a range of about 3 Å to about 90 Å. If the thickness of the electron injection layer EIL satisfies the above described range, satisfactory electron injection properties may be obtained without inducing substantial increase of a driving voltage.

The second electrode EL2 is provided on the electron transport region ETR. The second electrode EL2 may be a common electrode. The second electrode EL2 may be a cathode or an anode, but an embodiment of the inventive concept is not limited thereto. For example, if the first electrode EL1 is an anode, the second cathode EL2 may be a cathode, and if the first electrode EL1 is a cathode, the second electrode EL2 may be an anode.

The second electrode EL2 may be a transmissive electrode, a transflective electrode, or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, compounds thereof, or mixtures thereof (for example, AgMg, AgYb, or MgAg). Otherwise, the second electrode EL2 may have a multilayered structure including a reflective layer or a transflective layer formed using the above-described materials and a transparent conductive layer formed using ITO, IZO, ZnO, ITZO, etc. For example, the second electrode EL2 may include the aforementioned metal materials, combinations of two or more metal materials selected from the aforementioned metal materials, or oxides of the aforementioned metal materials.

Though not shown, the second electrode EL2 may be connected with an auxiliary electrode. If the second electrode EL2 is connected with the auxiliary electrode, the resistance of the second electrode EL2 may decrease.

On the second electrode EL2 in the light emitting element ED of an embodiment, a capping layer CPL may be further disposed. The capping layer CPL may include a multilayer or a single layer.

In an embodiment, the capping layer CPL may be an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol sol-9-yl) triphenylamine (TCTA), etc., or includes an epoxy resin, or acrylate such as methacrylate. A capping layer CPL may include at least one among Compounds P1 to P5 below, but an embodiment of the inventive concept is not limited thereto.

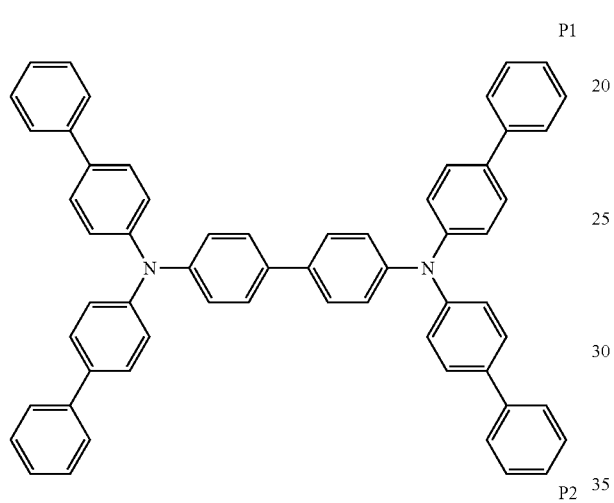

P1

P2

P3

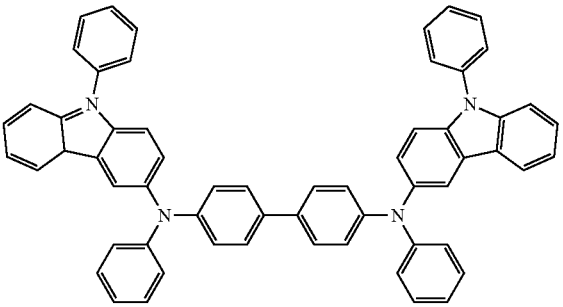

-continued

P4

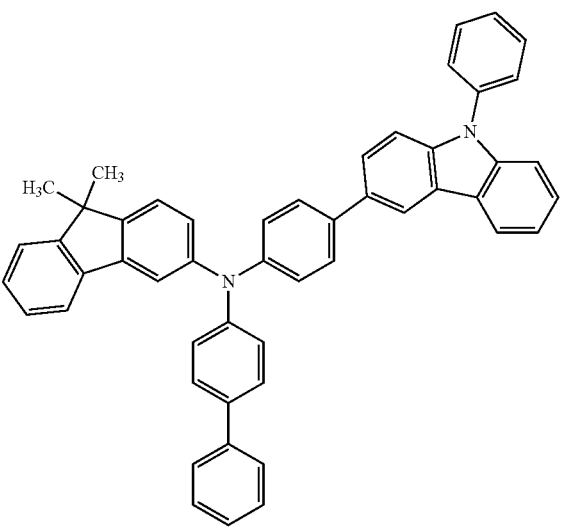

P5

A refractive index of the capping layer CPL may be equal to or greater than about 1.6. For example, the refractive index of the capping layer CPL with respect to light in a wavelength range of about 550 nm to about 660 nm may be equal to or greater than about 1.6.

Figure 8:
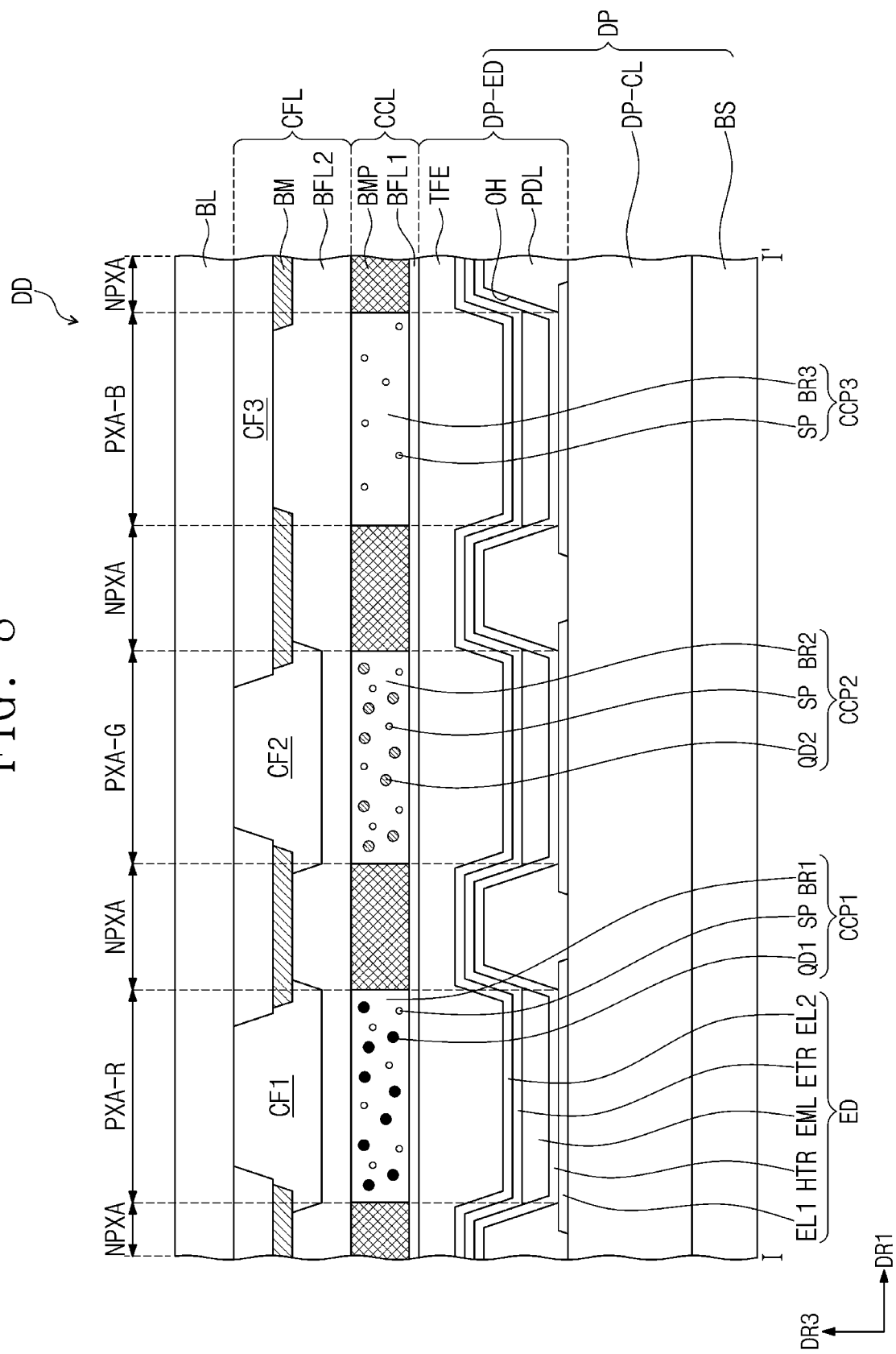
FIG. 8 is a schematic cross-sectional view of a display apparatus according to an embodiment.
Figure 9:
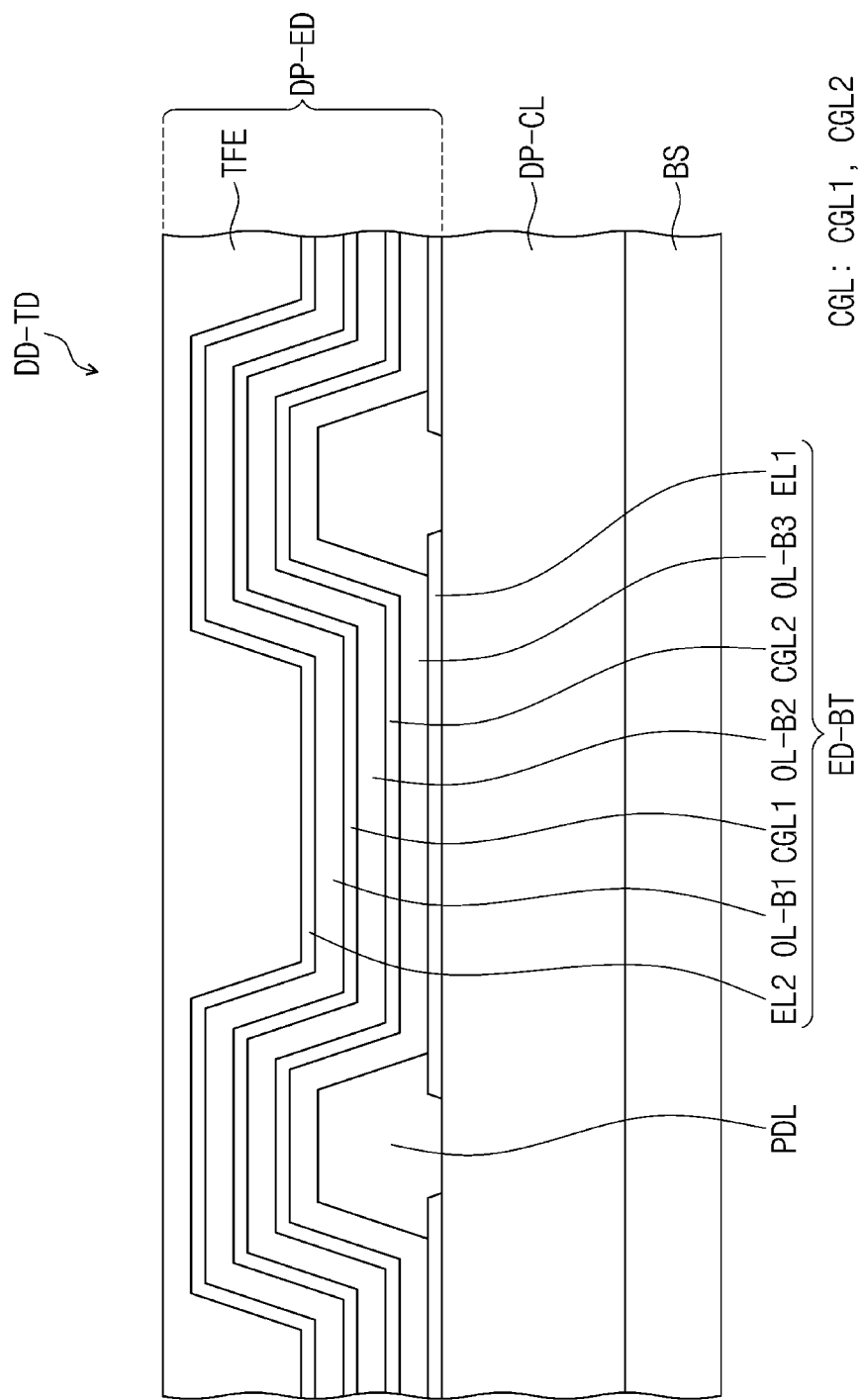
FIG. 9 is a schematic cross-sectional view of a display apparatus according to an embodiment.

FIG. 8 and FIG. 9 are schematic cross-sectional views of display apparatuses according to embodiments, respectively. In the explanation on the display apparatuses of embodiments, referring to FIG. 8 and FIG. 9, the overlapping parts with the explanation on FIG. 1 to FIG. 7 will not be explained again, and the different features will be explained chiefly.

Referring to FIG. 8, the display apparatus DD according to an embodiment may include a display panel DP including a display device layer DP-ED, a light controlling layer CCL disposed on the display panel DP and a color filter layer CFL.

In an embodiment shown in FIG. 8, the display panel DP includes a base layer BS, a circuit layer DP-CL provided on the base layer BS and a display device layer DP-ED, and the display device layer DP-ED may include a light emitting element ED.

The light emitting element ED may include a first electrode EL1, a hole transport region HTR disposed on the first electrode EL1, an emission layer EML disposed on the hole transport region HTR, an electron transport region ETR disposed on the emission layer EIL, and a second electrode EL2 disposed on the electron transport region ETR. The same structures of the light emitting elements of FIG. 4 to FIG. 7 may be applied to the structure of the light emitting element ED shown in FIG. 8.

Referring to FIG. 8, the emission layer EIL may be disposed in an opening part OH defined in a pixel definition layer PDL. For example, the emission layer EIL divided by the pixel definition layer PDL and correspondingly provided to each of luminous areas PXA-R, PXA-G, and PXA-B may emit light in the same wavelength region. In the display apparatus DD of an embodiment, the emission layer EIL may emit blue light. Different from the drawings, in an embodiment, the emission layer EMIL may be provided as a common layer for all luminous areas PXA-R, PXA-G, and PXA-B.

The light controlling layer CCL may be disposed on the display panel DP. The light controlling layer CCL may include a light converter. The light converter may be a quantum dot or a phosphor. The light converter may transform the wavelength of light provided and emit the converted light. For example, the light controlling layer CCL may be a layer including a quantum dot or a layer including a phosphor.

The light controlling layer CCL may include multiple light controlling parts CCP1, CCP2, and CCP3. The light controlling parts CCP1, CCP2, and CCP3 may be separated from one another.

Referring to FIG. 8, a partition pattern BMP may be disposed between the separated light controlling parts CCP1, CCP2, and CCP3, but an embodiment of the inventive concept is not limited thereto. In FIG. 8, the partition pattern BMP is shown as not overlapping the light controlling parts CCP1, CCP2, and CCP3, but at least a portion of the edge of the light controlling parts CCP1, CCP2, and CCP3 may be overlapped with the partition pattern BMP.

The light controlling layer CCL may include a first light controlling part CCP1 including a first quantum dot QD1 converting first color light provided from the light emitting element ED into second color light, a second light controlling part CCP2 including a second quantum dot QD2 converting first color light into third color light, and a third light controlling part CCP3 transmitting first color light.

In an embodiment, the first light controlling part CCP1 may provide red light which is the second color light, and the second light controlling part CCP2 may provide green light which is the third color light. The third color light controlling part CCP3 may transmit and provide blue light which is the first color light provided from the light emitting element ED. For example, the first quantum dot QD1 may be a red quantum dot, and the second quantum dot QD2 may be a green quantum dot. On the quantum dots QD1 and QD2, the same contents as those described above may be applied.

The light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but may include the scatterer SP.

The scatterer SP may be an inorganic particle. For example, the scatterer SP may include at least one among $TiO_2$, ZnO, $Al_2O_3$, $SiO_2$, and hollow silica. The scatterer SP may include at least one among $TiO_2$, ZnO, $Al_2O_3$, $SiO_2$, and hollow silica, or may be a mixture of two or more materials selected among $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2, and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2, and BR3 are mediums in which the quantum dots QD1 and QD2 and the scatterer SP are dispersed, and may be composed of various resin compositions which may be generally referred to as a binder. For example, the base resins BR1, BR2, and BR3 may be acrylic resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 may be the same or different from each other.

The light controlling layer CCL may include a barrier layer BFL1. The barrier layer BFL1 may play the role of blocking the penetration of moisture and/or oxygen (hereinafter, will be referred to as "humidity/oxygen"). The barrier layer BFL1 may be disposed on the light controlling parts CCP1, CCP2, and CCP3 to block the exposure of light controlling parts CCP1, CCP2, and CCP3 to humidity/oxygen. The barrier layer BFL1 may cover the light controlling parts CCP1, CCP2, and CCP3. The barrier layer BFL2 may be provided between the light controlling parts CCP1, CCP2, and CCP3 and a color filter layer CFL.

The barrier layers BFL1 and BFL2 may include at least one inorganic layer. For example, the barrier layers BFL1 and BFL2 may be formed by including an inorganic material. For example, the barrier layers BFL1 and BFL2 may be formed by including silicon nitride, aluminum nitride, zirconium nitride, titanium nitride, hafnium nitride, tantalum nitride, silicon oxide, aluminum oxide, titanium oxide, tin oxide, cerium oxide and silicon oxynitride, or a metal thin film securing light transmittance. The barrier layers BFL1 and BFL2 may further include an organic layer. The barrier layers BFL1 and BFL2 may be composed of a single layer or of multiple layers.

In the display apparatus DD of an embodiment, the color filter layer CFL may be disposed on the light controlling layer CCL. For example, the color filter layer CFL may be disposed directly on the light controlling layer CCL. In an embodiment, the barrier layer BFL2 may be omitted.

The color filter layer CFL may include a light blocking part BM and filters CF-B, CF-G, and CF-R. The color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. Each of the filters CF1, CF2, and CF3 may include a polymer photosensitive resin and a pigment or dye. The first filter CF1 may include a red pigment or dye, the second filter CF2 may include a green pigment or dye, and the third filter CF3 may include a blue pigment or dye. However, an embodiment of the inventive concept is not limited thereto, and the third filter CF3 may not include the pigment or dye. The third filter CF3 may include a polymer photosensitive resin and not include a pigment or dye. The third filter CF3 may be transparent. The third filter CF3 may be formed using a transparent photosensitive resin.

In an embodiment, the first filter CF1 and the second filter CF2 may be yellow filters. The first filter CF1 and the second filter CF2 may be provided in one body without distinction.

The light blocking part BM may be a black matrix. The light blocking part BM may be formed by including an organic light blocking material or an inorganic light blocking material including a black pigment or black dye. The light blocking part BM may prevent light leakage phenomenon and define the boundaries among adjacent filters CF1, CF2, and CF3. In an embodiment, the light blocking part BM may be formed as a blue filter.

Each of the first to third filters CF1, CF2, and CF3 may be disposed corresponding to each of a red luminous area PXA-R, green luminous area PXA-G, and blue luminous area PXA-B.

On the color filter layer CFL, a base substrate BL may be disposed. The base substrate BL may be a member providing a base surface on which the color filter layer CFL, the light controlling layer CCL, etc. are disposed. The base substrate BL may be a glass substrate, a metal substrate, a plastic substrate, etc. However, an embodiment of the inventive concept is not limited thereto, and the base substrate BL may be an inorganic layer, an organic layer, or a composite material layer. Different from the drawing, the base substrate BL may be omitted in an embodiment.

FIG. 9 is a schematic cross-sectional view showing a portion of the display apparatus according to an embodiment. In FIG. 9, the schematic cross-sectional view of a portion corresponding to the display panel DP in FIG. 8 is shown. In a display apparatus DD-TD of an embodiment, the light emitting element ED-BT may include multiple light emitting structures OL-B1, OL-B2, and OL-B3. The light emitting element ED-BT may include oppositely disposed first electrode EL1 and second electrode EL2, and the multiple light emitting structures OL-B1, OL-B2, and OL-B3 stacked in order in a thickness direction and provided between the first electrode EL1 and the second electrode EL2. In this embodiment, the first electrode EL1 and the second electrode EL2 are disposed to face each other. Each of the light emitting structures OL-B1, OL-B2, and OL-B3 may include an emission layer EML (FIG. 8), and a hole transport region HTR and an electron transport region ETR disposed with the emission layer EML (FIG. 7) therebetween.

For example, the light emitting element ED-BT included in the display apparatus DD-TD of an embodiment may be a light emitting element of a tandem structure including multiple emission layers.

In an embodiment shown in FIG. 9, light emitted from the light emitting structures OL-B1, OL-B2, and OL-B3 may be all blue light. However, an embodiment of the inventive concept is not limited thereto, and the wavelength regions of light emitted from the light emitting structures OL-B1, OL-B2, and OL-B3 may be different from each other. For example, the light emitting element ED-BT including the multiple light emitting structures OL-B1, OL-B2, and OL-B3 emitting light in different wavelength regions may emit white light.

Between neighboring light emitting structures OL-B1, OL-B2, and OL-B3, a charge generating layer CGL may be disposed. In an embodiment, the charge generating layer CGL may include charge generating layers CGL1 and CGL2. Charge generating layer CGL1 may be disposed between light emitting structures OL-B1 and OL-B2, and charge generating layer CGL2 may be disposed between light emitting structures OL-B2 and OL-B3. The charge generating layer CGL may include a p-type charge generating layer and/or an n-type charge generating layer.

Hereinafter, the monoamine compound according to an embodiment and the light emitting element of an embodiment, including the monoamine compound of an embodiment of the inventive concept will be explained referring to embodiments and comparative embodiments. The following embodiments are only examples to assist the understanding of the inventive concept, and the scope of the inventive concept is not limited thereto.

EXAMPLES

1. Synthesis of Monoamine Compound of an Embodiment

First, the synthetic method of monoamine compounds according to the embodiments will be explained in particular illustrating the synthetic methods of Compounds 1, 2, 13, 18, 19 and 20. The synthetic methods of the compounds explained hereinafter are embodiments, and the synthetic method of the compound according to an embodiment of the inventive concept is not limited to the following embodiments.

1-1 Synthesis of Compound 1

Compound 1 of an embodiment may be synthesized, for example, by Reaction 1 below.

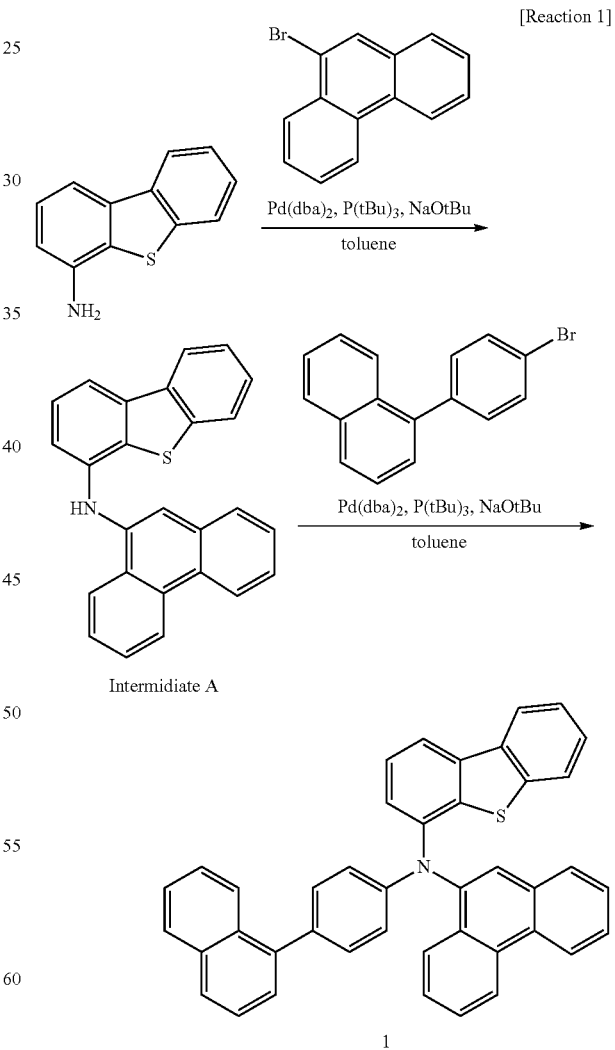

Under an argon (Ar) atmosphere, in a 1,000 ml, three-neck flask, dibenzothiophen-4-amine (20.0 g), 9-bromophenanthrene (25.8 g), bis(dibenzylideneacetone)palladium(O) (Pd(dba)₂, 2.89 g), and sodium tert-butoxide (NaOtBu, 9.65 g) were dissolved in a toluene solvent (500 ml), and tri-tert-butylphosphine (P(tBu)₃, 2.0 M in toluene, 5.0 ml) was added thereto, followed by heating and refluxing for about 2 hours. After finishing the reaction, an organic layer was extracted from the mixture thus produced using water and CH₂Cl₂, the extracted organic layer was dried with MgSO₄, and solvents were distilled under a reduced pressure to obtain a crude Intermediate A. The crude Intermediate A thus obtained was separated by silica gel column chromatography to obtain 30.5 g (yield 81%) of Intermediate A. The molecular weight of Intermediate A measured by FAB-MS measurement was 375.

Under an argon atmosphere, to a 300 ml, three-neck flask, Intermediate A (5.0 g), 1-(4-bromophenyl)naphthalene (3.8 g), Pd(dba)₃ (0.38 g), and NaOtBu (1.28 g) were added and dissolved in toluene (100 ml). P(tBu)₃ (2.0 M in toluene, 0.7 ml) was added thereto, followed by heating and refluxing for about 4 hours. After finishing the reaction, an organic layer was extracted from the mixture thus produced using water and CH₂Cl₂, the extracted organic layer was dried with MgSO₄, and solvents were distilled under a reduced pressure to obtain a crude Compound 1. The crude Compound 1 thus obtained was separated by silica gel column chromatography to obtain 5.5 g (yield 72%) of Compound 1. The molecular weight of Compound 1 measured by FAB-MS measurement was 577.

1-2. Synthesis of Compound 2

Compound 2 of an embodiment may be synthesized, for example, by Reaction 2 below.

5.4 g (yield 70%) of Compound 2 was obtained by performing the same method as the method for preparing Compound 1 under the same conditions except for adding 2-(4-bromophenyl) naphthalene (3.8 g) to Intermediate A (5.0 g). The molecular weight of Compound 2 measured by FAB-MS measurement was 577.

1-3. Synthesis of Compound 13

Compound 13 of an embodiment may be synthesized, for example, by Reaction 3 below.

[Reaction 3]

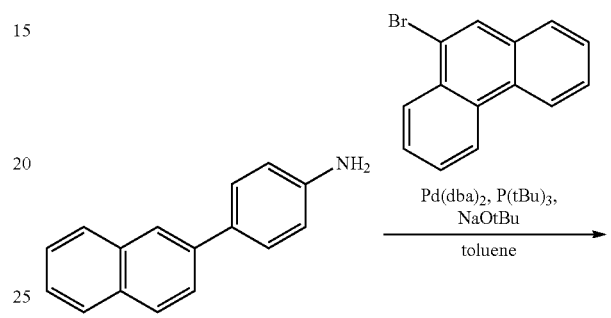

[Reaction 2]

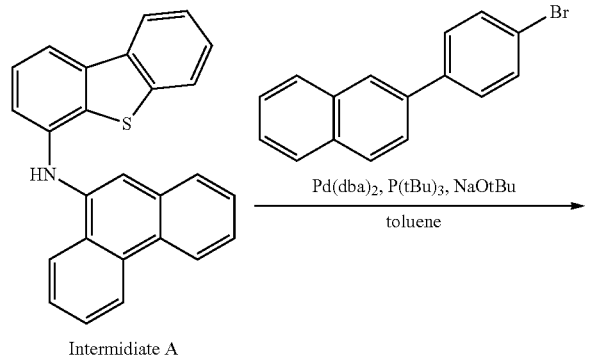

Under an argon atmosphere, to a 1,000 ml, three-neck flask, 4-(naphthalen-2-yl)aniline (20.0 g), 9-bromophenanthrene (23.5 g), Pd(dba)$_2$ (2.62 g), and NaOtBu (8.77 g) were added and dissolved in toluene (450 ml), and P(tBu)$_3$ (2.0 M in toluene, 4.6 ml) was added thereto, followed by heating and refluxing for about 2 hours. After finishing the reaction, an organic layer was extracted from the mixture thus produced using water and CH$_2$Cl$_2$, the extracted organic layer was dried with MgSO$_4$, and solvents were distilled under a reduced pressure to obtain a crude Intermediate B. The crude Intermediate B thus obtained was separated by silica gel column chromatography to obtain 25.3 g (yield 70%) of Intermediate B. The molecular weight of Intermediate B measured by FAB-MS measurement was 395.

Under an argon atmosphere, to a 200 ml, three-neck flask, Intermediate B (5.0 g), 4-bromo-1-phenyldibenzothiophene (4.29 g), Pd(dba)$_2$ (0.36 g), and NaOtBu (1.21 g) were added and dissolved in toluene (80 ml). P(tBu)$_3$ (2.0 M in toluene, 0.6 ml) was added thereto, and heating and refluxing were performed for about 4 hours. After finishing the reaction, an organic layer was extracted from the mixture thus produced using water and CH$_2$Cl$_2$, the extracted organic layer was dried with MgSO$_4$, and solvents were distilled under a reduced pressure to obtain a crude Compound 13. The crude Compound 13 thus obtained was separated by silica gel column chromatography to obtain 5.4 g (yield 65%) of Compound 13. The molecular weight of Compound 13 measured by FAB-MS measurement was 653.

1-4. Synthesis of Compound 18

Compound 18 of an embodiment may be synthesized, for example, by Reaction 4 below.

4.9 g (yield 59%) of Compound 18 was obtained by performing the same method as the method for preparing Compound 13 under the same conditions except for adding 4-bromo-6-phenyldibenzothiophene (4.3 g) to Intermediate B (5.0 g). The molecular weight of Compound 18 measured by FAB-MS measurement was 653.

1-5. Synthesis of Compound 19

Compound 19 of an embodiment may be synthesized, for example, by Reaction 5 below.

[Reaction 5]

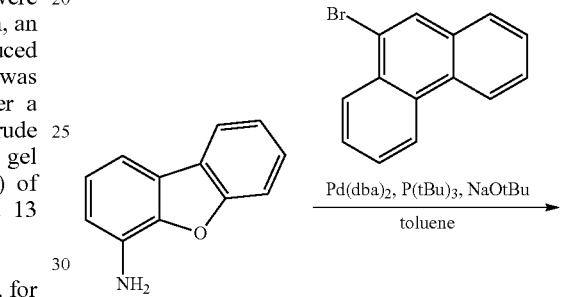

[Reaction 4]

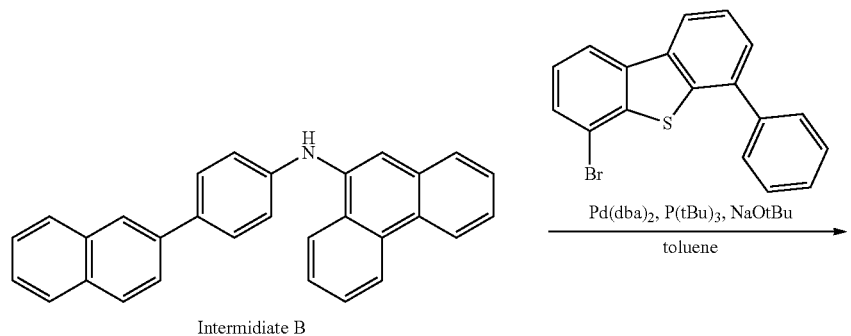

18

1-6. Synthesis of Compound 20

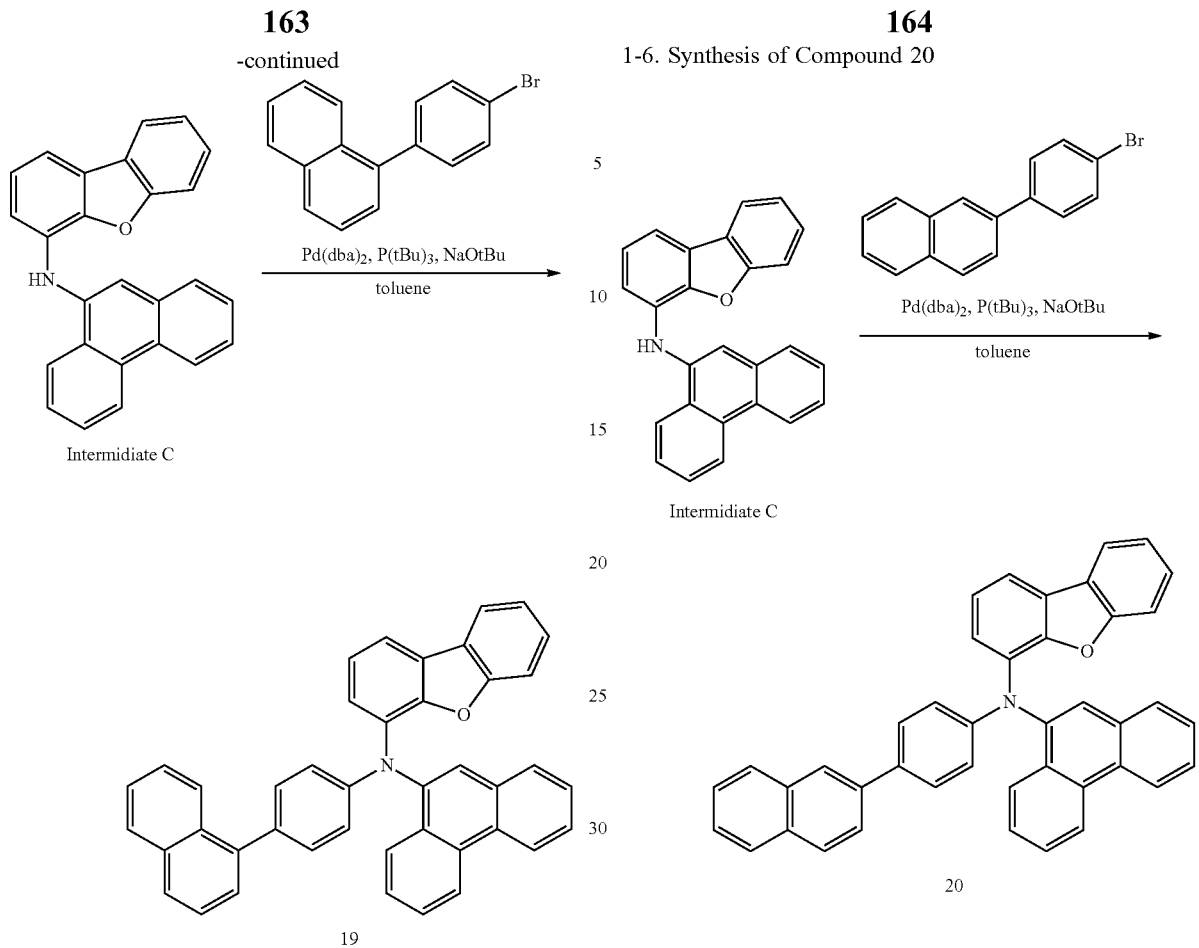

Under an argon atmosphere, to a 1,000 ml, three-neck flask, dibenzofuran-4-amine (20.0 g), 9-bromophenanthrene (28.1 g), Pd(dba)$_2$ (3.13 g), and NaOtBu (10.5 g) were added and dissolved in toluene (500 ml), and P(tBu)$_3$ (2.0 M in toluene, 5.5 ml) was added thereto, followed by heating and refluxing for about 3 hours. After finishing the reaction, an organic layer was extracted from the mixture thus produced using water and CH$_2$Cl$_2$, the extracted organic layer was dried with MgSO$_4$, and solvents were distilled under a reduced pressure to obtain a crude Intermediate C. The crude Intermediate C thus obtained was separated by silica gel column chromatography to obtain 31.4 g (yield 80%) of Intermediate C. The molecular weight of Intermediate C measured by FAB-MS measurement was 359.

Under an argon atmosphere, to a 300 ml, three-neck flask, Intermediate C (5.0 g), 1-(4-bromophenyl)naphthalene (3.9 g), Pd(dba)$_2$ (0.40 g), and NaOtBu (1.35 g) were added and dissolved in toluene (100 ml). P(tBu)$_3$ (2.0 M in toluene, 0.7 ml) was added thereto, and heating and refluxing were performed for about 4 hours. After finishing the reaction, an organic layer was extracted from the mixture thus produced using water and CH$_2$Cl$_2$, the extracted organic layer was dried with MgSO$_4$, and solvents were distilled under a reduced pressure to obtain a crude Compound 19. The crude Compound 19 thus obtained was separated by silica gel column chromatography to obtain 6.3 g (yield 80%) of Compound 19. The molecular weight of Compound 19 measured by FAB-MS measurement was 561.

5.8 g (yield 75%) of Compound 20 was obtained by performing the same method as the method for preparing Compound 19 under the same conditions except for adding 2-(4-bromophenyl)naphthalene (3.9 g) to Intermediate C (5.0 g). The molecular weight of Compound 20 measured by FAB-MS measurement was 577.

2. Evaluation of Physical Properties of Compounds

The levels of HOMO, lowest unoccupied molecular orbital (LUMO), S1, and T1 on Example Compounds 1, 2, 13, 18, 19 and 20 and Comparative Compounds X-1 to X-4 are shown in Table 1. The levels of HOMO, LUMO, S1, and T1 were calculated by a non-empirical molecular orbital method. The calculation was conducted using Gaussian09 which is a product of Gaussian Co., a functional of B3LYP, and a basis function of 6-31G(d).

TABLE 1

| Compound | HOMO (eV) | LUMO (eV) | S1 (eV) | T1 (eV) |
|---|---|---|---|---|
| Example Compound 1 | −5.04 | −1.20 | 3.27 | 2.56 |
| Example Compound 2 | −5.01 | −1.21 | 3.24 | 2.54 |
| Example Compound 13 | −5.00 | −1.21 | 3.23 | 2.54 |
| Example Compound 18 | −4.99 | −1.19 | 3.23 | 2.54 |
| Example Compound 19 | −5.02 | −1.13 | 3.34 | 2.58 |
| Example Compound 20 | −5.00 | −1.15 | 3.31 | 2.55 |
| Comparative Compound X-1 | −4.92 | −1.11 | 3.35 | 2.67 |
| Comparative Compound X-2 | −4.87 | −1.18 | 3.14 | 2.45 |

TABLE 1-continued

| Compound | HOMO (eV) | LUMO (eV) | S1 (eV) | T1 (eV) |
|---|---|---|---|---|
| Comparative Compound X-3 | −5.02 | −1.14 | 3.34 | 2.51 |
| Comparative Compound X-4 | −5.01 | −1.21 | 3.23 | 2.57 |

[Comparative Compounds]

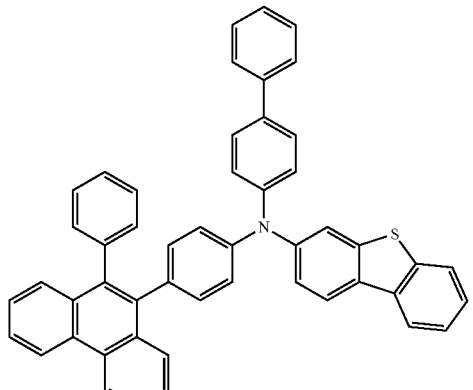

X-1

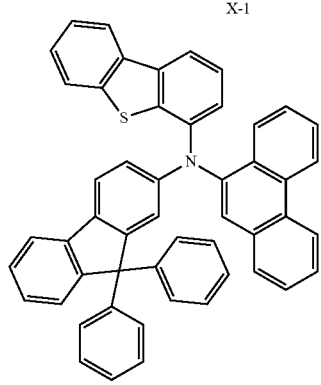

X-2

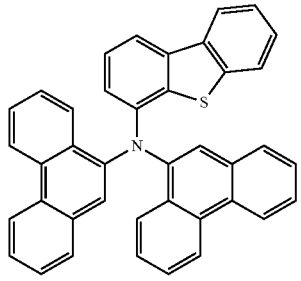

X-3

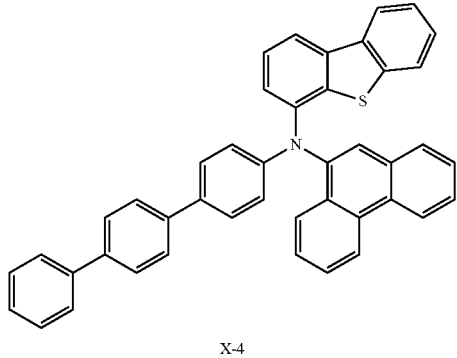

X-4

The Example Compounds have equal or lower levels of a HOMO energy level and a LUMO energy level compared to Comparative Compounds X-1 to X-2.

3. Manufacture and Evaluation of Light Emitting Element
(Manufacture of Light Emitting Element)

On a glass substrate, ITO with a thickness of about 1,500 Å was patterned and washed with ultra-pure water, cleaned with ultrasonic waves, exposed to UV for about 30 minutes and treated with ozone. 2-TNATA was deposited to a thickness of about 600 Å, at least one among the compounds according to embodiments of the inventive concept was deposited to a thickness of about 300 Å to form a hole transport region. On the hole transport region, a compound including TBP and ADN in a ratio of 3:97 was co-deposited as a host material to a thickness of about 250 Å to form an emission layer. After that, on the emission layer, a layer with a thickness of about 250 Å was formed using $Alq_3$, and a layer with a thickness of about 10 Å was formed using LiF to form an electron transport region. A second electrode with a thickness of about 1,000 Å was formed using aluminum (Al).

In the Examples, the hole transport region, the emission layer, the electron transport region, and the second electrode were formed using a vacuum deposition apparatus.

(Evaluation of Properties of Light Emitting Element)

In order to evaluate the emission efficiency of Examples 1 to 6 and Comparative Examples 1 to 4, measurement was conducted using an external quantum efficiency measurement apparatus of C9920-12 of Hamamatsu Photonics Co. The device life LT50 represents time required to decrease initial brightness to 50%.

TABLE 2

| Device manufacturing example | HTL | Emission efficiency (@10 mA/cm$^2$) | Device life (LT50) |
|---|---|---|---|
| Example 1 | Example Compound 1 | 111% | 112% |
| Example 2 | Example Compound 2 | 109% | 130% |
| Example 3 | Example Compound 13 | 109% | 118% |
| Example 4 | Example Compound 18 | 107% | 150% |
| Example 5 | Example Compound 19 | 110% | 120% |
| Example 6 | Example Compound 20 | 108% | 130% |
| Comparative Example 1 | Comparative Compound X-1 | 100% | 100% |
| Comparative Example 2 | Comparative Compound X-2 | 101% | 95% |
| Comparative Example 3 | Comparative Compound X-3 | 104% | 20% |
| Comparative Example 4 | Comparative Compound X-4 | 105% | 60% |

In comparison to Comparative Examples 1 and 2, the Examples showed high emission efficiency and long life. This is considered due to a low HOMO energy level. In the compounds with a low HOMO energy level, hole transport is somewhat restricted, and efficient recombination at the interface of a hole transport layer and an emission layer is considered to generate, and emission efficiency is increased.

Comparative Examples 1 and 2 had a high HOMO energy level and showed low emission efficiency when compared with the Examples. Comparative Examples 3 and 4 had the same level of a HOMO energy level as the Examples and showed higher emission efficiency when compared with Comparative Example 1 and Comparative Example 2. However, in Comparative Example 3, it was confirmed that due to the steric hindrance of 9-phenanthrene, molecular stability was degraded, and life was reduced, and accordingly, lower emission efficiency was shown when compared with the Examples. In Comparative Example 4, a naphthyl group was not present, and electron tolerance was reduced when compared with the Examples, and short life characteristic was shown.

Accordingly, it could be confirmed that when compared with the Comparative Compounds, the Example Compounds include a phenanthryl group and a dibenzoheterole group which were directly bonded to the nitrogen of an amine and a naphthyl group which was bonded to the nitrogen of an amine via a linker in a hole transport layer, and had low HOMO energy, excellent molecular stability, and high electron tolerance, thereby showing high emission efficiency properties and long life characteristics.

An embodiment may provide a light emitting element having high emission efficiency and long life by including a monoamine compound having a high HOMO energy level, high molecular stability, and large electron tolerance in a hole transport region.

An embodiment may provide a monoamine compound having a low HOMO energy level, high molecular stability, and large electron tolerance by including a phenanthryl group and a dibenzoheterole group which are directly bonded to the nitrogen of an amine and a naphthyl group which is bonded to the nitrogen of an amine via a linker.

The light emitting element of an embodiment includes the monoamine compound of an embodiment in a hole transport layer and may show high emission efficiency properties and long-life characteristics in a blue wavelength region.

The monoamine compound of an embodiment has low HOMO energy and a stable molecular structure, and may have high emission efficiency and long-life characteristics.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting element, comprising:
   a first electrode;
   a second electrode facing the first electrode; and
   a plurality of functional layers disposed between the first electrode and the second electrode, wherein
   at least one functional layer among the plurality of functional layers comprises a monoamine compound comprising:
      a phenanthryl group directly bonded to a nitrogen atom;
      a dibenzoheterole group, that is a dibenzothiophene group directly bonded to the nitrogen atom at a 1-, 2-, 3-, or 4-position with respect to a sulfur atom thereof or a dibenzofuran group directly bonded to the nitrogen atom at a 1-, 3-, or 4-position with respect to an oxygen atom thereof; and
      a naphthyl group bonded to the nitrogen atom via a linker,
   the phenanthryl group is an unsubstituted phenanthryl group or a phenanthryl group substituted with a deuterium atom,
   the naphthyl group is an unsubstituted naphthyl group, a naphthyl group substituted with a substituted or unsubstituted phenyl group, a naphthyl group substituted with a substituted or unsubstituted naphthyl group, or a naphthyl group substituted with a deuterium atom,
   provided that when the naphthyl group is substituted with a substituted or unsubstituted phenyl group and when the naphthyl group is bonded to the linker at a 1-position, the substituted or unsubstituted phenyl group is not bonded to the naphthyl group at an 8-position, and
   the dibenzoheterole group is substituted with at least one substituted or unsubstituted phenyl group.

2. The light emitting element of claim 1, wherein the linker is a substituted or unsubstituted phenylene group or a substituted or unsubstituted divalent biphenyl group.

3. The light emitting element of claim 2, wherein
   the linker is an unsubstituted phenylene group, and
   the naphthyl group is bonded to the phenylene group at a para position with respect to the nitrogen atom.

4. The light emitting element of claim 1, wherein
   the naphthyl group is an unsubstituted naphthyl group, a naphthyl group substituted with a phenyl group, or a naphthyl group substituted with a deuterium atom,
   provided that when the naphthyl group is substituted with a substituted or unsubstituted phenyl group and when the naphthyl group is bonded to the linker at a 1-position, the substituted or unsubstituted phenyl group is not bonded to the naphthyl group at an 8-position.

5. The light emitting element of claim 1, wherein the monoamine compound is one selected from Compound Group 1:

[Compound Group 1]

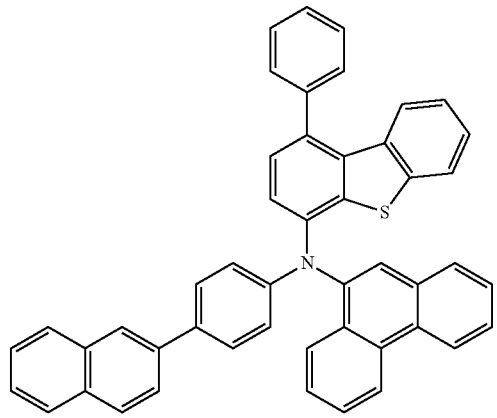

13

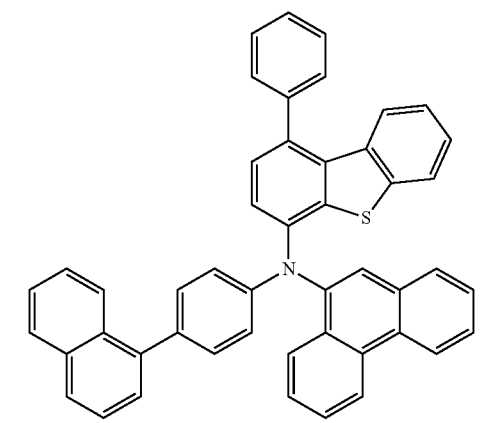

14

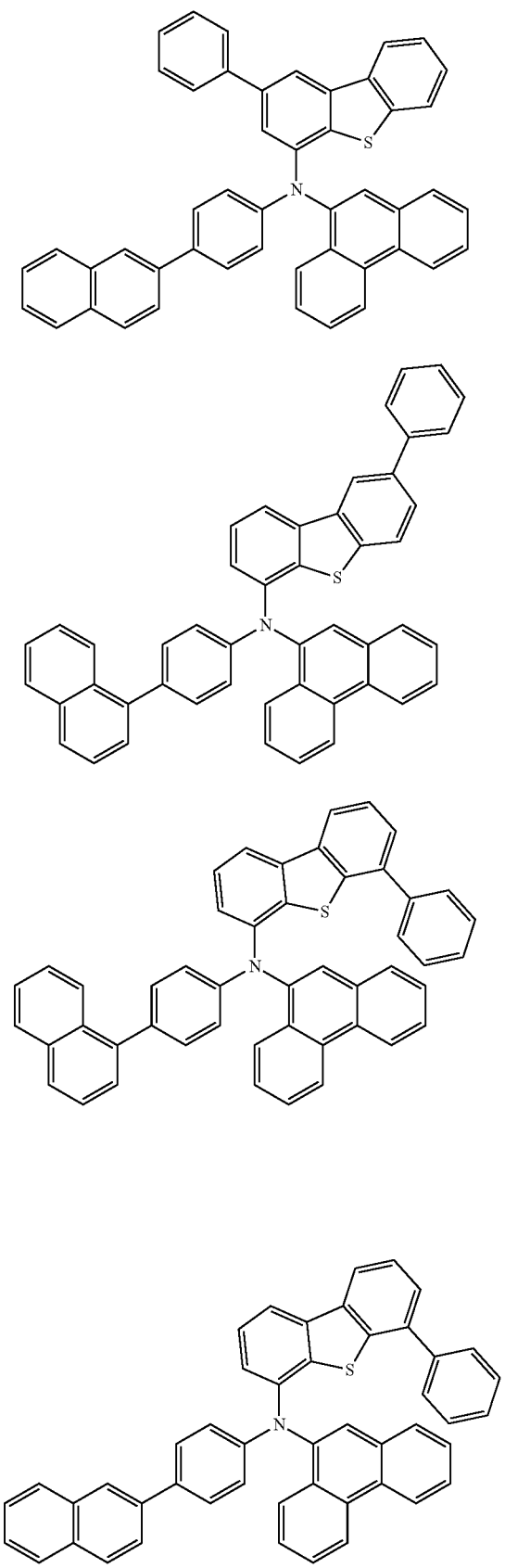
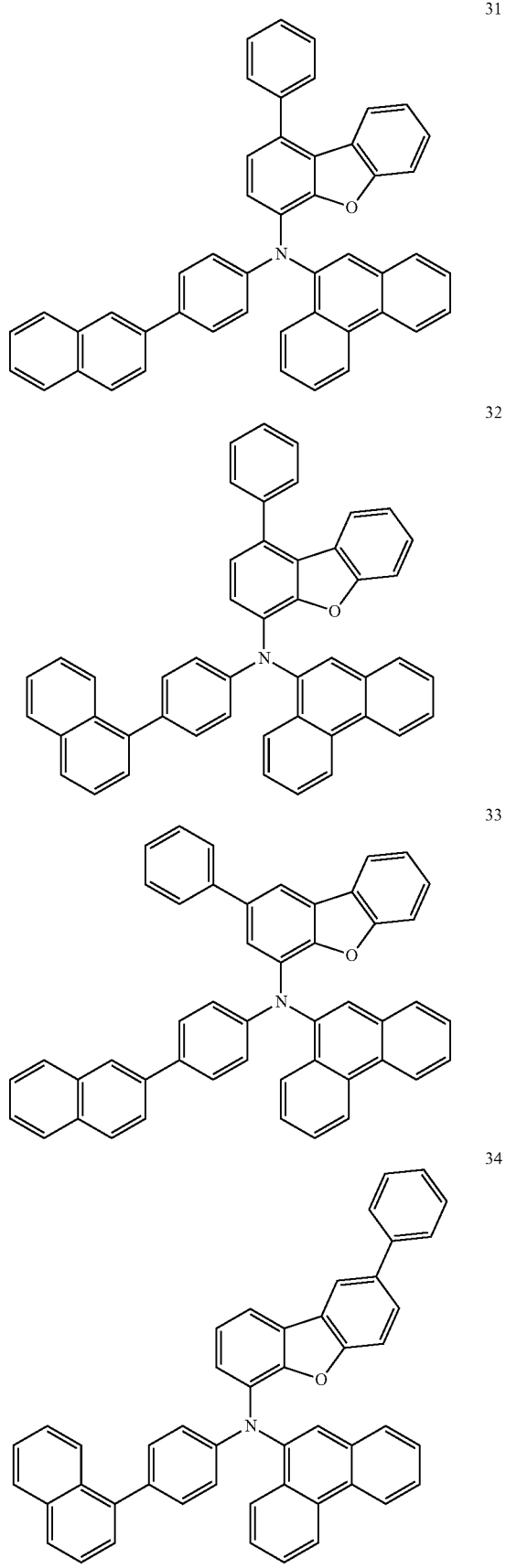

171
-continued

35

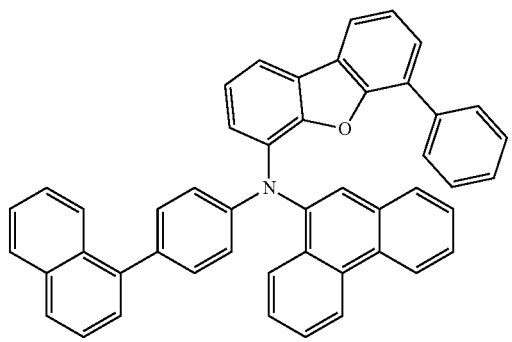

36

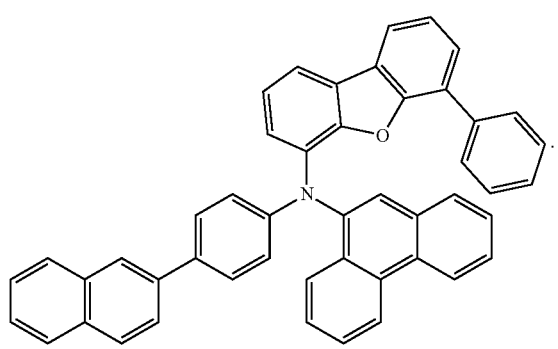

172
-continued

[Formula 3-2]

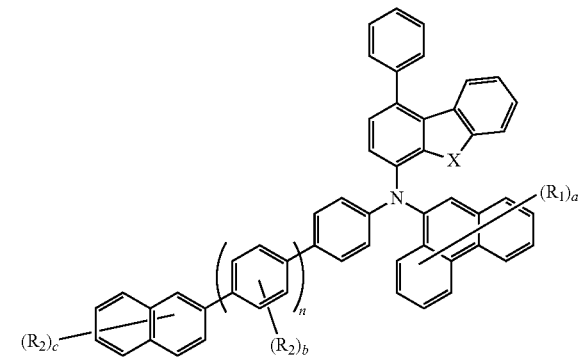

[Formula 3-3]

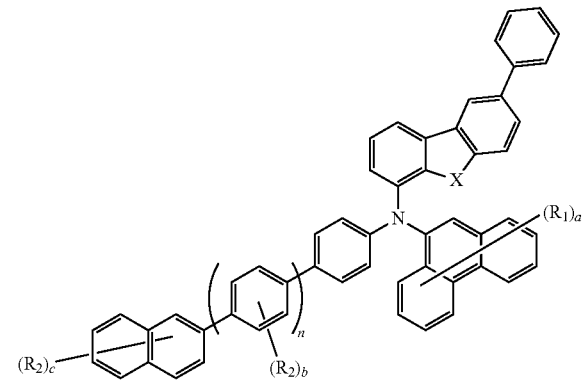

[Formula 3-4]

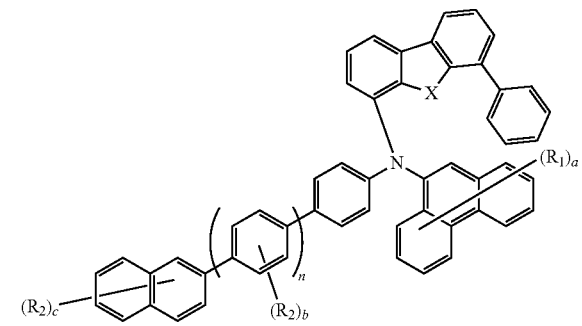

wherein in Formula 3-1 to Formula 3-4,

X is O or S, n is 0 or 1, a is an integer from 0 to 9, b is an integer from 0 to 4, c is an integer from 0 to 7, $R_1$ to $R_3$ are each independently a substituted or unsubstituted alkyl group of 1 to 15 carbon atoms, a substituted or unsubstituted aryl group of 6 to 30 carbon atoms, a substituted or unsubstituted heteroaryl group of 1 to 30 carbon atoms, a substituted or unsubstituted silyl group, a halogen atom, a hydrogen atom, or a deuterium atom, and when X is O, the dibenzofuran group is directly bonded to the nitrogen atom at a 1-, 3-, or 4-position with respect to the oxygen atom.

6. A light emitting element, comprising:

a first electrode;

a second electrode facing the first electrode; and a plurality of functional layers disposed between the first electrode and the second electrode, wherein at least one functional layer among the plurality of functional layers comprises a monoamine compound represented by one of Formula 3-1 to Formula 3-4:

[Formula 3-1]

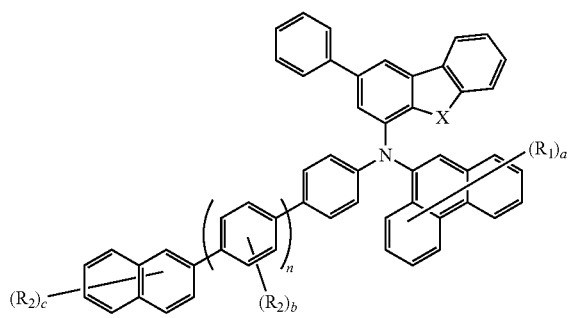

7. The light emitting element of claim 6, wherein the functional layers comprise:
   a hole transport region; and
   an emission layer disposed on the hole transport region, and
   the hole transport region comprises the monoamine compound.

8. The light emitting element of claim 7, wherein the hole transport region comprises a plurality of hole transport layers, and
   a hole transport layer adjacent to the emission layer among the plurality of hole transport layers comprises the monoamine compound.

9. The light emitting element of claim 7, wherein the emission layer emits blue light.

10. The light emitting element of claim 6, wherein the monoamine compound has a highest occupied molecular orbital (HOMO) energy level in a range of about −5.02 eV to about −4.80 eV.

11. The light emitting element of claim 6, wherein at least one functional layer among the plurality of functional layers comprises at least one monoamine compound represented by Compound Group 1:

[Compound Group 1]

13
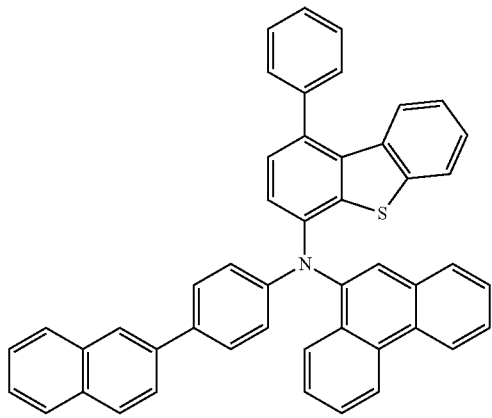

14

-continued

15
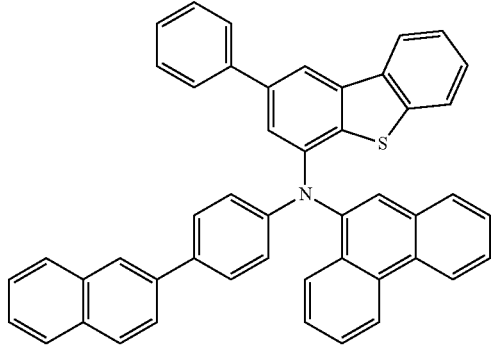

16
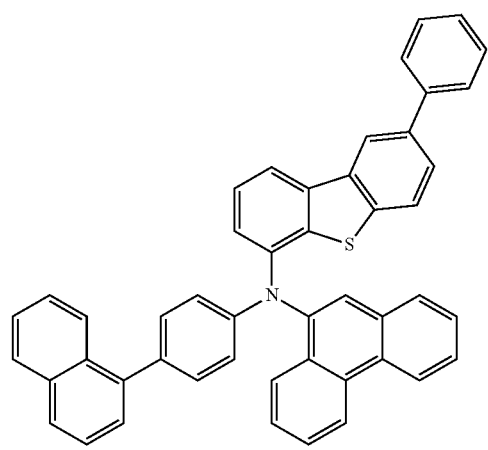

17
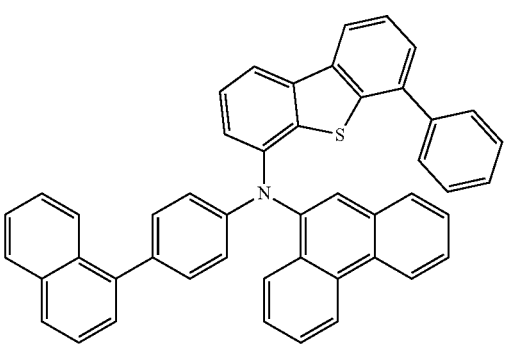

18
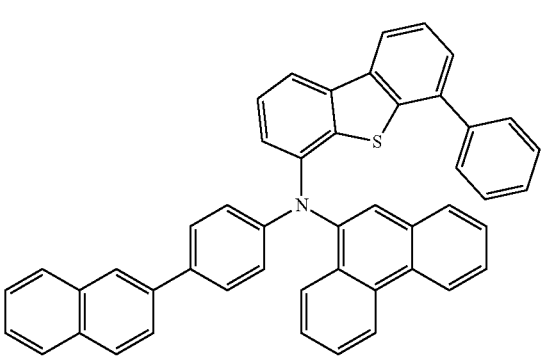

31
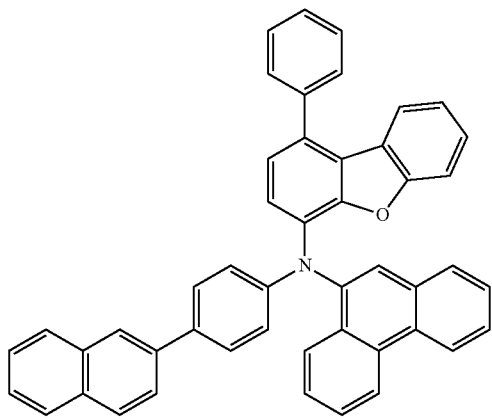
32
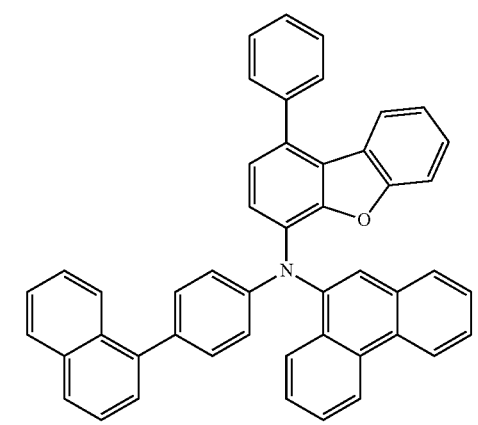
33
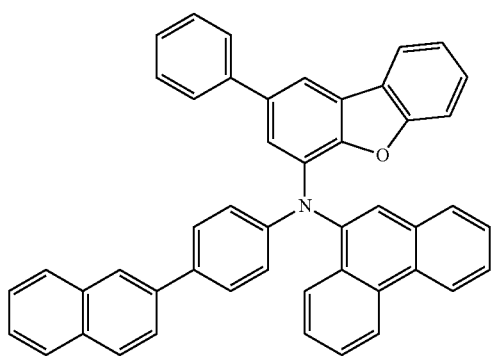
34
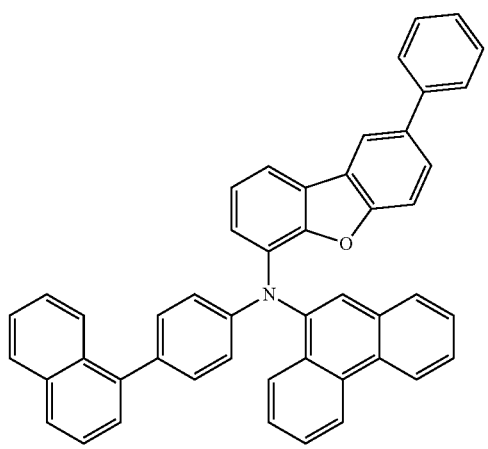
35
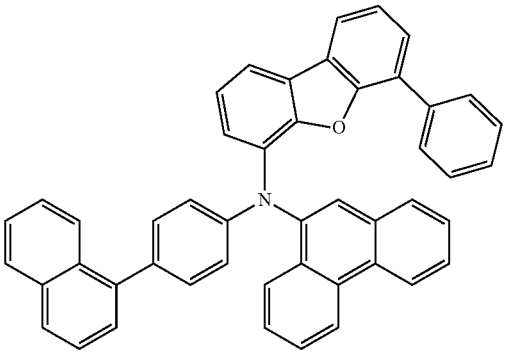
36
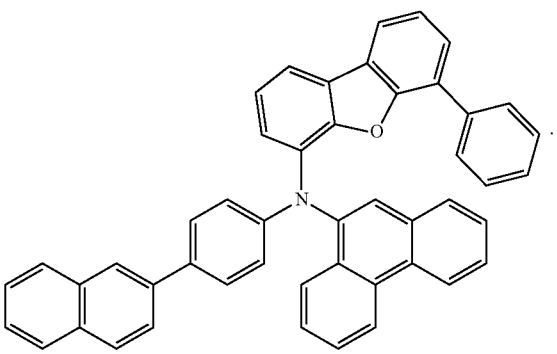
12. A monoamine compound represented by one of Formula 3-1 to Formula 3-4:
[Formula 3-1]
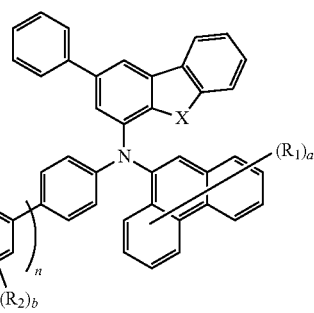

177
-continued

[Formula 3-2]

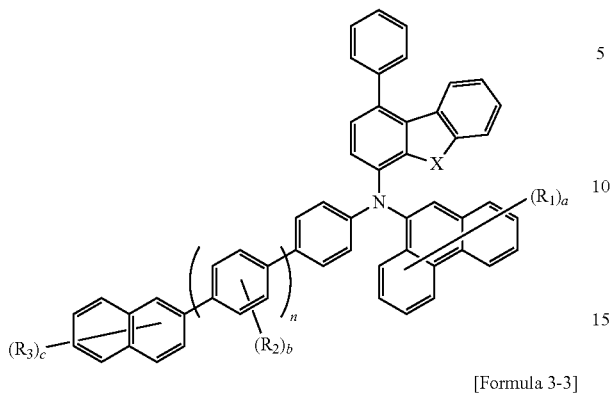

[Formula 3-3]

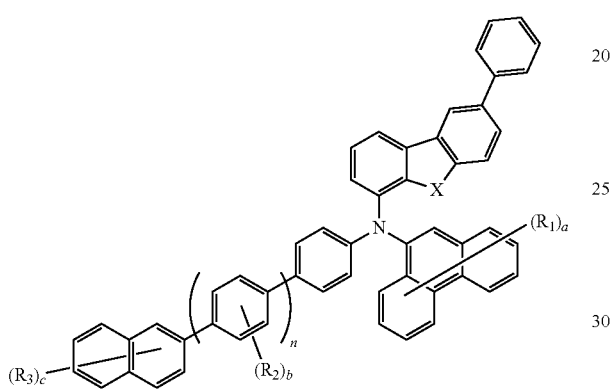

[Formula 3-4]

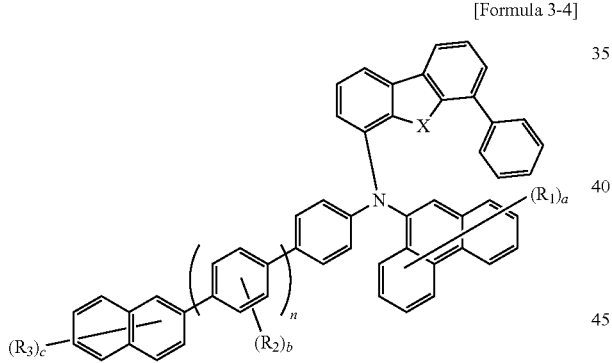

wherein in Formula 3-1 to Formula 3-4,

X is O or S, n is 0 or 1, a is an integer from 0 to 9, b is an integer from 0 to 4, c is an integer from 0 to 7, $R_1$ to $R_3$ are each independently a substituted or unsubstituted alkyl group of 1 to 15 carbon atoms, a substituted or unsubstituted aryl group of 6 to 30 carbon atoms, a substituted or unsubstituted heteroaryl group of 1 to 30 carbon atoms, a substituted or unsubstituted silyl group, a halogen atom, a hydrogen atom, or a deuterium atom, and when X is O, the dibenzofuran group is directly bonded to the nitrogen atom at a 1-, 3-, or 4-position with respect to the oxygen atom.

178

13. The monoamine compound of claim 12, wherein the monoamine compound is selected from Compound Group 1:

[Compound Group 1]

13

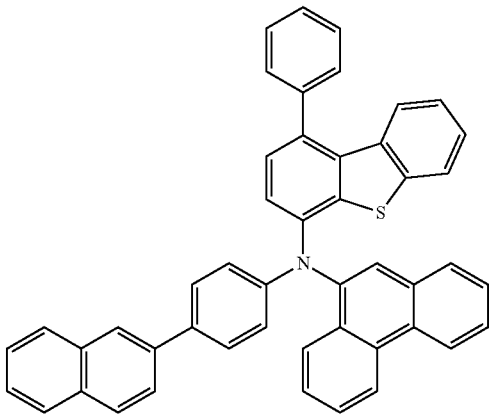

14

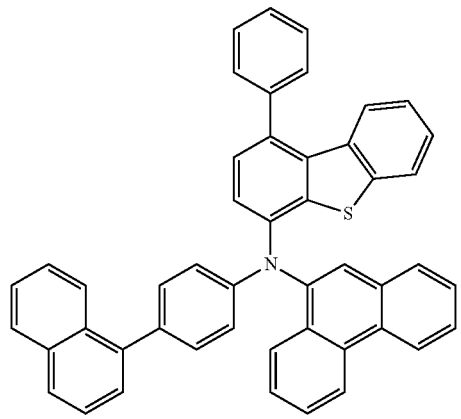

15

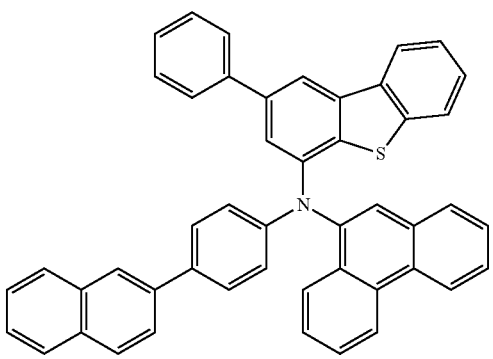

| 16 | 32 |
|---|---|
| 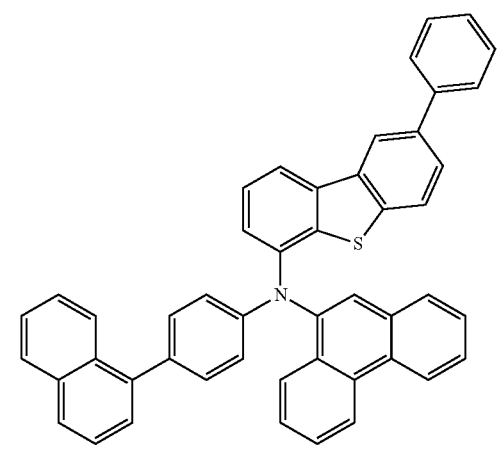 | 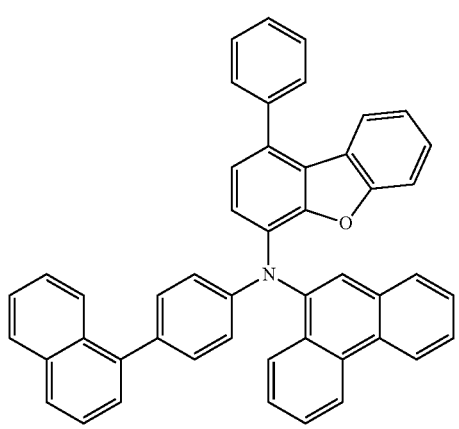 |
| 17 | 33 |
| 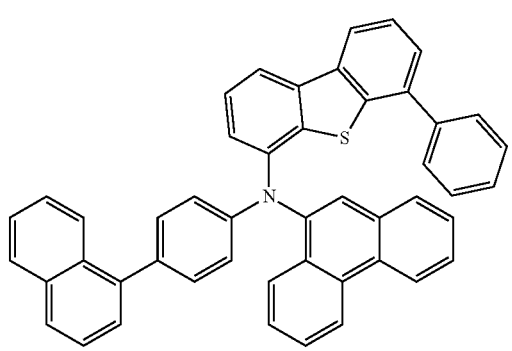 | 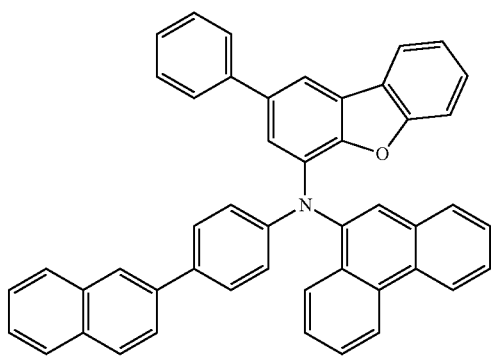 |
| 18 | 34 |
| 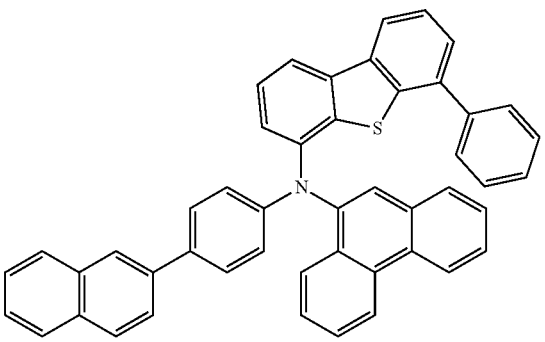 | 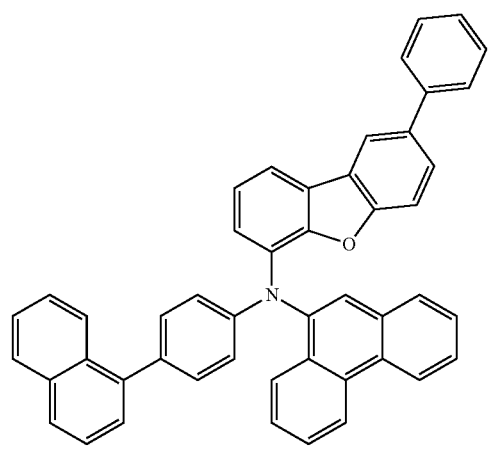 |
| 31 | 35 |
| 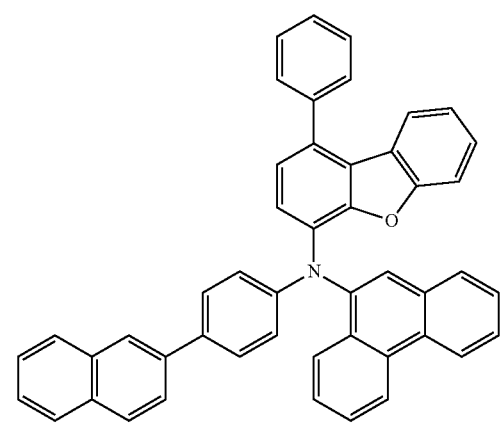 | 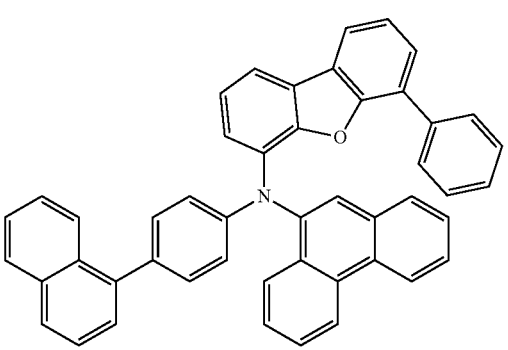 |

-continued

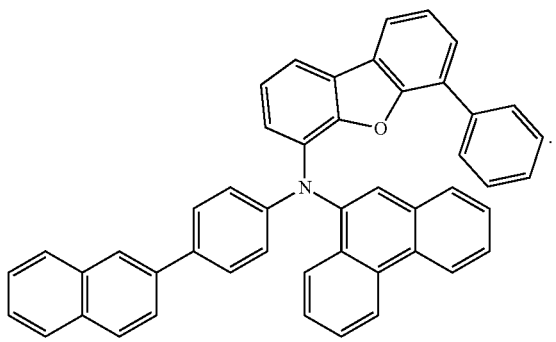

14. A display apparatus including a light emitting element, wherein the light emitting element comprises:
a first electrode;
a second electrode facing the first electrode; and
a plurality of functional layers disposed between the first electrode and the second electrode,
at least one functional layer among the plurality of functional layers comprises a monoamine compound comprising:
a phenanthryl group directly bonded to a nitrogen atom;
a dibenzoheterole group, that is a dibenzothiophene group directly bonded to the nitrogen atom at a 1-, 2-, 3-, or 4-position with respect to a sulfur atom thereof or a dibenzofuran group directly bonded to the nitrogen atom at a 1-, 3-, or 4-position with respect to an oxygen atom thereof; and
a naphthyl group bonded to the nitrogen atom via a linker,
the phenanthryl group is an unsubstituted phenanthryl group or a phenanthryl group substituted with a deuterium atom,
the naphthyl group is an unsubstituted naphthyl group, a naphthyl group substituted with a substituted or unsubstituted phenyl group, a naphthyl group substituted with a substituted or unsubstituted naphthyl group, or a naphthyl group substituted with a deuterium atom,
provided that when the naphthyl group is substituted with a substituted or unsubstituted phenyl group and when the naphthyl group is bonded to the linker at a 1-position, the substituted or unsubstituted phenyl group is not bonded to the naphthyl group at an 8-position, and
the dibenzoheterole group is substituted with at least one substituted or unsubstituted phenyl group.

* * * * *